(12) United States Patent
Frederick et al.

(10) Patent No.: US 7,220,309 B2
(45) Date of Patent: May 22, 2007

(54) RECEPTOR LINKED PROTEIN TYROSINE PHOSPHATASES

(75) Inventors: Christin Frederick, Newton, MA (US); Haruo Saito, Newton, MA (US)

(73) Assignee: Dana Farber Cancer Insitute, Boston, MA (US)

( * ) Notice: Subject to any disclaimer, the term of this patent is extended or adjusted under 35 U.S.C. 154(b) by 259 days.

(21) Appl. No.: 10/385,206

(22) Filed: Mar. 10, 2003

(65) Prior Publication Data

US 2003/0224335 A1 Dec. 4, 2003

Related U.S. Application Data

(60) Provisional application No. 60/362,594, filed on Mar. 8, 2002.

(51) Int. Cl.
*C30B 29/14* (2006.01)
(52) U.S. Cl. .............................. 117/68; 117/69; 117/929
(58) Field of Classification Search .................. 117/68, 117/69, 929
See application file for complete search history.

(56) References Cited

OTHER PUBLICATIONS

Jiang et al., "Receptor-like Protein Phosphatase Homodimerizes on the Cell Surface", Molecular and Cellular Biology Aug. 200 pp. 5917-5929.*
Blom et al., "Characterization of a Human Basophil-Like Cell Line", Scand. J. Immunol. vol. 44 1996 pp. 54-61.*
Li et al., "Efficient Total Synthese of Pulchellactam, A CD45 Protein Tyrosine Phosphatase Inhibitor", J. Org. Chem vol. 67 No. 14. 2002 pp. 4702-4706.*
Nam et al., Crystal Structure of the Tandem Phosphatase Domains of RPTP LAR, Cell, vol. 97 May 1999 pp. 449-457.*

* cited by examiner

*Primary Examiner*—Robert Kunemund
(74) *Attorney, Agent, or Firm*—Peter F. Corless; Edwards Angell Palmer & Dodge LLP

(57) ABSTRACT

The crystal structures of CD45 and LAR, described herein, provide a basis for kinetic and functional studies. Identification of the crystal structures of cellular molecules is important in to determine functional roles in immunity, phosphorylation events, disease initiation mechanism. The isolated crystals and methods for crystallization thereof, are also important in identifying small molecule interactions with cellular molecules for new drug discovery.

24 Claims, 131 Drawing Sheets

ACTIVE SITE (A) COORDINATES

```
ATOM    483  N    ASN A 654      2.085  -17.209   27.627  1.00 55.68      A
ATOM    484  CA   ASN A 654      1.592  -16.373   26.527  1.00 55.68      A
ATOM    485  CB   ASN A 654      0.090  -16.627   26.301  1.00 55.68      A
ATOM    486  CG   ASN A 654     -0.201  -18.034   25.797  1.00 55.68      A
ATOM    487  OD1  ASN A 654      0.126  -18.382   24.658  1.00 55.68      A
ATOM    488  ND2  ASN A 654     -0.813  -18.855   26.648  1.00 55.68      A
ATOM    489  C    ASN A 654      1.808  -14.867   26.701  1.00 55.68      A
ATOM    490  O    ASN A 654      0.945  -14.083   26.318  1.00 55.68      A
ATOM    491  N    LYS A 655      2.939  -14.460   27.273  1.00 55.68      A
ATOM    492  CA   LYS A 655      3.235  -13.039   27.469  1.00 55.68      A
ATOM    493  CB   LYS A 655      3.124  -12.651   28.944  1.00 55.68      A
ATOM    494  CG   LYS A 655      1.703  -12.569   29.462  1.00 55.68      A
ATOM    495  CD   LYS A 655      1.674  -12.233   30.940  1.00 55.68      A
ATOM    496  CE   LYS A 655      0.252  -12.246   31.486  1.00 55.68      A
ATOM    497  NZ   LYS A 655      0.195  -12.146   32.977  1.00 55.68      A
ATOM    498  C    LYS A 655      4.631  -12.722   26.965  1.00 55.68      A
ATOM    499  O    LYS A 655      5.083  -11.581   27.003  1.00 55.68      A
ATOM    500  N    ASN A 656      5.310  -13.752   26.487  1.00 55.68      A
ATOM    501  CA   ASN A 656      6.645  -13.588   25.958  1.00 55.68      A
ATOM    502  CB   ASN A 656      7.634  -14.387   26.789  1.00 55.68      A
ATOM    503  CG   ASN A 656      7.902  -13.745   28.105  1.00 55.68      A
ATOM    504  OD1  ASN A 656      7.981  -12.518   28.196  1.00 55.68      A
ATOM    505  ND2  ASN A 656      8.052  -14.553   29.140  1.00 55.68      A
ATOM    506  C    ASN A 656      6.737  -14.020   24.507  1.00 55.68      A
ATOM    507  O    ASN A 656      6.243  -15.085   24.138  1.00 55.68      A
ATOM    508  N    ARG A 657      7.377  -13.195   23.686  1.00 55.68      A
ATOM    509  CA   ARG A 657      7.531  -13.507   22.281  1.00 55.68      A
ATOM    510  CB   ARG A 657      8.015  -12.275   21.537  1.00 55.68      A
ATOM    511  CG   ARG A 657      6.893  -11.303   21.275  1.00 55.68      A
ATOM    512  CD   ARG A 657      7.396   -9.992   20.755  1.00 55.68      A
ATOM    513  NE   ARG A 657      6.338   -9.191   20.150  1.00 55.68      A
ATOM    514  CZ   ARG A 657      5.894   -9.362   18.912  1.00 55.68      A
ATOM    515  NH1  ARG A 657      6.410  -10.306   18.144  1.00 55.68      A
ATOM    516  NH2  ARG A 657      4.948   -8.576   18.434  1.00 55.68      A
ATOM    517  C    ARG A 657      8.460  -14.688   22.050  1.00 55.68      A
ATOM    518  O    ARG A 657      8.112  -15.629   21.329  1.00 55.68      A
ATOM    519  N    TYR A 658      9.637  -14.654   22.661  1.00 55.68      A
ATOM    520  CA   TYR A 658     10.589  -15.749   22.506  1.00 55.68      A
ATOM    521  CB   TYR A 658     11.851  -15.268   21.777  1.00 55.68      A
ATOM    522  CG   TYR A 658     11.568  -14.446   20.542  1.00 55.68      A
ATOM    523  CD1  TYR A 658     12.406  -13.398   20.169  1.00 55.68      A
ATOM    524  CE1  TYR A 658     12.093  -12.572   19.081  1.00 55.68      A
ATOM    525  CD2  TYR A 658     10.419  -14.660   19.789  1.00 55.68      A
ATOM    526  CE2  TYR A 658     10.093  -13.842   18.704  1.00 55.68      A
ATOM    527  CZ   TYR A 658     10.929  -12.797   18.358  1.00 55.68      A
ATOM    528  OH   TYR A 658     10.563  -11.954   17.329  1.00 55.68      A
ATOM    529  C    TYR A 658     10.947  -16.260   23.892  1.00 55.68      A
ATOM    530  O    TYR A 658     11.423  -15.501   24.724  1.00 55.68      A
ATOM    531  N    VAL A 659     10.710  -17.542   24.141  1.00 55.68      A
ATOM    532  CA   VAL A 659     11.010  -18.134   25.437  1.00 55.68      A
ATOM    533  CB   VAL A 659     10.386  -19.523   25.564  1.00 55.68      A
ATOM    534  CG1  VAL A 659      8.876  -19.385   25.623  1.00 55.68      A
ATOM    535  CG2  VAL A 659     10.822  -20.407   24.389  1.00 55.68      A
ATOM    536  C    VAL A 659     12.503  -18.233   25.727  1.00 55.68      A
```

Figure 4 A

ACTIVE SITE (A) COORDINATES

| | | | | | | | | | | |
|---|---|---|---|---|---|---|---|---|---|---|
| ATOM | 483 | N | ASN | A | 654 | 2.085 | -17.209 | 27.627 | 1.00 55.68 | A |
| ATOM | 484 | CA | ASN | A | 654 | 1.592 | -16.373 | 26.527 | 1.00 55.68 | A |
| ATOM | 485 | CB | ASN | A | 654 | 0.090 | -16.627 | 26.301 | 1.00 55.68 | A |
| ATOM | 486 | CG | ASN | A | 654 | -0.201 | -18.034 | 25.797 | 1.00 55.68 | A |
| ATOM | 487 | OD1 | ASN | A | 654 | 0.126 | -18.382 | 24.658 | 1.00 55.68 | A |
| ATOM | 488 | ND2 | ASN | A | 654 | -0.813 | -18.855 | 26.648 | 1.00 55.68 | A |
| ATOM | 489 | C | ASN | A | 654 | 1.808 | -14.867 | 26.701 | 1.00 55.68 | A |
| ATOM | 490 | O | ASN | A | 654 | 0.945 | -14.083 | 26.318 | 1.00 55.68 | A |
| ATOM | 491 | N | LYS | A | 655 | 2.939 | -14.460 | 27.273 | 1.00 55.68 | A |
| ATOM | 492 | CA | LYS | A | 655 | 3.235 | -13.039 | 27.469 | 1.00 55.68 | A |
| ATOM | 493 | CB | LYS | A | 655 | 3.124 | -12.651 | 28.944 | 1.00 55.68 | A |
| ATOM | 494 | CG | LYS | A | 655 | 1.703 | -12.569 | 29.462 | 1.00 55.68 | A |
| ATOM | 495 | CD | LYS | A | 655 | 1.674 | -12.233 | 30.940 | 1.00 55.68 | A |
| ATOM | 496 | CE | LYS | A | 655 | 0.252 | -12.246 | 31.486 | 1.00 55.68 | A |
| ATOM | 497 | NZ | LYS | A | 655 | 0.195 | -12.146 | 32.977 | 1.00 55.68 | A |
| ATOM | 498 | C | LYS | A | 655 | 4.631 | -12.722 | 26.965 | 1.00 55.68 | A |
| ATOM | 499 | O | LYS | A | 655 | 5.083 | -11.581 | 27.003 | 1.00 55.68 | A |
| ATOM | 500 | N | ASN | A | 656 | 5.310 | -13.752 | 26.487 | 1.00 55.68 | A |
| ATOM | 501 | CA | ASN | A | 656 | 6.645 | -13.588 | 25.958 | 1.00 55.68 | A |
| ATOM | 502 | CB | ASN | A | 656 | 7.634 | -14.387 | 26.789 | 1.00 55.68 | A |
| ATOM | 503 | CG | ASN | A | 656 | 7.902 | -13.745 | 28.105 | 1.00 55.68 | A |
| ATOM | 504 | OD1 | ASN | A | 656 | 7.981 | -12.518 | 28.196 | 1.00 55.68 | A |
| ATOM | 505 | ND2 | ASN | A | 656 | 8.052 | -14.553 | 29.140 | 1.00 55.68 | A |
| ATOM | 506 | C | ASN | A | 656 | 6.737 | -14.020 | 24.507 | 1.00 55.68 | A |
| ATOM | 507 | O | ASN | A | 656 | 6.243 | -15.085 | 24.138 | 1.00 55.68 | A |
| ATOM | 508 | N | ARG | A | 657 | 7.377 | -13.195 | 23.686 | 1.00 55.68 | A |
| ATOM | 509 | CA | ARG | A | 657 | 7.531 | -13.507 | 22.281 | 1.00 55.68 | A |
| ATOM | 510 | CB | ARG | A | 657 | 8.015 | -12.275 | 21.537 | 1.00 55.68 | A |
| ATOM | 511 | CG | ARG | A | 657 | 6.893 | -11.303 | 21.275 | 1.00 55.68 | A |
| ATOM | 512 | CD | ARG | A | 657 | 7.396 | -9.992 | 20.755 | 1.00 55.68 | A |
| ATOM | 513 | NE | ARG | A | 657 | 6.338 | -9.191 | 20.150 | 1.00 55.68 | A |
| ATOM | 514 | CZ | ARG | A | 657 | 5.894 | -9.362 | 18.912 | 1.00 55.68 | A |
| ATOM | 515 | NH1 | ARG | A | 657 | 6.410 | -10.306 | 18.144 | 1.00 55.68 | A |
| ATOM | 516 | NH2 | ARG | A | 657 | 4.948 | -8.576 | 18.434 | 1.00 55.68 | A |
| ATOM | 517 | C | ARG | A | 657 | 8.460 | -14.688 | 22.050 | 1.00 55.68 | A |
| ATOM | 518 | O | ARG | A | 657 | 8.112 | -15.629 | 21.329 | 1.00 55.68 | A |
| ATOM | 519 | N | TYR | A | 658 | 9.637 | -14.654 | 22.661 | 1.00 55.68 | A |
| ATOM | 520 | CA | TYR | A | 658 | 10.589 | -15.749 | 22.506 | 1.00 55.68 | A |
| ATOM | 521 | CB | TYR | A | 658 | 11.851 | -15.268 | 21.777 | 1.00 55.68 | A |
| ATOM | 522 | CG | TYR | A | 658 | 11.568 | -14.446 | 20.542 | 1.00 55.68 | A |
| ATOM | 523 | CD1 | TYR | A | 658 | 12.406 | -13.398 | 20.169 | 1.00 55.68 | A |
| ATOM | 524 | CE1 | TYR | A | 658 | 12.093 | -12.572 | 19.081 | 1.00 55.68 | A |
| ATOM | 525 | CD2 | TYR | A | 658 | 10.419 | -14.660 | 19.789 | 1.00 55.68 | A |
| ATOM | 526 | CE2 | TYR | A | 658 | 10.093 | -13.842 | 18.704 | 1.00 55.68 | A |
| ATOM | 527 | CZ | TYR | A | 658 | 10.929 | -12.797 | 18.358 | 1.00 55.68 | A |
| ATOM | 528 | OH | TYR | A | 658 | 10.563 | -11.954 | 17.329 | 1.00 55.68 | A |
| ATOM | 529 | C | TYR | A | 658 | 10.947 | -16.260 | 23.892 | 1.00 55.68 | A |
| ATOM | 530 | O | TYR | A | 658 | 11.423 | -15.501 | 24.724 | 1.00 55.68 | A |
| ATOM | 531 | N | VAL | A | 659 | 10.710 | -17.542 | 24.141 | 1.00 55.68 | A |
| ATOM | 532 | CA | VAL | A | 659 | 11.010 | -18.134 | 25.437 | 1.00 55.68 | A |
| ATOM | 533 | CB | VAL | A | 659 | 10.386 | -19.523 | 25.564 | 1.00 55.68 | A |
| ATOM | 534 | CG1 | VAL | A | 659 | 8.876 | -19.385 | 25.623 | 1.00 55.68 | A |
| ATOM | 535 | CG2 | VAL | A | 659 | 10.822 | -20.407 | 24.389 | 1.00 55.68 | A |
| ATOM | 536 | C | VAL | A | 659 | 12.503 | -18.233 | 25.727 | 1.00 55.68 | A |

Figure 4 A
(Continued)

| | | | | | | | | | |
|---|---|---|---|---|---|---|---|---|---|
| ATOM | 537 | O | VAL A 659 | 12.957 | -19.127 | 26.437 | 1.00 | 55.68 | A |
| ATOM | 538 | N | ASP A 660 | 13.264 | -17.309 | 25.163 | 1.00 | 55.68 | A |
| ATOM | 539 | CA | ASP A 660 | 14.698 | -17.264 | 25.382 | 1.00 | 55.68 | A |
| ATOM | 540 | CB | ASP A 660 | 15.460 | -17.335 | 24.060 | 1.00 | 55.68 | A |
| ATOM | 541 | CG | ASP A 660 | 15.680 | -18.754 | 23.588 | 1.00 | 55.68 | A |
| ATOM | 542 | OD1 | ASP A 660 | 14.686 | -19.499 | 23.449 | 1.00 | 55.68 | A |
| ATOM | 543 | OD2 | ASP A 660 | 16.850 | -19.120 | 23.351 | 1.00 | 55.68 | A |
| ATOM | 544 | C | ASP A 660 | 14.970 | -15.935 | 26.038 | 1.00 | 55.68 | A |
| ATOM | 545 | O | ASP A 660 | 15.558 | -15.867 | 27.113 | 1.00 | 55.68 | A |
| ATOM | 546 | N | ILE A 661 | 14.532 | -14.878 | 25.369 | 1.00 | 55.68 | A |
| ATOM | 547 | CA | ILE A 661 | 14.705 | -13.533 | 25.865 | 1.00 | 55.68 | A |
| ATOM | 548 | CB | ILE A 661 | 14.298 | -12.505 | 24.799 | 1.00 | 55.68 | A |
| ATOM | 549 | CG2 | ILE A 661 | 14.949 | -11.172 | 25.085 | 1.00 | 55.68 | A |
| ATOM | 550 | CG1 | ILE A 661 | 14.740 | -12.979 | 23.416 | 1.00 | 55.68 | A |
| ATOM | 551 | CD1 | ILE A 661 | 16.193 | -13.317 | 23.315 | 1.00 | 55.68 | A |
| ATOM | 552 | C | ILE A 661 | 13.782 | -13.411 | 27.063 | 1.00 | 55.68 | A |
| ATOM | 553 | O | ILE A 661 | 12.565 | -13.440 | 26.908 | 1.00 | 55.68 | A |
| ATOM | 554 | N | LEU A 662 | 14.363 | -13.282 | 28.255 | 1.00 | 55.68 | A |
| ATOM | 555 | CA | LEU A 662 | 13.585 | -13.178 | 29.491 | 1.00 | 55.68 | A |
| ATOM | 556 | CB | LEU A 662 | 13.348 | -14.581 | 30.044 | 1.00 | 55.68 | A |
| ATOM | 557 | CG | LEU A 662 | 12.525 | -15.462 | 29.097 | 1.00 | 55.68 | A |
| ATOM | 558 | CD1 | LEU A 662 | 12.775 | -16.921 | 29.385 | 1.00 | 55.68 | A |
| ATOM | 559 | CD2 | LEU A 662 | 11.059 | -15.111 | 29.235 | 1.00 | 55.68 | A |
| ATOM | 560 | C | LEU A 662 | 14.204 | -12.267 | 30.562 | 1.00 | 55.68 | A |
| ATOM | 561 | O | LEU A 662 | 15.393 | -12.344 | 30.861 | 1.00 | 55.68 | A |
| ATOM | 562 | N | PRO A 663 | 13.376 | -11.409 | 31.166 | 1.00 | 55.68 | A |
| ATOM | 563 | CD | PRO A 663 | 11.920 | -11.588 | 31.091 | 1.00 | 55.68 | A |
| ATOM | 564 | CA | PRO A 663 | 13.696 | -10.432 | 32.196 | 1.00 | 55.68 | A |
| ATOM | 565 | CB | PRO A 663 | 12.350 | -9.813 | 32.474 | 1.00 | 55.68 | A |
| ATOM | 566 | CG | PRO A 663 | 11.465 | -10.987 | 32.373 | 1.00 | 55.68 | A |
| ATOM | 567 | C | PRO A 663 | 14.306 | -11.015 | 33.454 | 1.00 | 55.68 | A |
| ATOM | 568 | O | PRO A 663 | 13.818 | -12.019 | 33.973 | 1.00 | 55.68 | A |
| ATOM | 1087 | N | THR A 727 | 11.523 | 0.416 | 15.813 | 1.00 | 55.68 | A |
| ATOM | 1088 | CA | THR A 727 | 11.146 | -0.581 | 14.802 | 1.00 | 55.68 | A |
| ATOM | 1089 | CB | THR A 727 | 10.917 | -1.956 | 15.425 | 1.00 | 55.68 | A |
| ATOM | 1090 | OG1 | THR A 727 | 10.737 | -2.926 | 14.388 | 1.00 | 55.68 | A |
| ATOM | 1091 | CG2 | THR A 727 | 9.670 | -1.927 | 16.280 | 1.00 | 55.68 | A |
| ATOM | 1092 | C | THR A 727 | 9.866 | -0.224 | 14.030 | 1.00 | 55.68 | A |
| ATOM | 1093 | O | THR A 727 | 9.306 | 0.867 | 14.183 | 1.00 | 55.68 | A |
| ATOM | 1094 | N | ARG A 728 | 9.415 | -1.148 | 13.186 | 1.00 | 55.68 | A |
| ATOM | 1095 | CA | ARG A 728 | 8.188 | -0.954 | 12.423 | 1.00 | 55.68 | A |
| ATOM | 1096 | CB | ARG A 728 | 8.437 | -0.922 | 10.911 | 1.00 | 55.68 | A |
| ATOM | 1097 | CG | ARG A 728 | 9.275 | 0.259 | 10.408 | 1.00 | 55.68 | A |
| ATOM | 1098 | CD | ARG A 728 | 9.281 | 0.342 | 8.881 | 1.00 | 55.68 | A |
| ATOM | 1099 | NE | ARG A 728 | 9.588 | -0.932 | 8.238 | 1.00 | 55.68 | A |
| ATOM | 1100 | CZ | ARG A 728 | 10.718 | -1.609 | 8.408 | 1.00 | 55.68 | A |
| ATOM | 1101 | NH1 | ARG A 728 | 11.666 | -1.142 | 9.203 | 1.00 | 55.68 | A |
| ATOM | 1102 | NH2 | ARG A 728 | 10.904 | -2.756 | 7.782 | 1.00 | 55.68 | A |
| ATOM | 1103 | C | ARG A 728 | 7.379 | -2.180 | 12.770 | 1.00 | 55.68 | A |
| ATOM | 1104 | O | ARG A 728 | 7.877 | -3.294 | 12.724 | 1.00 | 55.68 | A |
| ATOM | 1105 | N | CYS A 729 | 6.129 | -1.960 | 13.129 | 1.00 | 55.68 | A |
| ATOM | 1106 | CA | CYS A 729 | 5.244 | -3.028 | 13.521 | 1.00 | 55.68 | A |
| ATOM | 1107 | CB | CYS A 729 | 3.822 | -2.582 | 13.275 | 1.00 | 55.68 | A |
| ATOM | 1108 | SG | CYS A 729 | 3.570 | -0.899 | 13.854 | 1.00 | 55.68 | A |
| ATOM | 1109 | C | CYS A 729 | 5.560 | -4.316 | 12.791 | 1.00 | 55.68 | A |
| ATOM | 1110 | O | CYS A 729 | 5.991 | -5.278 | 13.409 | 1.00 | 55.68 | A |
| ATOM | 1111 | N | GLU A 730 | 5.364 | -4.348 | 11.479 | 1.00 | 55.68 | A |

Figure 4 A (Continued)

| | | | | | | | | | | |
|---|---|---|---|---|---|---|---|---|---|---|
| ATOM | 1112 | CA | GLU | A | 730 | 5.663 | -5.563 | 10.715 | 1.00 55.68 | A |
| ATOM | 1113 | CB | GLU | A | 730 | 4.407 | -6.097 | 10.019 | 1.00 55.68 | A |
| ATOM | 1114 | CG | GLU | A | 730 | 3.597 | -7.077 | 10.888 | 1.00 55.68 | A |
| ATOM | 1115 | CD | GLU | A | 730 | 2.126 | -7.175 | 10.478 | 1.00 55.68 | A |
| ATOM | 1116 | OE1 | GLU | A | 730 | 1.844 | -7.556 | 9.316 | 1.00 55.68 | A |
| ATOM | 1117 | OE2 | GLU | A | 730 | 1.252 | -6.864 | 11.322 | 1.00 55.68 | A |
| ATOM | 1118 | C | GLU | A | 730 | 6.775 | -5.332 | 9.709 | 1.00 55.68 | A |
| ATOM | 1119 | O | GLU | A | 730 | 6.696 | -4.450 | 8.853 | 1.00 55.68 | A |
| ATOM | 1120 | N | GLU | A | 731 | 7.813 | -6.150 | 9.829 | 1.00 55.68 | A |
| ATOM | 1121 | CA | GLU | A | 731 | 8.990 | -6.037 | 8.988 | 1.00 55.68 | A |
| ATOM | 1122 | CB | GLU | A | 731 | 10.171 | -5.556 | 9.829 | 1.00 55.68 | A |
| ATOM | 1123 | CG | GLU | A | 731 | 9.869 | -4.279 | 10.595 | 1.00 55.68 | A |
| ATOM | 1124 | CD | GLU | A | 731 | 10.966 | -3.922 | 11.559 | 1.00 55.68 | A |
| ATOM | 1125 | OE1 | GLU | A | 731 | 11.488 | -4.855 | 12.207 | 1.00 55.68 | A |
| ATOM | 1126 | OE2 | GLU | A | 731 | 11.297 | -2.722 | 11.676 | 1.00 55.68 | A |
| ATOM | 1127 | C | GLU | A | 731 | 9.362 | -7.330 | 8.295 | 1.00 55.68 | A |
| ATOM | 1128 | O | GLU | A | 731 | 9.499 | -8.372 | 8.938 | 1.00 55.68 | A |
| ATOM | 1129 | N | GLY | A | 732 | 9.548 | -7.240 | 6.977 | 1.00 55.68 | A |
| ATOM | 1130 | CA | GLY | A | 732 | 9.893 | -8.413 | 6.206 | 1.00 55.68 | A |
| ATOM | 1131 | C | GLY | A | 732 | 8.839 | -9.469 | 6.466 | 1.00 55.68 | A |
| ATOM | 1132 | O | GLY | A | 732 | 9.099 | -10.464 | 7.150 | 1.00 55.68 | A |
| ATOM | 1133 | N | ASN | A | 733 | 7.643 | -9.221 | 5.932 | 1.00 55.68 | A |
| ATOM | 1134 | CA | ASN | A | 733 | 6.485 | -10.109 | 6.058 | 1.00 55.68 | A |
| ATOM | 1135 | CB | ASN | A | 733 | 6.148 | -10.694 | 4.679 | 1.00 55.68 | A |
| ATOM | 1136 | CG | ASN | A | 733 | 5.611 | -9.630 | 3.705 | 1.00 55.68 | A |
| ATOM | 1137 | OD1 | ASN | A | 733 | 6.031 | -8.465 | 3.736 | 1.00 55.68 | A |
| ATOM | 1138 | ND2 | ASN | A | 733 | 4.692 | -10.033 | 2.832 | 1.00 55.68 | A |
| ATOM | 1139 | C | ASN | A | 733 | 6.591 | -11.219 | 7.114 | 1.00 55.68 | A |
| ATOM | 1140 | O | ASN | A | 733 | 6.723 | -12.405 | 6.799 | 1.00 55.68 | A |
| ATOM | 1141 | N | ARG | A | 734 | 6.511 | -10.788 | 8.372 | 1.00 55.68 | A |
| ATOM | 1142 | CA | ARG | A | 734 | 6.574 | -11.633 | 9.560 | 1.00 55.68 | A |
| ATOM | 1143 | CB | ARG | A | 734 | 8.031 | -12.022 | 9.829 | 1.00 55.68 | A |
| ATOM | 1144 | CG | ARG | A | 734 | 8.261 | -12.745 | 11.128 | 1.00 55.68 | A |
| ATOM | 1145 | CD | ARG | A | 734 | 7.621 | -14.121 | 11.152 | 1.00 55.68 | A |
| ATOM | 1146 | NE | ARG | A | 734 | 7.289 | -14.530 | 12.521 | 1.00 55.68 | A |
| ATOM | 1147 | CZ | ARG | A | 734 | 6.080 | -14.415 | 13.079 | 1.00 55.68 | A |
| ATOM | 1148 | NH1 | ARG | A | 734 | 5.062 | -13.911 | 12.388 | 1.00 55.68 | A |
| ATOM | 1149 | NH2 | ARG | A | 734 | 5.892 | -14.792 | 14.340 | 1.00 55.68 | A |
| ATOM | 1150 | C | ARG | A | 734 | 6.016 | -10.712 | 10.660 | 1.00 55.68 | A |
| ATOM | 1151 | O | ARG | A | 734 | 5.843 | -9.513 | 10.407 | 1.00 55.68 | A |
| ATOM | 1152 | N | ASN | A | 735 | 5.710 | -11.244 | 11.849 | 1.00 55.68 | A |
| ATOM | 1153 | CA | ASN | A | 735 | 5.173 | -10.413 | 12.948 | 1.00 55.68 | A |
| ATOM | 1154 | CB | ASN | A | 735 | 4.174 | -11.192 | 13.820 | 1.00 55.68 | A |
| ATOM | 1155 | CG | ASN | A | 735 | 2.776 | -11.287 | 13.198 | 1.00 55.68 | A |
| ATOM | 1156 | OD1 | ASN | A | 735 | 1.816 | -11.674 | 13.862 | 1.00 55.68 | A |
| ATOM | 1157 | ND2 | ASN | A | 735 | 2.664 | -10.950 | 11.923 | 1.00 55.68 | A |
| ATOM | 1158 | C | ASN | A | 735 | 6.295 | -9.903 | 13.837 | 1.00 55.68 | A |
| ATOM | 1159 | O | ASN | A | 735 | 7.244 | -10.631 | 14.120 | 1.00 55.68 | A |
| ATOM | 1160 | N | LYS | A | 736 | 6.193 | -8.656 | 14.282 | 1.00 55.68 | A |
| ATOM | 1161 | CA | LYS | A | 736 | 7.237 | -8.092 | 15.128 | 1.00 55.68 | A |
| ATOM | 1162 | CB | LYS | A | 736 | 8.219 | -7.272 | 14.286 | 1.00 55.68 | A |
| ATOM | 1163 | CG | LYS | A | 736 | 9.129 | -8.101 | 13.383 | 1.00 55.68 | A |
| ATOM | 1164 | CD | LYS | A | 736 | 10.018 | -9.058 | 14.169 | 1.00 55.68 | A |
| ATOM | 1165 | CE | LYS | A | 736 | 10.922 | -9.853 | 13.239 | 1.00 55.68 | A |
| ATOM | 1166 | NZ | LYS | A | 736 | 11.720 | -10.901 | 13.921 | 1.00 55.68 | A |
| ATOM | 1167 | C | LYS | A | 736 | 6.750 | -7.247 | 16.302 | 1.00 55.68 | A |
| ATOM | 1168 | O | LYS | A | 736 | 7.497 | -7.018 | 17.239 | 1.00 55.68 | A |

Figure 4 A
(Continued)

| | | | | | | | | | | |
|---|---|---|---|---|---|---|---|---|---|---|
| ATOM | 1169 | N | CYS | A | 737 | 5.504 | -6.791 | 16.258 | 1.00 55.68 | A |
| ATOM | 1170 | CA | CYS | A | 737 | 4.944 | -5.979 | 17.333 | 1.00 55.68 | A |
| ATOM | 1171 | CB | CYS | A | 737 | 5.873 | -4.835 | 17.698 | 1.00 55.68 | A |
| ATOM | 1172 | SG | CYS | A | 737 | 5.024 | -3.469 | 18.527 | 1.00 55.68 | A |
| ATOM | 1173 | C | CYS | A | 737 | 3.628 | -5.387 | 16.926 | 1.00 55.68 | A |
| ATOM | 1174 | O | CYS | A | 737 | 3.591 | -4.346 | 16.284 | 1.00 55.68 | A |
| ATOM | 1619 | N | THR | A | 792 | 12.122 | 4.432 | 11.913 | 1.00 55.68 | A |
| ATOM | 1620 | CA | THR | A | 792 | 11.638 | 3.821 | 10.689 | 1.00 55.68 | A |
| ATOM | 1621 | CB | THR | A | 792 | 10.893 | 4.862 | 9.862 | 1.00 55.68 | A |
| ATOM | 1622 | OG1 | THR | A | 792 | 11.801 | 5.918 | 9.525 | 1.00 55.68 | A |
| ATOM | 1623 | CG2 | THR | A | 792 | 9.723 | 5.442 | 10.650 | 1.00 55.68 | A |
| ATOM | 1624 | C | THR | A | 792 | 12.719 | 3.218 | 9.803 | 1.00 55.68 | A |
| ATOM | 1625 | O | THR | A | 792 | 12.583 | 2.099 | 9.312 | 1.00 55.68 | A |
| ATOM | 1626 | N | SER | A | 793 | 13.793 | 3.962 | 9.600 | 1.00 55.68 | A |
| ATOM | 1627 | CA | SER | A | 793 | 14.855 | 3.497 | 8.732 | 1.00 55.68 | A |
| ATOM | 1628 | CB | SER | A | 793 | 15.805 | 4.666 | 8.425 | 1.00 55.68 | A |
| ATOM | 1629 | OG | SER | A | 793 | 15.122 | 5.712 | 7.748 | 1.00 55.68 | A |
| ATOM | 1630 | C | SER | A | 793 | 15.660 | 2.266 | 9.159 | 1.00 55.68 | A |
| ATOM | 1631 | O | SER | A | 793 | 16.683 | 1.964 | 8.552 | 1.00 55.68 | A |
| ATOM | 1632 | N | TRP | A | 794 | 15.225 | 1.542 | 10.180 | 1.00 55.68 | A |
| ATOM | 1633 | CA | TRP | A | 794 | 16.003 | 0.372 | 10.570 | 1.00 55.68 | A |
| ATOM | 1634 | CB | TRP | A | 794 | 15.639 | -0.121 | 11.976 | 1.00 55.68 | A |
| ATOM | 1635 | CG | TRP | A | 794 | 16.658 | -1.094 | 12.536 | 1.00 55.68 | A |
| ATOM | 1636 | CD2 | TRP | A | 794 | 17.593 | -0.858 | 13.607 | 1.00 55.68 | A |
| ATOM | 1637 | CE2 | TRP | A | 794 | 18.358 | -2.034 | 13.760 | 1.00 55.68 | A |
| ATOM | 1638 | CE3 | TRP | A | 794 | 17.859 | 0.233 | 14.447 | 1.00 55.68 | A |
| ATOM | 1639 | CD1 | TRP | A | 794 | 16.894 | -2.364 | 12.103 | 1.00 55.68 | A |
| ATOM | 1640 | NE1 | TRP | A | 794 | 17.913 | -2.935 | 12.831 | 1.00 55.68 | A |
| ATOM | 1641 | CZ2 | TRP | A | 794 | 19.362 | -2.154 | 14.715 | 1.00 55.68 | A |
| ATOM | 1642 | CZ3 | TRP | A | 794 | 18.864 | 0.111 | 15.397 | 1.00 55.68 | A |
| ATOM | 1643 | CH2 | TRP | A | 794 | 19.600 | -1.075 | 15.520 | 1.00 55.68 | A |
| ATOM | 1644 | C | TRP | A | 794 | 15.759 | -0.730 | 9.563 | 1.00 55.68 | A |
| ATOM | 1645 | O | TRP | A | 794 | 14.662 | -1.290 | 9.490 | 1.00 55.68 | A |
| ATOM | 1646 | N | PRO | A | 795 | 16.793 | -1.066 | 8.781 | 1.00 55.68 | A |
| ATOM | 1647 | CD | PRO | A | 795 | 18.184 | -0.699 | 9.075 | 1.00 55.68 | A |
| ATOM | 1648 | CA | PRO | A | 795 | 16.765 | -2.094 | 7.744 | 1.00 55.68 | A |
| ATOM | 1649 | CB | PRO | A | 795 | 18.231 | -2.165 | 7.294 | 1.00 55.68 | A |
| ATOM | 1650 | CG | PRO | A | 795 | 18.952 | -1.880 | 8.519 | 1.00 55.68 | A |
| ATOM | 1651 | C | PRO | A | 795 | 16.227 | -3.449 | 8.182 | 1.00 55.68 | A |
| ATOM | 1652 | O | PRO | A | 795 | 16.574 | -3.938 | 9.248 | 1.00 55.68 | A |
| ATOM | 1653 | N | ASP | A | 796 | 15.338 | -4.017 | 7.370 | 1.00 55.68 | A |
| ATOM | 1654 | CA | ASP | A | 796 | 14.802 | -5.347 | 7.614 | 1.00 55.68 | A |
| ATOM | 1655 | CB | ASP | A | 796 | 14.063 | -5.857 | 6.376 | 1.00 55.68 | A |
| ATOM | 1656 | CG | ASP | A | 796 | 12.791 | -5.101 | 6.106 | 1.00 55.68 | A |
| ATOM | 1657 | OD1 | ASP | A | 796 | 11.792 | -5.426 | 6.783 | 1.00 55.68 | A |
| ATOM | 1658 | OD2 | ASP | A | 796 | 12.787 | -4.195 | 5.225 | 1.00 55.68 | A |
| ATOM | 1659 | C | ASP | A | 796 | 16.032 | -6.222 | 7.840 | 1.00 55.68 | A |
| ATOM | 1660 | O | ASP | A | 796 | 16.680 | -6.648 | 6.884 | 1.00 55.68 | A |
| ATOM | 1661 | N | HIS | A | 797 | 16.390 | -6.455 | 9.099 | 1.00 55.68 | A |
| ATOM | 1662 | CA | HIS | A | 797 | 17.541 | -7.309 | 9.398 | 1.00 55.68 | A |
| ATOM | 1663 | CB | HIS | A | 797 | 17.411 | -8.651 | 8.638 | 1.00 55.68 | A |
| ATOM | 1664 | CG | HIS | A | 797 | 18.637 | -9.490 | 8.646 | 1.00 55.68 | A |
| ATOM | 1665 | CD2 | HIS | A | 797 | 19.856 | -9.305 | 9.236 | 1.00 55.68 | A |
| ATOM | 1666 | ND1 | HIS | A | 797 | 18.739 | -10.679 | 7.953 | 1.00 55.68 | A |
| ATOM | 1667 | CE1 | HIS | A | 797 | 19.947 | -11.179 | 8.107 | 1.00 55.68 | A |
| ATOM | 1668 | NE2 | HIS | A | 797 | 20.647 | -10.354 | 8.885 | 1.00 55.68 | A |
| ATOM | 1669 | C | HIS | A | 797 | 18.817 | -6.614 | 8.976 | 1.00 55.68 | A |

Figure 4 A
(Continued)

| | | | | | | | | | |
|---|---|---|---|---|---|---|---|---|---|
| ATOM | 1670 | O | HIS | A | 797 | 18.979 | -6.271 | 7.809 | 1.00 55.68 | A |
| ATOM | 1671 | N | GLY | A | 798 | 19.729 | -6.464 | 9.933 | 1.00 55.68 | A |
| ATOM | 1672 | CA | GLY | A | 798 | 21.008 | -5.829 | 9.686 | 1.00 55.68 | A |
| ATOM | 1673 | C | GLY | A | 798 | 21.241 | -4.630 | 10.587 | 1.00 55.68 | A |
| ATOM | 1674 | O | GLY | A | 798 | 20.715 | -4.547 | 11.694 | 1.00 55.68 | A |
| ATOM | 1675 | N | VAL | A | 799 | 22.041 | -3.686 | 10.110 | 1.00 55.68 | A |
| ATOM | 1676 | CA | VAL | A | 799 | 22.345 | -2.488 | 10.877 | 1.00 55.68 | A |
| ATOM | 1677 | CB | VAL | A | 799 | 23.616 | -2.690 | 11.741 | 1.00 55.68 | A |
| ATOM | 1678 | CG1 | VAL | A | 799 | 23.611 | -4.088 | 12.344 | 1.00 55.68 | A |
| ATOM | 1679 | CG2 | VAL | A | 799 | 24.884 | -2.470 | 10.922 | 1.00 55.68 | A |
| ATOM | 1680 | C | VAL | A | 799 | 22.555 | -1.341 | 9.904 | 1.00 55.68 | A |
| ATOM | 1681 | O | VAL | A | 799 | 23.222 | -1.497 | 8.886 | 1.00 55.68 | A |
| ATOM | 1682 | N | PRO | A | 800 | 21.970 | -0.178 | 10.194 | 1.00 55.68 | A |
| ATOM | 1683 | CD | PRO | A | 800 | 21.062 | 0.009 | 11.332 | 1.00 55.68 | A |
| ATOM | 1684 | CA | PRO | A | 800 | 22.045 | 1.045 | 9.386 | 1.00 55.68 | A |
| ATOM | 1685 | CB | PRO | A | 800 | 21.413 | 2.074 | 10.300 | 1.00 55.68 | A |
| ATOM | 1686 | CG | PRO | A | 800 | 20.352 | 1.273 | 10.957 | 1.00 55.68 | A |
| ATOM | 1687 | C | PRO | A | 800 | 23.426 | 1.482 | 8.854 | 1.00 55.68 | A |
| ATOM | 1688 | O | PRO | A | 800 | 24.385 | 1.654 | 9.613 | 1.00 55.68 | A |
| ATOM | 1689 | N | GLU | A | 801 | 23.497 | 1.679 | 7.537 | 1.00 55.68 | A |
| ATOM | 1690 | CA | GLU | A | 801 | 24.727 | 2.075 | 6.855 | 1.00 55.68 | A |
| ATOM | 1691 | CB | GLU | A | 801 | 24.493 | 2.124 | 5.347 | 1.00 55.68 | A |
| ATOM | 1692 | CG | GLU | A | 801 | 24.512 | 0.772 | 4.648 | 1.00 55.68 | A |
| ATOM | 1693 | CD | GLU | A | 801 | 25.919 | 0.239 | 4.429 | 1.00 55.68 | A |
| ATOM | 1694 | OE1 | GLU | A | 801 | 26.874 | 1.051 | 4.490 | 1.00 55.68 | A |
| ATOM | 1695 | OE2 | GLU | A | 801 | 26.062 | -0.986 | 4.176 | 1.00 55.68 | A |
| ATOM | 1696 | C | GLU | A | 801 | 25.359 | 3.390 | 7.292 | 1.00 55.68 | A |
| ATOM | 1697 | O | GLU | A | 801 | 26.577 | 3.532 | 7.245 | 1.00 55.68 | A |
| ATOM | 1698 | N | ASP | A | 802 | 24.565 | 4.370 | 7.686 | 1.00 55.68 | A |
| ATOM | 1699 | CA | ASP | A | 802 | 25.181 | 5.613 | 8.110 | 1.00 55.68 | A |
| ATOM | 1700 | CB | ASP | A | 802 | 24.798 | 6.766 | 7.183 | 1.00 55.68 | A |
| ATOM | 1701 | CG | ASP | A | 802 | 25.939 | 7.753 | 6.995 | 1.00 55.68 | A |
| ATOM | 1702 | OD1 | ASP | A | 802 | 26.370 | 8.372 | 7.990 | 1.00 55.68 | A |
| ATOM | 1703 | OD2 | ASP | A | 802 | 26.415 | 7.900 | 5.851 | 1.00 55.68 | A |
| ATOM | 1704 | C | ASP | A | 802 | 24.783 | 5.917 | 9.539 | 1.00 55.68 | A |
| ATOM | 1705 | O | ASP | A | 802 | 23.828 | 6.652 | 9.802 | 1.00 55.68 | A |
| ATOM | 1706 | N | PRO | A | 803 | 25.525 | 5.343 | 10.488 | 1.00 55.68 | A |
| ATOM | 1707 | CD | PRO | A | 803 | 26.780 | 4.618 | 10.236 | 1.00 55.68 | A |
| ATOM | 1708 | CA | PRO | A | 803 | 25.317 | 5.495 | 11.914 | 1.00 55.68 | A |
| ATOM | 1709 | CB | PRO | A | 803 | 26.701 | 5.249 | 12.469 | 1.00 55.68 | A |
| ATOM | 1710 | CG | PRO | A | 803 | 27.164 | 4.143 | 11.614 | 1.00 55.68 | A |
| ATOM | 1711 | C | PRO | A | 803 | 24.743 | 6.829 | 12.329 | 1.00 55.68 | A |
| ATOM | 1712 | O | PRO | A | 803 | 24.155 | 6.929 | 13.400 | 1.00 55.68 | A |
| ATOM | 1913 | N | SER | A | 828 | 11.640 | -2.638 | 20.964 | 1.00 55.68 | A |
| ATOM | 1914 | CA | SER | A | 828 | 11.873 | -3.111 | 19.629 | 1.00 55.68 | A |
| ATOM | 1915 | CB | SER | A | 828 | 13.287 | -3.619 | 19.520 | 1.00 55.68 | A |
| ATOM | 1916 | OG | SER | A | 828 | 13.438 | -4.750 | 20.344 | 1.00 55.68 | A |
| ATOM | 1917 | C | SER | A | 828 | 10.917 | -4.269 | 19.516 | 1.00 55.68 | A |
| ATOM | 1918 | O | SER | A | 828 | 9.730 | -4.106 | 19.735 | 1.00 55.68 | A |
| ATOM | 1919 | N | SER | A | 829 | 11.437 | -5.445 | 19.187 | 1.00 55.68 | A |
| ATOM | 1920 | CA | SER | A | 829 | 10.608 | -6.642 | 19.084 | 1.00 55.68 | A |
| ATOM | 1921 | CB | SER | A | 829 | 10.869 | -7.396 | 17.770 | 1.00 55.68 | A |
| ATOM | 1922 | OG | SER | A | 829 | 12.221 | -7.796 | 17.643 | 1.00 55.68 | A |
| ATOM | 1923 | C | SER | A | 829 | 10.915 | -7.542 | 20.277 | 1.00 55.68 | A |
| ATOM | 1924 | O | SER | A | 829 | 10.220 | -7.492 | 21.290 | 1.00 55.68 | A |
| ATOM | 1925 | N | ALA | A | 830 | 11.960 | -8.353 | 20.172 | 1.00 55.68 | A |
| ATOM | 1926 | CA | ALA | A | 830 | 12.310 | -9.226 | 21.270 | 1.00 55.68 | A |

Figure 4 A
(Continued)

| | | | | | | | | | |
|---|---|---|---|---|---|---|---|---|---|
| ATOM | 1927 | CB | ALA A 830 | 13.496 | -10.073 | 20.913 | 1.00 | 55.68 | A |
| ATOM | 1928 | C | ALA A 830 | 12.628 | -8.351 | 22.461 | 1.00 | 55.68 | A |
| ATOM | 1929 | O | ALA A 830 | 12.280 | -8.691 | 23.588 | 1.00 | 55.68 | A |
| ATOM | 1930 | N | GLY A 831 | 13.282 | -7.217 | 22.206 | 1.00 | 55.68 | A |
| ATOM | 1931 | CA | GLY A 831 | 13.628 | -6.287 | 23.278 | 1.00 | 55.68 | A |
| ATOM | 1932 | C | GLY A 831 | 15.110 | -6.026 | 23.532 | 1.00 | 55.68 | A |
| ATOM | 1933 | O | GLY A 831 | 15.550 | -4.876 | 23.544 | 1.00 | 55.68 | A |
| ATOM | 1934 | N | VAL A 832 | 15.878 | -7.094 | 23.739 | 1.00 | 55.68 | A |
| ATOM | 1935 | CA | VAL A 832 | 17.310 | -6.999 | 24.009 | 1.00 | 55.68 | A |
| ATOM | 1936 | CB | VAL A 832 | 17.938 | -8.398 | 24.180 | 1.00 | 55.68 | A |
| ATOM | 1937 | CG1 | VAL A 832 | 17.596 | -8.962 | 25.546 | 1.00 | 55.68 | A |
| ATOM | 1938 | CG2 | VAL A 832 | 17.432 | -9.323 | 23.103 | 1.00 | 55.68 | A |
| ATOM | 1939 | C | VAL A 832 | 18.116 | -6.259 | 22.956 | 1.00 | 55.68 | A |
| ATOM | 1940 | O | VAL A 832 | 18.335 | -5.053 | 23.058 | 1.00 | 55.68 | A |
| ATOM | 1941 | N | GLY A 833 | 18.561 | -7.017 | 21.960 | 1.00 | 55.68 | A |
| ATOM | 1942 | CA | GLY A 833 | 19.356 | -6.489 | 20.868 | 1.00 | 55.68 | A |
| ATOM | 1943 | C | GLY A 833 | 19.071 | -5.052 | 20.503 | 1.00 | 55.68 | A |
| ATOM | 1944 | O | GLY A 833 | 19.333 | -4.147 | 21.289 | 1.00 | 55.68 | A |
| ATOM | 1945 | N | ARG A 834 | 18.533 | -4.847 | 19.310 | 1.00 | 55.68 | A |
| ATOM | 1946 | CA | ARG A 834 | 18.229 | -3.513 | 18.823 | 1.00 | 55.68 | A |
| ATOM | 1947 | CB | ARG A 834 | 16.912 | -3.518 | 18.080 | 1.00 | 55.68 | A |
| ATOM | 1948 | CG | ARG A 834 | 16.976 | -4.046 | 16.672 | 1.00 | 55.68 | A |
| ATOM | 1949 | CD | ARG A 834 | 15.625 | -3.854 | 16.065 | 1.00 | 55.68 | A |
| ATOM | 1950 | NE | ARG A 834 | 15.591 | -4.198 | 14.664 | 1.00 | 55.68 | A |
| ATOM | 1951 | CZ | ARG A 834 | 14.485 | -4.163 | 13.936 | 1.00 | 55.68 | A |
| ATOM | 1952 | NH1 | ARG A 834 | 13.340 | -3.801 | 14.505 | 1.00 | 55.68 | A |
| ATOM | 1953 | NH2 | ARG A 834 | 14.528 | -4.477 | 12.645 | 1.00 | 55.68 | A |
| ATOM | 1954 | C | ARG A 834 | 18.188 | -2.417 | 19.869 | 1.00 | 55.68 | A |
| ATOM | 1955 | O | ARG A 834 | 18.855 | -1.395 | 19.725 | 1.00 | 55.68 | A |
| ATOM | 1956 | N | THR A 835 | 17.401 | -2.620 | 20.919 | 1.00 | 55.68 | A |
| ATOM | 1957 | CA | THR A 835 | 17.293 | -1.623 | 21.976 | 1.00 | 55.68 | A |
| ATOM | 1958 | CB | THR A 835 | 16.399 | -2.107 | 23.111 | 1.00 | 55.68 | A |
| ATOM | 1959 | OG1 | THR A 835 | 15.160 | -2.568 | 22.578 | 1.00 | 55.68 | A |
| ATOM | 1960 | CG2 | THR A 835 | 16.108 | -0.981 | 24.055 | 1.00 | 55.68 | A |
| ATOM | 1961 | C | THR A 835 | 18.673 | -1.331 | 22.544 | 1.00 | 55.68 | A |
| ATOM | 1962 | O | THR A 835 | 19.131 | -0.179 | 22.542 | 1.00 | 55.68 | A |
| ATOM | 1963 | N | GLY A 836 | 19.332 | -2.383 | 23.026 | 1.00 | 55.68 | A |
| ATOM | 1964 | CA | GLY A 836 | 20.662 | -2.230 | 23.589 | 1.00 | 55.68 | A |
| ATOM | 1965 | C | GLY A 836 | 21.411 | -1.224 | 22.760 | 1.00 | 55.68 | A |
| ATOM | 1966 | O | GLY A 836 | 21.857 | -0.191 | 23.247 | 1.00 | 55.68 | A |
| ATOM | 1967 | N | THR A 837 | 21.509 | -1.529 | 21.480 | 1.00 | 55.68 | A |
| ATOM | 1968 | CA | THR A 837 | 22.184 | -0.670 | 20.541 | 1.00 | 55.68 | A |
| ATOM | 1969 | CB | THR A 837 | 21.831 | -1.065 | 19.129 | 1.00 | 55.68 | A |
| ATOM | 1970 | OG1 | THR A 837 | 22.266 | -2.405 | 18.895 | 1.00 | 55.68 | A |
| ATOM | 1971 | CG2 | THR A 837 | 22.499 | -0.140 | 18.145 | 1.00 | 55.68 | A |
| ATOM | 1972 | C | THR A 837 | 21.859 | 0.803 | 20.729 | 1.00 | 55.68 | A |
| ATOM | 1973 | O | THR A 837 | 22.755 | 1.615 | 20.890 | 1.00 | 55.68 | A |
| ATOM | 1974 | N | TYR A 838 | 20.585 | 1.165 | 20.707 | 1.00 | 55.68 | A |
| ATOM | 1975 | CA | TYR A 838 | 20.248 | 2.570 | 20.874 | 1.00 | 55.68 | A |
| ATOM | 1976 | CB | TYR A 838 | 18.760 | 2.823 | 20.687 | 1.00 | 55.68 | A |
| ATOM | 1977 | CG | TYR A 838 | 18.375 | 4.199 | 21.153 | 1.00 | 55.68 | A |
| ATOM | 1978 | CD1 | TYR A 838 | 18.858 | 5.331 | 20.516 | 1.00 | 55.68 | A |
| ATOM | 1979 | CE1 | TYR A 838 | 18.574 | 6.593 | 20.997 | 1.00 | 55.68 | A |
| ATOM | 1980 | CD2 | TYR A 838 | 17.595 | 4.369 | 22.277 | 1.00 | 55.68 | A |
| ATOM | 1981 | CE2 | TYR A 838 | 17.307 | 5.621 | 22.764 | 1.00 | 55.68 | A |
| ATOM | 1982 | CZ | TYR A 838 | 17.798 | 6.726 | 22.129 | 1.00 | 55.68 | A |
| ATOM | 1983 | OH | TYR A 838 | 17.522 | 7.955 | 22.669 | 1.00 | 55.68 | A |

Figure 4 A
(Continued)

| ATOM | 1984 | C | TYR A 838 | 20.641 | 3.073 | 22.241 | 1.00 | 55.68 | A |
|---|---|---|---|---|---|---|---|---|---|
| ATOM | 1985 | O | TYR A 838 | 20.845 | 4.267 | 22.438 | 1.00 | 55.68 | A |
| ATOM | 1986 | N | ILE A 839 | 20.735 | 2.161 | 23.194 | 1.00 | 55.68 | A |
| ATOM | 1987 | CA | ILE A 839 | 21.099 | 2.555 | 24.539 | 1.00 | 55.68 | A |
| ATOM | 1988 | CB | ILE A 839 | 20.624 | 1.529 | 25.551 | 1.00 | 55.68 | A |
| ATOM | 1989 | CG2 | ILE A 839 | 20.957 | 1.994 | 26.948 | 1.00 | 55.68 | A |
| ATOM | 1990 | CG1 | ILE A 839 | 19.118 | 1.362 | 25.427 | 1.00 | 55.68 | A |
| ATOM | 1991 | CD1 | ILE A 839 | 18.546 | 0.431 | 26.435 | 1.00 | 55.68 | A |
| ATOM | 1992 | C | ILE A 839 | 22.598 | 2.762 | 24.684 | 1.00 | 55.68 | A |
| ATOM | 1993 | O | ILE A 839 | 23.039 | 3.844 | 25.074 | 1.00 | 55.68 | A |
| ATOM | 1994 | N | GLY A 840 | 23.382 | 1.733 | 24.379 | 1.00 | 55.68 | A |
| ATOM | 1995 | CA | GLY A 840 | 24.823 | 1.877 | 24.476 | 1.00 | 55.68 | A |
| ATOM | 1996 | C | GLY A 840 | 25.199 | 3.234 | 23.919 | 1.00 | 55.68 | A |
| ATOM | 1997 | O | GLY A 840 | 25.843 | 4.047 | 24.580 | 1.00 | 55.68 | A |
| ATOM | 1998 | N | ILE A 841 | 24.765 | 3.473 | 22.686 | 1.00 | 55.68 | A |
| ATOM | 1999 | CA | ILE A 841 | 25.008 | 4.732 | 22.008 | 1.00 | 55.68 | A |
| ATOM | 2000 | CB | ILE A 841 | 24.064 | 4.906 | 20.806 | 1.00 | 55.68 | A |
| ATOM | 2001 | CG2 | ILE A 841 | 24.186 | 6.302 | 20.231 | 1.00 | 55.68 | A |
| ATOM | 2002 | CG1 | ILE A 841 | 24.386 | 3.852 | 19.753 | 1.00 | 55.68 | A |
| ATOM | 2003 | CD1 | ILE A 841 | 23.496 | 3.899 | 18.543 | 1.00 | 55.68 | A |
| ATOM | 2004 | C | ILE A 841 | 24.719 | 5.816 | 23.009 | 1.00 | 55.68 | A |
| ATOM | 2005 | O | ILE A 841 | 25.641 | 6.402 | 23.568 | 1.00 | 55.68 | A |
| ATOM | 2006 | N | ASP A 842 | 23.430 | 6.048 | 23.246 | 1.00 | 55.68 | A |
| ATOM | 2007 | CA | ASP A 842 | 22.963 | 7.064 | 24.182 | 1.00 | 55.68 | A |
| ATOM | 2008 | CB | ASP A 842 | 21.555 | 6.740 | 24.669 | 1.00 | 55.68 | A |
| ATOM | 2009 | CG | ASP A 842 | 20.866 | 7.941 | 25.277 | 1.00 | 55.68 | A |
| ATOM | 2010 | OD1 | ASP A 842 | 21.543 | 8.688 | 26.010 | 1.00 | 55.68 | A |
| ATOM | 2011 | OD2 | ASP A 842 | 19.653 | 8.140 | 25.028 | 1.00 | 55.68 | A |
| ATOM | 2012 | C | ASP A 842 | 23.890 | 7.149 | 25.379 | 1.00 | 55.68 | A |
| ATOM | 2013 | O | ASP A 842 | 24.829 | 7.943 | 25.384 | 1.00 | 55.68 | A |
| ATOM | 2233 | N | MET A 870 | 21.140 | -8.527 | 25.540 | 1.00 | 55.68 | A |
| ATOM | 2234 | CA | MET A 870 | 21.292 | -7.152 | 25.099 | 1.00 | 55.68 | A |
| ATOM | 2235 | CB | MET A 870 | 21.602 | -6.238 | 26.274 | 1.00 | 55.68 | A |
| ATOM | 2236 | CG | MET A 870 | 20.393 | -5.890 | 27.118 | 1.00 | 55.68 | A |
| ATOM | 2237 | SD | MET A 870 | 19.158 | -4.931 | 26.217 | 1.00 | 55.68 | A |
| ATOM | 2238 | CE | MET A 870 | 19.279 | -3.365 | 26.961 | 1.00 | 55.68 | A |
| ATOM | 2239 | C | MET A 870 | 22.403 | -7.071 | 24.082 | 1.00 | 55.68 | A |
| ATOM | 2240 | O | MET A 870 | 23.519 | -7.492 | 24.340 | 1.00 | 55.68 | A |
| ATOM | 2241 | N | VAL A 871 | 22.072 | -6.541 | 22.913 | 1.00 | 55.68 | A |
| ATOM | 2242 | CA | VAL A 871 | 23.015 | -6.394 | 21.814 | 1.00 | 55.68 | A |
| ATOM | 2243 | CB | VAL A 871 | 24.237 | -5.564 | 22.252 | 1.00 | 55.68 | A |
| ATOM | 2244 | CG1 | VAL A 871 | 25.171 | -5.372 | 21.088 | 1.00 | 55.68 | A |
| ATOM | 2245 | CG2 | VAL A 871 | 23.785 | -4.209 | 22.772 | 1.00 | 55.68 | A |
| ATOM | 2246 | C | VAL A 871 | 23.447 | -7.770 | 21.318 | 1.00 | 55.68 | A |
| ATOM | 2247 | O | VAL A 871 | 24.624 | -8.110 | 21.338 | 1.00 | 55.68 | A |
| ATOM | 2248 | N | GLN A 872 | 22.473 | -8.543 | 20.853 | 1.00 | 55.68 | A |
| ATOM | 2249 | CA | GLN A 872 | 22.694 | -9.906 | 20.378 | 1.00 | 55.68 | A |
| ATOM | 2250 | CB | GLN A 872 | 21.356 | -10.543 | 20.041 | 1.00 | 55.68 | A |
| ATOM | 2251 | CG | GLN A 872 | 20.751 | -10.015 | 18.758 | 1.00 | 55.68 | A |
| ATOM | 2252 | CD | GLN A 872 | 19.343 | -10.525 | 18.532 | 1.00 | 55.68 | A |
| ATOM | 2253 | OE1 | GLN A 872 | 19.094 | -11.734 | 18.544 | 1.00 | 55.68 | A |
| ATOM | 2254 | NE2 | GLN A 872 | 18.409 | -9.601 | 18.318 | 1.00 | 55.68 | A |
| ATOM | 2255 | C | GLN A 872 | 23.599 | -10.078 | 19.169 | 1.00 | 55.68 | A |
| ATOM | 2256 | O | GLN A 872 | 23.996 | -11.195 | 18.836 | 1.00 | 55.68 | A |
| ATOM | 2257 | N | VAL A 873 | 23.928 | -8.984 | 18.504 | 1.00 | 55.68 | A |
| ATOM | 2258 | CA | VAL A 873 | 24.751 | -9.095 | 17.319 | 1.00 | 55.68 | A |
| ATOM | 2259 | CB | VAL A 873 | 23.966 | -8.745 | 16.072 | 1.00 | 55.68 | A |

Figure 4 A
(Continued)

| ATOM | 2260 | CG1 | VAL A 873 | 24.827 | -9.019 | 14.850 | 1.00 | 55.68 | A |
|------|------|-----|-----------|--------|--------|--------|------|-------|---|
| ATOM | 2261 | CG2 | VAL A 873 | 22.683 | -9.555 | 16.039 | 1.00 | 55.68 | A |
| ATOM | 2262 | C   | VAL A 873 | 25.996 | -8.249 | 17.324 | 1.00 | 55.68 | A |
| ATOM | 2263 | O   | VAL A 873 | 25.967 | -7.054 | 17.629 | 1.00 | 55.68 | A |
| ATOM | 2264 | N   | GLU A 874 | 27.093 | -8.891 | 16.953 | 1.00 | 55.68 | A |
| ATOM | 2265 | CA  | GLU A 874 | 28.377 | -8.234 | 16.901 | 1.00 | 55.68 | A |
| ATOM | 2266 | CB  | GLU A 874 | 29.387 | -9.146 | 16.220 | 1.00 | 55.68 | A |
| ATOM | 2267 | CG  | GLU A 874 | 30.783 | -8.577 | 16.171 | 1.00 | 55.68 | A |
| ATOM | 2268 | CD  | GLU A 874 | 31.681 | -9.337 | 15.217 | 1.00 | 55.68 | A |
| ATOM | 2269 | OE1 | GLU A 874 | 32.894 | -9.027 | 15.183 | 1.00 | 55.68 | A |
| ATOM | 2270 | OE2 | GLU A 874 | 31.171 | -10.235| 14.502 | 1.00 | 55.68 | A |
| ATOM | 2271 | C   | GLU A 874 | 28.186 | -6.972 | 16.097 | 1.00 | 55.68 | A |
| ATOM | 2272 | O   | GLU A 874 | 28.582 | -5.891 | 16.514 | 1.00 | 55.68 | A |
| ATOM | 2273 | N   | ALA A 875 | 27.557 | -7.134 | 14.941 | 1.00 | 55.68 | A |
| ATOM | 2274 | CA  | ALA A 875 | 27.290 | -6.031 | 14.039 | 1.00 | 55.68 | A |
| ATOM | 2275 | CB  | ALA A 875 | 26.374 | -6.493 | 12.922 | 1.00 | 55.68 | A |
| ATOM | 2276 | C   | ALA A 875 | 26.654 | -4.882 | 14.801 | 1.00 | 55.68 | A |
| ATOM | 2277 | O   | ALA A 875 | 26.898 | -3.714 | 14.504 | 1.00 | 55.68 | A |
| ATOM | 2278 | N   | GLN A 876 | 25.835 | -5.219 | 15.789 | 1.00 | 55.68 | A |
| ATOM | 2279 | CA  | GLN A 876 | 25.174 | -4.201 | 16.590 | 1.00 | 55.68 | A |
| ATOM | 2280 | CB  | GLN A 876 | 24.106 | -4.840 | 17.483 | 1.00 | 55.68 | A |
| ATOM | 2281 | CG  | GLN A 876 | 23.102 | -5.700 | 16.712 | 1.00 | 55.68 | A |
| ATOM | 2282 | CD  | GLN A 876 | 21.758 | -5.831 | 17.409 | 1.00 | 55.68 | A |
| ATOM | 2283 | OE1 | GLN A 876 | 20.886 | -6.569 | 16.958 | 1.00 | 55.68 | A |
| ATOM | 2284 | NE2 | GLN A 876 | 21.582 | -5.109 | 18.509 | 1.00 | 55.68 | A |
| ATOM | 2285 | C   | GLN A 876 | 26.259 | -3.556 | 17.429 | 1.00 | 55.68 | A |
| ATOM | 2286 | O   | GLN A 876 | 26.379 | -2.330 | 17.499 | 1.00 | 55.68 | A |
| ATOM | 2287 | N   | TYR A 877 | 27.060 | -4.416 | 18.048 | 1.00 | 55.68 | A |
| ATOM | 2288 | CA  | TYR A 877 | 28.180 | -4.004 | 18.890 | 1.00 | 55.68 | A |
| ATOM | 2289 | CB  | TYR A 877 | 29.085 | -5.215 | 19.149 | 1.00 | 55.68 | A |
| ATOM | 2290 | CG  | TYR A 877 | 30.110 | -5.060 | 20.257 | 1.00 | 55.68 | A |
| ATOM | 2291 | CD1 | TYR A 877 | 30.779 | -3.851 | 20.466 | 1.00 | 55.68 | A |
| ATOM | 2292 | CE1 | TYR A 877 | 31.768 | -3.740 | 21.446 | 1.00 | 55.68 | A |
| ATOM | 2293 | CD2 | TYR A 877 | 30.458 | -6.153 | 21.061 | 1.00 | 55.68 | A |
| ATOM | 2294 | CE2 | TYR A 877 | 31.449 | -6.050 | 22.038 | 1.00 | 55.68 | A |
| ATOM | 2295 | CZ  | TYR A 877 | 32.099 | -4.844 | 22.224 | 1.00 | 55.68 | A |
| ATOM | 2296 | OH  | TYR A 877 | 33.091 | -4.754 | 23.173 | 1.00 | 55.68 | A |
| ATOM | 2297 | C   | TYR A 877 | 28.962 | -2.952 | 18.127 | 1.00 | 55.68 | A |
| ATOM | 2298 | O   | TYR A 877 | 29.144 | -1.826 | 18.578 | 1.00 | 55.68 | A |
| ATOM | 2299 | N   | ILE A 878 | 29.399 | -3.350 | 16.945 | 1.00 | 55.68 | A |
| ATOM | 2300 | CA  | ILE A 878 | 30.183 | -2.512 | 16.065 | 1.00 | 55.68 | A |
| ATOM | 2301 | CB  | ILE A 878 | 30.512 | -3.297 | 14.798 | 1.00 | 55.68 | A |
| ATOM | 2302 | CG2 | ILE A 878 | 31.470 | -2.513 | 13.934 | 1.00 | 55.68 | A |
| ATOM | 2303 | CG1 | ILE A 878 | 31.107 | -4.653 | 15.211 | 1.00 | 55.68 | A |
| ATOM | 2304 | CD1 | ILE A 878 | 31.622 | -5.531 | 14.083 | 1.00 | 55.68 | A |
| ATOM | 2305 | C   | ILE A 878 | 29.557 | -1.167 | 15.710 | 1.00 | 55.68 | A |
| ATOM | 2306 | O   | ILE A 878 | 30.204 | -0.129 | 15.824 | 1.00 | 55.68 | A |
| ATOM | 2307 | N   | LEU A 879 | 28.300 | -1.174 | 15.287 | 1.00 | 55.68 | A |
| ATOM | 2308 | CA  | LEU A 879 | 27.647 | 0.074  | 14.930 | 1.00 | 55.68 | A |
| ATOM | 2309 | CB  | LEU A 879 | 26.155 | -0.157 | 14.689 | 1.00 | 55.68 | A |
| ATOM | 2310 | CG  | LEU A 879 | 25.358 | 0.940  | 13.980 | 1.00 | 55.68 | A |
| ATOM | 2311 | CD1 | LEU A 879 | 23.922 | 0.487  | 13.817 | 1.00 | 55.68 | A |
| ATOM | 2312 | CD2 | LEU A 879 | 25.408 | 2.224  | 14.768 | 1.00 | 55.68 | A |
| ATOM | 2313 | C   | LEU A 879 | 27.862 | 1.071  | 16.061 | 1.00 | 55.68 | A |
| ATOM | 2314 | O   | LEU A 879 | 28.133 | 2.241  | 15.811 | 1.00 | 55.68 | A |
| ATOM | 2315 | N   | ILE A 880 | 27.771 | 0.594  | 17.304 | 1.00 | 55.68 | A |
| ATOM | 2316 | CA  | ILE A 880 | 27.950 | 1.456  | 18.483 | 1.00 | 55.68 | A |

Figure 4 A
(Continued)

| ATOM | 2317 | CB | ILE A 880 | 27.974 | 0.654 | 19.813 | 1.00 | 55.68 | A |
|------|------|------|-----------|--------|--------|--------|------|-------|---|
| ATOM | 2318 | CG2 | ILE A 880 | 27.892 | 1.613 | 20.986 | 1.00 | 55.68 | A |
| ATOM | 2319 | CG1 | ILE A 880 | 26.800 | -0.327 | 19.869 | 1.00 | 55.68 | A |
| ATOM | 2320 | CD1 | ILE A 880 | 26.695 | -1.115 | 21.157 | 1.00 | 55.68 | A |
| ATOM | 2321 | C | ILE A 880 | 29.267 | 2.203 | 18.372 | 1.00 | 55.68 | A |
| ATOM | 2322 | O | ILE A 880 | 29.296 | 3.421 | 18.202 | 1.00 | 55.68 | A |
| ATOM | 2323 | N | HIS A 881 | 30.359 | 1.460 | 18.481 | 1.00 | 55.68 | A |
| ATOM | 2324 | CA | HIS A 881 | 31.678 | 2.045 | 18.354 | 1.00 | 55.68 | A |
| ATOM | 2325 | CB | HIS A 881 | 32.713 | 0.953 | 18.089 | 1.00 | 55.68 | A |
| ATOM | 2326 | CG | HIS A 881 | 32.998 | 0.083 | 19.272 | 1.00 | 55.68 | A |
| ATOM | 2327 | CD2 | HIS A 881 | 32.735 | -1.223 | 19.502 | 1.00 | 55.68 | A |
| ATOM | 2328 | ND1 | HIS A 881 | 33.654 | 0.542 | 20.391 | 1.00 | 55.68 | A |
| ATOM | 2329 | CE1 | HIS A 881 | 33.785 | -0.443 | 21.259 | 1.00 | 55.68 | A |
| ATOM | 2330 | NE2 | HIS A 881 | 33.235 | -1.525 | 20.743 | 1.00 | 55.68 | A |
| ATOM | 2331 | C | HIS A 881 | 31.644 | 3.003 | 17.167 | 1.00 | 55.68 | A |
| ATOM | 2332 | O | HIS A 881 | 31.942 | 4.191 | 17.304 | 1.00 | 55.68 | A |
| ATOM | 2333 | N | GLN A 882 | 31.258 | 2.473 | 16.006 | 1.00 | 55.68 | A |
| ATOM | 2334 | CA | GLN A 882 | 31.192 | 3.269 | 14.790 | 1.00 | 55.68 | A |
| ATOM | 2335 | CB | GLN A 882 | 30.351 | 2.568 | 13.720 | 1.00 | 55.68 | A |
| ATOM | 2336 | CG | GLN A 882 | 31.057 | 1.378 | 13.088 | 1.00 | 55.68 | A |
| ATOM | 2337 | CD | GLN A 882 | 30.364 | 0.837 | 11.854 | 1.00 | 55.68 | A |
| ATOM | 2338 | OE1 | GLN A 882 | 29.843 | 1.596 | 11.051 | 1.00 | 55.68 | A |
| ATOM | 2339 | NE2 | GLN A 882 | 30.377 | -0.483 | 11.688 | 1.00 | 55.68 | A |
| ATOM | 2340 | C | GLN A 882 | 30.614 | 4.622 | 15.095 | 1.00 | 55.68 | A |
| ATOM | 2341 | O | GLN A 882 | 31.341 | 5.580 | 15.273 | 1.00 | 55.68 | A |
| ATOM | 2342 | N | ALA A 883 | 29.300 | 4.697 | 15.175 | 1.00 | 55.68 | A |
| ATOM | 2343 | CA | ALA A 883 | 28.667 | 5.965 | 15.455 | 1.00 | 55.68 | A |
| ATOM | 2344 | CB | ALA A 883 | 27.290 | 5.752 | 15.990 | 1.00 | 55.68 | A |
| ATOM | 2345 | C | ALA A 883 | 29.503 | 6.671 | 16.477 | 1.00 | 55.68 | A |
| ATOM | 2346 | O | ALA A 883 | 29.960 | 7.782 | 16.255 | 1.00 | 55.68 | A |
| ATOM | 9848 | S | SO4 S2001 | 15.227 | -6.517 | 18.891 | 1.00 | 55.68 | S |
| ATOM | 9849 | O1 | SO4 S2001 | 14.732 | -7.643 | 19.695 | 1.00 | 55.68 | S |
| ATOM | 9850 | O2 | SO4 S2001 | 16.290 | -6.969 | 17.973 | 1.00 | 55.68 | S |
| ATOM | 9851 | O3 | SO4 S2001 | 15.784 | -5.481 | 19.771 | 1.00 | 55.68 | S |
| ATOM | 9852 | O4 | SO4 S2001 | 14.105 | -5.972 | 18.118 | 1.00 | 55.68 | S |

Figure 4 A
(Continued)

ACTIVE SITE (B) COORDINATES

```
ATOM   461  N    ASN A 654    -13.059 -16.139   3.738  1.00109.13      A
ATOM   462  CA   ASN A 654    -13.535 -15.420   2.548  1.00109.13      A
ATOM   463  CB   ASN A 654    -15.027 -15.695   2.300  1.00109.13      A
ATOM   464  CG   ASN A 654    -15.413 -17.139   2.557  1.00109.13      A
ATOM   465  OD1  ASN A 654    -15.343 -17.621   3.693  1.00109.13      A
ATOM   466  ND2  ASN A 654    -15.830 -17.840   1.502  1.00109.13      A
ATOM   467  C    ASN A 654    -13.365 -13.919   2.767  1.00109.13      A
ATOM   468  O    ASN A 654    -14.212 -13.132   2.347  1.00109.13      A
ATOM   469  N    LYS A 655    -12.284 -13.529   3.436  1.00109.13      A
ATOM   470  CA   LYS A 655    -12.030 -12.129   3.730  1.00109.13      A
ATOM   471  CB   LYS A 655    -11.980 -11.912   5.233  1.00109.13      A
ATOM   472  CG   LYS A 655    -13.309 -11.940   5.931  1.00109.13      A
ATOM   473  CD   LYS A 655    -13.741 -10.532   6.270  1.00109.13      A
ATOM   474  CE   LYS A 655    -14.689 -10.539   7.456  1.00109.13      A
ATOM   475  NZ   LYS A 655    -14.936  -9.177   8.009  1.00109.13      A
ATOM   476  C    LYS A 655    -10.726 -11.658   3.134  1.00109.13      A
ATOM   477  O    LYS A 655    -10.382 -10.488   3.243  1.00109.13      A
ATOM   478  N    ASN A 656     -9.980 -12.565   2.522  1.00109.13      A
ATOM   479  CA   ASN A 656     -8.724 -12.170   1.922  1.00109.13      A
ATOM   480  CB   ASN A 656     -7.576 -12.970   2.515  1.00109.13      A
ATOM   481  CG   ASN A 656     -7.583 -12.948   4.014  1.00109.13      A
ATOM   482  OD1  ASN A 656     -8.447 -13.557   4.648  1.00109.13      A
ATOM   483  ND2  ASN A 656     -6.632 -12.232   4.600  1.00109.13      A
ATOM   484  C    ASN A 656     -8.825 -12.432   0.448  1.00109.13      A
ATOM   485  O    ASN A 656     -9.711 -13.157   0.010  1.00109.13      A
ATOM   486  N    ARG A 657     -7.920 -11.841  -0.320  1.00109.13      A
ATOM   487  CA   ARG A 657     -7.925 -12.019  -1.768  1.00109.13      A
ATOM   488  CB   ARG A 657     -7.459 -10.753  -2.466  1.00109.13      A
ATOM   489  CG   ARG A 657     -8.150 -10.509  -3.768  1.00109.13      A
ATOM   490  CD   ARG A 657     -7.656  -9.229  -4.367  1.00109.13      A
ATOM   491  NE   ARG A 657     -8.543  -8.756  -5.416  1.00109.13      A
ATOM   492  CZ   ARG A 657     -9.759  -8.287  -5.192  1.00109.13      A
ATOM   493  NH1  ARG A 657    -10.225  -8.230  -3.952  1.00109.13      A
ATOM   494  NH2  ARG A 657    -10.505  -7.879  -6.207  1.00109.13      A
ATOM   495  C    ARG A 657     -7.005 -13.147  -2.156  1.00109.13      A
ATOM   496  O    ARG A 657     -7.131 -13.717  -3.228  1.00109.13      A
ATOM   497  N    TYR A 658     -6.071 -13.456  -1.270  1.00109.13      A
ATOM   498  CA   TYR A 658     -5.110 -14.517  -1.501  1.00109.13      A
ATOM   499  CB   TYR A 658     -3.850 -13.928  -2.134  1.00109.13      A
ATOM   500  CG   TYR A 658     -4.152 -13.085  -3.353  1.00109.13      A
ATOM   501  CD1  TYR A 658     -4.584 -13.669  -4.544  1.00109.13      A
ATOM   502  CE1  TYR A 658     -4.918 -12.888  -5.659  1.00109.13      A
ATOM   503  CD2  TYR A 658     -4.056 -11.699  -3.304  1.00109.13      A
ATOM   504  CE2  TYR A 658     -4.385 -10.912  -4.411  1.00109.13      A
ATOM   505  CZ   TYR A 658     -4.813 -11.512  -5.582  1.00109.13      A
ATOM   506  OH   TYR A 658     -5.122 -10.733  -6.667  1.00109.13      A
ATOM   507  C    TYR A 658     -4.785 -15.158  -0.158  1.00109.13      A
ATOM   508  O    TYR A 658     -4.611 -14.464   0.830  1.00109.13      A
ATOM   509  N    VAL A 659     -4.725 -16.482  -0.115  1.00109.13      A
ATOM   510  CA   VAL A 659     -4.412 -17.189   1.120  1.00109.13      A
ATOM   511  CB   VAL A 659     -4.756 -18.679   0.994  1.00109.13      A
ATOM   512  CG1  VAL A 659     -3.970 -19.296  -0.163  1.00109.13      A
ATOM   513  CG2  VAL A 659     -4.454 -19.396   2.296  1.00109.13      A
ATOM   514  C    VAL A 659     -2.929 -17.043   1.486  1.00109.13      A
```

Figure 4 B

| ATOM | 515 | O | VAL A 659 | -2.534 | -17.273 | 2.626 | 1.00 | 109.13 | A |
|------|-----|----|-----------|--------|---------|-------|------|--------|---|
| ATOM | 516 | N | ASP A 660 | -2.105 | -16.651 | 0.521 | 1.00 | 109.13 | A |
| ATOM | 517 | CA | ASP A 660 | -0.682 | -16.471 | 0.777 | 1.00 | 109.13 | A |
| ATOM | 518 | CB | ASP A 660 | 0.091 | -16.395 | -0.552 | 1.00 | 109.13 | A |
| ATOM | 519 | CG | ASP A 660 | 1.514 | -15.840 | -0.386 | 1.00 | 109.13 | A |
| ATOM | 520 | OD1 | ASP A 660 | 2.121 | -16.055 | 0.695 | 1.00 | 109.13 | A |
| ATOM | 521 | OD2 | ASP A 660 | 2.031 | -15.200 | -1.339 | 1.00 | 109.13 | A |
| ATOM | 522 | C | ASP A 660 | -0.434 | -15.210 | 1.595 | 1.00 | 109.13 | A |
| ATOM | 523 | O | ASP A 660 | 0.065 | -15.274 | 2.722 | 1.00 | 109.13 | A |
| ATOM | 524 | N | ILE A 661 | -0.790 | -14.068 | 1.016 | 1.00 | 109.13 | A |
| ATOM | 525 | CA | ILE A 661 | -0.608 | -12.776 | 1.658 | 1.00 | 109.13 | A |
| ATOM | 526 | CB | ILE A 661 | -0.791 | -11.627 | 0.650 | 1.00 | 109.13 | A |
| ATOM | 527 | CG2 | ILE A 661 | -0.989 | -10.318 | 1.374 | 1.00 | 109.13 | A |
| ATOM | 528 | CG1 | ILE A 661 | 0.440 | -11.518 | -0.250 | 1.00 | 109.13 | A |
| ATOM | 529 | CD1 | ILE A 661 | 0.678 | -12.710 | -1.144 | 1.00 | 109.13 | A |
| ATOM | 530 | C | ILE A 661 | -1.554 | -12.543 | 2.820 | 1.00 | 109.13 | A |
| ATOM | 531 | O | ILE A 661 | -2.743 | -12.296 | 2.624 | 1.00 | 109.13 | A |
| ATOM | 532 | N | LEU A 662 | -1.019 | -12.610 | 4.034 | 1.00 | 109.13 | A |
| ATOM | 533 | CA | LEU A 662 | -1.824 | -12.386 | 5.222 | 1.00 | 109.13 | A |
| ATOM | 534 | CB | LEU A 662 | -2.083 | -13.705 | 5.939 | 1.00 | 109.13 | A |
| ATOM | 535 | CG | LEU A 662 | -2.914 | -14.681 | 5.098 | 1.00 | 109.13 | A |
| ATOM | 536 | CD1 | LEU A 662 | -3.237 | -15.917 | 5.906 | 1.00 | 109.13 | A |
| ATOM | 537 | CD2 | LEU A 662 | -4.197 | -13.999 | 4.647 | 1.00 | 109.13 | A |
| ATOM | 538 | C | LEU A 662 | -1.165 | -11.383 | 6.148 | 1.00 | 109.13 | A |
| ATOM | 539 | O | LEU A 662 | 0.058 | -11.278 | 6.202 | 1.00 | 109.13 | A |
| ATOM | 540 | N | PRO A 663 | -1.974 | -10.617 | 6.883 | 1.00 | 109.13 | A |
| ATOM | 541 | CD | PRO A 663 | -3.446 | -10.622 | 6.894 | 1.00 | 109.13 | A |
| ATOM | 542 | CA | PRO A 663 | -1.453 | -9.612 | 7.801 | 1.00 | 109.13 | A |
| ATOM | 543 | CB | PRO A 663 | -2.655 | -8.704 | 7.996 | 1.00 | 109.13 | A |
| ATOM | 544 | CG | PRO A 663 | -3.771 | -9.680 | 8.019 | 1.00 | 109.13 | A |
| ATOM | 545 | C | PRO A 663 | -0.923 | -10.180 | 9.125 | 1.00 | 109.13 | A |
| ATOM | 546 | O | PRO A 663 | -1.461 | -11.154 | 9.663 | 1.00 | 109.13 | A |
| ATOM | 1065 | N | THR A 727 | -3.368 | 0.513 | -8.704 | 1.00 | 109.13 | A |
| ATOM | 1066 | CA | THR A 727 | -3.786 | -0.619 | -9.522 | 1.00 | 109.13 | A |
| ATOM | 1067 | CB | THR A 727 | -4.055 | -1.836 | -8.650 | 1.00 | 109.13 | A |
| ATOM | 1068 | OG1 | THR A 727 | -4.392 | -2.943 | -9.480 | 1.00 | 109.13 | A |
| ATOM | 1069 | CG2 | THR A 727 | -5.215 | -1.566 | -7.720 | 1.00 | 109.13 | A |
| ATOM | 1070 | C | THR A 727 | -5.053 | -0.352 | -10.344 | 1.00 | 109.13 | A |
| ATOM | 1071 | O | THR A 727 | -5.706 | 0.683 | -10.214 | 1.00 | 109.13 | A |
| ATOM | 1072 | N | ARG A 728 | -5.396 | -1.300 | -11.198 | 1.00 | 109.13 | A |
| ATOM | 1073 | CA | ARG A 728 | -6.583 | -1.172 | -12.009 | 1.00 | 109.13 | A |
| ATOM | 1074 | CB | ARG A 728 | -6.219 | -1.259 | -13.493 | 1.00 | 109.13 | A |
| ATOM | 1075 | CG | ARG A 728 | -5.962 | 0.109 | -14.147 | 1.00 | 109.13 | A |
| ATOM | 1076 | CD | ARG A 728 | -5.268 | 0.018 | -15.511 | 1.00 | 109.13 | A |
| ATOM | 1077 | NE | ARG A 728 | -3.846 | -0.282 | -15.361 | 1.00 | 109.13 | A |
| ATOM | 1078 | CZ | ARG A 728 | -2.960 | -0.266 | -16.352 | 1.00 | 109.13 | A |
| ATOM | 1079 | NH1 | ARG A 728 | -3.349 | 0.039 | -17.583 | 1.00 | 109.13 | A |
| ATOM | 1080 | NH2 | ARG A 728 | -1.683 | -0.545 | -16.107 | 1.00 | 109.13 | A |
| ATOM | 1081 | C | ARG A 728 | -7.469 | -2.317 | -11.590 | 1.00 | 109.13 | A |
| ATOM | 1082 | O | ARG A 728 | -7.017 | -3.444 | -11.509 | 1.00 | 109.13 | A |
| ATOM | 1083 | N | CYS A 729 | -8.734 | -2.024 | -11.319 | 1.00 | 109.13 | A |
| ATOM | 1084 | CA | CYS A 729 | -9.661 | -3.047 | -10.874 | 1.00 | 109.13 | A |
| ATOM | 1085 | CB | CYS A 729 | -11.080 | -2.505 | -10.813 | 1.00 | 109.13 | A |
| ATOM | 1086 | SG | CYS A 729 | -11.248 | -0.971 | -9.942 | 1.00 | 109.13 | A |
| ATOM | 1087 | C | CYS A 729 | -9.688 | -4.288 | -11.729 | 1.00 | 109.13 | A |
| ATOM | 1088 | O | CYS A 729 | -9.094 | -4.354 | -12.820 | 1.00 | 109.13 | A |
| ATOM | 1089 | N | GLU A 730 | -10.420 | -5.262 | -11.188 | 1.00 | 109.13 | A |

Figure 4 B
(Continued)

| | | | | | | | | | |
|---|---|---|---|---|---|---|---|---|---|
| ATOM | 1090 | CA | GLU | A | 730 | -10.690 | -6.593 | -11.769 | 1.00109.13 A |
| ATOM | 1091 | CB | GLU | A | 730 | -10.334 | -6.629 | -13.288 | 1.00109.13 A |
| ATOM | 1092 | CG | GLU | A | 730 | -11.081 | -7.727 | -14.089 | 1.00109.13 A |
| ATOM | 1093 | CD | GLU | A | 730 | -12.610 | -7.694 | -13.901 | 1.00109.13 A |
| ATOM | 1094 | OE1 | GLU | A | 730 | -13.269 | -6.829 | -14.517 | 1.00109.13 A |
| ATOM | 1095 | OE2 | GLU | A | 730 | -13.147 | -8.530 | -13.129 | 1.00109.13 A |
| ATOM | 1096 | C | GLU | A | 730 | -10.034 | -7.777 | -11.018 | 1.00109.13 A |
| ATOM | 1097 | O | GLU | A | 730 | -8.889 | -7.683 | -10.567 | 1.00109.13 A |
| ATOM | 1098 | N | GLU | A | 731 | -10.805 | -8.855 | -10.860 | 1.00109.13 A |
| ATOM | 1099 | CA | GLU | A | 731 | -10.358 | -10.082 | -10.215 | 1.00109.13 A |
| ATOM | 1100 | CB | GLU | A | 731 | -10.579 | -11.274 | -11.163 | 1.00109.13 A |
| ATOM | 1101 | CG | GLU | A | 731 | -10.319 | -10.992 | -12.672 | 1.00109.13 A |
| ATOM | 1102 | CD | GLU | A | 731 | -8.845 | -10.985 | -13.094 | 1.00109.13 A |
| ATOM | 1103 | OE1 | GLU | A | 731 | -8.378 | -9.961 | -13.645 | 1.00109.13 A |
| ATOM | 1104 | OE2 | GLU | A | 731 | -8.165 | -12.013 | -12.895 | 1.00109.13 A |
| ATOM | 1105 | C | GLU | A | 731 | -8.908 | -10.100 | -9.731 | 1.00109.13 A |
| ATOM | 1106 | O | GLU | A | 731 | -8.004 | -9.553 | -10.368 | 1.00109.13 A |
| ATOM | 1107 | N | GLY | A | 732 | -8.692 | -10.760 | -8.599 | 1.00109.13 A |
| ATOM | 1108 | CA | GLY | A | 732 | -7.357 | -10.857 | -8.050 | 1.00109.13 A |
| ATOM | 1109 | C | GLY | A | 732 | -6.386 | -11.420 | -9.068 | 1.00109.13 A |
| ATOM | 1110 | O | GLY | A | 732 | -5.744 | -10.661 | -9.802 | 1.00109.13 A |
| ATOM | 1111 | N | ASN | A | 733 | -6.301 | -12.753 | -9.109 | 1.00109.13 A |
| ATOM | 1112 | CA | ASN | A | 733 | -5.414 | -13.508 | -10.012 | 1.00109.13 A |
| ATOM | 1113 | CB | ASN | A | 733 | -6.261 | -14.446 | -10.903 | 1.00109.13 A |
| ATOM | 1114 | CG | ASN | A | 733 | -5.582 | -15.801 | -11.158 | 1.00109.13 A |
| ATOM | 1115 | OD1 | ASN | A | 733 | -4.466 | -15.862 | -11.686 | 1.00109.13 A |
| ATOM | 1116 | ND2 | ASN | A | 733 | -6.260 | -16.889 | -10.781 | 1.00109.13 A |
| ATOM | 1117 | C | ASN | A | 733 | -4.510 | -12.605 | -10.880 | 1.00109.13 A |
| ATOM | 1118 | O | ASN | A | 733 | -4.943 | -12.107 | -11.931 | 1.00109.13 A |
| ATOM | 1119 | N | ARG | A | 734 | -3.260 | -12.413 | -10.437 | 1.00109.13 A |
| ATOM | 1120 | CA | ARG | A | 734 | -2.273 | -11.558 | -11.126 | 1.00109.13 A |
| ATOM | 1121 | CB | ARG | A | 734 | -2.091 | -11.959 | -12.616 | 1.00109.13 A |
| ATOM | 1122 | CG | ARG | A | 734 | -1.605 | -10.773 | -13.496 | 1.00109.13 A |
| ATOM | 1123 | CD | ARG | A | 734 | -1.362 | -11.117 | -14.954 | 1.00109.13 A |
| ATOM | 1124 | NE | ARG | A | 734 | -0.908 | -9.948 | -15.713 | 1.00109.13 A |
| ATOM | 1125 | CZ | ARG | A | 734 | -0.316 | -9.998 | -16.910 | 1.00109.13 A |
| ATOM | 1126 | NH1 | ARG | A | 734 | -0.094 | -11.162 | -17.505 | 1.00109.13 A |
| ATOM | 1127 | NH2 | ARG | A | 734 | 0.058 | -8.879 | -17.523 | 1.00109.13 A |
| ATOM | 1128 | C | ARG | A | 734 | -2.649 | -10.066 | -11.063 | 1.00109.13 A |
| ATOM | 1129 | O | ARG | A | 734 | -1.942 | -9.253 | -10.448 | 1.00109.13 A |
| ATOM | 1130 | N | ASN | A | 735 | -3.758 | -9.722 | -11.721 | 1.00109.13 A |
| ATOM | 1131 | CA | ASN | A | 735 | -4.226 | -8.350 | -11.778 | 1.00109.13 A |
| ATOM | 1132 | CB | ASN | A | 735 | -5.126 | -8.130 | -13.017 | 1.00109.13 A |
| ATOM | 1133 | CG | ASN | A | 735 | -4.755 | -6.852 | -13.819 | 1.00109.13 A |
| ATOM | 1134 | OD1 | ASN | A | 735 | -3.604 | -6.395 | -13.779 | 1.00109.13 A |
| ATOM | 1135 | ND2 | ASN | A | 735 | -5.736 | -6.291 | -14.559 | 1.00109.13 A |
| ATOM | 1136 | C | ASN | A | 735 | -4.893 | -7.934 | -10.467 | 1.00109.13 A |
| ATOM | 1137 | O | ASN | A | 735 | -4.154 | -7.777 | -9.511 | 1.00109.13 A |
| ATOM | 1138 | N | LYS | A | 736 | -6.221 | -7.780 | -10.330 | 1.00109.13 A |
| ATOM | 1139 | CA | LYS | A | 736 | -6.627 | -7.277 | -9.019 | 1.00109.13 A |
| ATOM | 1140 | CB | LYS | A | 736 | -5.974 | -5.897 | -8.887 | 1.00109.13 A |
| ATOM | 1141 | CG | LYS | A | 736 | -5.843 | -5.113 | -10.200 | 1.00109.13 A |
| ATOM | 1142 | CD | LYS | A | 736 | -4.426 | -5.163 | -10.854 | 1.00109.13 A |
| ATOM | 1143 | CE | LYS | A | 736 | -4.284 | -4.191 | -12.062 | 1.00109.13 A |
| ATOM | 1144 | NZ | LYS | A | 736 | -2.947 | -4.199 | -12.749 | 1.00109.13 A |
| ATOM | 1145 | C | LYS | A | 736 | -7.927 | -7.177 | -8.200 | 1.00109.13 A |
| ATOM | 1146 | O | LYS | A | 736 | -8.449 | -8.147 | -7.693 | 1.00109.13 A |

Figure 4 B
(Continued)

| | | | | | | | | | |
|---|---|---|---|---|---|---|---|---|---|
| ATOM | 1147 | N | CYS | A | 737 | -8.376 | -5.932 | -8.090 | 1.00 109.13 A |
| ATOM | 1148 | CA | CYS | A | 737 | -9.413 | -5.362 | -7.225 | 1.00 109.13 A |
| ATOM | 1149 | CB | CYS | A | 737 | -8.755 | -4.092 | -6.682 | 1.00 109.13 A |
| ATOM | 1150 | SG | CYS | A | 737 | -9.804 | -2.842 | -5.973 | 1.00 109.13 A |
| ATOM | 1151 | C | CYS | A | 737 | -10.851 | -5.039 | -7.636 | 1.00 109.13 A |
| ATOM | 1152 | O | CYS | A | 737 | -11.147 | -4.882 | -8.812 | 1.00 109.13 A |
| ATOM | 1597 | N | THR | A | 792 | -3.087 | 4.291 | -13.004 | 1.00 109.13 A |
| ATOM | 1598 | CA | THR | A | 792 | -3.458 | 3.383 | -14.087 | 1.00 109.13 A |
| ATOM | 1599 | CB | THR | A | 792 | -4.609 | 3.986 | -14.900 | 1.00 109.13 A |
| ATOM | 1600 | OG1 | THR | A | 792 | -4.504 | 5.417 | -14.877 | 1.00 109.13 A |
| ATOM | 1601 | CG2 | THR | A | 792 | -5.939 | 3.554 | -14.338 | 1.00 109.13 A |
| ATOM | 1602 | C | THR | A | 792 | -2.347 | 3.016 | -15.067 | 1.00 109.13 A |
| ATOM | 1603 | O | THR | A | 792 | -2.618 | 2.495 | -16.150 | 1.00 109.13 A |
| ATOM | 1604 | N | SER | A | 793 | -1.101 | 3.272 | -14.698 | 1.00 109.13 A |
| ATOM | 1605 | CA | SER | A | 793 | 0.005 | 2.967 | -15.597 | 1.00 109.13 A |
| ATOM | 1606 | CB | SER | A | 793 | 0.757 | 4.264 | -15.932 | 1.00 109.13 A |
| ATOM | 1607 | OG | SER | A | 793 | -0.148 | 5.302 | -16.296 | 1.00 109.13 A |
| ATOM | 1608 | C | SER | A | 793 | 0.976 | 1.928 | -15.032 | 1.00 109.13 A |
| ATOM | 1609 | O | SER | A | 793 | 2.002 | 1.645 | -15.638 | 1.00 109.13 A |
| ATOM | 1610 | N | TRP | A | 794 | 0.650 | 1.355 | -13.876 | 1.00 109.13 A |
| ATOM | 1611 | CA | TRP | A | 794 | 1.529 | 0.365 | -13.255 | 1.00 109.13 A |
| ATOM | 1612 | CB | TRP | A | 794 | 1.533 | 0.500 | -11.731 | 1.00 109.13 A |
| ATOM | 1613 | CG | TRP | A | 794 | 2.743 | -0.116 | -11.111 | 1.00 109.13 A |
| ATOM | 1614 | CD2 | TRP | A | 794 | 3.516 | 0.405 | -10.023 | 1.00 109.13 A |
| ATOM | 1615 | CE2 | TRP | A | 794 | 4.587 | -0.494 | -9.804 | 1.00 109.13 A |
| ATOM | 1616 | CE3 | TRP | A | 794 | 3.412 | 1.544 | -9.213 | 1.00 109.13 A |
| ATOM | 1617 | CD1 | TRP | A | 794 | 3.354 | -1.276 | -11.490 | 1.00 109.13 A |
| ATOM | 1618 | NE1 | TRP | A | 794 | 4.464 | -1.509 | -10.713 | 1.00 109.13 A |
| ATOM | 1619 | CZ2 | TRP | A | 794 | 5.544 | -0.291 | -8.811 | 1.00 109.13 A |
| ATOM | 1620 | CZ3 | TRP | A | 794 | 4.365 | 1.748 | -8.225 | 1.00 109.13 A |
| ATOM | 1621 | CH2 | TRP | A | 794 | 5.418 | 0.834 | -8.033 | 1.00 109.13 A |
| ATOM | 1622 | C | TRP | A | 794 | 1.131 | -1.053 | -13.600 | 1.00 109.13 A |
| ATOM | 1623 | O | TRP | A | 794 | 0.081 | -1.532 | -13.169 | 1.00 109.13 A |
| ATOM | 1624 | N | PRO | A | 795 | 1.980 | -1.755 | -14.370 | 1.00 109.13 A |
| ATOM | 1625 | CD | PRO | A | 795 | 3.254 | -1.328 | -14.978 | 1.00 109.13 A |
| ATOM | 1626 | CA | PRO | A | 795 | 1.664 | -3.132 | -14.745 | 1.00 109.13 A |
| ATOM | 1627 | CB | PRO | A | 795 | 2.845 | -3.537 | -15.634 | 1.00 109.13 A |
| ATOM | 1628 | CG | PRO | A | 795 | 3.963 | -2.645 | -15.179 | 1.00 109.13 A |
| ATOM | 1629 | C | PRO | A | 795 | 1.404 | -4.107 | -13.594 | 1.00 109.13 A |
| ATOM | 1630 | O | PRO | A | 795 | 2.043 | -4.091 | -12.541 | 1.00 109.13 A |
| ATOM | 1631 | N | ASP | A | 796 | 0.405 | -4.936 | -13.859 | 1.00 109.13 A |
| ATOM | 1632 | CA | ASP | A | 796 | -0.139 | -6.004 | -13.018 | 1.00 109.13 A |
| ATOM | 1633 | CB | ASP | A | 796 | -0.827 | -7.019 | -13.979 | 1.00 109.13 A |
| ATOM | 1634 | CG | ASP | A | 796 | -0.548 | -6.709 | -15.505 | 1.00 109.13 A |
| ATOM | 1635 | OD1 | ASP | A | 796 | 0.617 | -6.834 | -15.976 | 1.00 109.13 A |
| ATOM | 1636 | OD2 | ASP | A | 796 | -1.497 | -6.329 | -16.242 | 1.00 109.13 A |
| ATOM | 1637 | C | ASP | A | 796 | 0.785 | -6.750 | -12.022 | 1.00 109.13 A |
| ATOM | 1638 | O | ASP | A | 796 | 0.299 | -7.420 | -11.097 | 1.00 109.13 A |
| ATOM | 1639 | N | HIS | A | 797 | 2.100 | -6.622 | -12.205 | 1.00 109.13 A |
| ATOM | 1640 | CA | HIS | A | 797 | 3.069 | -7.330 | -11.364 | 1.00 109.13 A |
| ATOM | 1641 | CB | HIS | A | 797 | 3.014 | -8.824 | -11.691 | 1.00 109.13 A |
| ATOM | 1642 | CG | HIS | A | 797 | 2.623 | -9.689 | -10.536 | 1.00 109.13 A |
| ATOM | 1643 | CD2 | HIS | A | 797 | 1.458 | -10.317 | -10.246 | 1.00 109.13 A |
| ATOM | 1644 | ND1 | HIS | A | 797 | 3.499 | -10.014 | -9.523 | 1.00 109.13 A |
| ATOM | 1645 | CE1 | HIS | A | 797 | 2.891 | -10.810 | -8.660 | 1.00 109.13 A |
| ATOM | 1646 | NE2 | HIS | A | 797 | 1.652 | -11.009 | -9.075 | 1.00 109.13 A |
| ATOM | 1647 | C | HIS | A | 797 | 4.502 | -6.851 | -11.586 | 1.00 109.13 A |

Figure 4 B
(Continued)

| ATOM | 1648 | O   | HIS A 797 | 5.424  | -7.389 | -10.970 | 1.00 | 109.13 | A |
|------|------|-----|-----------|--------|--------|---------|------|--------|---|
| ATOM | 1649 | N   | GLY A 798 | 4.679  | -5.857 | -12.464 | 1.00 | 109.13 | A |
| ATOM | 1650 | CA  | GLY A 798 | 6.005  | -5.337 | -12.780 | 1.00 | 109.13 | A |
| ATOM | 1651 | C   | GLY A 798 | 6.261  | -3.860 | -12.523 | 1.00 | 109.13 | A |
| ATOM | 1652 | O   | GLY A 798 | 5.780  | -3.302 | -11.546 | 1.00 | 109.13 | A |
| ATOM | 1653 | N   | VAL A 799 | 7.021  | -3.213 | -13.397 | 1.00 | 109.13 | A |
| ATOM | 1654 | CA  | VAL A 799 | 7.335  | -1.801 | -13.194 | 1.00 | 109.13 | A |
| ATOM | 1655 | CB  | VAL A 799 | 8.848  | -1.613 | -12.926 | 1.00 | 109.13 | A |
| ATOM | 1656 | CG1 | VAL A 799 | 9.276  | -2.516 | -11.802 | 1.00 | 109.13 | A |
| ATOM | 1657 | CG2 | VAL A 799 | 9.655  | -1.900 | -14.182 | 1.00 | 109.13 | A |
| ATOM | 1658 | C   | VAL A 799 | 6.924  | -0.837 | -14.314 | 1.00 | 109.13 | A |
| ATOM | 1659 | O   | VAL A 799 | 6.995  | -1.161 | -15.497 | 1.00 | 109.13 | A |
| ATOM | 1660 | N   | PRO A 800 | 6.483  | 0.372  | -13.942 | 1.00 | 109.13 | A |
| ATOM | 1661 | CD  | PRO A 800 | 6.073  | 0.769  | -12.587 | 1.00 | 109.13 | A |
| ATOM | 1662 | CA  | PRO A 800 | 6.069  | 1.381  | -14.916 | 1.00 | 109.13 | A |
| ATOM | 1663 | CB  | PRO A 800 | 5.519  | 2.497  | -14.040 | 1.00 | 109.13 | A |
| ATOM | 1664 | CG  | PRO A 800 | 4.984  | 1.755  | -12.874 | 1.00 | 109.13 | A |
| ATOM | 1665 | C   | PRO A 800 | 7.229  | 1.873  | -15.769 | 1.00 | 109.13 | A |
| ATOM | 1666 | O   | PRO A 800 | 8.377  | 1.851  | -15.342 | 1.00 | 109.13 | A |
| ATOM | 1667 | N   | GLU A 801 | 6.922  | 2.314  | -16.981 | 1.00 | 109.13 | A |
| ATOM | 1668 | CA  | GLU A 801 | 7.942  | 2.848  | -17.871 | 1.00 | 109.13 | A |
| ATOM | 1669 | CB  | GLU A 801 | 7.345  | 3.124  | -19.261 | 1.00 | 109.13 | A |
| ATOM | 1670 | CG  | GLU A 801 | 7.034  | 1.881  | -20.092 | 1.00 | 109.13 | A |
| ATOM | 1671 | CD  | GLU A 801 | 8.284  | 1.060  | -20.404 | 1.00 | 109.13 | A |
| ATOM | 1672 | OE1 | GLU A 801 | 8.898  | 0.531  | -19.436 | 1.00 | 109.13 | A |
| ATOM | 1673 | OE2 | GLU A 801 | 8.648  | 0.951  | -21.607 | 1.00 | 109.13 | A |
| ATOM | 1674 | C   | GLU A 801 | 8.455  | 4.158  | -17.264 | 1.00 | 109.13 | A |
| ATOM | 1675 | O   | GLU A 801 | 7.667  | 4.983  | -16.793 | 1.00 | 109.13 | A |
| ATOM | 1676 | N   | ASP A 802 | 9.770  | 4.351  | -17.286 | 1.00 | 109.13 | A |
| ATOM | 1677 | CA  | ASP A 802 | 10.386 | 5.560  | -16.728 | 1.00 | 109.13 | A |
| ATOM | 1678 | CB  | ASP A 802 | 9.936  | 6.810  | -17.508 | 1.00 | 109.13 | A |
| ATOM | 1679 | CG  | ASP A 802 | 10.674 | 8.080  | -17.068 | 1.00 | 109.13 | A |
| ATOM | 1680 | OD1 | ASP A 802 | 11.916 | 8.145  | -17.228 | 1.00 | 109.13 | A |
| ATOM | 1681 | OD2 | ASP A 802 | 10.006 | 9.015  | -16.563 | 1.00 | 109.13 | A |
| ATOM | 1682 | C   | ASP A 802 | 10.045 | 5.723  | -15.234 | 1.00 | 109.13 | A |
| ATOM | 1683 | O   | ASP A 802 | 8.916  | 6.065  | -14.868 | 1.00 | 109.13 | A |
| ATOM | 1684 | N   | PRO A 803 | 11.028 | 5.477  | -14.353 | 1.00 | 109.13 | A |
| ATOM | 1685 | CD  | PRO A 803 | 12.416 | 5.053  | -14.598 | 1.00 | 109.13 | A |
| ATOM | 1686 | CA  | PRO A 803 | 10.790 | 5.607  | -12.923 | 1.00 | 109.13 | A |
| ATOM | 1687 | CB  | PRO A 803 | 12.181 | 5.444  | -12.342 | 1.00 | 109.13 | A |
| ATOM | 1688 | CG  | PRO A 803 | 12.796 | 4.477  | -13.267 | 1.00 | 109.13 | A |
| ATOM | 1689 | C   | PRO A 803 | 10.166 | 6.943  | -12.577 | 1.00 | 109.13 | A |
| ATOM | 1690 | O   | PRO A 803 | 9.342  | 7.025  | -11.681 | 1.00 | 109.13 | A |
| ATOM | 1891 | N   | SER A 828 | -3.245 | -2.027 | -3.191  | 1.00 | 109.13 | A |
| ATOM | 1892 | CA  | SER A 828 | -3.071 | -2.545 | -4.546  | 1.00 | 109.13 | A |
| ATOM | 1893 | CB  | SER A 828 | -1.610 | -2.906 | -4.795  | 1.00 | 109.13 | A |
| ATOM | 1894 | OG  | SER A 828 | -1.203 | -3.989 | -3.989  | 1.00 | 109.13 | A |
| ATOM | 1895 | C   | SER A 828 | -3.955 | -3.794 | -4.703  | 1.00 | 109.13 | A |
| ATOM | 1896 | O   | SER A 828 | -5.122 | -3.795 | -4.320  | 1.00 | 109.13 | A |
| ATOM | 1897 | N   | SER A 829 | -3.409 | -4.863 | -5.256  | 1.00 | 109.13 | A |
| ATOM | 1898 | CA  | SER A 829 | -4.196 | -6.069 | -5.420  | 1.00 | 109.13 | A |
| ATOM | 1899 | CB  | SER A 829 | -3.721 | -6.854 | -6.631  | 1.00 | 109.13 | A |
| ATOM | 1900 | OG  | SER A 829 | -4.425 | -8.079 | -6.743  | 1.00 | 109.13 | A |
| ATOM | 1901 | C   | SER A 829 | -4.103 | -6.956 | -4.195  | 1.00 | 109.13 | A |
| ATOM | 1902 | O   | SER A 829 | -5.097 | -7.537 | -3.771  | 1.00 | 109.13 | A |
| ATOM | 1903 | N   | ALA A 830 | -2.899 | -7.071 | -3.637  | 1.00 | 109.13 | A |
| ATOM | 1904 | CA  | ALA A 830 | -2.659 | -7.892 | -2.447  | 1.00 | 109.13 | A |

Figure 4 B
(Continued)

| ATOM | 1905 | CB | ALA A 830 | -1.766 | -9.058 | -2.789 | 1.00 | 109.13 | A |
|---|---|---|---|---|---|---|---|---|---|
| ATOM | 1906 | C | ALA A 830 | -2.015 | -7.063 | -1.353 | 1.00 | 109.13 | A |
| ATOM | 1907 | O | ALA A 830 | -1.410 | -7.593 | -0.434 | 1.00 | 109.13 | A |
| ATOM | 1908 | N | GLY A 831 | -2.147 | -5.751 | -1.472 | 1.00 | 109.13 | A |
| ATOM | 1909 | CA | GLY A 831 | -1.583 | -4.858 | -0.491 | 1.00 | 109.13 | A |
| ATOM | 1910 | C | GLY A 831 | -0.089 | -4.706 | -0.647 | 1.00 | 109.13 | A |
| ATOM | 1911 | O | GLY A 831 | 0.393 | -3.641 | -1.009 | 1.00 | 109.13 | A |
| ATOM | 1912 | N | VAL A 832 | 0.634 | -5.790 | -0.397 | 1.00 | 109.13 | A |
| ATOM | 1913 | CA | VAL A 832 | 2.092 | -5.817 | -0.452 | 1.00 | 109.13 | A |
| ATOM | 1914 | CB | VAL A 832 | 2.566 | -7.255 | -0.214 | 1.00 | 109.13 | A |
| ATOM | 1915 | CG1 | VAL A 832 | 2.203 | -7.676 | 1.183 | 1.00 | 109.13 | A |
| ATOM | 1916 | CG2 | VAL A 832 | 1.892 | -8.187 | -1.181 | 1.00 | 109.13 | A |
| ATOM | 1917 | C | VAL A 832 | 2.839 | -5.230 | -1.673 | 1.00 | 109.13 | A |
| ATOM | 1918 | O | VAL A 832 | 3.093 | -4.023 | -1.748 | 1.00 | 109.13 | A |
| ATOM | 1919 | N | GLY A 833 | 3.214 | -6.102 | -2.604 | 1.00 | 109.13 | A |
| ATOM | 1920 | CA | GLY A 833 | 3.935 | -5.709 | -3.803 | 1.00 | 109.13 | A |
| ATOM | 1921 | C | GLY A 833 | 3.973 | -4.260 | -4.261 | 1.00 | 109.13 | A |
| ATOM | 1922 | O | GLY A 833 | 4.762 | -3.467 | -3.763 | 1.00 | 109.13 | A |
| ATOM | 1923 | N | ARG A 834 | 3.118 | -3.921 | -5.220 | 1.00 | 109.13 | A |
| ATOM | 1924 | CA | ARG A 834 | 3.088 | -2.586 | -5.799 | 1.00 | 109.13 | A |
| ATOM | 1925 | CB | ARG A 834 | 1.946 | -2.465 | -6.801 | 1.00 | 109.13 | A |
| ATOM | 1926 | CG | ARG A 834 | 2.278 | -2.974 | -8.190 | 1.00 | 109.13 | A |
| ATOM | 1927 | CD | ARG A 834 | 1.080 | -2.842 | -9.136 | 1.00 | 109.13 | A |
| ATOM | 1928 | NE | ARG A 834 | 0.001 | -3.774 | -8.806 | 1.00 | 109.13 | A |
| ATOM | 1929 | CZ | ARG A 834 | -1.216 | -3.727 | -9.332 | 1.00 | 109.13 | A |
| ATOM | 1930 | NH1 | ARG A 834 | -1.521 | -2.794 | -10.218 | 1.00 | 109.13 | A |
| ATOM | 1931 | NH2 | ARG A 834 | -2.127 | -4.612 | -8.968 | 1.00 | 109.13 | A |
| ATOM | 1932 | C | ARG A 834 | 3.023 | -1.422 | -4.847 | 1.00 | 109.13 | A |
| ATOM | 1933 | O | ARG A 834 | 3.689 | -0.417 | -5.058 | 1.00 | 109.13 | A |
| ATOM | 1934 | N | THR A 835 | 2.216 | -1.529 | -3.806 | 1.00 | 109.13 | A |
| ATOM | 1935 | CA | THR A 835 | 2.122 | -0.422 | -2.868 | 1.00 | 109.13 | A |
| ATOM | 1936 | CB | THR A 835 | 0.989 | -0.619 | -1.853 | 1.00 | 109.13 | A |
| ATOM | 1937 | OG1 | THR A 835 | 1.399 | -1.575 | -0.877 | 1.00 | 109.13 | A |
| ATOM | 1938 | CG2 | THR A 835 | -0.273 | -1.129 | -2.543 | 1.00 | 109.13 | A |
| ATOM | 1939 | C | THR A 835 | 3.439 | -0.382 | -2.121 | 1.00 | 109.13 | A |
| ATOM | 1940 | O | THR A 835 | 4.042 | 0.680 | -1.945 | 1.00 | 109.13 | A |
| ATOM | 1941 | N | GLY A 836 | 3.880 | -1.562 | -1.697 | 1.00 | 109.13 | A |
| ATOM | 1942 | CA | GLY A 836 | 5.128 | -1.682 | -0.971 | 1.00 | 109.13 | A |
| ATOM | 1943 | C | GLY A 836 | 6.242 | -0.943 | -1.669 | 1.00 | 109.13 | A |
| ATOM | 1944 | O | GLY A 836 | 7.041 | -0.259 | -1.044 | 1.00 | 109.13 | A |
| ATOM | 1945 | N | THR A 837 | 6.297 | -1.077 | -2.981 | 1.00 | 109.13 | A |
| ATOM | 1946 | CA | THR A 837 | 7.316 | -0.391 | -3.741 | 1.00 | 109.13 | A |
| ATOM | 1947 | CB | THR A 837 | 7.229 | -0.769 | -5.216 | 1.00 | 109.13 | A |
| ATOM | 1948 | OG1 | THR A 837 | 7.226 | -2.198 | -5.335 | 1.00 | 109.13 | A |
| ATOM | 1949 | CG2 | THR A 837 | 8.419 | -0.212 | -5.978 | 1.00 | 109.13 | A |
| ATOM | 1950 | C | THR A 837 | 7.129 | 1.114 | -3.581 | 1.00 | 109.13 | A |
| ATOM | 1951 | O | THR A 837 | 8.081 | 1.830 | -3.279 | 1.00 | 109.13 | A |
| ATOM | 1952 | N | TYR A 838 | 5.898 | 1.587 | -3.768 | 1.00 | 109.13 | A |
| ATOM | 1953 | CA | TYR A 838 | 5.590 | 3.016 | -3.634 | 1.00 | 109.13 | A |
| ATOM | 1954 | CB | TYR A 838 | 4.097 | 3.275 | -3.822 | 1.00 | 109.13 | A |
| ATOM | 1955 | CG | TYR A 838 | 3.668 | 4.638 | -3.330 | 1.00 | 109.13 | A |
| ATOM | 1956 | CD1 | TYR A 838 | 4.359 | 5.778 | -3.697 | 1.00 | 109.13 | A |
| ATOM | 1957 | CE1 | TYR A 838 | 3.976 | 7.018 | -3.240 | 1.00 | 109.13 | A |
| ATOM | 1958 | CD2 | TYR A 838 | 2.575 | 4.781 | -2.494 | 1.00 | 109.13 | A |
| ATOM | 1959 | CE2 | TYR A 838 | 2.186 | 6.018 | -2.037 | 1.00 | 109.13 | A |
| ATOM | 1960 | CZ | TYR A 838 | 2.891 | 7.130 | -2.411 | 1.00 | 109.13 | A |
| ATOM | 1961 | OH | TYR A 838 | 2.522 | 8.359 | -1.939 | 1.00 | 109.13 | A |

Figure 4 B
(Continued)

| | | | | | | | | | |
|---|---|---|---|---|---|---|---|---|---|
| ATOM | 1962 | C | TYR | A | 838 | 6.006 | 3.552 | -2.277 | 1.00109.13 | A |
| ATOM | 1963 | O | TYR | A | 838 | 6.794 | 4.498 | -2.188 | 1.00109.13 | A |
| ATOM | 1964 | N | ILE | A | 839 | 5.439 | 2.955 | -1.231 | 1.00109.13 | A |
| ATOM | 1965 | CA | ILE | A | 839 | 5.747 | 3.314 | 0.142 | 1.00109.13 | A |
| ATOM | 1966 | CB | ILE | A | 839 | 5.167 | 2.264 | 1.102 | 1.00109.13 | A |
| ATOM | 1967 | CG2 | ILE | A | 839 | 5.566 | 2.576 | 2.517 | 1.00109.13 | A |
| ATOM | 1968 | CG1 | ILE | A | 839 | 3.651 | 2.236 | 0.983 | 1.00109.13 | A |
| ATOM | 1969 | CD1 | ILE | A | 839 | 2.989 | 1.241 | 1.897 | 1.00109.13 | A |
| ATOM | 1970 | C | ILE | A | 839 | 7.273 | 3.370 | 0.312 | 1.00109.13 | A |
| ATOM | 1971 | O | ILE | A | 839 | 7.824 | 4.326 | 0.869 | 1.00109.13 | A |
| ATOM | 1972 | N | GLY | A | 840 | 7.945 | 2.334 | -0.187 | 1.00109.13 | A |
| ATOM | 1973 | CA | GLY | A | 840 | 9.392 | 2.256 | -0.107 | 1.00109.13 | A |
| ATOM | 1974 | C | GLY | A | 840 | 10.051 | 3.471 | -0.709 | 1.00109.13 | A |
| ATOM | 1975 | O | GLY | A | 840 | 10.964 | 4.035 | -0.130 | 1.00109.13 | A |
| ATOM | 1976 | N | ILE | A | 841 | 9.590 | 3.885 | -1.877 | 1.00109.13 | A |
| ATOM | 1977 | CA | ILE | A | 841 | 10.167 | 5.054 | -2.511 | 1.00109.13 | A |
| ATOM | 1978 | CB | ILE | A | 841 | 9.657 | 5.242 | -3.947 | 1.00109.13 | A |
| ATOM | 1979 | CG2 | ILE | A | 841 | 10.454 | 6.334 | -4.639 | 1.00109.13 | A |
| ATOM | 1980 | CG1 | ILE | A | 841 | 9.812 | 3.935 | -4.723 | 1.00109.13 | A |
| ATOM | 1981 | CD1 | ILE | A | 841 | 9.404 | 4.027 | -6.168 | 1.00109.13 | A |
| ATOM | 1982 | C | ILE | A | 841 | 9.806 | 6.293 | -1.709 | 1.00109.13 | A |
| ATOM | 1983 | O | ILE | A | 841 | 10.688 | 7.000 | -1.238 | 1.00109.13 | A |
| ATOM | 1984 | N | ASP | A | 842 | 8.512 | 6.552 | -1.549 | 1.00109.13 | A |
| ATOM | 1985 | CA | ASP | A | 842 | 8.060 | 7.723 | -0.802 | 1.00109.13 | A |
| ATOM | 1986 | CB | ASP | A | 842 | 6.584 | 7.594 | -0.420 | 1.00109.13 | A |
| ATOM | 1987 | CG | ASP | A | 842 | 6.052 | 8.829 | 0.301 | 1.00109.13 | A |
| ATOM | 1988 | OD1 | ASP | A | 842 | 4.819 | 8.924 | 0.506 | 1.00109.13 | A |
| ATOM | 1989 | OD2 | ASP | A | 842 | 6.864 | 9.705 | 0.659 | 1.00109.13 | A |
| ATOM | 1990 | C | ASP | A | 842 | 8.873 | 7.900 | 0.460 | 1.00109.13 | A |
| ATOM | 1991 | O | ASP | A | 842 | 9.261 | 9.018 | 0.794 | 1.00109.13 | A |
| ATOM | 2211 | N | MET | A | 870 | 6.041 | -7.600 | 1.208 | 1.00109.13 | A |
| ATOM | 2212 | CA | MET | A | 870 | 6.072 | -6.208 | 0.732 | 1.00109.13 | A |
| ATOM | 2213 | CB | MET | A | 870 | 6.265 | -5.218 | 1.896 | 1.00109.13 | A |
| ATOM | 2214 | CG | MET | A | 870 | 5.046 | -4.959 | 2.797 | 1.00109.13 | A |
| ATOM | 2215 | SD | MET | A | 870 | 3.907 | -3.640 | 2.286 | 1.00109.13 | A |
| ATOM | 2216 | CE | MET | A | 870 | 4.762 | -2.220 | 2.765 | 1.00109.13 | A |
| ATOM | 2217 | C | MET | A | 870 | 7.232 | -6.050 | -0.262 | 1.00109.13 | A |
| ATOM | 2218 | O | MET | A | 870 | 8.341 | -6.510 | -0.003 | 1.00109.13 | A |
| ATOM | 2219 | N | VAL | A | 871 | 6.974 | -5.404 | -1.397 | 1.00109.13 | A |
| ATOM | 2220 | CA | VAL | A | 871 | 7.992 | -5.216 | -2.424 | 1.00109.13 | A |
| ATOM | 2221 | CB | VAL | A | 871 | 9.182 | -4.424 | -1.862 | 1.00109.13 | A |
| ATOM | 2222 | CG1 | VAL | A | 871 | 10.360 | -4.499 | -2.802 | 1.00109.13 | A |
| ATOM | 2223 | CG2 | VAL | A | 871 | 8.777 | -2.978 | -1.666 | 1.00109.13 | A |
| ATOM | 2224 | C | VAL | A | 871 | 8.427 | -6.601 | -2.872 | 1.00109.13 | A |
| ATOM | 2225 | O | VAL | A | 871 | 9.484 | -7.085 | -2.484 | 1.00109.13 | A |
| ATOM | 2226 | N | GLN | A | 872 | 7.600 | -7.230 | -3.702 | 1.00109.13 | A |
| ATOM | 2227 | CA | GLN | A | 872 | 7.849 | -8.592 | -4.172 | 1.00109.13 | A |
| ATOM | 2228 | CB | GLN | A | 872 | 6.548 | -9.391 | -4.098 | 1.00109.13 | A |
| ATOM | 2229 | CG | GLN | A | 872 | 5.348 | -8.695 | -4.710 | 1.00109.13 | A |
| ATOM | 2230 | CD | GLN | A | 872 | 4.697 | -9.517 | -5.801 | 1.00109.13 | A |
| ATOM | 2231 | OE1 | GLN | A | 872 | 4.454 | -10.717 | -5.638 | 1.00109.13 | A |
| ATOM | 2232 | NE2 | GLN | A | 872 | 4.401 | -8.872 | -6.924 | 1.00109.13 | A |
| ATOM | 2233 | C | GLN | A | 872 | 8.480 | -8.846 | -5.539 | 1.00109.13 | A |
| ATOM | 2234 | O | GLN | A | 872 | 8.207 | -9.875 | -6.159 | 1.00109.13 | A |
| ATOM | 2235 | N | VAL | A | 873 | 9.327 | -7.935 | -6.005 | 1.00109.13 | A |
| ATOM | 2236 | CA | VAL | A | 873 | 9.982 | -8.109 | -7.303 | 1.00109.13 | A |
| ATOM | 2237 | CB | VAL | A | 873 | 9.041 | -7.748 | -8.479 | 1.00109.13 | A |

Figure 4 B
(Continued)

| | | | | | | | | | |
|---|---|---|---|---|---|---|---|---|---|
| ATOM | 2238 | CG1 | VAL | A | 873 | 9.849 | -7.654 | -9.766 | 1.00 109.13 A |
| ATOM | 2239 | CG2 | VAL | A | 873 | 7.943 | -8.805 | -8.632 | 1.00 109.13 A |
| ATOM | 2240 | C | VAL | A | 873 | 11.261 | -7.290 | -7.457 | 1.00 109.13 A |
| ATOM | 2241 | O | VAL | A | 873 | 11.246 | -6.068 | -7.374 | 1.00 109.13 A |
| ATOM | 2242 | N | GLU | A | 874 | 12.359 | -8.001 | -7.690 | 1.00 109.13 A |
| ATOM | 2243 | CA | GLU | A | 874 | 13.693 | -7.437 | -7.882 | 1.00 109.13 A |
| ATOM | 2244 | CB | GLU | A | 874 | 14.603 | -8.444 | -8.586 | 1.00 109.13 A |
| ATOM | 2245 | CG | GLU | A | 874 | 14.092 | -9.871 | -8.505 | 1.00 109.13 A |
| ATOM | 2246 | CD | GLU | A | 874 | 12.598 | -9.981 | -8.867 | 1.00 109.13 A |
| ATOM | 2247 | OE1 | GLU | A | 874 | 12.209 | -9.530 | -9.978 | 1.00 109.13 A |
| ATOM | 2248 | OE2 | GLU | A | 874 | 11.816 | -10.501 | -8.024 | 1.00 109.13 A |
| ATOM | 2249 | C | GLU | A | 874 | 13.563 | -6.212 | -8.746 | 1.00 109.13 A |
| ATOM | 2250 | O | GLU | A | 874 | 14.268 | -5.223 | -8.536 | 1.00 109.13 A |
| ATOM | 2251 | N | ALA | A | 875 | 12.663 | -6.297 | -9.725 | 1.00 109.13 A |
| ATOM | 2252 | CA | ALA | A | 875 | 12.413 | -5.196 | -10.637 | 1.00 109.13 A |
| ATOM | 2253 | CB | ALA | A | 875 | 11.383 | -5.599 | -11.647 | 1.00 109.13 A |
| ATOM | 2254 | C | ALA | A | 875 | 11.908 | -4.039 | -9.797 | 1.00 109.13 A |
| ATOM | 2255 | O | ALA | A | 875 | 12.406 | -2.916 | -9.885 | 1.00 109.13 A |
| ATOM | 2256 | N | GLN | A | 876 | 10.915 | -4.329 | -8.969 | 1.00 109.13 A |
| ATOM | 2257 | CA | GLN | A | 876 | 10.358 | -3.322 | -8.077 | 1.00 109.13 A |
| ATOM | 2258 | CB | GLN | A | 876 | 9.196 | -3.916 | -7.278 | 1.00 109.13 A |
| ATOM | 2259 | CG | GLN | A | 876 | 8.081 | -4.436 | -8.166 | 1.00 109.13 A |
| ATOM | 2260 | CD | GLN | A | 876 | 6.951 | -5.065 | -7.396 | 1.00 109.13 A |
| ATOM | 2261 | OE1 | GLN | A | 876 | 6.006 | -5.588 | -7.985 | 1.00 109.13 A |
| ATOM | 2262 | NE2 | GLN | A | 876 | 7.036 | -5.022 | -6.072 | 1.00 109.13 A |
| ATOM | 2263 | C | GLN | A | 876 | 11.476 | -2.885 | -7.137 | 1.00 109.13 A |
| ATOM | 2264 | O | GLN | A | 876 | 11.587 | -1.711 | -6.780 | 1.00 109.13 A |
| ATOM | 2265 | N | TYR | A | 877 | 12.307 | -3.850 | -6.750 | 1.00 109.13 A |
| ATOM | 2266 | CA | TYR | A | 877 | 13.436 | -3.588 | -5.869 | 1.00 109.13 A |
| ATOM | 2267 | CB | TYR | A | 877 | 14.275 | -4.847 | -5.665 | 1.00 109.13 A |
| ATOM | 2268 | CG | TYR | A | 877 | 15.326 | -4.693 | -4.589 | 1.00 109.13 A |
| ATOM | 2269 | CD1 | TYR | A | 877 | 15.017 | -4.923 | -3.244 | 1.00 109.13 A |
| ATOM | 2270 | CE1 | TYR | A | 877 | 15.970 | -4.738 | -2.245 | 1.00 109.13 A |
| ATOM | 2271 | CD2 | TYR | A | 877 | 16.616 | -4.277 | -4.907 | 1.00 109.13 A |
| ATOM | 2272 | CE2 | TYR | A | 877 | 17.577 | -4.088 | -3.918 | 1.00 109.13 A |
| ATOM | 2273 | CZ | TYR | A | 877 | 17.250 | -4.317 | -2.587 | 1.00 109.13 A |
| ATOM | 2274 | OH | TYR | A | 877 | 18.201 | -4.108 | -1.602 | 1.00 109.13 A |
| ATOM | 2275 | C | TYR | A | 877 | 14.291 | -2.545 | -6.541 | 1.00 109.13 A |
| ATOM | 2276 | O | TYR | A | 877 | 14.577 | -1.502 | -5.975 | 1.00 109.13 A |
| ATOM | 2277 | N | ILE | A | 878 | 14.694 | -2.844 | -7.765 | 1.00 109.13 A |
| ATOM | 2278 | CA | ILE | A | 878 | 15.514 | -1.935 | -8.538 | 1.00 109.13 A |
| ATOM | 2279 | CB | ILE | A | 878 | 15.864 | -2.549 | -9.918 | 1.00 109.13 A |
| ATOM | 2280 | CG2 | ILE | A | 878 | 16.788 | -1.609 | -10.704 | 1.00 109.13 A |
| ATOM | 2281 | CG1 | ILE | A | 878 | 16.543 | -3.910 | -9.719 | 1.00 109.13 A |
| ATOM | 2282 | CD1 | ILE | A | 878 | 16.943 | -4.612 | -11.017 | 1.00 109.13 A |
| ATOM | 2283 | C | ILE | A | 878 | 14.780 | -0.616 | -8.739 | 1.00 109.13 A |
| ATOM | 2284 | O | ILE | A | 878 | 15.377 | 0.459 | -8.685 | 1.00 109.13 A |
| ATOM | 2285 | N | LEU | A | 879 | 13.475 | -0.698 | -8.950 | 1.00 109.13 A |
| ATOM | 2286 | CA | LEU | A | 879 | 12.691 | 0.505 | -9.173 | 1.00 109.13 A |
| ATOM | 2287 | CB | LEU | A | 879 | 11.189 | 0.178 | -9.184 | 1.00 109.13 A |
| ATOM | 2288 | CG | LEU | A | 879 | 10.339 | 0.868 | -10.265 | 1.00 109.13 A |
| ATOM | 2289 | CD1 | LEU | A | 879 | 8.893 | 0.453 | -10.087 | 1.00 109.13 A |
| ATOM | 2290 | CD2 | LEU | A | 879 | 10.476 | 2.383 | -10.195 | 1.00 109.13 A |
| ATOM | 2291 | C | LEU | A | 879 | 12.993 | 1.550 | -8.105 | 1.00 109.13 A |
| ATOM | 2292 | O | LEU | A | 879 | 13.373 | 2.684 | -8.423 | 1.00 109.13 A |
| ATOM | 2293 | N | ILE | A | 880 | 12.832 | 1.158 | -6.841 | 1.00 109.13 A |
| ATOM | 2294 | CA | ILE | A | 880 | 13.069 | 2.061 | -5.722 | 1.00 109.13 A |

Figure 4 B
(Continued)

| ATOM | 2295 | CB | ILE A 880 | 12.982 | 1.333 | -4.384 | 1.00 | 109.13 | A |
|------|------|------|-----------|--------|-------|--------|------|--------|---|
| ATOM | 2296 | CG2 | ILE A 880 | 13.088 | 2.323 | -3.254 | 1.00 | 109.13 | A |
| ATOM | 2297 | CG1 | ILE A 880 | 11.660 | 0.585 | -4.293 | 1.00 | 109.13 | A |
| ATOM | 2298 | CD1 | ILE A 880 | 11.453 | -0.121 | -2.981 | 1.00 | 109.13 | A |
| ATOM | 2299 | C | ILE A 880 | 14.445 | 2.682 | -5.835 | 1.00 | 109.13 | A |
| ATOM | 2300 | O | ILE A 880 | 14.631 | 3.848 | -5.491 | 1.00 | 109.13 | A |
| ATOM | 2301 | N | HIS A 881 | 15.402 | 1.899 | -6.331 | 1.00 | 109.13 | A |
| ATOM | 2302 | CA | HIS A 881 | 16.776 | 2.366 | -6.491 | 1.00 | 109.13 | A |
| ATOM | 2303 | CB | HIS A 881 | 17.724 | 1.177 | -6.726 | 1.00 | 109.13 | A |
| ATOM | 2304 | CG | HIS A 881 | 18.023 | 0.375 | -5.485 | 1.00 | 109.13 | A |
| ATOM | 2305 | CD2 | HIS A 881 | 17.536 | -0.814 | -5.050 | 1.00 | 109.13 | A |
| ATOM | 2306 | ND1 | HIS A 881 | 18.927 | 0.785 | -4.527 | 1.00 | 109.13 | A |
| ATOM | 2307 | CE1 | HIS A 881 | 18.987 | -0.114 | -3.561 | 1.00 | 109.13 | A |
| ATOM | 2308 | NE2 | HIS A 881 | 18.152 | -1.094 | -3.854 | 1.00 | 109.13 | A |
| ATOM | 2309 | C | HIS A 881 | 16.889 | 3.381 | -7.625 | 1.00 | 109.13 | A |
| ATOM | 2310 | O | HIS A 881 | 17.408 | 4.482 | -7.419 | 1.00 | 109.13 | A |
| ATOM | 2311 | N | GLN A 882 | 16.387 | 3.026 | -8.808 | 1.00 | 109.13 | A |
| ATOM | 2312 | CA | GLN A 882 | 16.435 | 3.935 | -9.959 | 1.00 | 109.13 | A |
| ATOM | 2313 | CB | GLN A 882 | 15.664 | 3.358 | -11.148 | 1.00 | 109.13 | A |
| ATOM | 2314 | CG | GLN A 882 | 15.840 | 1.862 | -11.374 | 1.00 | 109.13 | A |
| ATOM | 2315 | CD | GLN A 882 | 14.928 | 1.320 | -12.472 | 1.00 | 109.13 | A |
| ATOM | 2316 | OE1 | GLN A 882 | 13.725 | 1.588 | -12.491 | 1.00 | 109.13 | A |
| ATOM | 2317 | NE2 | GLN A 882 | 15.501 | 0.542 | -13.384 | 1.00 | 109.13 | A |
| ATOM | 2318 | C | GLN A 882 | 15.790 | 5.250 | -9.559 | 1.00 | 109.13 | A |
| ATOM | 2319 | O | GLN A 882 | 16.391 | 6.312 | -9.672 | 1.00 | 109.13 | A |
| ATOM | 2320 | N | ALA A 883 | 14.556 | 5.153 | -9.084 | 1.00 | 109.13 | A |
| ATOM | 2321 | CA | ALA A 883 | 13.783 | 6.308 | -8.648 | 1.00 | 109.13 | A |
| ATOM | 2322 | CB | ALA A 883 | 12.591 | 5.835 | -7.822 | 1.00 | 109.13 | A |
| ATOM | 2323 | C | ALA A 883 | 14.614 | 7.304 | -7.835 | 1.00 | 109.13 | A |
| ATOM | 2324 | O | ALA A 883 | 14.597 | 8.521 | -8.085 | 1.00 | 109.13 | A |
| ATOM | 18981 | N | PTY P2001 | 1.032 | -15.800 | -6.223 | 1.00 | 109.13 | P |
| ATOM | 18982 | CA | PTY P2001 | 1.152 | -14.390 | -6.559 | 1.00 | 109.13 | P |
| ATOM | 18983 | CB | PTY P2001 | 0.889 | -13.540 | -5.291 | 1.00 | 109.13 | P |
| ATOM | 18984 | CG | PTY P2001 | 0.515 | -12.073 | -5.556 | 1.00 | 109.13 | P |
| ATOM | 18985 | CD1 | PTY P2001 | -0.786 | -11.717 | -5.973 | 1.00 | 109.13 | P |
| ATOM | 18986 | CE1 | PTY P2001 | -1.162 | -10.355 | -6.220 | 1.00 | 109.13 | P |
| ATOM | 18987 | CD2 | PTY P2001 | 1.493 | -11.030 | -5.376 | 1.00 | 109.13 | P |
| ATOM | 18988 | CE2 | PTY P2001 | 1.132 | -9.669 | -5.619 | 1.00 | 109.13 | P |
| ATOM | 18989 | CZ | PTY P2001 | -0.175 | -9.320 | -6.034 | 1.00 | 109.13 | P |
| ATOM | 18990 | OH | PTY P2001 | -0.559 | -7.906 | -6.283 | 1.00 | 109.13 | P |
| ATOM | 18991 | OR1 | PTY P2001 | 0.129 | -6.753 | -4.272 | 1.00 | 109.13 | P |
| ATOM | 18992 | OR2 | PTY P2001 | -0.480 | -5.411 | -6.223 | 1.00 | 109.13 | P |
| ATOM | 18993 | OR3 | PTY P2001 | 1.658 | -6.640 | -6.173 | 1.00 | 109.13 | P |
| ATOM | 18994 | PR | PTY P2001 | 0.268 | -6.592 | -5.744 | 1.00 | 109.13 | P |
| ATOM | 18995 | C | PTY P2001 | 2.546 | -14.099 | -7.179 | 1.00 | 109.13 | P |
| ATOM | 18996 | O | PTY P2001 | 2.769 | -14.237 | -8.397 | 1.00 | 109.13 | P |

Figure 4 B
(Continued)

ACTIVE SITE (C) COORDINATES

```
ATOM   2840  N    SER A 945      22.092    8.354  -48.122  1.00109.13       A
ATOM   2841  CA   SER A 945      21.710    9.527  -48.902  1.00109.13       A
ATOM   2842  CB   SER A 945      22.149    9.374  -50.369  1.00109.13       A
ATOM   2843  OG   SER A 945      23.572    9.399  -50.509  1.00109.13       A
ATOM   2844  C    SER A 945      20.210    9.756  -48.823  1.00109.13       A
ATOM   2845  O    SER A 945      19.649   10.526  -49.600  1.00109.13       A
ATOM   2846  N    LYS A 946      19.576    9.065  -47.878  1.00109.13       A
ATOM   2847  CA   LYS A 946      18.138    9.180  -47.621  1.00109.13       A
ATOM   2848  CB   LYS A 946      17.517    7.800  -47.365  1.00109.13       A
ATOM   2849  CG   LYS A 946      17.566    6.827  -48.539  1.00109.13       A
ATOM   2850  CD   LYS A 946      16.900    5.495  -48.177  1.00109.13       A
ATOM   2851  CE   LYS A 946      16.919    4.496  -49.329  1.00109.13       A
ATOM   2852  NZ   LYS A 946      16.274    3.191  -48.979  1.00109.13       A
ATOM   2853  C    LYS A 946      17.946   10.053  -46.373  1.00109.13       A
ATOM   2854  O    LYS A 946      16.850   10.146  -45.825  1.00109.13       A
ATOM   2855  N    ASN A 947      19.029   10.685  -45.932  1.00109.13       A
ATOM   2856  CA   ASN A 947      19.018   11.540  -44.747  1.00109.13       A
ATOM   2857  CB   ASN A 947      19.949   10.978  -43.655  1.00109.13       A
ATOM   2858  CG   ASN A 947      19.532    9.596  -43.153  1.00109.13       A
ATOM   2859  OD1  ASN A 947      20.215    9.000  -42.309  1.00109.13       A
ATOM   2860  ND2  ASN A 947      18.416    9.082  -43.666  1.00109.13       A
ATOM   2861  C    ASN A 947      19.517   12.932  -45.097  1.00109.13       A
ATOM   2862  O    ASN A 947      20.698   13.102  -45.415  1.00109.13       A
ATOM   2863  N    ARG A 948      18.639   13.928  -45.035  1.00109.13       A
ATOM   2864  CA   ARG A 948      19.066   15.291  -45.321  1.00109.13       A
ATOM   2865  CB   ARG A 948      17.944   16.277  -45.029  1.00109.13       A
ATOM   2866  CG   ARG A 948      18.307   17.713  -45.350  1.00109.13       A
ATOM   2867  CD   ARG A 948      17.954   18.053  -46.785  1.00109.13       A
ATOM   2868  NE   ARG A 948      16.561   17.715  -47.039  1.00109.13       A
ATOM   2869  CZ   ARG A 948      15.872   18.136  -48.089  1.00109.13       A
ATOM   2870  NH1  ARG A 948      16.452   18.922  -48.989  1.00109.13       A
ATOM   2871  NH2  ARG A 948      14.606   17.760  -48.240  1.00109.13       A
ATOM   2872  C    ARG A 948      20.259   15.580  -44.401  1.00109.13       A
ATOM   2873  O    ARG A 948      21.169   16.326  -44.757  1.00109.13       A
ATOM   2874  N    ASN A 949      20.235   14.983  -43.210  1.00109.13       A
ATOM   2875  CA   ASN A 949      21.317   15.131  -42.246  1.00109.13       A
ATOM   2876  CB   ASN A 949      20.842   15.829  -40.969  1.00109.13       A
ATOM   2877  CG   ASN A 949      21.953   15.970  -39.922  1.00109.13       A
ATOM   2878  OD1  ASN A 949      21.838   16.747  -38.975  1.00109.13       A
ATOM   2879  ND2  ASN A 949      23.022   15.212  -40.086  1.00109.13       A
ATOM   2880  C    ASN A 949      21.822   13.740  -41.911  1.00109.13       A
ATOM   2881  O    ASN A 949      21.046   12.854  -41.554  1.00109.13       A
ATOM   2882  N    SER A 950      23.135   13.567  -42.034  1.00109.13       A
ATOM   2883  CA   SER A 950      23.804   12.299  -41.766  1.00109.13       A
ATOM   2884  CB   SER A 950      25.292   12.421  -42.107  1.00109.13       A
ATOM   2885  OG   SER A 950      26.023   11.304  -41.615  1.00109.13       A
ATOM   2886  C    SER A 950      23.665   11.760  -40.340  1.00109.13       A
ATOM   2887  O    SER A 950      23.122   10.670  -40.144  1.00109.13       A
ATOM   2888  N    ASN A 951      24.161   12.512  -39.354  1.00109.13       A
ATOM   2889  CA   ASN A 951      24.110   12.073  -37.957  1.00109.13       A
ATOM   2890  CB   ASN A 951      24.981   12.988  -37.073  1.00109.13       A
ATOM   2891  CG   ASN A 951      24.463   14.409  -37.001  1.00109.13       A
ATOM   2892  OD1  ASN A 951      23.396   14.676  -36.431  1.00109.13       A
ATOM   2893  ND2  ASN A 951      25.221   15.336  -37.580  1.00109.13       A
```

Figure 4 C

```
ATOM   2894  C    ASN A  951      22.694  11.956 -37.378  1.00109.13      A
ATOM   2895  O    ASN A  951      22.405  11.028 -36.609  1.00109.13      A
ATOM   2896  N    VAL A  952      21.813  12.884 -37.745  1.00109.13      A
ATOM   2897  CA   VAL A  952      20.440  12.834 -37.257  1.00109.13      A
ATOM   2898  CB   VAL A  952      19.694  14.147 -37.550  1.00109.13      A
ATOM   2899  CG1  VAL A  952      18.275  14.081 -36.989  1.00109.13      A
ATOM   2900  CG2  VAL A  952      20.451  15.307 -36.937  1.00109.13      A
ATOM   2901  C    VAL A  952      19.697  11.665 -37.908  1.00109.13      A
ATOM   2902  O    VAL A  952      19.134  11.789 -38.999  1.00109.13      A
ATOM   2903  N    ILE A  953      19.719  10.524 -37.230  1.00109.13      A
ATOM   2904  CA   ILE A  953      19.060   9.334 -37.723  1.00109.13      A
ATOM   2905  CB   ILE A  953      20.095   8.278 -38.193  1.00109.13      A
ATOM   2906  CG2  ILE A  953      19.383   7.088 -38.843  1.00109.13      A
ATOM   2907  CG1  ILE A  953      21.072   8.913 -39.187  1.00109.13      A
ATOM   2908  CD1  ILE A  953      22.203   8.001 -39.632  1.00109.13      A
ATOM   2909  C    ILE A  953      18.242   8.767 -36.579  1.00109.13      A
ATOM   2910  O    ILE A  953      18.671   8.796 -35.427  1.00109.13      A
ATOM   2911  N    PRO A  954      17.038   8.263 -36.879  1.00109.13      A
ATOM   2912  CD   PRO A  954      16.330   8.341 -38.168  1.00109.13      A
ATOM   2913  CA   PRO A  954      16.171   7.689 -35.849  1.00109.13      A
ATOM   2914  CB   PRO A  954      14.840   7.498 -36.589  1.00109.13      A
ATOM   2915  CG   PRO A  954      15.258   7.295 -38.002  1.00109.13      A
ATOM   2916  C    PRO A  954      16.700   6.386 -35.235  1.00109.13      A
ATOM   2917  O    PRO A  954      17.359   5.596 -35.910  1.00109.13      A
ATOM   3454  N    THR A1037       9.517  24.383 -42.303  1.00109.13      A
ATOM   3455  CA   THR A1037      10.521  24.968 -43.178  1.00109.13      A
ATOM   3456  CB   THR A1037      11.508  23.919 -43.670  1.00109.13      A
ATOM   3457  OG1  THR A1037      10.793  22.921 -44.411  1.00109.13      A
ATOM   3458  CG2  THR A1037      12.249  23.282 -42.494  1.00109.13      A
ATOM   3459  C    THR A1037       9.934  25.625 -44.412  1.00109.13      A
ATOM   3460  O    THR A1037       8.742  25.503 -44.711  1.00109.13      A
ATOM   3461  N    GLU A1038      10.805  26.313 -45.135  1.00109.13      A
ATOM   3462  CA   GLU A1038      10.427  27.007 -46.347  1.00109.13      A
ATOM   3463  CB   GLU A1038      10.900  28.459 -46.269  1.00109.13      A
ATOM   3464  CG   GLU A1038      10.326  29.364 -47.336  1.00109.13      A
ATOM   3465  CD   GLU A1038       8.808  29.324 -47.386  1.00109.13      A
ATOM   3466  OE1  GLU A1038       8.253  28.281 -47.804  1.00109.13      A
ATOM   3467  OE2  GLU A1038       8.171  30.337 -47.005  1.00109.13      A
ATOM   3468  C    GLU A1038      11.069  26.296 -47.535  1.00109.13      A
ATOM   3469  O    GLU A1038      12.179  26.641 -47.940  1.00109.13      A
ATOM   3470  N    LEU A1039      10.368  25.292 -48.066  1.00109.13      A
ATOM   3471  CA   LEU A1039      10.813  24.495 -49.221  1.00109.13      A
ATOM   3472  CB   LEU A1039       9.987  24.850 -50.464  1.00109.13      A
ATOM   3473  CG   LEU A1039       8.506  24.480 -50.471  1.00109.13      A
ATOM   3474  CD1  LEU A1039       7.661  25.743 -50.553  1.00109.13      A
ATOM   3475  CD2  LEU A1039       8.228  23.558 -51.648  1.00109.13      A
ATOM   3476  C    LEU A1039      12.294  24.601 -49.588  1.00109.13      A
ATOM   3477  O    LEU A1039      13.111  23.763 -49.199  1.00109.13      A
ATOM   3478  N    LYS A1040      12.628  25.631 -50.359  1.00109.13      A
ATOM   3479  CA   LYS A1040      14.000  25.839 -50.790  1.00109.13      A
ATOM   3480  CB   LYS A1040      14.149  25.450 -52.275  1.00109.13      A
ATOM   3481  CG   LYS A1040      13.387  26.352 -53.262  1.00109.13      A
ATOM   3482  CD   LYS A1040      13.351  25.781 -54.691  1.00109.13      A
ATOM   3483  CE   LYS A1040      12.267  24.692 -54.860  1.00109.13      A
ATOM   3484  NZ   LYS A1040      10.840  25.175 -54.750  1.00109.13      A
ATOM   3485  C    LYS A1040      14.419  27.288 -50.586  1.00109.13      A
ATOM   3486  O    LYS A1040      15.067  27.872 -51.443  1.00109.13      A
```

Figure 4 C
(Continued)

| | | | | | | | | |
|---|---|---|---|---|---|---|---|---|
| ATOM | 3487 | N | HIS A1041 | 14.053 | 27.876 | -49.456 | 1.00 109.13 | A |
| ATOM | 3488 | CA | HIS A1041 | 14.440 | 29.261 | -49.208 | 1.00 109.13 | A |
| ATOM | 3489 | CB | HIS A1041 | 13.813 | 29.791 | -47.904 | 1.00 109.13 | A |
| ATOM | 3490 | CG | HIS A1041 | 13.431 | 31.246 | -47.957 | 1.00 109.13 | A |
| ATOM | 3491 | CD2 | HIS A1041 | 12.271 | 31.878 | -47.643 | 1.00 109.13 | A |
| ATOM | 3492 | ND1 | HIS A1041 | 14.302 | 32.234 | -48.375 | 1.00 109.13 | A |
| ATOM | 3493 | CE1 | HIS A1041 | 13.695 | 33.409 | -48.316 | 1.00 109.13 | A |
| ATOM | 3494 | NE2 | HIS A1041 | 12.463 | 33.221 | -47.875 | 1.00 109.13 | A |
| ATOM | 3495 | C | HIS A1041 | 15.971 | 29.297 | -49.117 | 1.00 109.13 | A |
| ATOM | 3496 | O | HIS A1041 | 16.623 | 28.245 | -49.030 | 1.00 109.13 | A |
| ATOM | 3497 | N | GLY A1042 | 16.540 | 30.502 | -49.138 | 1.00 109.13 | A |
| ATOM | 3498 | CA | GLY A1042 | 17.983 | 30.632 | -49.087 | 1.00 109.13 | A |
| ATOM | 3499 | C | GLY A1042 | 18.627 | 29.928 | -50.275 | 1.00 109.13 | A |
| ATOM | 3500 | O | GLY A1042 | 19.729 | 29.391 | -50.145 | 1.00 109.13 | A |
| ATOM | 3501 | N | ASP A1043 | 17.937 | 29.924 | -51.422 | 1.00 109.13 | A |
| ATOM | 3502 | CA | ASP A1043 | 18.420 | 29.289 | -52.651 | 1.00 109.13 | A |
| ATOM | 3503 | CB | ASP A1043 | 19.801 | 29.843 | -53.022 | 1.00 109.13 | A |
| ATOM | 3504 | CG | ASP A1043 | 20.709 | 28.784 | -53.662 | 1.00 109.13 | A |
| ATOM | 3505 | OD1 | ASP A1043 | 20.306 | 28.204 | -54.700 | 1.00 109.13 | A |
| ATOM | 3506 | OD2 | ASP A1043 | 21.821 | 28.530 | -53.120 | 1.00 109.13 | A |
| ATOM | 3507 | C | ASP A1043 | 18.501 | 27.761 | -52.590 | 1.00 109.13 | A |
| ATOM | 3508 | O | ASP A1043 | 18.000 | 27.065 | -53.477 | 1.00 109.13 | A |
| ATOM | 3509 | N | GLN A1044 | 19.172 | 27.261 | -51.554 | 1.00 109.13 | A |
| ATOM | 3510 | CA | GLN A1044 | 19.370 | 25.831 | -51.321 | 1.00 109.13 | A |
| ATOM | 3511 | CB | GLN A1044 | 20.198 | 25.617 | -50.051 | 1.00 109.13 | A |
| ATOM | 3512 | CG | GLN A1044 | 21.658 | 25.966 | -50.176 | 1.00 109.13 | A |
| ATOM | 3513 | CD | GLN A1044 | 22.402 | 24.985 | -51.062 | 1.00 109.13 | A |
| ATOM | 3514 | OE1 | GLN A1044 | 22.323 | 23.760 | -50.861 | 1.00 109.13 | A |
| ATOM | 3515 | NE2 | GLN A1044 | 23.139 | 25.513 | -52.045 | 1.00 109.13 | A |
| ATOM | 3516 | C | GLN A1044 | 18.037 | 25.131 | -51.144 | 1.00 109.13 | A |
| ATOM | 3517 | O | GLN A1044 | 17.020 | 25.783 | -50.901 | 1.00 109.13 | A |
| ATOM | 3518 | N | GLU A1045 | 18.046 | 23.804 | -51.245 | 1.00 109.13 | A |
| ATOM | 3519 | CA | GLU A1045 | 16.818 | 23.030 | -51.074 | 1.00 109.13 | A |
| ATOM | 3520 | CB | GLU A1045 | 16.826 | 21.802 | -51.997 | 1.00 109.13 | A |
| ATOM | 3521 | CG | GLU A1045 | 15.450 | 21.345 | -52.494 | 1.00 109.13 | A |
| ATOM | 3522 | CD | GLU A1045 | 14.803 | 22.338 | -53.480 | 1.00 109.13 | A |
| ATOM | 3523 | OE1 | GLU A1045 | 15.549 | 23.012 | -54.250 | 1.00 109.13 | A |
| ATOM | 3524 | OE2 | GLU A1045 | 13.544 | 22.425 | -53.495 | 1.00 109.13 | A |
| ATOM | 3525 | C | GLU A1045 | 16.713 | 22.586 | -49.606 | 1.00 109.13 | A |
| ATOM | 3526 | O | GLU A1045 | 17.300 | 21.574 | -49.203 | 1.00 109.13 | A |
| ATOM | 3527 | N | ILE A1046 | 15.980 | 23.358 | -48.806 | 1.00 109.13 | A |
| ATOM | 3528 | CA | ILE A1046 | 15.793 | 23.046 | -47.390 | 1.00 109.13 | A |
| ATOM | 3529 | CB | ILE A1046 | 15.237 | 24.245 | -46.646 | 1.00 109.13 | A |
| ATOM | 3530 | CG2 | ILE A1046 | 14.966 | 23.865 | -45.206 | 1.00 109.13 | A |
| ATOM | 3531 | CG1 | ILE A1046 | 16.217 | 25.414 | -46.753 | 1.00 109.13 | A |
| ATOM | 3532 | CD1 | ILE A1046 | 15.749 | 26.663 | -46.043 | 1.00 109.13 | A |
| ATOM | 3533 | C | ILE A1046 | 14.803 | 21.901 | -47.256 | 1.00 109.13 | A |
| ATOM | 3534 | O | ILE A1046 | 14.890 | 21.067 | -46.355 | 1.00 109.13 | A |
| ATOM | 3535 | N | CYS A1047 | 13.858 | 21.888 | -48.180 | 1.00 109.13 | A |
| ATOM | 3536 | CA | CYS A1047 | 12.834 | 20.874 | -48.244 | 1.00 109.13 | A |
| ATOM | 3537 | CB | CYS A1047 | 11.579 | 21.351 | -47.518 | 1.00 109.13 | A |
| ATOM | 3538 | SG | CYS A1047 | 10.275 | 20.113 | -47.405 | 1.00 109.13 | A |
| ATOM | 3539 | C | CYS A1047 | 12.549 | 20.685 | -49.728 | 1.00 109.13 | A |
| ATOM | 3540 | O | CYS A1047 | 12.974 | 21.500 | -50.551 | 1.00 109.13 | A |
| ATOM | 3969 | N | THR A1098 | 5.872 | 29.680 | -41.704 | 1.00 109.13 | A |
| ATOM | 3970 | CA | THR A1098 | 7.030 | 30.325 | -42.300 | 1.00 109.13 | A |
| ATOM | 3971 | CB | THR A1098 | 6.549 | 31.452 | -43.216 | 1.00 109.13 | A |

Figure 4 C
(Continued)

| ATOM | 3972 | OG1 | THR A1098 | 5.807 | 32.398 | -42.440 | 1.00 | 109.13 | A |
|------|------|-----|-----------|-------|--------|---------|------|--------|---|
| ATOM | 3973 | CG2 | THR A1098 | 5.637 | 30.900 | -44.313 | 1.00 | 109.13 | A |
| ATOM | 3974 | C   | THR A1098 | 8.100 | 30.882 | -41.343 | 1.00 | 109.13 | A |
| ATOM | 3975 | O   | THR A1098 | 9.205 | 30.338 | -41.260 | 1.00 | 109.13 | A |
| ATOM | 3976 | N   | ASN A1099 | 7.764 | 31.970 | -40.645 | 1.00 | 109.13 | A |
| ATOM | 3977 | CA  | ASN A1099 | 8.650 | 32.660 | -39.704 | 1.00 | 109.13 | A |
| ATOM | 3978 | CB  | ASN A1099 | 7.878 | 32.994 | -38.441 | 1.00 | 109.13 | A |
| ATOM | 3979 | CG  | ASN A1099 | 6.930 | 34.152 | -38.643 | 1.00 | 109.13 | A |
| ATOM | 3980 | OD1 | ASN A1099 | 6.008 | 34.083 | -39.455 | 1.00 | 109.13 | A |
| ATOM | 3981 | ND2 | ASN A1099 | 7.158 | 35.236 | -37.906 | 1.00 | 109.13 | A |
| ATOM | 3982 | C   | ASN A1099 | 9.987 | 32.033 | -39.320 | 1.00 | 109.13 | A |
| ATOM | 3983 | O   | ASN A1099 | 11.024 | 32.704 | -39.399 | 1.00 | 109.13 | A |
| ATOM | 3984 | N   | TRP A1100 | 9.976 | 30.773 | -38.887 | 1.00 | 109.13 | A |
| ATOM | 3985 | CA  | TRP A1100 | 11.221 | 30.093 | -38.512 | 1.00 | 109.13 | A |
| ATOM | 3986 | CB  | TRP A1100 | 10.930 | 28.677 | -38.017 | 1.00 | 109.13 | A |
| ATOM | 3987 | CG  | TRP A1100 | 11.158 | 28.481 | -36.547 | 1.00 | 109.13 | A |
| ATOM | 3988 | CD2 | TRP A1100 | 10.362 | 27.694 | -35.667 | 1.00 | 109.13 | A |
| ATOM | 3989 | CE2 | TRP A1100 | 10.981 | 27.728 | -34.398 | 1.00 | 109.13 | A |
| ATOM | 3990 | CE3 | TRP A1100 | 9.186 | 26.961 | -35.827 | 1.00 | 109.13 | A |
| ATOM | 3991 | CD1 | TRP A1100 | 12.203 | 28.955 | -35.798 | 1.00 | 109.13 | A |
| ATOM | 3992 | NE1 | TRP A1100 | 12.104 | 28.506 | -34.506 | 1.00 | 109.13 | A |
| ATOM | 3993 | CZ2 | TRP A1100 | 10.461 | 27.053 | -33.298 | 1.00 | 109.13 | A |
| ATOM | 3994 | CZ3 | TRP A1100 | 8.672 | 26.295 | -34.738 | 1.00 | 109.13 | A |
| ATOM | 3995 | CH2 | TRP A1100 | 9.308 | 26.343 | -33.486 | 1.00 | 109.13 | A |
| ATOM | 3996 | C   | TRP A1100 | 12.238 | 30.009 | -39.660 | 1.00 | 109.13 | A |
| ATOM | 3997 | O   | TRP A1100 | 11.882 | 29.718 | -40.806 | 1.00 | 109.13 | A |
| ATOM | 3998 | N   | SER A1101 | 13.509 | 30.243 | -39.344 | 1.00 | 109.13 | A |
| ATOM | 3999 | CA  | SER A1101 | 14.552 | 30.193 | -40.363 | 1.00 | 109.13 | A |
| ATOM | 4000 | CB  | SER A1101 | 14.983 | 31.620 | -40.741 | 1.00 | 109.13 | A |
| ATOM | 4001 | OG  | SER A1101 | 13.984 | 32.271 | -41.512 | 1.00 | 109.13 | A |
| ATOM | 4002 | C   | SER A1101 | 15.789 | 29.360 | -39.991 | 1.00 | 109.13 | A |
| ATOM | 4003 | O   | SER A1101 | 15.680 | 28.200 | -39.554 | 1.00 | 109.13 | A |
| ATOM | 4004 | N   | VAL A1102 | 16.961 | 29.971 | -40.196 | 1.00 | 109.13 | A |
| ATOM | 4005 | CA  | VAL A1102 | 18.257 | 29.345 | -39.923 | 1.00 | 109.13 | A |
| ATOM | 4006 | CB  | VAL A1102 | 19.360 | 29.900 | -40.891 | 1.00 | 109.13 | A |
| ATOM | 4007 | CG1 | VAL A1102 | 18.980 | 29.595 | -42.342 | 1.00 | 109.13 | A |
| ATOM | 4008 | CG2 | VAL A1102 | 19.535 | 31.403 | -40.700 | 1.00 | 109.13 | A |
| ATOM | 4009 | C   | VAL A1102 | 18.676 | 29.576 | -38.470 | 1.00 | 109.13 | A |
| ATOM | 4010 | O   | VAL A1102 | 19.092 | 28.649 | -37.766 | 1.00 | 109.13 | A |
| ATOM | 4011 | N   | GLU A1103 | 18.569 | 30.828 | -38.033 | 1.00 | 109.13 | A |
| ATOM | 4012 | CA  | GLU A1103 | 18.903 | 31.195 | -36.664 | 1.00 | 109.13 | A |
| ATOM | 4013 | CB  | GLU A1103 | 19.232 | 32.706 | -36.572 | 1.00 | 109.13 | A |
| ATOM | 4014 | CG  | GLU A1103 | 18.129 | 33.648 | -36.039 | 1.00 | 109.13 | A |
| ATOM | 4015 | CD  | GLU A1103 | 16.965 | 33.883 | -37.004 | 1.00 | 109.13 | A |
| ATOM | 4016 | OE1 | GLU A1103 | 17.221 | 34.174 | -38.195 | 1.00 | 109.13 | A |
| ATOM | 4017 | OE2 | GLU A1103 | 15.794 | 33.798 | -36.562 | 1.00 | 109.13 | A |
| ATOM | 4018 | C   | GLU A1103 | 17.626 | 30.844 | -35.922 | 1.00 | 109.13 | A |
| ATOM | 4019 | O   | GLU A1103 | 17.467 | 31.108 | -34.725 | 1.00 | 109.13 | A |
| ATOM | 4020 | N   | GLN A1104 | 16.729 | 30.213 | -36.677 | 1.00 | 109.13 | A |
| ATOM | 4021 | CA  | GLN A1104 | 15.431 | 29.792 | -36.181 | 1.00 | 109.13 | A |
| ATOM | 4022 | CB  | GLN A1104 | 15.589 | 28.694 | -35.106 | 1.00 | 109.13 | A |
| ATOM | 4023 | CG  | GLN A1104 | 15.612 | 27.249 | -35.677 | 1.00 | 109.13 | A |
| ATOM | 4024 | CD  | GLN A1104 | 16.718 | 26.995 | -36.726 | 1.00 | 109.13 | A |
| ATOM | 4025 | OE1 | GLN A1104 | 17.914 | 26.991 | -36.404 | 1.00 | 109.13 | A |
| ATOM | 4026 | NE2 | GLN A1104 | 16.314 | 26.774 | -37.979 | 1.00 | 109.13 | A |
| ATOM | 4027 | C   | GLN A1104 | 14.680 | 31.008 | -35.638 | 1.00 | 109.13 | A |
| ATOM | 4028 | O   | GLN A1104 | 14.111 | 31.783 | -36.426 | 1.00 | 109.13 | A |

Figure 4 C
(Continued)

| ATOM | 4029 | N | LEU | A1105 | 14.692 | 31.182 | -34.314 | 1.00 | 109.13 | A |
|------|------|-----|-----|-------|--------|--------|---------|------|--------|---|
| ATOM | 4030 | CA | LEU | A1105 | 14.006 | 32.308 | -33.678 | 1.00 | 109.13 | A |
| ATOM | 4031 | CB | LEU | A1105 | 14.885 | 33.557 | -33.748 | 1.00 | 109.13 | A |
| ATOM | 4032 | CG | LEU | A1105 | 16.236 | 33.428 | -33.054 | 1.00 | 109.13 | A |
| ATOM | 4033 | CD1 | LEU | A1105 | 17.029 | 34.708 | -33.267 | 1.00 | 109.13 | A |
| ATOM | 4034 | CD2 | LEU | A1105 | 16.028 | 33.153 | -31.562 | 1.00 | 109.13 | A |
| ATOM | 4035 | C | LEU | A1105 | 12.673 | 32.566 | -34.390 | 1.00 | 109.13 | A |
| ATOM | 4036 | O | LEU | A1105 | 12.609 | 33.348 | -35.353 | 1.00 | 109.13 | A |
| ATOM | 4037 | N | PRO | A1106 | 11.592 | 31.911 | -33.929 | 1.00 | 109.13 | A |
| ATOM | 4038 | CD | PRO | A1106 | 11.531 | 30.996 | -32.776 | 1.00 | 109.13 | A |
| ATOM | 4039 | CA | PRO | A1106 | 10.269 | 32.075 | -34.536 | 1.00 | 109.13 | A |
| ATOM | 4040 | CB | PRO | A1106 | 9.441 | 31.008 | -33.822 | 1.00 | 109.13 | A |
| ATOM | 4041 | CG | PRO | A1106 | 10.061 | 30.970 | -32.466 | 1.00 | 109.13 | A |
| ATOM | 4042 | C | PRO | A1106 | 9.667 | 33.490 | -34.418 | 1.00 | 109.13 | A |
| ATOM | 4043 | O | PRO | A1106 | 8.442 | 33.662 | -34.497 | 1.00 | 109.13 | A |
| ATOM | 4044 | N | ALA | A1107 | 10.533 | 34.496 | -34.269 | 1.00 | 109.13 | A |
| ATOM | 4045 | CA | ALA | A1107 | 10.100 | 35.882 | -34.121 | 1.00 | 109.13 | A |
| ATOM | 4046 | CB | ALA | A1107 | 9.234 | 36.303 | -35.300 | 1.00 | 109.13 | A |
| ATOM | 4047 | C | ALA | A1107 | 9.302 | 35.952 | -32.820 | 1.00 | 109.13 | A |
| ATOM | 4048 | O | ALA | A1107 | 9.861 | 35.750 | -31.725 | 1.00 | 109.13 | A |
| ATOM | 4049 | N | GLU | A1108 | 7.995 | 36.192 | -32.946 | 1.00 | 109.13 | A |
| ATOM | 4050 | CA | GLU | A1108 | 7.105 | 36.298 | -31.786 | 1.00 | 109.13 | A |
| ATOM | 4051 | CB | GLU | A1108 | 6.162 | 37.495 | -31.967 | 1.00 | 109.13 | A |
| ATOM | 4052 | CG | GLU | A1108 | 6.880 | 38.784 | -32.393 | 1.00 | 109.13 | A |
| ATOM | 4053 | CD | GLU | A1108 | 8.056 | 39.167 | -31.489 | 1.00 | 109.13 | A |
| ATOM | 4054 | OE1 | GLU | A1108 | 8.801 | 40.116 | -31.838 | 1.00 | 109.13 | A |
| ATOM | 4055 | OE2 | GLU | A1108 | 8.234 | 38.524 | -30.431 | 1.00 | 109.13 | A |
| ATOM | 4056 | C | GLU | A1108 | 6.289 | 35.036 | -31.467 | 1.00 | 109.13 | A |
| ATOM | 4057 | O | GLU | A1108 | 5.653 | 34.444 | -32.337 | 1.00 | 109.13 | A |
| ATOM | 4058 | N | PRO | A1109 | 6.293 | 34.622 | -30.193 | 1.00 | 109.13 | A |
| ATOM | 4059 | CD | PRO | A1109 | 6.865 | 35.367 | -29.055 | 1.00 | 109.13 | A |
| ATOM | 4060 | CA | PRO | A1109 | 5.564 | 33.435 | -29.730 | 1.00 | 109.13 | A |
| ATOM | 4061 | CB | PRO | A1109 | 5.604 | 33.579 | -28.205 | 1.00 | 109.13 | A |
| ATOM | 4062 | CG | PRO | A1109 | 6.889 | 34.320 | -27.966 | 1.00 | 109.13 | A |
| ATOM | 4063 | C | PRO | A1109 | 4.134 | 33.429 | -30.261 | 1.00 | 109.13 | A |
| ATOM | 4064 | O | PRO | A1109 | 3.761 | 32.594 | -31.083 | 1.00 | 109.13 | A |
| ATOM | 4288 | N | ILE | A1142 | 4.944 | 16.046 | -37.985 | 1.00 | 109.13 | A |
| ATOM | 4289 | CA | ILE | A1142 | 5.683 | 17.298 | -38.070 | 1.00 | 109.13 | A |
| ATOM | 4290 | CB | ILE | A1142 | 5.922 | 17.852 | -36.663 | 1.00 | 109.13 | A |
| ATOM | 4291 | CG2 | ILE | A1142 | 6.664 | 19.171 | -36.731 | 1.00 | 109.13 | A |
| ATOM | 4292 | CG1 | ILE | A1142 | 4.581 | 18.014 | -35.956 | 1.00 | 109.13 | A |
| ATOM | 4293 | CD1 | ILE | A1142 | 4.679 | 18.217 | -34.494 | 1.00 | 109.13 | A |
| ATOM | 4294 | C | ILE | A1142 | 7.019 | 17.107 | -38.768 | 1.00 | 109.13 | A |
| ATOM | 4295 | O | ILE | A1142 | 7.605 | 16.041 | -38.693 | 1.00 | 109.13 | A |
| ATOM | 4296 | N | HIS | A1143 | 7.497 | 18.133 | -39.463 | 1.00 | 109.13 | A |
| ATOM | 4297 | CA | HIS | A1143 | 8.776 | 18.030 | -40.153 | 1.00 | 109.13 | A |
| ATOM | 4298 | CB | HIS | A1143 | 8.656 | 17.139 | -41.407 | 1.00 | 109.13 | A |
| ATOM | 4299 | CG | HIS | A1143 | 7.958 | 17.779 | -42.576 | 1.00 | 109.13 | A |
| ATOM | 4300 | CD2 | HIS | A1143 | 6.783 | 17.475 | -43.186 | 1.00 | 109.13 | A |
| ATOM | 4301 | ND1 | HIS | A1143 | 8.501 | 18.824 | -43.295 | 1.00 | 109.13 | A |
| ATOM | 4302 | CE1 | HIS | A1143 | 7.694 | 19.132 | -44.297 | 1.00 | 109.13 | A |
| ATOM | 4303 | NE2 | HIS | A1143 | 6.644 | 18.329 | -44.253 | 1.00 | 109.13 | A |
| ATOM | 4304 | C | HIS | A1143 | 9.422 | 19.359 | -40.517 | 1.00 | 109.13 | A |
| ATOM | 4305 | O | HIS | A1143 | 8.750 | 20.362 | -40.763 | 1.00 | 109.13 | A |
| ATOM | 4306 | N | CYS | A1144 | 10.750 | 19.341 | -40.509 | 1.00 | 109.13 | A |
| ATOM | 4307 | CA | CYS | A1144 | 11.584 | 20.488 | -40.841 | 1.00 | 109.13 | A |
| ATOM | 4308 | CB | CYS | A1144 | 11.963 | 21.279 | -39.571 | 1.00 | 109.13 | A |

Figure 4 C
(Continued)

| | | | | | | | | |
|---|---|---|---|---|---|---|---|---|
| ATOM | 4309 | SG | CYS | A1144 | 12.780 | 20.367 | -38.215 | 1.00 109.13 | A |
| ATOM | 4310 | C | CYS | A1144 | 12.818 | 19.895 | -41.509 | 1.00 109.13 | A |
| ATOM | 4311 | O | CYS | A1144 | 12.777 | 18.747 | -41.940 | 1.00 109.13 | A |
| ATOM | 4312 | N | ARG | A1145 | 13.902 | 20.657 | -41.608 | 1.00 109.13 | A |
| ATOM | 4313 | CA | ARG | A1145 | 15.125 | 20.141 | -42.220 | 1.00 109.13 | A |
| ATOM | 4314 | CB | ARG | A1145 | 16.331 | 21.019 | -41.854 | 1.00 109.13 | A |
| ATOM | 4315 | CG | ARG | A1145 | 16.334 | 22.441 | -42.417 | 1.00 109.13 | A |
| ATOM | 4316 | CD | ARG | A1145 | 17.659 | 23.170 | -42.049 | 1.00 109.13 | A |
| ATOM | 4317 | NE | ARG | A1145 | 17.882 | 24.435 | -42.765 | 1.00 109.13 | A |
| ATOM | 4318 | CZ | ARG | A1145 | 17.310 | 25.608 | -42.473 | 1.00 109.13 | A |
| ATOM | 4319 | NH1 | ARG | A1145 | 16.453 | 25.728 | -41.454 | 1.00 109.13 | A |
| ATOM | 4320 | NH2 | ARG | A1145 | 17.600 | 26.673 | -43.216 | 1.00 109.13 | A |
| ATOM | 4321 | C | ARG | A1145 | 15.416 | 18.689 | -41.787 | 1.00 109.13 | A |
| ATOM | 4322 | O | ARG | A1145 | 15.150 | 17.757 | -42.538 | 1.00 109.13 | A |
| ATOM | 4323 | N | ASP | A1146 | 15.947 | 18.507 | -40.576 | 1.00 109.13 | A |
| ATOM | 4324 | CA | ASP | A1146 | 16.294 | 17.187 | -40.048 | 1.00 109.13 | A |
| ATOM | 4325 | CB | ASP | A1146 | 17.526 | 17.297 | -39.164 | 1.00 109.13 | A |
| ATOM | 4326 | CG | ASP | A1146 | 17.403 | 18.406 | -38.148 | 1.00 109.13 | A |
| ATOM | 4327 | OD1 | ASP | A1146 | 16.264 | 18.725 | -37.752 | 1.00 109.13 | A |
| ATOM | 4328 | OD2 | ASP | A1146 | 18.440 | 18.959 | -37.736 | 1.00 109.13 | A |
| ATOM | 4329 | C | ASP | A1146 | 15.189 | 16.510 | -39.248 | 1.00 109.13 | A |
| ATOM | 4330 | O | ASP | A1146 | 15.314 | 15.345 | -38.883 | 1.00 109.13 | A |
| ATOM | 4331 | N | GLY | A1147 | 14.119 | 17.242 | -38.951 | 1.00 109.13 | A |
| ATOM | 4332 | CA | GLY | A1147 | 13.005 | 16.673 | -38.200 | 1.00 109.13 | A |
| ATOM | 4333 | C | GLY | A1147 | 13.135 | 16.725 | -36.690 | 1.00 109.13 | A |
| ATOM | 4334 | O | GLY | A1147 | 12.351 | 16.107 | -35.976 | 1.00 109.13 | A |
| ATOM | 4335 | N | SER | A1148 | 14.122 | 17.471 | -36.210 | 1.00 109.13 | A |
| ATOM | 4336 | CA | SER | A1148 | 14.352 | 17.590 | -34.787 | 1.00 109.13 | A |
| ATOM | 4337 | CB | SER | A1148 | 15.536 | 16.708 | -34.376 | 1.00 109.13 | A |
| ATOM | 4338 | OG | SER | A1148 | 15.283 | 15.333 | -34.630 | 1.00 109.13 | A |
| ATOM | 4339 | C | SER | A1148 | 14.622 | 19.036 | -34.395 | 1.00 109.13 | A |
| ATOM | 4340 | O | SER | A1148 | 14.052 | 19.553 | -33.429 | 1.00 109.13 | A |
| ATOM | 4341 | N | GLN | A1149 | 15.495 | 19.689 | -35.145 | 1.00 109.13 | A |
| ATOM | 4342 | CA | GLN | A1149 | 15.836 | 21.078 | -34.867 | 1.00 109.13 | A |
| ATOM | 4343 | CB | GLN | A1149 | 16.404 | 21.726 | -36.146 | 1.00 109.13 | A |
| ATOM | 4344 | CG | GLN | A1149 | 17.055 | 23.108 | -35.958 | 1.00 109.13 | A |
| ATOM | 4345 | CD | GLN | A1149 | 18.479 | 23.046 | -35.414 | 1.00 109.13 | A |
| ATOM | 4346 | OE1 | GLN | A1149 | 19.073 | 24.073 | -35.097 | 1.00 109.13 | A |
| ATOM | 4347 | NE2 | GLN | A1149 | 19.030 | 21.841 | -35.315 | 1.00 109.13 | A |
| ATOM | 4348 | C | GLN | A1149 | 14.606 | 21.859 | -34.364 | 1.00 109.13 | A |
| ATOM | 4349 | O | GLN | A1149 | 14.437 | 22.063 | -33.162 | 1.00 109.13 | A |
| ATOM | 4350 | N | GLN | A1150 | 13.752 | 22.270 | -35.298 | 1.00 109.13 | A |
| ATOM | 4351 | CA | GLN | A1150 | 12.548 | 23.031 | -34.997 | 1.00 109.13 | A |
| ATOM | 4352 | CB | GLN | A1150 | 12.081 | 23.796 | -36.240 | 1.00 109.13 | A |
| ATOM | 4353 | CG | GLN | A1150 | 12.878 | 25.064 | -36.545 | 1.00 109.13 | A |
| ATOM | 4354 | CD | GLN | A1150 | 12.843 | 25.457 | -38.022 | 1.00 109.13 | A |
| ATOM | 4355 | OE1 | GLN | A1150 | 13.303 | 26.539 | -38.411 | 1.00 109.13 | A |
| ATOM | 4356 | NE2 | GLN | A1150 | 12.309 | 24.572 | -38.850 | 1.00 109.13 | A |
| ATOM | 4357 | C | GLN | A1150 | 11.431 | 22.139 | -34.508 | 1.00 109.13 | A |
| ATOM | 4358 | O | GLN | A1150 | 10.659 | 22.535 | -33.642 | 1.00 109.13 | A |
| ATOM | 4359 | N | THR | A1151 | 11.338 | 20.939 | -35.062 | 1.00 109.13 | A |
| ATOM | 4360 | CA | THR | A1151 | 10.295 | 20.006 | -34.658 | 1.00 109.13 | A |
| ATOM | 4361 | CB | THR | A1151 | 10.447 | 18.643 | -35.368 | 1.00 109.13 | A |
| ATOM | 4362 | OG1 | THR | A1151 | 10.024 | 18.768 | -36.727 | 1.00 109.13 | A |
| ATOM | 4363 | CG2 | THR | A1151 | 9.606 | 17.578 | -34.693 | 1.00 109.13 | A |
| ATOM | 4364 | C | THR | A1151 | 10.315 | 19.787 | -33.150 | 1.00 109.13 | A |
| ATOM | 4365 | O | THR | A1151 | 9.266 | 19.698 | -32.520 | 1.00 109.13 | A |

Figure 4 C
(Continued)

| | | | | | | | | |
|---|---|---|---|---|---|---|---|---|
| ATOM | 4366 | N | GLY | A1152 | 11.509 | 19.704 | -32.569 | 1.00 109.13 | A |
| ATOM | 4367 | CA | GLY | A1152 | 11.621 | 19.503 | -31.134 | 1.00 109.13 | A |
| ATOM | 4368 | C | GLY | A1152 | 10.851 | 20.586 | -30.413 | 1.00 109.13 | A |
| ATOM | 4369 | O | GLY | A1152 | 10.047 | 20.307 | -29.538 | 1.00 109.13 | A |
| ATOM | 4370 | N | ILE | A1153 | 11.088 | 21.829 | -30.810 | 1.00 109.13 | A |
| ATOM | 4371 | CA | ILE | A1153 | 10.427 | 22.973 | -30.215 | 1.00 109.13 | A |
| ATOM | 4372 | CB | ILE | A1153 | 10.864 | 24.274 | -30.898 | 1.00 109.13 | A |
| ATOM | 4373 | CG2 | ILE | A1153 | 10.382 | 25.458 | -30.117 | 1.00 109.13 | A |
| ATOM | 4374 | CG1 | ILE | A1153 | 12.384 | 24.321 | -30.992 | 1.00 109.13 | A |
| ATOM | 4375 | CD1 | ILE | A1153 | 13.101 | 24.122 | -29.692 | 1.00 109.13 | A |
| ATOM | 4376 | C | ILE | A1153 | 8.922 | 22.842 | -30.336 | 1.00 109.13 | A |
| ATOM | 4377 | O | ILE | A1153 | 8.183 | 23.221 | -29.431 | 1.00 109.13 | A |
| ATOM | 4378 | N | PHE | A1154 | 8.460 | 22.294 | -31.449 | 1.00 109.13 | A |
| ATOM | 4379 | CA | PHE | A1154 | 7.024 | 22.144 | -31.642 | 1.00 109.13 | A |
| ATOM | 4380 | CB | PHE | A1154 | 6.696 | 21.855 | -33.113 | 1.00 109.13 | A |
| ATOM | 4381 | CG | PHE | A1154 | 5.299 | 22.247 | -33.518 | 1.00 109.13 | A |
| ATOM | 4382 | CD1 | PHE | A1154 | 4.942 | 23.583 | -33.609 | 1.00 109.13 | A |
| ATOM | 4383 | CD2 | PHE | A1154 | 4.350 | 21.286 | -33.811 | 1.00 109.13 | A |
| ATOM | 4384 | CE1 | PHE | A1154 | 3.661 | 23.954 | -33.985 | 1.00 109.13 | A |
| ATOM | 4385 | CE2 | PHE | A1154 | 3.068 | 21.650 | -34.188 | 1.00 109.13 | A |
| ATOM | 4386 | CZ | PHE | A1154 | 2.724 | 22.986 | -34.275 | 1.00 109.13 | A |
| ATOM | 4387 | C | PHE | A1154 | 6.456 | 21.035 | -30.763 | 1.00 109.13 | A |
| ATOM | 4388 | O | PHE | A1154 | 5.548 | 21.263 | -29.969 | 1.00 109.13 | A |
| ATOM | 4389 | N | CYS | A1155 | 6.992 | 19.833 | -30.902 | 1.00 109.13 | A |
| ATOM | 4390 | CA | CYS | A1155 | 6.503 | 18.719 | -30.118 | 1.00 109.13 | A |
| ATOM | 4391 | CB | CYS | A1155 | 7.393 | 17.497 | -30.313 | 1.00 109.13 | A |
| ATOM | 4392 | SG | CYS | A1155 | 7.229 | 16.706 | -31.917 | 1.00 109.13 | A |
| ATOM | 4393 | C | CYS | A1155 | 6.447 | 19.095 | -28.651 | 1.00 109.13 | A |
| ATOM | 4394 | O | CYS | A1155 | 5.465 | 18.811 | -27.967 | 1.00 109.13 | A |
| ATOM | 4395 | N | ALA | A1156 | 7.492 | 19.744 | -28.162 | 1.00 109.13 | A |
| ATOM | 4396 | CA | ALA | A1156 | 7.511 | 20.136 | -26.764 | 1.00 109.13 | A |
| ATOM | 4397 | CB | ALA | A1156 | 8.784 | 20.885 | -26.443 | 1.00 109.13 | A |
| ATOM | 4398 | C | ALA | A1156 | 6.309 | 21.011 | -26.482 | 1.00 109.13 | A |
| ATOM | 4399 | O | ALA | A1156 | 5.390 | 20.602 | -25.782 | 1.00 109.13 | A |
| ATOM | 4400 | N | LEU | A1157 | 6.317 | 22.212 | -27.045 | 1.00 109.13 | A |
| ATOM | 4401 | CA | LEU | A1157 | 5.230 | 23.145 | -26.840 | 1.00 109.13 | A |
| ATOM | 4402 | CB | LEU | A1157 | 5.218 | 24.203 | -27.923 | 1.00 109.13 | A |
| ATOM | 4403 | CG | LEU | A1157 | 6.284 | 25.279 | -27.810 | 1.00 109.13 | A |
| ATOM | 4404 | CD1 | LEU | A1157 | 6.085 | 26.302 | -28.917 | 1.00 109.13 | A |
| ATOM | 4405 | CD2 | LEU | A1157 | 6.176 | 25.947 | -26.453 | 1.00 109.13 | A |
| ATOM | 4406 | C | LEU | A1157 | 3.904 | 22.444 | -26.828 | 1.00 109.13 | A |
| ATOM | 4407 | O | LEU | A1157 | 3.033 | 22.779 | -26.043 | 1.00 109.13 | A |
| ATOM | 4408 | N | LEU | A1158 | 3.742 | 21.466 | -27.706 | 1.00 109.13 | A |
| ATOM | 4409 | CA | LEU | A1158 | 2.485 | 20.724 | -27.770 | 1.00 109.13 | A |
| ATOM | 4410 | CB | LEU | A1158 | 2.521 | 19.702 | -28.907 | 1.00 109.13 | A |
| ATOM | 4411 | CG | LEU | A1158 | 2.248 | 20.237 | -30.305 | 1.00 109.13 | A |
| ATOM | 4412 | CD1 | LEU | A1158 | 2.366 | 19.116 | -31.310 | 1.00 109.13 | A |
| ATOM | 4413 | CD2 | LEU | A1158 | 0.856 | 20.825 | -30.347 | 1.00 109.13 | A |
| ATOM | 4414 | C | LEU | A1158 | 2.187 | 19.999 | -26.465 | 1.00 109.13 | A |
| ATOM | 4415 | O | LEU | A1158 | 1.105 | 20.155 | -25.884 | 1.00 109.13 | A |
| ATOM | 4416 | N | ASN | A1159 | 3.159 | 19.207 | -26.016 | 1.00 109.13 | A |
| ATOM | 4417 | CA | ASN | A1159 | 3.025 | 18.436 | -24.793 | 1.00 109.13 | A |
| ATOM | 4418 | CB | ASN | A1159 | 4.151 | 17.410 | -24.708 | 1.00 109.13 | A |
| ATOM | 4419 | CG | ASN | A1159 | 3.896 | 16.209 | -25.585 | 1.00 109.13 | A |
| ATOM | 4420 | OD1 | ASN | A1159 | 4.707 | 15.291 | -25.650 | 1.00 109.13 | A |
| ATOM | 4421 | ND2 | ASN | A1159 | 2.753 | 16.203 | -26.260 | 1.00 109.13 | A |
| ATOM | 4422 | C | ASN | A1159 | 2.967 | 19.275 | -23.527 | 1.00 109.13 | A |

Figure 4 C
(Continued)

| | | | | | | | | |
|---|---|---|---|---|---|---|---|---|
| ATOM | 4423 | O | ASN | A1159 | 2.496 | 18.814 | -22.496 | 1.00109.13 | A |
| ATOM | 4424 | N | LEU | A1160 | 3.439 | 20.508 | -23.592 | 1.00109.13 | A |
| ATOM | 4425 | CA | LEU | A1160 | 3.381 | 21.354 | -22.419 | 1.00109.13 | A |
| ATOM | 4426 | CB | LEU | A1160 | 4.470 | 22.422 | -22.461 | 1.00109.13 | A |
| ATOM | 4427 | CG | LEU | A1160 | 5.907 | 21.915 | -22.605 | 1.00109.13 | A |
| ATOM | 4428 | CD1 | LEU | A1160 | 6.855 | 23.071 | -22.381 | 1.00109.13 | A |
| ATOM | 4429 | CD2 | LEU | A1160 | 6.185 | 20.813 | -21.596 | 1.00109.13 | A |
| ATOM | 4430 | C | LEU | A1160 | 2.023 | 22.007 | -22.383 | 1.00109.13 | A |
| ATOM | 4431 | O | LEU | A1160 | 1.300 | 21.875 | -21.412 | 1.00109.13 | A |
| ATOM | 4432 | N | LEU | A1161 | 1.672 | 22.701 | -23.458 | 1.00109.13 | A |
| ATOM | 4433 | CA | LEU | A1161 | 0.385 | 23.377 | -23.538 | 1.00109.13 | A |
| ATOM | 4434 | CB | LEU | A1161 | 0.140 | 23.919 | -24.952 | 1.00109.13 | A |
| ATOM | 4435 | CG | LEU | A1161 | 1.095 | 24.998 | -25.463 | 1.00109.13 | A |
| ATOM | 4436 | CD1 | LEU | A1161 | 0.782 | 25.275 | -26.924 | 1.00109.13 | A |
| ATOM | 4437 | CD2 | LEU | A1161 | 0.965 | 26.265 | -24.632 | 1.00109.13 | A |
| ATOM | 4438 | C | LEU | A1161 | -0.745 | 22.436 | -23.143 | 1.00109.13 | A |
| ATOM | 4439 | O | LEU | A1161 | -1.747 | 22.874 | -22.585 | 1.00109.13 | A |
| ATOM | 4440 | N | GLU | A1162 | -0.597 | 21.147 | -23.427 | 1.00109.13 | A |
| ATOM | 4441 | CA | GLU | A1162 | -1.642 | 20.208 | -23.060 | 1.00109.13 | A |
| ATOM | 4442 | CB | GLU | A1162 | -1.318 | 18.801 | -23.563 | 1.00109.13 | A |
| ATOM | 4443 | CG | GLU | A1162 | -2.087 | 18.377 | -24.815 | 1.00109.13 | A |
| ATOM | 4444 | CD | GLU | A1162 | -3.586 | 18.219 | -24.582 | 1.00109.13 | A |
| ATOM | 4445 | OE1 | GLU | A1162 | -3.978 | 17.460 | -23.674 | 1.00109.13 | A |
| ATOM | 4446 | OE2 | GLU | A1162 | -4.378 | 18.846 | -25.313 | 1.00109.13 | A |
| ATOM | 4447 | C | GLU | A1162 | -1.747 | 20.209 | -21.548 | 1.00109.13 | A |
| ATOM | 4448 | O | GLU | A1162 | -2.725 | 20.711 | -20.983 | 1.00109.13 | A |
| ATOM | 4449 | N | SER | A1163 | -0.716 | 19.673 | -20.895 | 1.00109.13 | A |
| ATOM | 4450 | CA | SER | A1163 | -0.676 | 19.585 | -19.436 | 1.00109.13 | A |
| ATOM | 4451 | CB | SER | A1163 | 0.645 | 18.981 | -18.965 | 1.00109.13 | A |
| ATOM | 4452 | OG | SER | A1163 | 1.709 | 19.878 | -19.174 | 1.00109.13 | A |
| ATOM | 4453 | C | SER | A1163 | -0.865 | 20.929 | -18.772 | 1.00109.13 | A |
| ATOM | 4454 | O | SER | A1163 | -1.242 | 20.992 | -17.618 | 1.00109.13 | A |
| ATOM | 4455 | N | ALA | A1164 | -0.605 | 22.008 | -19.495 | 1.00109.13 | A |
| ATOM | 4456 | CA | ALA | A1164 | -0.763 | 23.338 | -18.926 | 1.00109.13 | A |
| ATOM | 4457 | CB | ALA | A1164 | -0.064 | 24.374 | -19.790 | 1.00109.13 | A |
| ATOM | 4458 | C | ALA | A1164 | -2.231 | 23.685 | -18.798 | 1.00109.13 | A |
| ATOM | 4459 | O | ALA | A1164 | -2.596 | 24.574 | -18.034 | 1.00109.13 | A |
| ATOM | 4460 | N | GLU | A1165 | -3.077 | 22.985 | -19.542 | 1.00109.13 | A |
| ATOM | 4461 | CA | GLU | A1165 | -4.497 | 23.268 | -19.486 | 1.00109.13 | A |
| ATOM | 4462 | CB | GLU | A1165 | -5.065 | 23.481 | -20.903 | 1.00109.13 | A |
| ATOM | 4463 | CG | GLU | A1165 | -5.167 | 24.980 | -21.293 | 1.00109.13 | A |
| ATOM | 4464 | CD | GLU | A1165 | -5.153 | 25.241 | -22.793 | 1.00109.13 | A |
| ATOM | 4465 | OE1 | GLU | A1165 | -5.981 | 24.646 | -23.525 | 1.00109.13 | A |
| ATOM | 4466 | OE2 | GLU | A1165 | -4.309 | 26.057 | -23.235 | 1.00109.13 | A |
| ATOM | 4467 | C | GLU | A1165 | -5.257 | 22.197 | -18.744 | 1.00109.13 | A |
| ATOM | 4468 | O | GLU | A1165 | -6.381 | 22.422 | -18.302 | 1.00109.13 | A |
| ATOM | 4469 | N | THR | A1166 | -4.638 | 21.035 | -18.587 | 1.00109.13 | A |
| ATOM | 4470 | CA | THR | A1166 | -5.282 | 19.948 | -17.858 | 1.00109.13 | A |
| ATOM | 4471 | CB | THR | A1166 | -5.186 | 18.598 | -18.620 | 1.00109.13 | A |
| ATOM | 4472 | OG1 | THR | A1166 | -3.821 | 18.186 | -18.720 | 1.00109.13 | A |
| ATOM | 4473 | CG2 | THR | A1166 | -5.771 | 18.731 | -20.004 | 1.00109.13 | A |
| ATOM | 4474 | C | THR | A1166 | -4.706 | 19.752 | -16.446 | 1.00109.13 | A |
| ATOM | 4475 | O | THR | A1166 | -5.132 | 18.849 | -15.732 | 1.00109.13 | A |
| ATOM | 4476 | N | GLU | A1167 | -3.765 | 20.603 | -16.031 | 1.00109.13 | A |
| ATOM | 4477 | CA | GLU | A1167 | -3.162 | 20.463 | -14.710 | 1.00109.13 | A |
| ATOM | 4478 | CB | GLU | A1167 | -2.293 | 19.205 | -14.662 | 1.00109.13 | A |
| ATOM | 4479 | CG | GLU | A1167 | -3.010 | 17.950 | -14.212 | 1.00109.13 | A |

Figure 4 C
(Continued)

| | | | | | | | | |
|---|---|---|---|---|---|---|---|---|
| ATOM | 4480 | CD | GLU | A1167 | -2.057 | 16.816 | -13.858 | 1.00 109.13 | A |
| ATOM | 4481 | OE1 | GLU | A1167 | -1.355 | 16.300 | -14.757 | 1.00 109.13 | A |
| ATOM | 4482 | OE2 | GLU | A1167 | -2.012 | 16.446 | -12.666 | 1.00 109.13 | A |
| ATOM | 4483 | C | GLU | A1167 | -2.317 | 21.606 | -14.165 | 1.00 109.13 | A |
| ATOM | 4484 | O | GLU | A1167 | -1.645 | 21.413 | -13.166 | 1.00 109.13 | A |
| ATOM | 4485 | N | GLU | A1168 | -2.329 | 22.780 | -14.782 | 1.00 109.13 | A |
| ATOM | 4486 | CA | GLU | A1168 | -1.504 | 23.890 | -14.289 | 1.00 109.13 | A |
| ATOM | 4487 | CB | GLU | A1168 | -2.035 | 24.454 | -12.967 | 1.00 109.13 | A |
| ATOM | 4488 | CG | GLU | A1168 | -3.305 | 25.257 | -13.047 | 1.00 109.13 | A |
| ATOM | 4489 | CD | GLU | A1168 | -4.522 | 24.398 | -13.266 | 1.00 109.13 | A |
| ATOM | 4490 | OE1 | GLU | A1168 | -5.638 | 24.893 | -13.004 | 1.00 109.13 | A |
| ATOM | 4491 | OE2 | GLU | A1168 | -4.367 | 23.237 | -13.702 | 1.00 109.13 | A |
| ATOM | 4492 | C | GLU | A1168 | -0.048 | 23.492 | -14.051 | 1.00 109.13 | A |
| ATOM | 4493 | O | GLU | A1168 | 0.727 | 24.275 | -13.517 | 1.00 109.13 | A |
| ATOM | 4494 | N | VAL | A1169 | 0.319 | 22.273 | -14.423 | 1.00 109.13 | A |
| ATOM | 4495 | CA | VAL | A1169 | 1.683 | 21.805 | -14.224 | 1.00 109.13 | A |
| ATOM | 4496 | CB | VAL | A1169 | 1.702 | 20.320 | -13.749 | 1.00 109.13 | A |
| ATOM | 4497 | CG1 | VAL | A1169 | 3.096 | 19.918 | -13.317 | 1.00 109.13 | A |
| ATOM | 4498 | CG2 | VAL | A1169 | 0.743 | 20.128 | -12.596 | 1.00 109.13 | A |
| ATOM | 4499 | C | VAL | A1169 | 2.463 | 21.932 | -15.531 | 1.00 109.13 | A |
| ATOM | 4500 | O | VAL | A1169 | 1.894 | 21.840 | -16.615 | 1.00 109.13 | A |
| ATOM | 4501 | N | VAL | A1170 | 3.764 | 22.162 | -15.421 | 1.00 109.13 | A |
| ATOM | 4502 | CA | VAL | A1170 | 4.632 | 22.293 | -16.581 | 1.00 109.13 | A |
| ATOM | 4503 | CB | VAL | A1170 | 4.859 | 23.773 | -16.946 | 1.00 109.13 | A |
| ATOM | 4504 | CG1 | VAL | A1170 | 5.689 | 23.879 | -18.204 | 1.00 109.13 | A |
| ATOM | 4505 | CG2 | VAL | A1170 | 3.536 | 24.473 | -17.135 | 1.00 109.13 | A |
| ATOM | 4506 | C | VAL | A1170 | 5.959 | 21.705 | -16.147 | 1.00 109.13 | A |
| ATOM | 4507 | O | VAL | A1170 | 6.511 | 22.143 | -15.148 | 1.00 109.13 | A |
| ATOM | 4508 | N | ASP | A1171 | 6.472 | 20.710 | -16.866 | 1.00 109.13 | A |
| ATOM | 4509 | CA | ASP | A1171 | 7.754 | 20.137 | -16.481 | 1.00 109.13 | A |
| ATOM | 4510 | CB | ASP | A1171 | 7.709 | 18.614 | -16.464 | 1.00 109.13 | A |
| ATOM | 4511 | CG | ASP | A1171 | 8.926 | 18.010 | -15.762 | 1.00 109.13 | A |
| ATOM | 4512 | OD1 | ASP | A1171 | 10.040 | 18.132 | -16.303 | 1.00 109.13 | A |
| ATOM | 4513 | OD2 | ASP | A1171 | 8.783 | 17.427 | -14.663 | 1.00 109.13 | A |
| ATOM | 4514 | C | ASP | A1171 | 8.879 | 20.596 | -17.387 | 1.00 109.13 | A |
| ATOM | 4515 | O | ASP | A1171 | 9.942 | 20.990 | -16.913 | 1.00 109.13 | A |
| ATOM | 4516 | N | ILE | A1172 | 8.657 | 20.543 | -18.690 | 1.00 109.13 | A |
| ATOM | 4517 | CA | ILE | A1172 | 9.676 | 20.992 | -19.623 | 1.00 109.13 | A |
| ATOM | 4518 | CB | ILE | A1172 | 10.065 | 22.459 | -19.340 | 1.00 109.13 | A |
| ATOM | 4519 | CG2 | ILE | A1172 | 11.227 | 22.869 | -20.210 | 1.00 109.13 | A |
| ATOM | 4520 | CG1 | ILE | A1172 | 8.863 | 23.363 | -19.599 | 1.00 109.13 | A |
| ATOM | 4521 | CD1 | ILE | A1172 | 9.083 | 24.799 | -19.272 | 1.00 109.13 | A |
| ATOM | 4522 | C | ILE | A1172 | 10.928 | 20.128 | -19.579 | 1.00 109.13 | A |
| ATOM | 4523 | O | ILE | A1172 | 11.281 | 19.504 | -20.576 | 1.00 109.13 | A |
| ATOM | 4524 | N | PHE | A1173 | 11.593 | 20.085 | -18.428 | 1.00 109.13 | A |
| ATOM | 4525 | CA | PHE | A1173 | 12.806 | 19.296 | -18.292 | 1.00 109.13 | A |
| ATOM | 4526 | CB | PHE | A1173 | 13.324 | 19.352 | -16.865 | 1.00 109.13 | A |
| ATOM | 4527 | CG | PHE | A1173 | 14.738 | 18.870 | -16.723 | 1.00 109.13 | A |
| ATOM | 4528 | CD1 | PHE | A1173 | 15.803 | 19.746 | -16.879 | 1.00 109.13 | A |
| ATOM | 4529 | CD2 | PHE | A1173 | 15.006 | 17.533 | -16.430 | 1.00 109.13 | A |
| ATOM | 4530 | CE1 | PHE | A1173 | 17.107 | 19.300 | -16.739 | 1.00 109.13 | A |
| ATOM | 4531 | CE2 | PHE | A1173 | 16.306 | 17.077 | -16.290 | 1.00 109.13 | A |
| ATOM | 4532 | CZ | PHE | A1173 | 17.358 | 17.961 | -16.444 | 1.00 109.13 | A |
| ATOM | 4533 | C | PHE | A1173 | 12.592 | 17.842 | -18.693 | 1.00 109.13 | A |
| ATOM | 4534 | O | PHE | A1173 | 13.240 | 17.344 | -19.600 | 1.00 109.13 | A |
| ATOM | 4535 | N | GLN | A1174 | 11.689 | 17.147 | -18.021 | 1.00 109.13 | A |
| ATOM | 4536 | CA | GLN | A1174 | 11.431 | 15.753 | -18.365 | 1.00 109.13 | A |

Figure 4 C
(Continued)

| ATOM | 4537 | CB | GLN A1174 | 10.454 | 15.129 | -17.359 | 1.00109.13 | A |
|------|------|------|-----------|--------|--------|---------|------------|---|
| ATOM | 4538 | CG | GLN A1174 | 11.077 | 14.680 | -16.042 | 1.00109.13 | A |
| ATOM | 4539 | CD | GLN A1174 | 11.858 | 13.376 | -16.168 | 1.00109.13 | A |
| ATOM | 4540 | OE1 | GLN A1174 | 12.553 | 12.964 | -15.239 | 1.00109.13 | A |
| ATOM | 4541 | NE2 | GLN A1174 | 11.741 | 12.718 | -17.317 | 1.00109.13 | A |
| ATOM | 4542 | C | GLN A1174 | 10.865 | 15.650 | -19.781 | 1.00109.13 | A |
| ATOM | 4543 | O | GLN A1174 | 11.164 | 14.706 | -20.506 | 1.00109.13 | A |
| ATOM | 4544 | N | VAL A1175 | 10.046 | 16.630 | -20.164 | 1.00109.13 | A |
| ATOM | 4545 | CA | VAL A1175 | 9.433 | 16.681 | -21.494 | 1.00109.13 | A |
| ATOM | 4546 | CB | VAL A1175 | 8.582 | 17.924 | -21.652 | 1.00109.13 | A |
| ATOM | 4547 | CG1 | VAL A1175 | 7.684 | 17.764 | -22.835 | 1.00109.13 | A |
| ATOM | 4548 | CG2 | VAL A1175 | 7.801 | 18.177 | -20.381 | 1.00109.13 | A |
| ATOM | 4549 | C | VAL A1175 | 10.511 | 16.716 | -22.568 | 1.00109.13 | A |
| ATOM | 4550 | O | VAL A1175 | 10.359 | 16.117 | -23.626 | 1.00109.13 | A |
| ATOM | 4551 | N | VAL A1176 | 11.590 | 17.445 | -22.284 | 1.00109.13 | A |
| ATOM | 4552 | CA | VAL A1176 | 12.736 | 17.557 | -23.184 | 1.00109.13 | A |
| ATOM | 4553 | CB | VAL A1176 | 13.611 | 18.771 | -22.837 | 1.00109.13 | A |
| ATOM | 4554 | CG1 | VAL A1176 | 14.815 | 18.827 | -23.747 | 1.00109.13 | A |
| ATOM | 4555 | CG2 | VAL A1176 | 12.796 | 20.040 | -22.946 | 1.00109.13 | A |
| ATOM | 4556 | C | VAL A1176 | 13.587 | 16.308 | -23.021 | 1.00109.13 | A |
| ATOM | 4557 | O | VAL A1176 | 14.110 | 15.778 | -23.992 | 1.00109.13 | A |
| ATOM | 4558 | N | LYS A1177 | 13.723 | 15.849 | -21.778 | 1.00109.13 | A |
| ATOM | 4559 | CA | LYS A1177 | 14.496 | 14.651 | -21.468 | 1.00109.13 | A |
| ATOM | 4560 | CB | LYS A1177 | 14.499 | 14.387 | -19.958 | 1.00109.13 | A |
| ATOM | 4561 | CG | LYS A1177 | 14.973 | 12.987 | -19.552 | 1.00109.13 | A |
| ATOM | 4562 | CD | LYS A1177 | 14.917 | 12.788 | -18.037 | 1.00109.13 | A |
| ATOM | 4563 | CE | LYS A1177 | 14.939 | 11.306 | -17.641 | 1.00109.13 | A |
| ATOM | 4564 | NZ | LYS A1177 | 13.648 | 10.584 | -17.898 | 1.00109.13 | A |
| ATOM | 4565 | C | LYS A1177 | 13.839 | 13.496 | -22.182 | 1.00109.13 | A |
| ATOM | 4566 | O | LYS A1177 | 14.449 | 12.465 | -22.435 | 1.00109.13 | A |
| ATOM | 4567 | N | ALA A1178 | 12.573 | 13.691 | -22.508 | 1.00109.13 | A |
| ATOM | 4568 | CA | ALA A1178 | 11.794 | 12.680 | -23.192 | 1.00109.13 | A |
| ATOM | 4569 | CB | ALA A1178 | 10.321 | 12.954 | -22.967 | 1.00109.13 | A |
| ATOM | 4570 | C | ALA A1178 | 12.117 | 12.676 | -24.683 | 1.00109.13 | A |
| ATOM | 4571 | O | ALA A1178 | 12.601 | 11.679 | -25.224 | 1.00109.13 | A |
| ATOM | 4572 | N | LEU A1179 | 11.833 | 13.795 | -25.341 | 1.00109.13 | A |
| ATOM | 4573 | CA | LEU A1179 | 12.102 | 13.928 | -26.759 | 1.00109.13 | A |
| ATOM | 4574 | CB | LEU A1179 | 11.917 | 15.377 | -27.196 | 1.00109.13 | A |
| ATOM | 4575 | CG | LEU A1179 | 10.497 | 15.920 | -27.232 | 1.00109.13 | A |
| ATOM | 4576 | CD1 | LEU A1179 | 10.533 | 17.396 | -27.569 | 1.00109.13 | A |
| ATOM | 4577 | CD2 | LEU A1179 | 9.697 | 15.149 | -28.266 | 1.00109.13 | A |
| ATOM | 4578 | C | LEU A1179 | 13.541 | 13.521 | -26.961 | 1.00109.13 | A |
| ATOM | 4579 | O | LEU A1179 | 13.852 | 12.692 | -27.807 | 1.00109.13 | A |
| ATOM | 4580 | N | ARG A1180 | 14.412 | 14.112 | -26.155 | 1.00109.13 | A |
| ATOM | 4581 | CA | ARG A1180 | 15.837 | 13.840 | -26.206 | 1.00109.13 | A |
| ATOM | 4582 | CB | ARG A1180 | 16.509 | 14.433 | -24.956 | 1.00109.13 | A |
| ATOM | 4583 | CG | ARG A1180 | 17.939 | 14.968 | -25.129 | 1.00109.13 | A |
| ATOM | 4584 | CD | ARG A1180 | 18.001 | 16.179 | -26.052 | 1.00109.13 | A |
| ATOM | 4585 | NE | ARG A1180 | 19.175 | 17.017 | -25.803 | 1.00109.13 | A |
| ATOM | 4586 | CZ | ARG A1180 | 19.308 | 17.817 | -24.749 | 1.00109.13 | A |
| ATOM | 4587 | NH1 | ARG A1180 | 18.342 | 17.889 | -23.850 | 1.00109.13 | A |
| ATOM | 4588 | NH2 | ARG A1180 | 20.399 | 18.548 | -24.585 | 1.00109.13 | A |
| ATOM | 4589 | C | ARG A1180 | 16.068 | 12.326 | -26.276 | 1.00109.13 | A |
| ATOM | 4590 | O | ARG A1180 | 16.809 | 11.853 | -27.132 | 1.00109.13 | A |
| ATOM | 4591 | N | LYS A1181 | 15.422 | 11.568 | -25.393 | 1.00109.13 | A |
| ATOM | 4592 | CA | LYS A1181 | 15.593 | 10.119 | -25.383 | 1.00109.13 | A |
| ATOM | 4593 | CB | LYS A1181 | 15.019 | 9.514 | -24.099 | 1.00109.13 | A |

Figure 4 C
(Continued)

| | | | | | | | | |
|---|---|---|---|---|---|---|---|---|
| ATOM | 4594 | CG | LYS | A1181 | 15.889 | 9.735 | -22.865 | 1.00109.13 | A |
| ATOM | 4595 | CD | LYS | A1181 | 15.331 | 9.023 | -21.626 | 1.00109.13 | A |
| ATOM | 4596 | CE | LYS | A1181 | 16.331 | 9.026 | -20.445 | 1.00109.13 | A |
| ATOM | 4597 | NZ | LYS | A1181 | 16.680 | 10.384 | -19.927 | 1.00109.13 | A |
| ATOM | 4598 | C | LYS | A1181 | 14.948 | 9.442 | -26.576 | 1.00109.13 | A |
| ATOM | 4599 | O | LYS | A1181 | 15.217 | 8.278 | -26.847 | 1.00109.13 | A |
| ATOM | 4600 | N | ALA | A1182 | 14.109 | 10.178 | -27.295 | 1.00109.13 | A |
| ATOM | 4601 | CA | ALA | A1182 | 13.402 | 9.632 | -28.449 | 1.00109.13 | A |
| ATOM | 4602 | CB | ALA | A1182 | 11.961 | 10.102 | -28.415 | 1.00109.13 | A |
| ATOM | 4603 | C | ALA | A1182 | 14.002 | 9.909 | -29.840 | 1.00109.13 | A |
| ATOM | 4604 | O | ALA | A1182 | 13.611 | 9.271 | -30.818 | 1.00109.13 | A |
| ATOM | 4605 | N | ARG | A1183 | 14.947 | 10.843 | -29.933 | 1.00109.13 | A |
| ATOM | 4606 | CA | ARG | A1183 | 15.564 | 11.187 | -31.221 | 1.00109.13 | A |
| ATOM | 4607 | CB | ARG | A1183 | 14.486 | 11.738 | -32.154 | 1.00109.13 | A |
| ATOM | 4608 | CG | ARG | A1183 | 14.931 | 12.202 | -33.533 | 1.00109.13 | A |
| ATOM | 4609 | CD | ARG | A1183 | 13.752 | 12.886 | -34.209 | 1.00109.13 | A |
| ATOM | 4610 | NE | ARG | A1183 | 13.461 | 12.370 | -35.541 | 1.00109.13 | A |
| ATOM | 4611 | CZ | ARG | A1183 | 14.099 | 12.745 | -36.641 | 1.00109.13 | A |
| ATOM | 4612 | NH1 | ARG | A1183 | 15.071 | 13.643 | -36.568 | 1.00109.13 | A |
| ATOM | 4613 | NH2 | ARG | A1183 | 13.758 | 12.231 | -37.813 | 1.00109.13 | A |
| ATOM | 4614 | C | ARG | A1183 | 16.663 | 12.230 | -31.017 | 1.00109.13 | A |
| ATOM | 4615 | O | ARG | A1183 | 16.582 | 13.049 | -30.100 | 1.00109.13 | A |
| ATOM | 4616 | N | LEU | A1184 | 17.681 | 12.216 | -31.870 | 1.00109.13 | A |
| ATOM | 4617 | CA | LEU | A1184 | 18.773 | 13.169 | -31.725 | 1.00109.13 | A |
| ATOM | 4618 | CB | LEU | A1184 | 19.994 | 12.653 | -32.482 | 1.00109.13 | A |
| ATOM | 4619 | CG | LEU | A1184 | 21.396 | 13.177 | -32.113 | 1.00109.13 | A |
| ATOM | 4620 | CD1 | LEU | A1184 | 21.826 | 14.292 | -33.073 | 1.00109.13 | A |
| ATOM | 4621 | CD2 | LEU | A1184 | 21.409 | 13.638 | -30.638 | 1.00109.13 | A |
| ATOM | 4622 | C | LEU | A1184 | 18.427 | 14.581 | -32.194 | 1.00109.13 | A |
| ATOM | 4623 | O | LEU | A1184 | 17.326 | 14.837 | -32.665 | 1.00109.13 | A |
| ATOM | 4624 | N | GLY | A1185 | 19.373 | 15.498 | -32.038 | 1.00109.13 | A |
| ATOM | 4625 | CA | GLY | A1185 | 19.174 | 16.868 | -32.468 | 1.00109.13 | A |
| ATOM | 4626 | C | GLY | A1185 | 18.137 | 17.657 | -31.697 | 1.00109.13 | A |
| ATOM | 4627 | O | GLY | A1185 | 18.184 | 18.888 | -31.693 | 1.00109.13 | A |
| ATOM | 4628 | N | MET | A1186 | 17.208 | 16.958 | -31.048 | 1.00109.13 | A |
| ATOM | 4629 | CA | MET | A1186 | 16.131 | 17.581 | -30.267 | 1.00109.13 | A |
| ATOM | 4630 | CB | MET | A1186 | 15.323 | 16.498 | -29.564 | 1.00109.13 | A |
| ATOM | 4631 | CG | MET | A1186 | 13.843 | 16.697 | -29.635 | 1.00109.13 | A |
| ATOM | 4632 | SD | MET | A1186 | 13.309 | 16.370 | -31.273 | 1.00109.13 | A |
| ATOM | 4633 | CE | MET | A1186 | 13.304 | 14.604 | -31.285 | 1.00109.13 | A |
| ATOM | 4634 | C | MET | A1186 | 16.629 | 18.572 | -29.213 | 1.00109.13 | A |
| ATOM | 4635 | O | MET | A1186 | 17.354 | 18.195 | -28.299 | 1.00109.13 | A |
| ATOM | 4636 | N | VAL | A1187 | 16.215 | 19.828 | -29.319 | 1.00109.13 | A |
| ATOM | 4637 | CA | VAL | A1187 | 16.647 | 20.853 | -28.366 | 1.00109.13 | A |
| ATOM | 4638 | CB | VAL | A1187 | 15.843 | 20.774 | -27.046 | 1.00109.13 | A |
| ATOM | 4639 | CG1 | VAL | A1187 | 16.327 | 21.833 | -26.082 | 1.00109.13 | A |
| ATOM | 4640 | CG2 | VAL | A1187 | 14.368 | 20.978 | -27.324 | 1.00109.13 | A |
| ATOM | 4641 | C | VAL | A1187 | 18.142 | 20.690 | -28.069 | 1.00109.13 | A |
| ATOM | 4642 | O | VAL | A1187 | 18.540 | 20.126 | -27.053 | 1.00109.13 | A |
| ATOM | 4643 | N | SER | A1188 | 18.961 | 21.202 | -28.980 | 1.00109.13 | A |
| ATOM | 4644 | CA | SER | A1188 | 20.412 | 21.110 | -28.898 | 1.00109.13 | A |
| ATOM | 4645 | CB | SER | A1188 | 21.012 | 21.233 | -30.310 | 1.00109.13 | A |
| ATOM | 4646 | OG | SER | A1188 | 20.263 | 20.503 | -31.271 | 1.00109.13 | A |
| ATOM | 4647 | C | SER | A1188 | 21.070 | 22.150 | -27.999 | 1.00109.13 | A |
| ATOM | 4648 | O | SER | A1188 | 22.127 | 21.895 | -27.431 | 1.00109.13 | A |
| ATOM | 4649 | N | THR | A1189 | 20.461 | 23.321 | -27.869 | 1.00109.13 | A |
| ATOM | 4650 | CA | THR | A1189 | 21.071 | 24.374 | -27.063 | 1.00109.13 | A |

Figure 4 C
(Continued)

| | | | | | | | | | |
|---|---|---|---|---|---|---|---|---|---|
| ATOM | 4651 | CB | THR | A1189 | 21.588 | 25.519 | -27.918 | 1.00 109.13 | A |
| ATOM | 4652 | OG1 | THR | A1189 | 20.487 | 26.113 | -28.630 | 1.00 109.13 | A |
| ATOM | 4653 | CG2 | THR | A1189 | 22.662 | 25.022 | -28.871 | 1.00 109.13 | A |
| ATOM | 4654 | C | THR | A1189 | 20.198 | 25.036 | -26.043 | 1.00 109.13 | A |
| ATOM | 4655 | O | THR | A1189 | 18.985 | 25.083 | -26.185 | 1.00 109.13 | A |
| ATOM | 4656 | N | PHE | A1190 | 20.857 | 25.596 | -25.037 | 1.00 109.13 | A |
| ATOM | 4657 | CA | PHE | A1190 | 20.186 | 26.299 | -23.970 | 1.00 109.13 | A |
| ATOM | 4658 | CB | PHE | A1190 | 21.222 | 26.986 | -23.081 | 1.00 109.13 | A |
| ATOM | 4659 | CG | PHE | A1190 | 20.667 | 28.130 | -22.278 | 1.00 109.13 | A |
| ATOM | 4660 | CD1 | PHE | A1190 | 20.787 | 29.441 | -22.739 | 1.00 109.13 | A |
| ATOM | 4661 | CD2 | PHE | A1190 | 19.999 | 27.898 | -21.075 | 1.00 109.13 | A |
| ATOM | 4662 | CE1 | PHE | A1190 | 20.250 | 30.496 | -22.014 | 1.00 109.13 | A |
| ATOM | 4663 | CE2 | PHE | A1190 | 19.458 | 28.947 | -20.344 | 1.00 109.13 | A |
| ATOM | 4664 | CZ | PHE | A1190 | 19.583 | 30.246 | -20.812 | 1.00 109.13 | A |
| ATOM | 4665 | C | PHE | A1190 | 19.207 | 27.329 | -24.533 | 1.00 109.13 | A |
| ATOM | 4666 | O | PHE | A1190 | 18.123 | 27.535 | -23.994 | 1.00 109.13 | A |
| ATOM | 4667 | N | GLU | A1191 | 19.591 | 27.977 | -25.623 | 1.00 109.13 | A |
| ATOM | 4668 | CA | GLU | A1191 | 18.736 | 28.983 | -26.241 | 1.00 109.13 | A |
| ATOM | 4669 | CB | GLU | A1191 | 19.333 | 29.405 | -27.584 | 1.00 109.13 | A |
| ATOM | 4670 | CG | GLU | A1191 | 20.726 | 30.060 | -27.449 | 1.00 109.13 | A |
| ATOM | 4671 | CD | GLU | A1191 | 21.820 | 29.082 | -26.985 | 1.00 109.13 | A |
| ATOM | 4672 | OE1 | GLU | A1191 | 22.310 | 28.301 | -27.838 | 1.00 109.13 | A |
| ATOM | 4673 | OE2 | GLU | A1191 | 22.178 | 29.090 | -25.776 | 1.00 109.13 | A |
| ATOM | 4674 | C | GLU | A1191 | 17.333 | 28.441 | -26.431 | 1.00 109.13 | A |
| ATOM | 4675 | O | GLU | A1191 | 16.380 | 28.958 | -25.869 | 1.00 109.13 | A |
| ATOM | 4676 | N | GLN | A1192 | 17.213 | 27.389 | -27.224 | 1.00 109.13 | A |
| ATOM | 4677 | CA | GLN | A1192 | 15.919 | 26.768 | -27.461 | 1.00 109.13 | A |
| ATOM | 4678 | CB | GLN | A1192 | 16.111 | 25.474 | -28.251 | 1.00 109.13 | A |
| ATOM | 4679 | CG | GLN | A1192 | 16.619 | 25.655 | -29.659 | 1.00 109.13 | A |
| ATOM | 4680 | CD | GLN | A1192 | 17.008 | 24.338 | -30.274 | 1.00 109.13 | A |
| ATOM | 4681 | OE1 | GLN | A1192 | 18.002 | 23.744 | -29.877 | 1.00 109.13 | A |
| ATOM | 4682 | NE2 | GLN | A1192 | 16.220 | 23.860 | -31.234 | 1.00 109.13 | A |
| ATOM | 4683 | C | GLN | A1192 | 15.235 | 26.458 | -26.126 | 1.00 109.13 | A |
| ATOM | 4684 | O | GLN | A1192 | 14.146 | 26.949 | -25.832 | 1.00 109.13 | A |
| ATOM | 4685 | N | TYR | A1193 | 15.890 | 25.620 | -25.333 | 1.00 109.13 | A |
| ATOM | 4686 | CA | TYR | A1193 | 15.395 | 25.231 | -24.026 | 1.00 109.13 | A |
| ATOM | 4687 | CB | TYR | A1193 | 16.569 | 24.749 | -23.152 | 1.00 109.13 | A |
| ATOM | 4688 | CG | TYR | A1193 | 16.193 | 24.195 | -21.790 | 1.00 109.13 | A |
| ATOM | 4689 | CD1 | TYR | A1193 | 15.531 | 22.973 | -21.664 | 1.00 109.13 | A |
| ATOM | 4690 | CE1 | TYR | A1193 | 15.146 | 22.483 | -20.411 | 1.00 109.13 | A |
| ATOM | 4691 | CD2 | TYR | A1193 | 16.467 | 24.914 | -20.627 | 1.00 109.13 | A |
| ATOM | 4692 | CE2 | TYR | A1193 | 16.082 | 24.436 | -19.371 | 1.00 109.13 | A |
| ATOM | 4693 | CZ | TYR | A1193 | 15.420 | 23.224 | -19.270 | 1.00 109.13 | A |
| ATOM | 4694 | OH | TYR | A1193 | 15.015 | 22.782 | -18.031 | 1.00 109.13 | A |
| ATOM | 4695 | C | TYR | A1193 | 14.747 | 26.465 | -23.420 | 1.00 109.13 | A |
| ATOM | 4696 | O | TYR | A1193 | 13.545 | 26.503 | -23.235 | 1.00 109.13 | A |
| ATOM | 4697 | N | GLN | A1194 | 15.550 | 27.492 | -23.162 | 1.00 109.13 | A |
| ATOM | 4698 | CA | GLN | A1194 | 15.069 | 28.734 | -22.560 | 1.00 109.13 | A |
| ATOM | 4699 | CB | GLN | A1194 | 16.148 | 29.816 | -22.607 | 1.00 109.13 | A |
| ATOM | 4700 | CG | GLN | A1194 | 15.787 | 31.042 | -21.795 | 1.00 109.13 | A |
| ATOM | 4701 | CD | GLN | A1194 | 16.587 | 32.262 | -22.188 | 1.00 109.13 | A |
| ATOM | 4702 | OE1 | GLN | A1194 | 17.811 | 32.215 | -22.268 | 1.00 109.13 | A |
| ATOM | 4703 | NE2 | GLN | A1194 | 15.894 | 33.372 | -22.429 | 1.00 109.13 | A |
| ATOM | 4704 | C | GLN | A1194 | 13.815 | 29.287 | -23.203 | 1.00 109.13 | A |
| ATOM | 4705 | O | GLN | A1194 | 12.987 | 29.882 | -22.531 | 1.00 109.13 | A |
| ATOM | 4706 | N | PHE | A1195 | 13.677 | 29.099 | -24.507 | 1.00 109.13 | A |
| ATOM | 4707 | CA | PHE | A1195 | 12.508 | 29.602 | -25.215 | 1.00 109.13 | A |

Figure 4 C
(Continued)

| ATOM | 4708 | CB | PHE | A1195 | 12.629 | 29.317 | -26.706 | 1.00 | 109.13 | A |
|------|------|-----|-----|-------|--------|--------|---------|------|--------|---|
| ATOM | 4709 | CG | PHE | A1195 | 11.417 | 29.707 | -27.498 | 1.00 | 109.13 | A |
| ATOM | 4710 | CD1 | PHE | A1195 | 10.871 | 30.985 | -27.380 | 1.00 | 109.13 | A |
| ATOM | 4711 | CD2 | PHE | A1195 | 10.838 | 28.807 | -28.389 | 1.00 | 109.13 | A |
| ATOM | 4712 | CE1 | PHE | A1195 | 9.766 | 31.362 | -28.141 | 1.00 | 109.13 | A |
| ATOM | 4713 | CE2 | PHE | A1195 | 9.728 | 29.169 | -29.160 | 1.00 | 109.13 | A |
| ATOM | 4714 | CZ | PHE | A1195 | 9.192 | 30.449 | -29.036 | 1.00 | 109.13 | A |
| ATOM | 4715 | C | PHE | A1195 | 11.241 | 28.962 | -24.693 | 1.00 | 109.13 | A |
| ATOM | 4716 | O | PHE | A1195 | 10.230 | 29.626 | -24.497 | 1.00 | 109.13 | A |
| ATOM | 4717 | N | LEU | A1196 | 11.305 | 27.658 | -24.486 | 1.00 | 109.13 | A |
| ATOM | 4718 | CA | LEU | A1196 | 10.168 | 26.912 | -23.982 | 1.00 | 109.13 | A |
| ATOM | 4719 | CB | LEU | A1196 | 10.598 | 25.479 | -23.673 | 1.00 | 109.13 | A |
| ATOM | 4720 | CG | LEU | A1196 | 11.222 | 24.767 | -24.874 | 1.00 | 109.13 | A |
| ATOM | 4721 | CD1 | LEU | A1196 | 11.667 | 23.359 | -24.505 | 1.00 | 109.13 | A |
| ATOM | 4722 | CD2 | LEU | A1196 | 10.203 | 24.726 | -25.980 | 1.00 | 109.13 | A |
| ATOM | 4723 | C | LEU | A1196 | 9.552 | 27.562 | -22.742 | 1.00 | 109.13 | A |
| ATOM | 4724 | O | LEU | A1196 | 8.339 | 27.746 | -22.682 | 1.00 | 109.13 | A |
| ATOM | 4725 | N | TYR | A1197 | 10.376 | 27.901 | -21.751 | 1.00 | 109.13 | A |
| ATOM | 4726 | CA | TYR | A1197 | 9.863 | 28.544 | -20.540 | 1.00 | 109.13 | A |
| ATOM | 4727 | CB | TYR | A1197 | 10.987 | 28.819 | -19.523 | 1.00 | 109.13 | A |
| ATOM | 4728 | CG | TYR | A1197 | 11.343 | 27.661 | -18.621 | 1.00 | 109.13 | A |
| ATOM | 4729 | CD1 | TYR | A1197 | 10.529 | 27.306 | -17.551 | 1.00 | 109.13 | A |
| ATOM | 4730 | CE1 | TYR | A1197 | 10.843 | 26.214 | -16.749 | 1.00 | 109.13 | A |
| ATOM | 4731 | CD2 | TYR | A1197 | 12.483 | 26.898 | -18.863 | 1.00 | 109.13 | A |
| ATOM | 4732 | CE2 | TYR | A1197 | 12.805 | 25.804 | -18.070 | 1.00 | 109.13 | A |
| ATOM | 4733 | CZ | TYR | A1197 | 11.985 | 25.465 | -17.021 | 1.00 | 109.13 | A |
| ATOM | 4734 | OH | TYR | A1197 | 12.308 | 24.358 | -16.275 | 1.00 | 109.13 | A |
| ATOM | 4735 | C | TYR | A1197 | 9.251 | 29.869 | -20.967 | 1.00 | 109.13 | A |
| ATOM | 4736 | O | TYR | A1197 | 8.065 | 30.119 | -20.774 | 1.00 | 109.13 | A |
| ATOM | 4737 | N | ASP | A1198 | 10.085 | 30.707 | -21.566 | 1.00 | 109.13 | A |
| ATOM | 4738 | CA | ASP | A1198 | 9.680 | 32.022 | -22.027 | 1.00 | 109.13 | A |
| ATOM | 4739 | CB | ASP | A1198 | 10.691 | 32.531 | -23.059 | 1.00 | 109.13 | A |
| ATOM | 4740 | CG | ASP | A1198 | 12.109 | 32.579 | -22.506 | 1.00 | 109.13 | A |
| ATOM | 4741 | OD1 | ASP | A1198 | 13.058 | 32.877 | -23.267 | 1.00 | 109.13 | A |
| ATOM | 4742 | OD2 | ASP | A1198 | 12.274 | 32.319 | -21.295 | 1.00 | 109.13 | A |
| ATOM | 4743 | C | ASP | A1198 | 8.272 | 32.023 | -22.606 | 1.00 | 109.13 | A |
| ATOM | 4744 | O | ASP | A1198 | 7.458 | 32.862 | -22.230 | 1.00 | 109.13 | A |
| ATOM | 4745 | N | VAL | A1199 | 7.981 | 31.075 | -23.501 | 1.00 | 109.13 | A |
| ATOM | 4746 | CA | VAL | A1199 | 6.658 | 30.984 | -24.132 | 1.00 | 109.13 | A |
| ATOM | 4747 | CB | VAL | A1199 | 6.679 | 30.072 | -25.386 | 1.00 | 109.13 | A |
| ATOM | 4748 | CG1 | VAL | A1199 | 7.319 | 30.793 | -26.520 | 1.00 | 109.13 | A |
| ATOM | 4749 | CG2 | VAL | A1199 | 7.430 | 28.795 | -25.102 | 1.00 | 109.13 | A |
| ATOM | 4750 | C | VAL | A1199 | 5.542 | 30.506 | -23.204 | 1.00 | 109.13 | A |
| ATOM | 4751 | O | VAL | A1199 | 4.531 | 31.186 | -23.046 | 1.00 | 109.13 | A |

Figure 4 C
(Continued)

ACTIVE SITE (D) COORDINATES

| ATOM | 7837 | N | SER | B | 945 | 70.107 | -1.769 | 89.636 | 1.00 | 56.04 | B |
|---|---|---|---|---|---|---|---|---|---|---|---|
| ATOM | 7838 | CA | SER | B | 945 | 69.996 | -2.939 | 90.495 | 1.00 | 56.04 | B |
| ATOM | 7839 | CB | SER | B | 945 | 70.456 | -2.569 | 91.900 | 1.00 | 56.04 | B |
| ATOM | 7840 | OG | SER | B | 945 | 69.592 | -1.578 | 92.455 | 1.00 | 56.04 | B |
| ATOM | 7841 | C | SER | B | 945 | 68.547 | -3.430 | 90.570 | 1.00 | 56.04 | B |
| ATOM | 7842 | O | SER | B | 945 | 68.238 | -4.336 | 91.347 | 1.00 | 56.04 | B |
| ATOM | 7843 | N | LYS | B | 946 | 67.669 | -2.822 | 89.766 | 1.00 | 56.04 | B |
| ATOM | 7844 | CA | LYS | B | 946 | 66.234 | -3.145 | 89.741 | 1.00 | 56.04 | B |
| ATOM | 7845 | CB | LYS | B | 946 | 65.428 | -1.840 | 89.689 | 1.00 | 56.04 | B |
| ATOM | 7846 | CG | LYS | B | 946 | 65.761 | -0.857 | 90.821 | 1.00 | 56.04 | B |
| ATOM | 7847 | CD | LYS | B | 946 | 64.894 | 0.412 | 90.755 | 1.00 | 56.04 | B |
| ATOM | 7848 | CE | LYS | B | 946 | 65.335 | 1.441 | 91.797 | 1.00 | 56.04 | B |
| ATOM | 7849 | NZ | LYS | B | 946 | 64.633 | 2.743 | 91.654 | 1.00 | 56.04 | B |
| ATOM | 7850 | C | LYS | B | 946 | 65.791 | -4.058 | 88.588 | 1.00 | 56.04 | B |
| ATOM | 7851 | O | LYS | B | 946 | 64.631 | -4.027 | 88.169 | 1.00 | 56.04 | B |
| ATOM | 7852 | N | ASN | B | 947 | 66.713 | -4.876 | 88.092 | 1.00 | 56.04 | B |
| ATOM | 7853 | CA | ASN | B | 947 | 66.418 | -5.770 | 86.985 | 1.00 | 56.04 | B |
| ATOM | 7854 | CB | ASN | B | 947 | 66.782 | -5.103 | 85.667 | 1.00 | 56.04 | B |
| ATOM | 7855 | CG | ASN | B | 947 | 66.149 | -3.745 | 85.525 | 1.00 | 56.04 | B |
| ATOM | 7856 | OD1 | ASN | B | 947 | 65.051 | -3.598 | 84.965 | 1.00 | 56.04 | B |
| ATOM | 7857 | ND2 | ASN | B | 947 | 66.825 | -2.732 | 86.063 | 1.00 | 56.04 | B |
| ATOM | 7858 | C | ASN | B | 947 | 67.202 | -7.043 | 87.111 | 1.00 | 56.04 | B |
| ATOM | 7859 | O | ASN | B | 947 | 68.361 | -7.104 | 86.707 | 1.00 | 56.04 | B |
| ATOM | 7860 | N | ARG | B | 948 | 66.559 | -8.059 | 87.666 | 1.00 | 56.04 | B |
| ATOM | 7861 | CA | ARG | B | 948 | 67.169 | -9.366 | 87.842 | 1.00 | 56.04 | B |
| ATOM | 7862 | CB | ARG | B | 948 | 66.078 | -10.372 | 88.184 | 1.00 | 56.04 | B |
| ATOM | 7863 | CG | ARG | B | 948 | 66.544 | -11.790 | 88.324 | 1.00 | 56.04 | B |
| ATOM | 7864 | CD | ARG | B | 948 | 65.331 | -12.696 | 88.379 | 1.00 | 56.04 | B |
| ATOM | 7865 | NE | ARG | B | 948 | 64.308 | -12.178 | 89.286 | 1.00 | 56.04 | B |
| ATOM | 7866 | CZ | ARG | B | 948 | 64.509 | -11.947 | 90.577 | 1.00 | 56.04 | B |
| ATOM | 7867 | NH1 | ARG | B | 948 | 65.694 | -12.188 | 91.114 | 1.00 | 56.04 | B |
| ATOM | 7868 | NH2 | ARG | B | 948 | 63.530 | -11.479 | 91.334 | 1.00 | 56.04 | B |
| ATOM | 7869 | C | ARG | B | 948 | 67.887 | -9.787 | 86.558 | 1.00 | 56.04 | B |
| ATOM | 7870 | O | ARG | B | 948 | 68.701 | -10.720 | 86.557 | 1.00 | 56.04 | B |
| ATOM | 7871 | N | ASN | B | 949 | 67.572 | -9.080 | 85.471 | 1.00 | 56.04 | B |
| ATOM | 7872 | CA | ASN | B | 949 | 68.148 | -9.337 | 84.153 | 1.00 | 56.04 | B |
| ATOM | 7873 | CB | ASN | B | 949 | 67.251 | -10.284 | 83.373 | 1.00 | 56.04 | B |
| ATOM | 7874 | CG | ASN | B | 949 | 67.907 | -10.777 | 82.124 | 1.00 | 56.04 | B |
| ATOM | 7875 | OD1 | ASN | B | 949 | 68.349 | -11.920 | 82.056 | 1.00 | 56.04 | B |
| ATOM | 7876 | ND2 | ASN | B | 949 | 68.003 | -9.911 | 81.128 | 1.00 | 56.04 | B |
| ATOM | 7877 | C | ASN | B | 949 | 68.334 | -8.057 | 83.332 | 1.00 | 56.04 | B |
| ATOM | 7878 | O | ASN | B | 949 | 67.608 | -7.828 | 82.364 | 1.00 | 56.04 | B |
| ATOM | 7879 | N | SER | B | 950 | 69.316 | -7.244 | 83.715 | 1.00 | 56.04 | B |
| ATOM | 7880 | CA | SER | B | 950 | 69.606 | -5.980 | 83.041 | 1.00 | 56.04 | B |
| ATOM | 7881 | CB | SER | B | 950 | 71.070 | -5.578 | 83.272 | 1.00 | 56.04 | B |
| ATOM | 7882 | OG | SER | B | 950 | 71.850 | -5.686 | 82.082 | 1.00 | 56.04 | B |
| ATOM | 7883 | C | SER | B | 950 | 69.335 | -5.970 | 81.544 | 1.00 | 56.04 | B |
| ATOM | 7884 | O | SER | B | 950 | 68.616 | -5.099 | 81.051 | 1.00 | 56.04 | B |
| ATOM | 7885 | N | ASN | B | 951 | 69.917 | -6.933 | 80.832 | 1.00 | 56.04 | B |
| ATOM | 7886 | CA | ASN | B | 951 | 69.766 | -7.014 | 79.380 | 1.00 | 56.04 | B |
| ATOM | 7887 | CB | ASN | B | 951 | 70.683 | -8.112 | 78.803 | 1.00 | 56.04 | B |
| ATOM | 7888 | CG | ASN | B | 951 | 70.532 | -9.442 | 79.517 | 1.00 | 56.04 | B |
| ATOM | 7889 | OD1 | ASN | B | 951 | 70.800 | -9.552 | 80.716 | 1.00 | 56.04 | B |
| ATOM | 7890 | ND2 | ASN | B | 951 | 70.104 | -10.462 | 78.779 | 1.00 | 56.04 | B |

Figure 4 D

| | | | | | | | | | | |
|---|---|---|---|---|---|---|---|---|---|---|
| ATOM | 7891 | C | ASN | B | 951 | 68.328 | -7.208 | 78.885 | 1.00 56.04 | B |
| ATOM | 7892 | O | ASN | B | 951 | 68.108 | -7.614 | 77.739 | 1.00 56.04 | B |
| ATOM | 7893 | N | VAL | B | 952 | 67.361 | -6.904 | 79.750 | 1.00 56.04 | B |
| ATOM | 7894 | CA | VAL | B | 952 | 65.942 | -7.005 | 79.419 | 1.00 56.04 | B |
| ATOM | 7895 | CB | VAL | B | 952 | 65.330 | -8.313 | 79.912 | 1.00 56.04 | B |
| ATOM | 7896 | CG1 | VAL | B | 952 | 63.803 | -8.245 | 79.827 | 1.00 56.04 | B |
| ATOM | 7897 | CG2 | VAL | B | 952 | 65.850 | -9.456 | 79.072 | 1.00 56.04 | B |
| ATOM | 7898 | C | VAL | B | 952 | 65.213 | -5.864 | 80.088 | 1.00 56.04 | B |
| ATOM | 7899 | O | VAL | B | 952 | 64.888 | -5.929 | 81.271 | 1.00 56.04 | B |
| ATOM | 7900 | N | ILE | B | 953 | 64.949 | -4.815 | 79.324 | 1.00 56.04 | B |
| ATOM | 7901 | CA | ILE | B | 953 | 64.273 | -3.649 | 79.864 | 1.00 56.04 | B |
| ATOM | 7902 | CB | ILE | B | 953 | 65.292 | -2.479 | 80.006 | 1.00 56.04 | B |
| ATOM | 7903 | CG2 | ILE | B | 953 | 64.568 | -1.126 | 80.119 | 1.00 56.04 | B |
| ATOM | 7904 | CG1 | ILE | B | 953 | 66.214 | -2.777 | 81.203 | 1.00 56.04 | B |
| ATOM | 7905 | CD1 | ILE | B | 953 | 67.453 | -1.889 | 81.323 | 1.00 56.04 | B |
| ATOM | 7906 | C | ILE | B | 953 | 63.059 | -3.232 | 79.041 | 1.00 56.04 | B |
| ATOM | 7907 | O | ILE | B | 953 | 63.016 | -3.411 | 77.827 | 1.00 56.04 | B |
| ATOM | 7908 | N | PRO | B | 954 | 62.042 | -2.690 | 79.712 | 1.00 56.04 | B |
| ATOM | 7909 | CD | PRO | B | 954 | 61.977 | -2.414 | 81.161 | 1.00 56.04 | B |
| ATOM | 7910 | CA | PRO | B | 954 | 60.821 | -2.249 | 79.043 | 1.00 56.04 | B |
| ATOM | 7911 | CB | PRO | B | 954 | 59.897 | -1.898 | 80.204 | 1.00 56.04 | B |
| ATOM | 7912 | CG | PRO | B | 954 | 60.877 | -1.369 | 81.242 | 1.00 56.04 | B |
| ATOM | 7913 | C | PRO | B | 954 | 61.101 | -1.046 | 78.178 | 1.00 56.04 | B |
| ATOM | 7914 | O | PRO | B | 954 | 61.825 | -0.138 | 78.586 | 1.00 56.04 | B |
| ATOM | 8468 | N | THR | B1037 | | 57.191 | -19.253 | 88.058 | 1.00 56.04 | B |
| ATOM | 8469 | CA | THR | B1037 | | 58.468 | -19.598 | 88.647 | 1.00 56.04 | B |
| ATOM | 8470 | CB | THR | B1037 | | 59.448 | -18.447 | 88.512 | 1.00 56.04 | B |
| ATOM | 8471 | OG1 | THR | B1037 | | 59.083 | -17.402 | 89.429 | 1.00 56.04 | B |
| ATOM | 8472 | CG2 | THR | B1037 | | 59.409 | -17.900 | 87.097 | 1.00 56.04 | B |
| ATOM | 8473 | C | THR | B1037 | | 58.367 | -19.906 | 90.117 | 1.00 56.04 | B |
| ATOM | 8474 | O | THR | B1037 | | 57.340 | -19.677 | 90.756 | 1.00 56.04 | B |
| ATOM | 8475 | N | GLU | B1038 | | 59.471 | -20.405 | 90.650 | 1.00 56.04 | B |
| ATOM | 8476 | CA | GLU | B1038 | | 59.555 | -20.739 | 92.053 | 1.00 56.04 | B |
| ATOM | 8477 | CB | GLU | B1038 | | 59.889 | -22.210 | 92.215 | 1.00 56.04 | B |
| ATOM | 8478 | CG | GLU | B1038 | | 59.008 | -23.095 | 91.390 | 1.00 56.04 | B |
| ATOM | 8479 | CD | GLU | B1038 | | 59.246 | -24.546 | 91.692 | 1.00 56.04 | B |
| ATOM | 8480 | OE1 | GLU | B1038 | | 59.025 | -24.937 | 92.860 | 1.00 56.04 | B |
| ATOM | 8481 | OE2 | GLU | B1038 | | 59.652 | -25.291 | 90.771 | 1.00 56.04 | B |
| ATOM | 8482 | C | GLU | B1038 | | 60.630 | -19.886 | 92.708 | 1.00 56.04 | B |
| ATOM | 8483 | O | GLU | B1038 | | 61.593 | -19.463 | 92.070 | 1.00 56.04 | B |
| ATOM | 8484 | N | LEU | B1039 | | 60.444 | -19.634 | 93.992 | 1.00 56.04 | B |
| ATOM | 8485 | CA | LEU | B1039 | | 61.366 | -18.834 | 94.759 | 1.00 56.04 | B |
| ATOM | 8486 | CB | LEU | B1039 | | 60.965 | -18.945 | 96.219 | 1.00 56.04 | B |
| ATOM | 8487 | CG | LEU | B1039 | | 59.470 | -18.645 | 96.348 | 1.00 56.04 | B |
| ATOM | 8488 | CD1 | LEU | B1039 | | 58.873 | -19.298 | 97.596 | 1.00 56.04 | B |
| ATOM | 8489 | CD2 | LEU | B1039 | | 59.288 | -17.139 | 96.350 | 1.00 56.04 | B |
| ATOM | 8490 | C | LEU | B1039 | | 62.816 | -19.277 | 94.534 | 1.00 56.04 | B |
| ATOM | 8491 | O | LEU | B1039 | | 63.676 | -18.444 | 94.255 | 1.00 56.04 | B |
| ATOM | 8492 | N | LYS | B1040 | | 63.098 | -20.575 | 94.662 | 1.00 56.04 | B |
| ATOM | 8493 | CA | LYS | B1040 | | 64.457 | -21.107 | 94.450 | 1.00 56.04 | B |
| ATOM | 8494 | CB | LYS | B1040 | | 65.188 | -21.322 | 95.784 | 1.00 56.04 | B |
| ATOM | 8495 | CG | LYS | B1040 | | 66.579 | -21.973 | 95.644 | 1.00 56.04 | B |
| ATOM | 8496 | CD | LYS | B1040 | | 67.208 | -22.362 | 96.995 | 1.00 56.04 | B |
| ATOM | 8497 | CE | LYS | B1040 | | 67.559 | -21.152 | 97.884 | 1.00 56.04 | B |
| ATOM | 8498 | NZ | LYS | B1040 | | 68.738 | -20.336 | 97.442 | 1.00 56.04 | B |
| ATOM | 8499 | C | LYS | B1040 | | 64.351 | -22.444 | 93.716 | 1.00 56.04 | B |
| ATOM | 8500 | O | LYS | B1040 | | 63.814 | -23.412 | 94.268 | 1.00 56.04 | B |

Figure 4 D
(Continued)

| | | | | | | | | | |
|---|---|---|---|---|---|---|---|---|---|
| ATOM | 8501 | N | HIS | B1041 | 64.874 | -22.495 | 92.486 | 1.00 56.04 | B |
| ATOM | 8502 | CA | HIS | B1041 | 64.813 | -23.711 | 91.652 | 1.00 56.04 | B |
| ATOM | 8503 | CB | HIS | B1041 | 63.600 | -23.614 | 90.675 | 1.00 56.04 | B |
| ATOM | 8504 | CG | HIS | B1041 | 62.914 | -24.925 | 90.364 | 1.00 56.04 | B |
| ATOM | 8505 | CD2 | HIS | B1041 | 62.478 | -25.928 | 91.167 | 1.00 56.04 | B |
| ATOM | 8506 | ND1 | HIS | B1041 | 62.526 | -25.274 | 89.083 | 1.00 56.04 | B |
| ATOM | 8507 | CE1 | HIS | B1041 | 61.884 | -26.430 | 89.111 | 1.00 56.04 | B |
| ATOM | 8508 | NE2 | HIS | B1041 | 61.841 | -26.848 | 90.364 | 1.00 56.04 | B |
| ATOM | 8509 | C | HIS | B1041 | 66.121 | -23.863 | 90.850 | 1.00 56.04 | B |
| ATOM | 8510 | O | HIS | B1041 | 66.180 | -24.643 | 89.890 | 1.00 56.04 | B |
| ATOM | 8511 | N | GLY | B1042 | 67.166 | -23.127 | 91.231 | 1.00 56.04 | B |
| ATOM | 8512 | CA | GLY | B1042 | 68.419 | -23.231 | 90.492 | 1.00 56.04 | B |
| ATOM | 8513 | C | GLY | B1042 | 69.630 | -22.538 | 91.098 | 1.00 56.04 | B |
| ATOM | 8514 | O | GLY | B1042 | 70.194 | -21.606 | 90.495 | 1.00 56.04 | B |
| ATOM | 8515 | N | ASP | B1043 | 70.023 | -23.011 | 92.285 | 1.00 56.04 | B |
| ATOM | 8516 | CA | ASP | B1043 | 71.173 | -22.494 | 93.054 | 1.00 56.04 | B |
| ATOM | 8517 | CB | ASP | B1043 | 72.336 | -22.091 | 92.096 | 1.00 56.04 | B |
| ATOM | 8518 | CG | ASP | B1043 | 73.725 | -22.101 | 92.774 | 1.00 56.04 | B |
| ATOM | 8519 | OD1 | ASP | B1043 | 74.689 | -21.657 | 92.107 | 1.00 56.04 | B |
| ATOM | 8520 | OD2 | ASP | B1043 | 73.857 | -22.545 | 93.946 | 1.00 56.04 | B |
| ATOM | 8521 | C | ASP | B1043 | 70.735 | -21.311 | 93.948 | 1.00 56.04 | B |
| ATOM | 8522 | O | ASP | B1043 | 70.530 | -21.485 | 95.152 | 1.00 56.04 | B |
| ATOM | 8523 | N | GLN | B1044 | 70.586 | -20.124 | 93.361 | 1.00 56.04 | B |
| ATOM | 8524 | CA | GLN | B1044 | 70.162 | -18.957 | 94.130 | 1.00 56.04 | B |
| ATOM | 8525 | CB | GLN | B1044 | 70.852 | -17.654 | 93.637 | 1.00 56.04 | B |
| ATOM | 8526 | CG | GLN | B1044 | 70.409 | -17.089 | 92.254 | 1.00 56.04 | B |
| ATOM | 8527 | CD | GLN | B1044 | 70.318 | -15.539 | 92.205 | 1.00 56.04 | B |
| ATOM | 8528 | OE1 | GLN | B1044 | 70.316 | -14.941 | 91.114 | 1.00 56.04 | B |
| ATOM | 8529 | NE2 | GLN | B1044 | 70.221 | -14.896 | 93.383 | 1.00 56.04 | B |
| ATOM | 8530 | C | GLN | B1044 | 68.653 | -18.776 | 94.071 | 1.00 56.04 | B |
| ATOM | 8531 | O | GLN | B1044 | 67.891 | -19.736 | 93.902 | 1.00 56.04 | B |
| ATOM | 8532 | N | GLU | B1045 | 68.245 | -17.521 | 94.196 | 1.00 56.04 | B |
| ATOM | 8533 | CA | GLU | B1045 | 66.857 | -17.115 | 94.186 | 1.00 56.04 | B |
| ATOM | 8534 | CB | GLU | B1045 | 66.660 | -16.044 | 95.250 | 1.00 56.04 | B |
| ATOM | 8535 | CG | GLU | B1045 | 65.350 | -15.313 | 95.146 | 1.00 56.04 | B |
| ATOM | 8536 | CD | GLU | B1045 | 65.529 | -13.882 | 94.683 | 1.00 56.04 | B |
| ATOM | 8537 | OE1 | GLU | B1045 | 65.882 | -13.025 | 95.531 | 1.00 56.04 | B |
| ATOM | 8538 | OE2 | GLU | B1045 | 65.327 | -13.621 | 93.472 | 1.00 56.04 | B |
| ATOM | 8539 | C | GLU | B1045 | 66.422 | -16.598 | 92.817 | 1.00 56.04 | B |
| ATOM | 8540 | O | GLU | B1045 | 67.103 | -15.767 | 92.201 | 1.00 56.04 | B |
| ATOM | 8541 | N | ILE | B1046 | 65.271 | -17.097 | 92.362 | 1.00 56.04 | B |
| ATOM | 8542 | CA | ILE | B1046 | 64.692 | -16.742 | 91.067 | 1.00 56.04 | B |
| ATOM | 8543 | CB | ILE | B1046 | 64.143 | -17.997 | 90.367 | 1.00 56.04 | B |
| ATOM | 8544 | CG2 | ILE | B1046 | 63.421 | -17.609 | 89.093 | 1.00 56.04 | B |
| ATOM | 8545 | CG1 | ILE | B1046 | 65.285 | -18.975 | 90.070 | 1.00 56.04 | B |
| ATOM | 8546 | CD1 | ILE | B1046 | 66.322 | -18.440 | 89.103 | 1.00 56.04 | B |
| ATOM | 8547 | C | ILE | B1046 | 63.561 | -15.712 | 91.165 | 1.00 56.04 | B |
| ATOM | 8548 | O | ILE | B1046 | 63.329 | -14.941 | 90.229 | 1.00 56.04 | B |
| ATOM | 8549 | N | CYS | B1047 | 62.854 | -15.700 | 92.290 | 1.00 56.04 | B |
| ATOM | 8550 | CA | CYS | B1047 | 61.761 | -14.756 | 92.476 | 1.00 56.04 | B |
| ATOM | 8551 | CB | CYS | B1047 | 60.469 | -15.351 | 91.891 | 1.00 56.04 | B |
| ATOM | 8552 | SG | CYS | B1047 | 58.947 | -14.344 | 91.994 | 1.00 56.04 | B |
| ATOM | 8553 | C | CYS | B1047 | 61.616 | -14.494 | 93.966 | 1.00 56.04 | B |
| ATOM | 8554 | O | CYS | B1047 | 61.777 | -15.409 | 94.772 | 1.00 56.04 | B |
| ATOM | 8983 | N | THR | B1098 | 53.623 | -24.192 | 88.633 | 1.00 56.04 | B |
| ATOM | 8984 | CA | THR | B1098 | 54.942 | -24.797 | 88.834 | 1.00 56.04 | B |
| ATOM | 8985 | CB | THR | B1098 | 54.942 | -25.738 | 90.067 | 1.00 56.04 | B |

Figure 4 D
(Continued)

| ATOM | 8986 | OG1 | THR | B1098 | 54.158 | -26.906 | 89.788 | 1.00 | 56.04 | B |
|------|------|-----|-----|-------|--------|---------|--------|------|-------|---|
| ATOM | 8987 | CG2 | THR | B1098 | 54.347 | -25.032 | 91.272 | 1.00 | 56.04 | B |
| ATOM | 8988 | C   | THR | B1098 | 55.470 | -25.599 | 87.651 | 1.00 | 56.04 | B |
| ATOM | 8989 | O   | THR | B1098 | 56.404 | -25.179 | 86.965 | 1.00 | 56.04 | B |
| ATOM | 8990 | N   | ASN | B1099 | 54.859 | -26.761 | 87.448 | 1.00 | 56.04 | B |
| ATOM | 8991 | CA  | ASN | B1099 | 55.203 | -27.720 | 86.405 | 1.00 | 56.04 | B |
| ATOM | 8992 | CB  | ASN | B1099 | 53.944 | -28.500 | 86.007 | 1.00 | 56.04 | B |
| ATOM | 8993 | CG  | ASN | B1099 | 53.356 | -29.294 | 87.174 | 1.00 | 56.04 | B |
| ATOM | 8994 | OD1 | ASN | B1099 | 53.947 | -30.270 | 87.639 | 1.00 | 56.04 | B |
| ATOM | 8995 | ND2 | ASN | B1099 | 52.194 | -28.865 | 87.658 | 1.00 | 56.04 | B |
| ATOM | 8996 | C   | ASN | B1099 | 55.913 | -27.204 | 85.164 | 1.00 | 56.04 | B |
| ATOM | 8997 | O   | ASN | B1099 | 56.477 | -27.995 | 84.413 | 1.00 | 56.04 | B |
| ATOM | 8998 | N   | TRP | B1100 | 55.886 | -25.898 | 84.922 | 1.00 | 56.04 | B |
| ATOM | 8999 | CA  | TRP | B1100 | 56.591 | -25.374 | 83.760 | 1.00 | 56.04 | B |
| ATOM | 9000 | CB  | TRP | B1100 | 56.256 | -23.906 | 83.484 | 1.00 | 56.04 | B |
| ATOM | 9001 | CG  | TRP | B1100 | 56.643 | -23.479 | 82.076 | 1.00 | 56.04 | B |
| ATOM | 9002 | CD2 | TRP | B1100 | 55.980 | -22.508 | 81.262 | 1.00 | 56.04 | B |
| ATOM | 9003 | CE2 | TRP | B1100 | 56.685 | -22.431 | 80.040 | 1.00 | 56.04 | B |
| ATOM | 9004 | CE3 | TRP | B1100 | 54.859 | -21.692 | 81.446 | 1.00 | 56.04 | B |
| ATOM | 9005 | CD1 | TRP | B1100 | 57.698 | -23.941 | 81.330 | 1.00 | 56.04 | B |
| ATOM | 9006 | NE1 | TRP | B1100 | 57.727 | -23.317 | 80.107 | 1.00 | 56.04 | B |
| ATOM | 9007 | CZ2 | TRP | B1100 | 56.304 | -21.575 | 79.013 | 1.00 | 56.04 | B |
| ATOM | 9008 | CZ3 | TRP | B1100 | 54.481 | -20.842 | 80.421 | 1.00 | 56.04 | B |
| ATOM | 9009 | CH2 | TRP | B1100 | 55.204 | -20.790 | 79.220 | 1.00 | 56.04 | B |
| ATOM | 9010 | C   | TRP | B1100 | 58.081 | -25.480 | 84.038 | 1.00 | 56.04 | B |
| ATOM | 9011 | O   | TRP | B1100 | 58.624 | -24.758 | 84.875 | 1.00 | 56.04 | B |
| ATOM | 9012 | N   | SER | B1101 | 58.725 | -26.394 | 83.325 | 1.00 | 56.04 | B |
| ATOM | 9013 | CA  | SER | B1101 | 60.152 | -26.631 | 83.453 | 1.00 | 56.04 | B |
| ATOM | 9014 | CB  | SER | B1101 | 60.648 | -27.351 | 82.198 | 1.00 | 56.04 | B |
| ATOM | 9015 | OG  | SER | B1101 | 60.166 | -26.715 | 81.021 | 1.00 | 56.04 | B |
| ATOM | 9016 | C   | SER | B1101 | 60.947 | -25.346 | 83.668 | 1.00 | 56.04 | B |
| ATOM | 9017 | O   | SER | B1101 | 61.910 | -25.325 | 84.445 | 1.00 | 56.04 | B |
| ATOM | 9018 | N   | VAL | B1102 | 60.532 | -24.284 | 82.980 | 1.00 | 56.04 | B |
| ATOM | 9019 | CA  | VAL | B1102 | 61.190 | -22.982 | 83.062 | 1.00 | 56.04 | B |
| ATOM | 9020 | CB  | VAL | B1102 | 61.631 | -22.668 | 84.534 | 1.00 | 56.04 | B |
| ATOM | 9021 | CG1 | VAL | B1102 | 62.355 | -21.328 | 84.610 | 1.00 | 56.04 | B |
| ATOM | 9022 | CG2 | VAL | B1102 | 60.407 | -22.646 | 85.446 | 1.00 | 56.04 | B |
| ATOM | 9023 | C   | VAL | B1102 | 62.408 | -23.009 | 82.131 | 1.00 | 56.04 | B |
| ATOM | 9024 | O   | VAL | B1102 | 62.800 | -22.000 | 81.537 | 1.00 | 56.04 | B |
| ATOM | 9025 | N   | GLU | B1103 | 62.995 | -24.190 | 82.013 | 1.00 | 56.04 | B |
| ATOM | 9026 | CA  | GLU | B1103 | 64.151 | -24.407 | 81.162 | 1.00 | 56.04 | B |
| ATOM | 9027 | CB  | GLU | B1103 | 65.415 | -24.643 | 82.011 | 1.00 | 56.04 | B |
| ATOM | 9028 | CG  | GLU | B1103 | 66.195 | -23.363 | 82.337 | 1.00 | 56.04 | B |
| ATOM | 9029 | CD  | GLU | B1103 | 66.990 | -22.825 | 81.140 | 1.00 | 56.04 | B |
| ATOM | 9030 | OE1 | GLU | B1103 | 66.496 | -22.884 | 79.985 | 1.00 | 56.04 | B |
| ATOM | 9031 | OE2 | GLU | B1103 | 68.115 | -22.330 | 81.359 | 1.00 | 56.04 | B |
| ATOM | 9032 | C   | GLU | B1103 | 63.822 | -25.628 | 80.325 | 1.00 | 56.04 | B |
| ATOM | 9033 | O   | GLU | B1103 | 63.865 | -26.758 | 80.805 | 1.00 | 56.04 | B |
| ATOM | 9034 | N   | GLN | B1104 | 63.477 | -25.381 | 79.070 | 1.00 | 56.04 | B |
| ATOM | 9035 | CA  | GLN | B1104 | 63.101 | -26.438 | 78.142 | 1.00 | 56.04 | B |
| ATOM | 9036 | CB  | GLN | B1104 | 63.898 | -27.715 | 78.442 | 1.00 | 56.04 | B· |
| ATOM | 9037 | CG  | GLN | B1104 | 65.419 | -27.504 | 78.405 | 1.00 | 56.04 | B |
| ATOM | 9038 | CD  | GLN | B1104 | 66.216 | -28.776 | 78.701 | 1.00 | 56.04 | B |
| ATOM | 9039 | OE1 | GLN | B1104 | 66.147 | -29.333 | 79.809 | 1.00 | 56.04 | B |
| ATOM | 9040 | NE2 | GLN | B1104 | 66.979 | -29.243 | 77.707 | 1.00 | 56.04 | B |
| ATOM | 9041 | C   | GLN | B1104 | 61.587 | -26.668 | 78.268 | 1.00 | 56.04 | B |
| ATOM | 9042 | O   | GLN | B1104 | 61.119 | -27.534 | 79.014 | 1.00 | 56.04 | B |

Figure 4 D
(Continued)

| ATOM | 9043 | N | LEU | B1105 | 60.845 | -25.855 | 77.519 | 1.00 | 56.04 | B |
|------|------|------|-----|-------|--------|---------|--------|------|-------|---|
| ATOM | 9044 | CA | LEU | B1105 | 59.386 | -25.862 | 77.486 | 1.00 | 56.04 | B |
| ATOM | 9045 | CB | LEU | B1105 | 58.896 | -25.137 | 76.233 | 1.00 | 56.04 | B |
| ATOM | 9046 | CG | LEU | B1105 | 59.429 | -23.717 | 76.077 | 1.00 | 56.04 | B |
| ATOM | 9047 | CD1 | LEU | B1105 | 58.600 | -23.028 | 75.011 | 1.00 | 56.04 | B |
| ATOM | 9048 | CD2 | LEU | B1105 | 59.357 | -22.957 | 77.410 | 1.00 | 56.04 | B |
| ATOM | 9049 | C | LEU | B1105 | 58.725 | -27.230 | 77.550 | 1.00 | 56.04 | B |
| ATOM | 9050 | O | LEU | B1105 | 59.264 | -28.217 | 77.020 | 1.00 | 56.04 | B |
| ATOM | 9051 | N | PRO | B1106 | 57.528 | -27.298 | 78.182 | 1.00 | 56.04 | B |
| ATOM | 9052 | CD | PRO | B1106 | 56.828 | -26.174 | 78.830 | 1.00 | 56.04 | B |
| ATOM | 9053 | CA | PRO | B1106 | 56.756 | -28.538 | 78.336 | 1.00 | 56.04 | B |
| ATOM | 9054 | CB | PRO | B1106 | 55.489 | -28.074 | 79.045 | 1.00 | 56.04 | B |
| ATOM | 9055 | CG | PRO | B1106 | 55.975 | -26.891 | 79.844 | 1.00 | 56.04 | B |
| ATOM | 9056 | C | PRO | B1106 | 56.448 | -29.163 | 76.991 | 1.00 | 56.04 | B |
| ATOM | 9057 | O | PRO | B1106 | 55.966 | -28.478 | 76.084 | 1.00 | 56.04 | B |
| ATOM | 9058 | N | ALA | B1107 | 56.748 | -30.455 | 76.855 | 1.00 | 56.04 | B |
| ATOM | 9059 | CA | ALA | B1107 | 56.470 | -31.174 | 75.609 | 1.00 | 56.04 | B |
| ATOM | 9060 | CB | ALA | B1107 | 56.746 | -32.666 | 75.781 | 1.00 | 56.04 | B |
| ATOM | 9061 | C | ALA | B1107 | 54.990 | -30.938 | 75.354 | 1.00 | 56.04 | B |
| ATOM | 9062 | O | ALA | B1107 | 54.520 | -30.900 | 74.208 | 1.00 | 56.04 | B |
| ATOM | 9063 | N | GLU | B1108 | 54.275 | -30.799 | 76.470 | 1.00 | 56.04 | B |
| ATOM | 9064 | CA | GLU | B1108 | 52.853 | -30.511 | 76.490 | 1.00 | 56.04 | B |
| ATOM | 9065 | CB | GLU | B1108 | 52.031 | -31.541 | 75.689 | 1.00 | 56.04 | B |
| ATOM | 9066 | CG | GLU | B1108 | 52.302 | -32.991 | 75.987 | 1.00 | 56.04 | B |
| ATOM | 9067 | CD | GLU | B1108 | 51.551 | -33.892 | 75.038 | 1.00 | 56.04 | B |
| ATOM | 9068 | OE1 | GLU | B1108 | 51.655 | -33.678 | 73.801 | 1.00 | 56.04 | B |
| ATOM | 9069 | OE2 | GLU | B1108 | 50.861 | -34.809 | 75.530 | 1.00 | 56.04 | B |
| ATOM | 9070 | C | GLU | B1108 | 52.315 | -30.381 | 77.907 | 1.00 | 56.04 | B |
| ATOM | 9071 | O | GLU | B1108 | 52.636 | -31.165 | 78.810 | 1.00 | 56.04 | B |
| ATOM | 9072 | N | PRO | B1109 | 51.541 | -29.316 | 78.125 | 1.00 | 56.04 | B |
| ATOM | 9073 | CD | PRO | B1109 | 51.772 | -28.081 | 77.350 | 1.00 | 56.04 | B |
| ATOM | 9074 | CA | PRO | B1109 | 50.904 | -28.982 | 79.393 | 1.00 | 56.04 | B |
| ATOM | 9075 | CB | PRO | B1109 | 51.656 | -27.732 | 79.804 | 1.00 | 56.04 | B |
| ATOM | 9076 | CG | PRO | B1109 | 51.731 | -26.977 | 78.441 | 1.00 | 56.04 | B |
| ATOM | 9077 | C | PRO | B1109 | 49.434 | -28.694 | 79.087 | 1.00 | 56.04 | B |
| ATOM | 9078 | O | PRO | B1109 | 48.971 | -27.559 | 79.220 | 1.00 | 56.04 | B |
| ATOM | 9303 | N | ILE | B1142 | 51.269 | -11.139 | 84.708 | 1.00 | 56.04 | B |
| ATOM | 9304 | CA | ILE | B1142 | 51.972 | -12.408 | 84.489 | 1.00 | 56.04 | B |
| ATOM | 9305 | CB | ILE | B1142 | 51.806 | -12.920 | 83.063 | 1.00 | 56.04 | B |
| ATOM | 9306 | CG2 | ILE | B1142 | 52.365 | -14.321 | 82.950 | 1.00 | 56.04 | B |
| ATOM | 9307 | CG1 | ILE | B1142 | 50.334 | -12.913 | 82.676 | 1.00 | 56.04 | B |
| ATOM | 9308 | CD1 | ILE | B1142 | 50.117 | -13.322 | 81.248 | 1.00 | 56.04 | B |
| ATOM | 9309 | C | ILE | B1142 | 53.458 | -12.188 | 84.696 | 1.00 | 56.04 | B |
| ATOM | 9310 | O | ILE | B1142 | 54.013 | -11.255 | 84.119 | 1.00 | 56.04 | B |
| ATOM | 9311 | N | HIS | B1143 | 54.111 | -13.031 | 85.499 | 1.00 | 56.04 | B |
| ATOM | 9312 | CA | HIS | B1143 | 55.546 | -12.854 | 85.727 | 1.00 | 56.04 | B |
| ATOM | 9313 | CB | HIS | B1143 | 55.805 | -11.946 | 86.942 | 1.00 | 56.04 | B |
| ATOM | 9314 | CG | HIS | B1143 | 55.751 | -12.651 | 88.266 | 1.00 | 56.04 | B |
| ATOM | 9315 | CD2 | HIS | B1143 | 56.729 | -13.218 | 89.011 | 1.00 | 56.04 | B |
| ATOM | 9316 | ND1 | HIS | B1143 | 54.583 | -12.815 | 88.981 | 1.00 | 56.04 | B |
| ATOM | 9317 | CE1 | HIS | B1143 | 54.843 | -13.450 | 90.109 | 1.00 | 56.04 | B |
| ATOM | 9318 | NE2 | HIS | B1143 | 56.138 | -13.707 | 90.152 | 1.00 | 56.04 | B |
| ATOM | 9319 | C | HIS | B1143 | 56.384 | -14.114 | 85.879 | 1.00 | 56.04 | B |
| ATOM | 9320 | O | HIS | B1143 | 55.872 | -15.203 | 86.171 | 1.00 | 56.04 | B |
| ATOM | 9321 | N | CYS | B1144 | 57.687 | -13.925 | 85.673 | 1.00 | 56.04 | B |
| ATOM | 9322 | CA | CYS | B1144 | 58.699 | -14.972 | 85.781 | 1.00 | 56.04 | B |
| ATOM | 9323 | CB | CYS | B1144 | 58.760 | -15.801 | 84.492 | 1.00 | 56.04 | B |

Figure 4 D
(Continued)

| | | | | | | | | | |
|---|---|---|---|---|---|---|---|---|---|
| ATOM | 9324 | SG | CYS | B1144 | 59.167 | -14.874 | 82.979 | 1.00 56.04 | B |
| ATOM | 9325 | C | CYS | B1144 | 60.038 | -14.273 | 86.032 | 1.00 56.04 | B |
| ATOM | 9326 | O | CYS | B1144 | 60.049 | -13.117 | 86.474 | 1.00 56.04 | B |
| ATOM | 9327 | N | ARG | B1145 | 61.157 | -14.950 | 85.765 | 1.00 56.04 | B |
| ATOM | 9328 | CA | ARG | B1145 | 62.461 | -14.324 | 85.979 | 1.00 56.04 | B |
| ATOM | 9329 | CB | ARG | B1145 | 63.599 | -15.148 | 85.360 | 1.00 56.04 | B |
| ATOM | 9330 | CG | ARG | B1145 | 64.040 | -16.389 | 86.138 | 1.00 56.04 | B |
| ATOM | 9331 | CD | ARG | B1145 | 63.696 | -17.702 | 85.393 | 1.00 56.04 | B |
| ATOM | 9332 | NE | ARG | B1145 | 64.253 | -18.922 | 86.011 | 1.00 56.04 | B |
| ATOM | 9333 | CZ | ARG | B1145 | 65.509 | -19.359 | 85.863 | 1.00 56.04 | B |
| ATOM | 9334 | NH1 | ARG | B1145 | 66.367 | -18.680 | 85.108 | 1.00 56.04 | B |
| ATOM | 9335 | NH2 | ARG | B1145 | 65.908 | -20.479 | 86.467 | 1.00 56.04 | B |
| ATOM | 9336 | C | ARG | B1145 | 62.439 | -12.966 | 85.303 | 1.00 56.04 | B |
| ATOM | 9337 | O | ARG | B1145 | 62.273 | -11.928 | 85.949 | 1.00 56.04 | B |
| ATOM | 9338 | N | ASP | B1146 | 62.571 | -13.008 | 83.981 | 1.00 56.04 | B |
| ATOM | 9339 | CA | ASP | B1146 | 62.617 | -11.821 | 83.136 | 1.00 56.04 | B |
| ATOM | 9340 | CB | ASP | B1146 | 63.440 | -12.140 | 81.900 | 1.00 56.04 | B |
| ATOM | 9341 | CG | ASP | B1146 | 62.855 | -13.298 | 81.109 | 1.00 56.04 | B |
| ATOM | 9342 | OD1 | ASP | B1146 | 63.512 | -13.779 | 80.150 | 1.00 56.04 | B |
| ATOM | 9343 | OD2 | ASP | B1146 | 61.723 | -13.724 | 81.455 | 1.00 56.04 | B |
| ATOM | 9344 | C | ASP | B1146 | 61.263 | -11.308 | 82.692 | 1.00 56.04 | B |
| ATOM | 9345 | O | ASP | B1146 | 61.184 | -10.319 | 81.970 | 1.00 56.04 | B |
| ATOM | 9346 | N | GLY | B1147 | 60.202 | -11.979 | 83.110 | 1.00 56.04 | B |
| ATOM | 9347 | CA | GLY | B1147 | 58.886 | -11.545 | 82.698 | 1.00 56.04 | B |
| ATOM | 9348 | C | GLY | B1147 | 58.856 | -11.459 | 81.187 | 1.00 56.04 | B |
| ATOM | 9349 | O | GLY | B1147 | 58.234 | -10.569 | 80.613 | 1.00 56.04 | B |
| ATOM | 9350 | N | SER | B1148 | 59.544 | -12.393 | 80.539 | 1.00 56.04 | B |
| ATOM | 9351 | CA | SER | B1148 | 59.599 | -12.420 | 79.085 | 1.00 56.04 | B |
| ATOM | 9352 | CB | SER | B1148 | 60.668 | -11.449 | 78.579 | 1.00 56.04 | B |
| ATOM | 9353 | OG | SER | B1148 | 60.438 | -10.140 | 79.060 | 1.00 56.04 | B |
| ATOM | 9354 | C | SER | B1148 | 59.864 | -13.809 | 78.508 | 1.00 56.04 | B |
| ATOM | 9355 | O | SER | B1148 | 59.036 | -14.333 | 77.766 | 1.00 56.04 | B |
| ATOM | 9356 | N | GLN | B1149 | 61.007 | -14.403 | 78.844 | 1.00 56.04 | B |
| ATOM | 9357 | CA | GLN | B1149 | 61.354 | -15.721 | 78.315 | 1.00 56.04 | B |
| ATOM | 9358 | CB | GLN | B1149 | 62.667 | -16.239 | 78.942 | 1.00 56.04 | B |
| ATOM | 9359 | CG | GLN | B1149 | 63.708 | -16.743 | 77.910 | 1.00 56.04 | B |
| ATOM | 9360 | CD | GLN | B1149 | 64.074 | -18.232 | 78.057 | 1.00 56.04 | B |
| ATOM | 9361 | OE1 | GLN | B1149 | 64.573 | -18.661 | 79.094 | 1.00 56.04 | B |
| ATOM | 9362 | NE2 | GLN | B1149 | 63.832 | -19.014 | 77.004 | 1.00 56.04 | B |
| ATOM | 9363 | C | GLN | B1149 | 60.232 | -16.734 | 78.539 | 1.00 56.04 | B |
| ATOM | 9364 | O | GLN | B1149 | 60.052 | -17.668 | 77.753 | 1.00 56.04 | B |
| ATOM | 9365 | N | GLN | B1150 | 59.476 | -16.551 | 79.611 | 1.00 56.04 | B |
| ATOM | 9366 | CA | GLN | B1150 | 58.396 | -17.467 | 79.886 | 1.00 56.04 | B |
| ATOM | 9367 | CB | GLN | B1150 | 58.589 | -18.118 | 81.239 | 1.00 56.04 | B |
| ATOM | 9368 | CG | GLN | B1150 | 57.921 | -19.472 | 81.347 | 1.00 56.04 | B |
| ATOM | 9369 | CD | GLN | B1150 | 58.186 | -20.131 | 82.683 | 1.00 56.04 | B |
| ATOM | 9370 | OE1 | GLN | B1150 | 59.296 | -20.039 | 83.222 | 1.00 56.04 | B |
| ATOM | 9371 | NE2 | GLN | B1150 | 57.178 | -20.809 | 83.225 | 1.00 56.04 | B |
| ATOM | 9372 | C | GLN | B1150 | 57.098 | -16.696 | 79.874 | 1.00 56.04 | B |
| ATOM | 9373 | O | GLN | B1150 | 56.137 | -17.089 | 79.207 | 1.00 56.04 | B |
| ATOM | 9374 | N | THR | B1151 | 57.076 | -15.593 | 80.619 | 1.00 56.04 | B |
| ATOM | 9375 | CA | THR | B1151 | 55.896 | -14.723 | 80.705 | 1.00 56.04 | B |
| ATOM | 9376 | CB | THR | B1151 | 56.251 | -13.321 | 81.282 | 1.00 56.04 | B |
| ATOM | 9377 | OG1 | THR | B1151 | 56.703 | -13.445 | 82.640 | 1.00 56.04 | B |
| ATOM | 9378 | CG2 | THR | B1151 | 55.034 | -12.401 | 81.230 | 1.00 56.04 | B |
| ATOM | 9379 | C | THR | B1151 | 55.314 | -14.514 | 79.317 | 1.00 56.04 | B |
| ATOM | 9380 | O | THR | B1151 | 54.097 | -14.518 | 79.135 | 1.00 56.04 | B |

Figure 4 D
(Continued)

| ATOM | 9381 | N | GLY B1152 | 56.202 | -14.321 | 78.347 | 1.00 | 56.04 | B |
|------|------|-----|----------|---------|---------|---------|------|-------|---|
| ATOM | 9382 | CA | GLY B1152 | 55.771 | -14.119 | 76.983 | 1.00 | 56.04 | B |
| ATOM | 9383 | C | GLY B1152 | 54.788 | -15.177 | 76.519 | 1.00 | 56.04 | B |
| ATOM | 9384 | O | GLY B1152 | 53.588 | -14.911 | 76.384 | 1.00 | 56.04 | B |
| ATOM | 9385 | N | ILE B1153 | 55.297 | -16.383 | 76.281 | 1.00 | 56.04 | B |
| ATOM | 9386 | CA | ILE B1153 | 54.481 | -17.496 | 75.819 | 1.00 | 56.04 | B |
| ATOM | 9387 | CB | ILE B1153 | 55.180 | -18.834 | 76.113 | 1.00 | 56.04 | B |
| ATOM | 9388 | CG2 | ILE B1153 | 54.216 | -19.994 | 75.909 | 1.00 | 56.04 | B |
| ATOM | 9389 | CG1 | ILE B1153 | 56.393 | -18.979 | 75.200 | 1.00 | 56.04 | B |
| ATOM | 9390 | CD1 | ILE B1153 | 57.063 | -20.308 | 75.300 | 1.00 | 56.04 | B |
| ATOM | 9391 | C | ILE B1153 | 53.071 | -17.519 | 76.400 | 1.00 | 56.04 | B |
| ATOM | 9392 | O | ILE B1153 | 52.135 | -17.947 | 75.734 | 1.00 | 56.04 | B |
| ATOM | 9393 | N | PHE B1154 | 52.910 | -17.064 | 77.635 | 1.00 | 56.04 | B |
| ATOM | 9394 | CA | PHE B1154 | 51.587 | -17.050 | 78.229 | 1.00 | 56.04 | B |
| ATOM | 9395 | CB | PHE B1154 | 51.641 | -16.555 | 79.675 | 1.00 | 56.04 | B |
| ATOM | 9396 | CG | PHE B1154 | 50.588 | -17.165 | 80.563 | 1.00 | 56.04 | B |
| ATOM | 9397 | CD1 | PHE B1154 | 50.434 | -18.545 | 80.634 | 1.00 | 56.04 | B |
| ATOM | 9398 | CD2 | PHE B1154 | 49.755 | -16.363 | 81.326 | 1.00 | 56.04 | B |
| ATOM | 9399 | CE1 | PHE B1154 | 49.473 | -19.110 | 81.443 | 1.00 | 56.04 | B |
| ATOM | 9400 | CE2 | PHE B1154 | 48.785 | -16.920 | 82.144 | 1.00 | 56.04 | B |
| ATOM | 9401 | CZ | PHE B1154 | 48.642 | -18.296 | 82.202 | 1.00 | 56.04 | B |
| ATOM | 9402 | C | PHE B1154 | 50.751 | -16.113 | 77.391 | 1.00 | 56.04 | B |
| ATOM | 9403 | O | PHE B1154 | 49.775 | -16.525 | 76.771 | 1.00 | 56.04 | B |
| ATOM | 9404 | N | CYS B1155 | 51.146 | -14.849 | 77.360 | 1.00 | 56.04 | B |
| ATOM | 9405 | CA | CYS B1155 | 50.427 | -13.864 | 76.573 | 1.00 | 56.04 | B |
| ATOM | 9406 | CB | CYS B1155 | 51.291 | -12.636 | 76.382 | 1.00 | 56.04 | B |
| ATOM | 9407 | SG | CYS B1155 | 51.769 | -11.982 | 77.965 | 1.00 | 56.04 | B |
| ATOM | 9408 | C | CYS B1155 | 50.058 | -14.457 | 75.231 | 1.00 | 56.04 | B |
| ATOM | 9409 | O | CYS B1155 | 48.880 | -14.562 | 74.894 | 1.00 | 56.04 | B |
| ATOM | 9410 | N | ALA B1156 | 51.070 | -14.864 | 74.477 | 1.00 | 56.04 | B |
| ATOM | 9411 | CA | ALA B1156 | 50.850 | -15.471 | 73.172 | 1.00 | 56.04 | B |
| ATOM | 9412 | CB | ALA B1156 | 52.043 | -16.332 | 72.794 | 1.00 | 56.04 | B |
| ATOM | 9413 | C | ALA B1156 | 49.588 | -16.320 | 73.174 | 1.00 | 56.04 | B |
| ATOM | 9414 | O | ALA B1156 | 48.550 | -15.907 | 72.673 | 1.00 | 56.04 | B |
| ATOM | 9415 | N | LEU B1157 | 49.684 | -17.509 | 73.745 | 1.00 | 56.04 | B |
| ATOM | 9416 | CA | LEU B1157 | 48.541 | -18.396 | 73.802 | 1.00 | 56.04 | B |
| ATOM | 9417 | CB | LEU B1157 | 48.854 | -19.603 | 74.681 | 1.00 | 56.04 | B |
| ATOM | 9418 | CG | LEU B1157 | 49.987 | -20.524 | 74.215 | 1.00 | 56.04 | B |
| ATOM | 9419 | CD1 | LEU B1157 | 50.268 | -21.557 | 75.302 | 1.00 | 56.04 | B |
| ATOM | 9420 | CD2 | LEU B1157 | 49.616 | -21.205 | 72.898 | 1.00 | 56.04 | B |
| ATOM | 9421 | C | LEU B1157 | 47.335 | -17.667 | 74.356 | 1.00 | 56.04 | B |
| ATOM | 9422 | O | LEU B1157 | 46.210 | -17.874 | 73.907 | 1.00 | 56.04 | B |
| ATOM | 9423 | N | LEU B1158 | 47.570 | -16.800 | 75.327 | 1.00 | 56.04 | B |
| ATOM | 9424 | CA | LEU B1158 | 46.468 | -16.082 | 75.925 | 1.00 | 56.04 | B |
| ATOM | 9425 | CB | LEU B1158 | 46.970 | -15.131 | 77.005 | 1.00 | 56.04 | B |
| ATOM | 9426 | CG | LEU B1158 | 45.943 | -14.785 | 78.089 | 1.00 | 56.04 | B |
| ATOM | 9427 | CD1 | LEU B1158 | 44.772 | -14.031 | 77.486 | 1.00 | 56.04 | B |
| ATOM | 9428 | CD2 | LEU B1158 | 45.461 | -16.064 | 78.758 | 1.00 | 56.04 | B |
| ATOM | 9429 | C | LEU B1158 | 45.694 | -15.317 | 74.868 | 1.00 | 56.04 | B |
| ATOM | 9430 | O | LEU B1158 | 44.466 | -15.282 | 74.892 | 1.00 | 56.04 | B |
| ATOM | 9643 | N | MET B1186 | 60.629 | -11.988 | 74.463 | 1.00 | 56.04 | B |
| ATOM | 9644 | CA | MET B1186 | 59.493 | -12.663 | 73.841 | 1.00 | 56.04 | B |
| ATOM | 9645 | CB | MET B1186 | 58.580 | -11.623 | 73.190 | 1.00 | 56.04 | B |
| ATOM | 9646 | CG | MET B1186 | 58.169 | -10.510 | 74.128 | 1.00 | 56.04 | B |
| ATOM | 9647 | SD | MET B1186 | 57.480 | -11.241 | 75.594 | 1.00 | 56.04 | B |
| ATOM | 9648 | CE | MET B1186 | 56.194 | -12.122 | 74.878 | 1.00 | 56.04 | B |
| ATOM | 9649 | C | MET B1186 | 59.957 | -13.658 | 72.789 | 1.00 | 56.04 | B |

Figure 4 D
(Continued)

| ATOM | 9650 | O   | MET B1186 | 60.870 | -13.361 | 72.019 | 1.00 | 56.04 | B |
| ---- | ---- | --- | --------- | ------ | ------- | ------ | ---- | ----- | - |
| ATOM | 9651 | N   | VAL B1187 | 59.312 | -14.823 | 72.763 | 1.00 | 56.04 | B |
| ATOM | 9652 | CA  | VAL B1187 | 59.648 | -15.891 | 71.830 | 1.00 | 56.04 | B |
| ATOM | 9653 | CB  | VAL B1187 | 58.524 | -16.183 | 70.851 | 1.00 | 56.04 | B |
| ATOM | 9654 | CG1 | VAL B1187 | 58.874 | -17.421 | 70.035 | 1.00 | 56.04 | B |
| ATOM | 9655 | CG2 | VAL B1187 | 57.233 | -16.362 | 71.592 | 1.00 | 56.04 | B |
| ATOM | 9656 | C   | VAL B1187 | 60.843 | -15.492 | 71.016 | 1.00 | 56.04 | B |
| ATOM | 9657 | O   | VAL B1187 | 60.739 | -14.649 | 70.134 | 1.00 | 56.04 | B |
| ATOM | 9658 | N   | SER B1188 | 61.984 | -16.085 | 71.305 | 1.00 | 56.04 | B |
| ATOM | 9659 | CA  | SER B1188 | 63.175 | -15.732 | 70.568 | 1.00 | 56.04 | B |
| ATOM | 9660 | CB  | SER B1188 | 64.161 | -15.050 | 71.509 | 1.00 | 56.04 | B |
| ATOM | 9661 | OG  | SER B1188 | 63.497 | -14.051 | 72.266 | 1.00 | 56.04 | B |
| ATOM | 9662 | C   | SER B1188 | 63.775 | -16.991 | 69.979 | 1.00 | 56.04 | B |
| ATOM | 9663 | O   | SER B1188 | 64.735 | -16.947 | 69.205 | 1.00 | 56.04 | B |
| ATOM | 9664 | N   | THR B1189 | 63.189 | -18.119 | 70.354 | 1.00 | 56.04 | B |
| ATOM | 9665 | CA  | THR B1189 | 63.671 | -19.395 | 69.877 | 1.00 | 56.04 | B |
| ATOM | 9666 | CB  | THR B1189 | 63.921 | -20.364 | 71.019 | 1.00 | 56.04 | B |
| ATOM | 9667 | OG1 | THR B1189 | 62.664 | -20.873 | 71.473 | 1.00 | 56.04 | B |
| ATOM | 9668 | CG2 | THR B1189 | 64.600 | -19.663 | 72.177 | 1.00 | 56.04 | B |
| ATOM | 9669 | C   | THR B1189 | 62.609 | -20.019 | 69.014 | 1.00 | 56.04 | B |
| ATOM | 9670 | O   | THR B1189 | 61.411 | -19.767 | 69.201 | 1.00 | 56.04 | B |
| ATOM | 9671 | N   | PHE B1190 | 63.057 | -20.839 | 68.069 | 1.00 | 56.04 | B |
| ATOM | 9672 | CA  | PHE B1190 | 62.149 | -21.541 | 67.183 | 1.00 | 56.04 | B |
| ATOM | 9673 | CB  | PHE B1190 | 62.940 | -22.306 | 66.118 | 1.00 | 56.04 | B |
| ATOM | 9674 | CG  | PHE B1190 | 62.096 | -23.227 | 65.287 | 1.00 | 56.04 | B |
| ATOM | 9675 | CD1 | PHE B1190 | 61.046 | -22.727 | 64.516 | 1.00 | 56.04 | B |
| ATOM | 9676 | CD2 | PHE B1190 | 62.327 | -24.598 | 65.305 | 1.00 | 56.04 | B |
| ATOM | 9677 | CE1 | PHE B1190 | 60.237 | -23.579 | 63.775 | 1.00 | 56.04 | B |
| ATOM | 9678 | CE2 | PHE B1190 | 61.527 | -25.459 | 64.572 | 1.00 | 56.04 | B |
| ATOM | 9679 | CZ  | PHE B1190 | 60.476 | -24.950 | 63.804 | 1.00 | 56.04 | B |
| ATOM | 9680 | C   | PHE B1190 | 61.354 | -22.510 | 68.058 | 1.00 | 56.04 | B |
| ATOM | 9681 | O   | PHE B1190 | 60.230 | -22.887 | 67.725 | 1.00 | 56.04 | B |
| ATOM | 9682 | N   | GLU B1191 | 61.949 | -22.912 | 69.180 | 1.00 | 56.04 | B |
| ATOM | 9683 | CA  | GLU B1191 | 61.278 | -23.817 | 70.098 | 1.00 | 56.04 | B |
| ATOM | 9684 | CB  | GLU B1191 | 62.120 | -24.100 | 71.348 | 1.00 | 56.04 | B |
| ATOM | 9685 | CG  | GLU B1191 | 63.397 | -24.909 | 71.170 | 1.00 | 56.04 | B |
| ATOM | 9686 | CD  | GLU B1191 | 63.746 | -25.689 | 72.439 | 1.00 | 56.04 | B |
| ATOM | 9687 | OE1 | GLU B1191 | 63.090 | -26.732 | 72.676 | 1.00 | 56.04 | B |
| ATOM | 9688 | OE2 | GLU B1191 | 64.656 | -25.260 | 73.199 | 1.00 | 56.04 | B |
| ATOM | 9689 | C   | GLU B1191 | 60.013 | -23.125 | 70.546 | 1.00 | 56.04 | B |
| ATOM | 9690 | O   | GLU B1191 | 58.913 | -23.547 | 70.217 | 1.00 | 56.04 | B |
| ATOM | 9691 | N   | GLN B1192 | 60.195 | -22.061 | 71.318 | 1.00 | 56.04 | B |
| ATOM | 9692 | CA  | GLN B1192 | 59.090 | -21.280 | 71.839 | 1.00 | 56.04 | B |
| ATOM | 9693 | CB  | GLN B1192 | 59.598 | -19.908 | 72.285 | 1.00 | 56.04 | B |
| ATOM | 9694 | CG  | GLN B1192 | 60.227 | -19.902 | 73.673 | 1.00 | 56.04 | B |
| ATOM | 9695 | CD  | GLN B1192 | 60.930 | -18.597 | 73.979 | 1.00 | 56.04 | B |
| ATOM | 9696 | OE1 | GLN B1192 | 61.121 | -18.233 | 75.147 | 1.00 | 56.04 | B |
| ATOM | 9697 | NE2 | GLN B1192 | 61.337 | -17.886 | 72.923 | 1.00 | 56.04 | B |
| ATOM | 9698 | C   | GLN B1192 | 58.038 | -21.128 | 70.759 | 1.00 | 56.04 | B |
| ATOM | 9699 | O   | GLN B1192 | 56.855 | -21.455 | 70.960 | 1.00 | 56.04 | B |
| ATOM | 9700 | N   | TYR B1193 | 58.496 | -20.638 | 69.609 | 1.00 | 56.04 | B |
| ATOM | 9701 | CA  | TYR B1193 | 57.644 | -20.430 | 68.449 | 1.00 | 56.04 | B |
| ATOM | 9702 | CB  | TYR B1193 | 58.492 | -20.018 | 67.249 | 1.00 | 56.04 | B |
| ATOM | 9703 | CG  | TYR B1193 | 57.678 | -19.463 | 66.102 | 1.00 | 56.04 | B |
| ATOM | 9704 | CD1 | TYR B1193 | 57.140 | -18.184 | 66.165 | 1.00 | 56.04 | B |
| ATOM | 9705 | CE1 | TYR B1193 | 56.389 | -17.667 | 65.123 | 1.00 | 56.04 | B |
| ATOM | 9706 | CD2 | TYR B1193 | 57.438 | -20.220 | 64.957 | 1.00 | 56.04 | B |

Figure 4 D
(Continued)

| | | | | | | | | | |
|---|---|---|---|---|---|---|---|---|---|
| ATOM | 9707 | CE2 | TYR | B1193 | 56.685 | -19.713 | 63.906 | 1.00 56.04 | B |
| ATOM | 9708 | CZ | TYR | B1193 | 56.162 | -18.432 | 63.997 | 1.00 56.04 | B |
| ATOM | 9709 | OH | TYR | B1193 | 55.404 | -17.910 | 62.969 | 1.00 56.04 | B |
| ATOM | 9710 | C | TYR | B1193 | 56.871 | -21.710 | 68.114 | 1.00 56.04 | B |
| ATOM | 9711 | O | TYR | B1193 | 55.637 | -21.734 | 68.185 | 1.00 56.04 | B |
| ATOM | 9712 | N | GLN | B1194 | 57.595 | -22.772 | 67.754 | 1.00 56.04 | B |
| ATOM | 9713 | CA | GLN | B1194 | 56.954 | -24.038 | 67.425 | 1.00 56.04 | B |
| ATOM | 9714 | CB | GLN | B1194 | 57.975 | -25.165 | 67.269 | 1.00 56.04 | B |
| ATOM | 9715 | CG | GLN | B1194 | 57.319 | -26.471 | 66.813 | 1.00 56.04 | B |
| ATOM | 9716 | CD | GLN | B1194 | 58.300 | -27.619 | 66.583 | 1.00 56.04 | B |
| ATOM | 9717 | OE1 | GLN | B1194 | 59.375 | -27.434 | 65.999 | 1.00 56.04 | B |
| ATOM | 9718 | NE2 | GLN | B1194 | 57.917 | -28.820 | 67.024 | 1.00 56.04 | B |
| ATOM | 9719 | C | GLN | B1194 | 55.956 | -24.440 | 68.499 | 1.00 56.04 | B |
| ATOM | 9720 | O | GLN | B1194 | 54.840 | -24.855 | 68.184 | 1.00 56.04 | B |
| ATOM | 9721 | N | PHE | B1195 | 56.348 | -24.318 | 69.766 | 1.00 56.04 | B |
| ATOM | 9722 | CA | PHE | B1195 | 55.451 | -24.685 | 70.854 | 1.00 56.04 | B |
| ATOM | 9723 | CB | PHE | B1195 | 55.907 | -24.119 | 72.189 | 1.00 56.04 | B |
| ATOM | 9724 | CG | PHE | B1195 | 54.995 | -24.489 | 73.325 | 1.00 56.04 | B |
| ATOM | 9725 | CD1 | PHE | B1195 | 54.714 | -25.829 | 73.594 | 1.00 56.04 | B |
| ATOM | 9726 | CD2 | PHE | B1195 | 54.413 | -23.509 | 74.126 | 1.00 56.04 | B |
| ATOM | 9727 | CE1 | PHE | B1195 | 53.864 | -26.185 | 74.650 | 1.00 56.04 | B |
| ATOM | 9728 | CE2 | PHE | B1195 | 53.563 | -23.856 | 75.182 | 1.00 56.04 | B |
| ATOM | 9729 | CZ | PHE | B1195 | 53.289 | -25.193 | 75.444 | 1.00 56.04 | B |
| ATOM | 9730 | C | PHE | B1195 | 54.078 | -24.140 | 70.571 | 1.00 56.04 | B |
| ATOM | 9731 | O | PHE | B1195 | 53.122 | -24.898 | 70.390 | 1.00 56.04 | B |
| ATOM | 9732 | N | LEU | B1196 | 54.002 | -22.813 | 70.538 | 1.00 56.04 | B |
| ATOM | 9733 | CA | LEU | B1196 | 52.757 | -22.120 | 70.269 | 1.00 56.04 | B |
| ATOM | 9734 | CB | LEU | B1196 | 53.054 | -20.781 | 69.608 | 1.00 56.04 | B |
| ATOM | 9735 | CG | LEU | B1196 | 53.974 | -19.901 | 70.445 | 1.00 56.04 | B |
| ATOM | 9736 | CD1 | LEU | B1196 | 54.120 | -18.547 | 69.799 | 1.00 56.04 | B |
| ATOM | 9737 | CD2 | LEU | B1196 | 53.391 | -19.755 | 71.829 | 1.00 56.04 | B |
| ATOM | 9738 | C | LEU | B1196 | 51.871 | -22.967 | 69.370 | 1.00 56.04 | B |
| ATOM | 9739 | O | LEU | B1196 | 50.815 | -23.444 | 69.794 | 1.00 56.04 | B |
| ATOM | 9740 | N | TYR | B1197 | 52.308 | -23.174 | 68.134 | 1.00 56.04 | B |
| ATOM | 9741 | CA | TYR | B1197 | 51.529 | -23.976 | 67.208 | 1.00 56.04 | B |
| ATOM | 9742 | CB | TYR | B1197 | 52.341 | -24.280 | 65.951 | 1.00 56.04 | B |
| ATOM | 9743 | CG | TYR | B1197 | 52.442 | -23.085 | 65.040 | 1.00 56.04 | B |
| ATOM | 9744 | CD1 | TYR | B1197 | 51.585 | -22.940 | 63.955 | 1.00 56.04 | B |
| ATOM | 9745 | CE1 | TYR | B1197 | 51.627 | -21.802 | 63.154 | 1.00 56.04 | B |
| ATOM | 9746 | CD2 | TYR | B1197 | 53.349 | -22.063 | 65.304 | 1.00 56.04 | B |
| ATOM | 9747 | CE2 | TYR | B1197 | 53.397 | -20.923 | 64.513 | 1.00 56.04 | B |
| ATOM | 9748 | CZ | TYR | B1197 | 52.535 | -20.798 | 63.440 | 1.00 56.04 | B |
| ATOM | 9749 | OH | TYR | B1197 | 52.584 | -19.671 | 62.653 | 1.00 56.04 | B |
| ATOM | 9750 | C | TYR | B1197 | 51.112 | -25.255 | 67.891 | 1.00 56.04 | B |
| ATOM | 9751 | O | TYR | B1197 | 50.022 | -25.322 | 68.468 | 1.00 56.04 | B |
| ATOM | 9752 | N | ASP | B1198 | 51.989 | -26.255 | 67.835 | 1.00 56.04 | B |
| ATOM | 9753 | CA | ASP | B1198 | 51.731 | -27.554 | 68.448 | 1.00 56.04 | B |
| ATOM | 9754 | CB | ASP | B1198 | 52.993 | -28.080 | 69.138 | 1.00 56.04 | B |
| ATOM | 9755 | CG | ASP | B1198 | 54.162 | -28.271 | 68.167 | 1.00 56.04 | B |
| ATOM | 9756 | OD1 | ASP | B1198 | 53.963 | -28.949 | 67.126 | 1.00 56.04 | B |
| ATOM | 9757 | OD2 | ASP | B1198 | 55.276 | -27.753 | 68.445 | 1.00 56.04 | B |
| ATOM | 9758 | C | ASP | B1198 | 50.621 | -27.392 | 69.462 | 1.00 56.04 | B |
| ATOM | 9759 | O | ASP | B1198 | 49.568 | -28.020 | 69.353 | 1.00 56.04 | B |
| ATOM | 9760 | N | VAL | B1199 | 50.860 | -26.516 | 70.432 | 1.00 56.04 | B |
| ATOM | 9761 | CA | VAL | B1199 | 49.880 | -26.239 | 71.458 | 1.00 56.04 | B |
| ATOM | 9762 | CB | VAL | B1199 | 50.253 | -24.996 | 72.256 | 1.00 56.04 | B |
| ATOM | 9763 | CG1 | VAL | B1199 | 49.298 | -24.808 | 73.398 | 1.00 56.04 | B |

Figure 4 D
(Continued)

| ATOM | 9764 | CG2 | VAL B1199 | 51.642 | -25.123 | 72.757 | 1.00 | 56.04 | B |
| ATOM | 9765 | C | VAL B1199 | 48.530 | -25.991 | 70.803 | 1.00 | 56.04 | B |
| ATOM | 9766 | O | VAL B1199 | 47.724 | -26.909 | 70.659 | 1.00 | 56.04 | B |

Figure 4 D
(Continued)

Refined atomic coordinates from space group P2(1)
a= 84.90 b=57.92 c= 159.29 alpha= 90.00
beta= 98.66 gamma= 90.00

(8a)Active site D1 domain molecule A

| ATOM | 461 | N   | ASN | A | 654 | 28.050 | -16.434 | 49.879 | 1.00 | 71.42 | A |
|------|-----|-----|-----|---|-----|--------|---------|--------|------|-------|---|
| ATOM | 462 | CA  | ASN | A | 654 | 28.688 | -15.938 | 51.090 | 1.00 | 70.77 | A |
| ATOM | 463 | CB  | ASN | A | 654 | 30.207 | -16.077 | 51.013 | 1.00 | 72.72 | A |
| ATOM | 464 | CG  | ASN | A | 654 | 30.678 | -17.439 | 51.428 | 1.00 | 74.05 | A |
| ATOM | 465 | OD1 | ASN | A | 654 | 30.352 | -18.437 | 50.797 | 1.00 | 76.12 | A |
| ATOM | 466 | ND2 | ASN | A | 654 | 31.446 | -17.493 | 52.503 | 1.00 | 75.61 | A |
| ATOM | 467 | C   | ASN | A | 654 | 28.335 | -14.469 | 51.247 | 1.00 | 69.16 | A |
| ATOM | 468 | O   | ASN | A | 654 | 28.587 | -13.876 | 52.287 | 1.00 | 69.13 | A |
| ATOM | 469 | N   | LYS | A | 655 | 27.743 | -13.892 | 50.208 | 1.00 | 66.96 | A |
| ATOM | 470 | CA  | LYS | A | 655 | 27.376 | -12.490 | 50.219 | 1.00 | 65.08 | A |
| ATOM | 471 | CB  | LYS | A | 655 | 27.375 | -11.963 | 48.795 | 1.00 | 63.20 | A |
| ATOM | 472 | CG  | LYS | A | 655 | 28.655 | -12.259 | 48.062 | 1.00 | 60.77 | A |
| ATOM | 473 | CD  | LYS | A | 655 | 28.631 | -11.705 | 46.666 | 1.00 | 59.76 | A |
| ATOM | 474 | CE  | LYS | A | 655 | 29.915 | -12.026 | 45.960 | 1.00 | 60.88 | A |
| ATOM | 475 | NZ  | LYS | A | 655 | 29.949 | -11.451 | 44.597 | 1.00 | 62.77 | A |
| ATOM | 476 | C   | LYS | A | 655 | 26.028 | -12.224 | 50.873 | 1.00 | 65.89 | A |
| ATOM | 477 | O   | LYS | A | 655 | 25.650 | -11.075 | 51.056 | 1.00 | 66.44 | A |
| ATOM | 478 | N   | ASN | A | 656 | 25.303 | -13.281 | 51.225 | 1.00 | 66.55 | A |
| ATOM | 479 | CA  | ASN | A | 656 | 24.004 | -13.132 | 51.872 | 1.00 | 66.91 | A |
| ATOM | 480 | CB  | ASN | A | 656 | 23.010 | -14.141 | 51.324 | 1.00 | 67.44 | A |

FIG. 8-1

| ATOM | 481 | CG | ASN | A | 656 | 22.734 | -13.928 | 49.866 | 1.00 | 68.17 | A |
|------|-----|-----|-----|---|-----|--------|---------|--------|------|-------|---|
| ATOM | 482 | OD1 | ASN | A | 656 | 22.357 | -12.833 | 49.454 | 1.00 | 68.34 | A |
| ATOM | 483 | ND2 | ASN | A | 656 | 22.920 | -14.970 | 49.067 | 1.00 | 68.13 | A |
| ATOM | 484 | C | ASN | A | 656 | 24.178 | -13.356 | 53.351 | 1.00 | 68.02 | A |
| ATOM | 485 | O | ASN | A | 656 | 25.133 | -14.000 | 53.770 | 1.00 | 69.36 | A |
| ATOM | 486 | N | ARG | A | 657 | 23.258 | -12.825 | 54.146 | 1.00 | 68.09 | A |
| ATOM | 487 | CA | ARG | A | 657 | 23.345 | -12.977 | 55.588 | 1.00 | 69.00 | A |
| ATOM | 488 | CB | ARG | A | 657 | 22.909 | -11.688 | 56.280 | 1.00 | 67.81 | A |
| ATOM | 489 | CG | ARG | A | 657 | 23.806 | -11.261 | 57.403 | 1.00 | 67.56 | A |
| ATOM | 490 | CD | ARG | A | 657 | 23.222 | -10.073 | 58.090 | 1.00 | 68.46 | A |
| ATOM | 491 | NE | ARG | A | 657 | 24.096 | -9.567 | 59.139 | 1.00 | 70.56 | A |
| ATOM | 492 | CZ | ARG | A | 657 | 25.255 | -8.957 | 58.919 | 1.00 | 70.95 | A |
| ATOM | 493 | NH1 | ARG | A | 657 | 25.687 | -8.774 | 57.685 | 1.00 | 70.47 | A |
| ATOM | 494 | NH2 | ARG | A | 657 | 25.980 | -8.521 | 59.935 | 1.00 | 71.24 | A |
| ATOM | 495 | C | ARG | A | 657 | 22.455 | -14.138 | 56.015 | 1.00 | 70.25 | A |
| ATOM | 496 | O | ARG | A | 657 | 22.782 | -14.877 | 56.948 | 1.00 | 70.95 | A |
| ATOM | 497 | N | TYR | A | 658 | 21.330 | -14.284 | 55.319 | 1.00 | 69.90 | A |
| ATOM | 498 | CA | TYR | A | 658 | 20.364 | -15.351 | 55.570 | 1.00 | 70.27 | A |
| ATOM | 499 | CB | TYR | A | 658 | 19.137 | -14.808 | 56.289 | 1.00 | 68.14 | A |
| ATOM | 500 | CG | TYR | A | 658 | 19.458 | -13.845 | 57.391 | 1.00 | 67.32 | A |
| ATOM | 501 | CD1 | TYR | A | 658 | 19.991 | -14.290 | 58.586 | 1.00 | 67.24 | A |
| ATOM | 502 | CE1 | TYR | A | 658 | 20.290 | -13.400 | 59.608 | 1.00 | 67.77 | A |
| ATOM | 503 | CD2 | TYR | A | 658 | 19.231 | -12.480 | 57.240 | 1.00 | 66.80 | A |
| ATOM | 504 | CE2 | TYR | A | 658 | 19.526 | -11.584 | 58.254 | 1.00 | 66.21 | A |
| ATOM | 505 | CZ | TYR | A | 658 | 20.053 | -12.051 | 59.435 | 1.00 | 66.90 | A |
| ATOM | 506 | OH | TYR | A | 658 | 20.324 | -11.187 | 60.462 | 1.00 | 65.94 | A |

FIG. 8-2

| | | | | | | | | | | |
|---|---|---|---|---|---|---|---|---|---|---|
| ATOM | 507 | C | TYR | A | 658 | 19.950 | -15.822 | 54.188 | 1.00 | 71.66 | A |
| ATOM | 508 | O | TYR | A | 658 | 19.815 | -15.006 | 53.290 | 1.00 | 74.26 | A |
| ATOM | 509 | N | VAL | A | 659 | 19.768 | -17.123 | 53.995 | 1.00 | 72.80 | A |
| ATOM | 510 | CA | VAL | A | 659 | 19.355 | -17.622 | 52.688 | 1.00 | 72.87 | A |
| ATOM | 511 | CB | VAL | A | 659 | 19.749 | -19.101 | 52.492 | 1.00 | 73.81 | A |
| ATOM | 512 | CG1 | VAL | A | 659 | 18.964 | -19.989 | 53.470 | 1.00 | 71.96 | A |
| ATOM | 513 | CG2 | VAL | A | 659 | 19.502 | -19.512 | 51.033 | 1.00 | 73.45 | A |
| ATOM | 514 | C | VAL | A | 659 | 17.836 | -17.499 | 52.623 | 1.00 | 72.67 | A |
| ATOM | 515 | O | VAL | A | 659 | 17.208 | -17.785 | 51.602 | 1.00 | 72.00 | A |
| ATOM | 516 | N | ASP | A | 660 | 17.257 | -17.068 | 53.738 | 1.00 | 71.85 | A |
| ATOM | 517 | CA | ASP | A | 660 | 15.817 | -16.887 | 53.850 | 1.00 | 71.06 | A |
| ATOM | 518 | CB | ASP | A | 660 | 15.448 | -16.639 | 55.327 | 1.00 | 73.28 | A |
| ATOM | 519 | CG | ASP | A | 660 | 13.979 | -16.941 | 55.633 | 1.00 | 75.91 | A |
| ATOM | 520 | OD1 | ASP | A | 660 | 13.555 | -18.108 | 55.459 | 1.00 | 77.99 | A |
| ATOM | 521 | OD2 | ASP | A | 660 | 13.244 | -16.022 | 56.052 | 1.00 | 76.97 | A |
| ATOM | 522 | C | ASP | A | 660 | 15.384 | -15.699 | 52.977 | 1.00 | 68.72 | A |
| ATOM | 523 | O | ASP | A | 660 | 14.325 | -15.730 | 52.347 | 1.00 | 67.92 | A |
| ATOM | 524 | N | ILE | A | 661 | 16.232 | -14.671 | 52.934 | 1.00 | 65.45 | A |
| ATOM | 525 | CA | ILE | A | 661 | 15.983 | -13.454 | 52.174 | 1.00 | 61.99 | A |
| ATOM | 526 | CB | ILE | A | 661 | 16.109 | -12.217 | 53.083 | 1.00 | 61.89 | A |
| ATOM | 527 | CG2 | ILE | A | 661 | 15.783 | -10.956 | 52.318 | 1.00 | 63.22 | A |
| ATOM | 528 | CG1 | ILE | A | 661 | 15.127 | -12.318 | 54.240 | 1.00 | 61.76 | A |
| ATOM | 529 | CD1 | ILE | A | 661 | 15.502 | -13.325 | 55.257 | 1.00 | 64.41 | A |
| ATOM | 530 | C | ILE | A | 661 | 16.941 | -13.287 | 50.998 | 1.00 | 60.47 | A |

FIG. 8-3

| ATOM | 531 | O   | ILE | A | 661 | 18.142 | -13.152 | 51.188 | 1.00 | 58.35 | A |
|------|-----|-----|-----|---|-----|--------|---------|--------|------|-------|---|
| ATOM | 532 | N   | LEU | A | 662 | 16.398 | -13.293 | 49.783 | 1.00 | 60.06 | A |
| ATOM | 533 | CA  | LEU | A | 662 | 17.202 | -13.131 | 48.572 | 1.00 | 60.58 | A |
| ATOM | 534 | CB  | LEU | A | 662 | 17.358 | -14.468 | 47.848 | 1.00 | 61.39 | A |
| ATOM | 535 | CG  | LEU | A | 662 | 17.977 | -15.585 | 48.679 | 1.00 | 62.30 | A |
| ATOM | 536 | CD1 | LEU | A | 662 | 18.056 | -16.827 | 47.841 | 1.00 | 63.00 | A |
| ATOM | 537 | CD2 | LEU | A | 662 | 19.354 | -15.172 | 49.160 | 1.00 | 63.33 | A |
| ATOM | 538 | C   | LEU | A | 662 | 16.536 | -12.119 | 47.649 | 1.00 | 60.56 | A |
| ATOM | 539 | O   | LEU | A | 662 | 15.322 | -12.114 | 47.491 | 1.00 | 61.00 | A |
| ATOM | 540 | N   | PRO | A | 663 | 17.328 | -11.247 | 47.016 | 1.00 | 60.85 | A |
| ATOM | 541 | CD  | PRO | A | 663 | 18.794 | -11.129 | 47.020 | 1.00 | 60.89 | A |
| ATOM | 542 | CA  | PRO | A | 663 | 16.738 | -10.253 | 46.129 | 1.00 | 61.44 | A |
| ATOM | 543 | CB  | PRO | A | 663 | 17.887 | -9.271  | 45.922 | 1.00 | 60.62 | A |
| ATOM | 544 | CG  | PRO | A | 663 | 19.048 | -10.161 | 45.882 | 1.00 | 60.18 | A |
| ATOM | 545 | C   | PRO | A | 663 | 16.206 | -10.823 | 44.819 | 1.00 | 62.58 | A |
| ATOM | 546 | O   | PRO | A | 663 | 16.806 | -11.721 | 44.223 | 1.00 | 62.37 | A |
| ATOM | 1065 | N   | THR | A | 727 | 18.782 | -0.393  | 62.840 | 1.00 | 66.57 | A |
| ATOM | 1066 | CA  | THR | A | 727 | 19.201 | -1.625  | 63.525 | 1.00 | 68.14 | A |
| ATOM | 1067 | CB  | THR | A | 727 | 19.495 | -2.798  | 62.522 | 1.00 | 67.12 | A |
| ATOM | 1068 | OG1 | THR | A | 727 | 19.587 | -4.037  | 63.230 | 1.00 | 65.28 | A |
| ATOM | 1069 | CG2 | THR | A | 727 | 20.819 | -2.588  | 61.821 | 1.00 | 66.36 | A |
| ATOM | 1070 | C   | THR | A | 727 | 20.480 | -1.379  | 64.320 | 1.00 | 69.88 | A |
| ATOM | 1071 | O   | THR | A | 727 | 21.056 | -0.287  | 64.298 | 1.00 | 70.47 | A |
| ATOM | 1072 | N   | ARG | A | 728 | 20.918 | -2.409  | 65.026 | 1.00 | 71.00 | A |
| ATOM | 1073 | CA  | ARG | A | 728 | 22.147 | -2.319  | 65.774 | 1.00 | 71.89 | A |
| ATOM | 1074 | CB  | ARG | A | 728 | 21.878 | -2.512  | 67.262 | 1.00 | 72.99 | A |

FIG. 8-4

| | | | | | | | | | |
|---|---|---|---|---|---|---|---|---|---|
| ATOM | 1075 | CG | ARG | A | 728 | 21.077 | -1.381 | 67.893 | 1.00 | 74.75 | A |
| ATOM | 1076 | CD | ARG | A | 728 | 21.210 | -1.402 | 69.407 | 1.00 | 75.06 | A |
| ATOM | 1077 | NE | ARG | A | 728 | 20.392 | -0.387 | 70.058 | 1.00 | 76.39 | A |
| ATOM | 1078 | CZ | ARG | A | 728 | 20.432 | -0.115 | 71.359 | 1.00 | 77.30 | A |
| ATOM | 1079 | NH1 | ARG | A | 728 | 21.257 | -0.782 | 72.153 | 1.00 | 77.53 | A |
| ATOM | 1080 | NH2 | ARG | A | 728 | 19.645 | 0.824 | 71.868 | 1.00 | 78.31 | A |
| ATOM | 1081 | C | ARG | A | 728 | 23.035 | -3.422 | 65.227 | 1.00 | 72.12 | A |
| ATOM | 1082 | O | ARG | A | 728 | 22.534 | -4.417 | 64.700 | 1.00 | 72.12 | A |
| ATOM | 1083 | N | CYS | A | 729 | 24.347 | -3.241 | 65.332 | 1.00 | 71.86 | A |
| ATOM | 1084 | CA | CYS | A | 729 | 25.291 | -4.235 | 64.827 | 1.00 | 72.85 | A |
| ATOM | 1085 | CB | CYS | A | 729 | 26.702 | -3.683 | 64.864 | 1.00 | 72.61 | A |
| ATOM | 1086 | SG | CYS | A | 729 | 26.877 | -2.199 | 63.935 | 1.00 | 74.04 | A |
| ATOM | 1087 | C | CYS | A | 729 | 25.256 | -5.534 | 65.610 | 1.00 | 73.87 | A |
| ATOM | 1088 | O | CYS | A | 729 | 25.520 | -6.609 | 65.072 | 1.00 | 72.73 | A |
| ATOM | 1089 | N | GLU | A | 730 | 24.942 | -5.425 | 66.892 | 1.00 | 75.15 | A |
| ATOM | 1090 | CA | GLU | A | 730 | 24.870 | -6.592 | 67.743 | 1.00 | 76.37 | A |
| ATOM | 1091 | CB | GLU | A | 730 | 25.981 | -6.529 | 68.787 | 1.00 | 77.54 | A |
| ATOM | 1092 | CG | GLU | A | 730 | 27.371 | -6.503 | 68.176 | 1.00 | 77.30 | A |
| ATOM | 1093 | CD | GLU | A | 730 | 27.711 | -7.793 | 67.456 | 1.00 | 77.53 | A |
| ATOM | 1094 | OE1 | GLU | A | 730 | 28.708 | -7.829 | 66.697 | 1.00 | 77.65 | A |
| ATOM | 1095 | OE2 | GLU | A | 730 | 26.980 | -8.779 | 67.659 | 1.00 | 78.09 | A |
| ATOM | 1096 | C | GLU | A | 730 | 23.504 | -6.648 | 68.404 | 1.00 | 77.19 | A |
| ATOM | 1097 | O | GLU | A | 730 | 22.973 | -5.627 | 68.849 | 1.00 | 76.64 | A |
| ATOM | 1098 | N | GLU | A | 731 | 22.939 | -7.850 | 68.450 | 1.00 | 78.92 | A |
| ATOM | 1099 | CA | GLU | A | 731 | 21.624 | -8.087 | 69.042 | 1.00 | 81.24 | A |
| ATOM | 1100 | CB | GLU | A | 731 | 20.529 | -7.904 | 67.998 | 1.00 | 82.58 | A |

FIG. 8-5

| ATOM | 1101 | CG  | GLU | A | 731 | 20.165 | -6.470  | 67.734 | 1.00 | 84.50 | A |
|------|------|-----|-----|---|-----|--------|---------|--------|------|-------|---|
| ATOM | 1102 | CD  | GLU | A | 731 | 19.060 | -6.341  | 66.709 | 1.00 | 84.89 | A |
| ATOM | 1103 | OE1 | GLU | A | 731 | 18.566 | -5.200  | 66.519 | 1.00 | 85.24 | A |
| ATOM | 1104 | OE2 | GLU | A | 731 | 18.700 | -7.377  | 66.098 | 1.00 | 84.01 | A |
| ATOM | 1105 | C   | GLU | A | 731 | 21.526 | -9.496  | 69.604 | 1.00 | 82.32 | A |
| ATOM | 1106 | O   | GLU | A | 731 | 21.454 | -10.476 | 68.849 | 1.00 | 82.59 | A |
| ATOM | 1107 | N   | GLY | A | 732 | 21.505 | -9.595  | 70.928 | 1.00 | 82.66 | A |
| ATOM | 1108 | CA  | GLY | A | 732 | 21.427 | -10.902 | 71.552 | 1.00 | 84.09 | A |
| ATOM | 1109 | C   | GLY | A | 732 | 22.745 | -11.649 | 71.427 | 1.00 | 84.34 | A |
| ATOM | 1110 | O   | GLY | A | 732 | 22.780 | -12.878 | 71.306 | 1.00 | 84.25 | A |
| ATOM | 1111 | N   | ASN | A | 733 | 23.842 | -10.900 | 71.453 | 1.00 | 84.26 | A |
| ATOM | 1112 | CA  | ASN | A | 733 | 25.153 | -11.509 | 71.337 | 1.00 | 83.84 | A |
| ATOM | 1113 | CB  | ASN | A | 733 | 25.372 | -12.469 | 72.497 | 1.00 | 86.43 | A |
| ATOM | 1114 | CG  | ASN | A | 733 | 25.154 | -11.793 | 73.849 | 1.00 | 88.39 | A |
| ATOM | 1115 | OD1 | ASN | A | 733 | 25.712 | -10.720 | 74.116 | 1.00 | 89.03 | A |
| ATOM | 1116 | ND2 | ASN | A | 733 | 24.341 | -12.416 | 74.708 | 1.00 | 88.80 | A |
| ATOM | 1117 | C   | ASN | A | 733 | 25.251 | -12.236 | 70.005 | 1.00 | 82.91 | A |
| ATOM | 1118 | O   | ASN | A | 733 | 26.075 | -13.151 | 69.834 | 1.00 | 83.44 | A |
| ATOM | 1119 | N   | ARG | A | 734 | 24.381 | -11.810 | 69.080 | 1.00 | 80.45 | A |
| ATOM | 1120 | CA  | ARG | A | 734 | 24.298 | -12.306 | 67.707 | 1.00 | 76.80 | A |
| ATOM | 1121 | CB  | ARG | A | 734 | 22.886 | -12.800 | 67.398 | 1.00 | 78.67 | A |
| ATOM | 1122 | CG  | ARG | A | 734 | 22.612 | -14.249 | 67.759 | 1.00 | 82.47 | A |
| ATOM | 1123 | CD  | ARG | A | 734 | 23.003 | -15.222 | 66.641 | 1.00 | 87.41 | A |
| ATOM | 1124 | NE  | ARG | A | 734 | 24.452 | -15.376 | 66.449 | 1.00 | 92.07 | A |
| ATOM | 1125 | CZ  | ARG | A | 734 | 25.225 | -14.585 | 65.694 | 1.00 | 93.81 | A |

FIG. 8-6

| ATOM | 1126 | NH1 | ARG | A | 734 | 24.706 | -13.556 | 65.032 | 1.00 | 94.21 | A |
|---|---|---|---|---|---|---|---|---|---|---|---|
| ATOM | 1127 | NH2 | ARG | A | 734 | 26.530 | -14.827 | 65.593 | 1.00 | 94.12 | A |
| ATOM | 1128 | C | ARG | A | 734 | 24.610 | -11.087 | 66.852 | 1.00 | 74.40 | A |
| ATOM | 1129 | O | ARG | A | 734 | 24.165 | -9.985 | 67.170 | 1.00 | 74.28 | A |
| ATOM | 1130 | N | ASN | A | 735 | 25.386 | -11.267 | 65.790 | 1.00 | 71.61 | A |
| ATOM | 1131 | CA | ASN | A | 735 | 25.741 | -10.152 | 64.915 | 1.00 | 69.66 | A |
| ATOM | 1132 | CB | ASN | A | 735 | 27.088 | -10.438 | 64.244 | 1.00 | 68.99 | A |
| ATOM | 1133 | CG | ASN | A | 735 | 27.604 | -9.269 | 63.438 | 1.00 | 68.46 | A |
| ATOM | 1134 | OD1 | ASN | A | 735 | 26.971 | -8.831 | 62.492 | 1.00 | 68.36 | A |
| ATOM | 1135 | ND2 | ASN | A | 735 | 28.767 | -8.766 | 63.809 | 1.00 | 69.46 | A |
| ATOM | 1136 | C | ASN | A | 735 | 24.647 | -9.922 | 63.866 | 1.00 | 68.55 | A |
| ATOM | 1137 | O | ASN | A | 735 | 24.213 | -10.847 | 63.176 | 1.00 | 69.13 | A |
| ATOM | 1138 | N | LYS | A | 736 | 24.184 | -8.687 | 63.753 | 1.00 | 66.42 | A |
| ATOM | 1139 | CA | LYS | A | 736 | 23.143 | -8.396 | 62.789 | 1.00 | 63.74 | A |
| ATOM | 1140 | CB | LYS | A | 736 | 21.929 | -7.776 | 63.504 | 1.00 | 63.56 | A |
| ATOM | 1141 | CG | LYS | A | 736 | 21.212 | -8.747 | 64.469 | 1.00 | 61.52 | A |
| ATOM | 1142 | CD | LYS | A | 736 | 20.954 | -10.087 | 63.793 | 1.00 | 59.23 | A |
| ATOM | 1143 | CE | LYS | A | 736 | 20.438 | -11.142 | 64.733 | 1.00 | 56.17 | A |
| ATOM | 1144 | NZ | LYS | A | 736 | 20.575 | -12.476 | 64.083 | 1.00 | 52.63 | A |
| ATOM | 1145 | C | LYS | A | 736 | 23.636 | -7.516 | 61.645 | 1.00 | 61.83 | A |
| ATOM | 1146 | O | LYS | A | 736 | 23.083 | -7.553 | 60.556 | 1.00 | 62.52 | A |
| ATOM | 1147 | N | CYS | A | 737 | 24.690 | -6.745 | 61.884 | 1.00 | 59.92 | A |
| ATOM | 1148 | CA | CYS | A | 737 | 25.250 | -5.876 | 60.854 | 1.00 | 57.69 | A |
| ATOM | 1149 | CB | CYS | A | 737 | 24.398 | -4.618 | 60.717 | 1.00 | 57.26 | A |
| ATOM | 1150 | SG | CYS | A | 737 | 24.971 | -3.480 | 59.457 | 1.00 | 56.50 | A |

FIG. 8-7

| ATOM | 1151 | C | CYS | A | 737 | 26.698 | -5.482 | 61.152 | 1.00 | 56.95 | A |
|---|---|---|---|---|---|---|---|---|---|---|---|
| ATOM | 1152 | O | CYS | A | 737 | 27.014 | -5.018 | 62.246 | 1.00 | 55.90 | A |
| ATOM | 1597 | N | THR | A | 792 | 18.306 | 3.329 | 67.037 | 1.00 | 56.52 | A |
| ATOM | 1598 | CA | THR | A | 792 | 18.583 | 2.253 | 67.966 | 1.00 | 57.85 | A |
| ATOM | 1599 | CB | THR | A | 792 | 19.788 | 2.600 | 68.811 | 1.00 | 57.33 | A |
| ATOM | 1600 | OG1 | THR | A | 792 | 19.858 | 4.020 | 68.961 | 1.00 | 56.51 | A |
| ATOM | 1601 | CG2 | THR | A | 792 | 21.044 | 2.084 | 68.169 | 1.00 | 55.11 | A |
| ATOM | 1602 | C | THR | A | 792 | 17.459 | 1.844 | 68.903 | 1.00 | 59.27 | A |
| ATOM | 1603 | O | THR | A | 792 | 17.643 | 0.971 | 69.744 | 1.00 | 60.51 | A |
| ATOM | 1604 | N | SER | A | 793 | 16.297 | 2.458 | 68.780 | 1.00 | 59.64 | A |
| ATOM | 1605 | CA | SER | A | 793 | 15.203 | 2.088 | 69.656 | 1.00 | 60.75 | A |
| ATOM | 1606 | CB | SER | A | 793 | 14.524 | 3.346 | 70.174 | 1.00 | 61.67 | A |
| ATOM | 1607 | OG | SER | A | 793 | 15.473 | 4.219 | 70.760 | 1.00 | 62.69 | A |
| ATOM | 1608 | C | SER | A | 793 | 14.201 | 1.201 | 68.919 | 1.00 | 61.76 | A |
| ATOM | 1609 | O | SER | A | 793 | 13.002 | 1.224 | 69.201 | 1.00 | 62.77 | A |
| ATOM | 1610 | N | TRP | A | 794 | 14.709 | 0.403 | 67.983 | 1.00 | 61.26 | A |
| ATOM | 1611 | CA | TRP | A | 794 | 13.880 | -0.488 | 67.181 | 1.00 | 60.42 | A |
| ATOM | 1612 | CB | TRP | A | 794 | 13.884 | -0.010 | 65.748 | 1.00 | 59.56 | A |
| ATOM | 1613 | CG | TRP | A | 794 | 12.808 | -0.564 | 64.955 | 1.00 | 58.39 | A |
| ATOM | 1614 | CD2 | TRP | A | 794 | 12.188 | 0.051 | 63.836 | 1.00 | 58.01 | A |
| ATOM | 1615 | CE2 | TRP | A | 794 | 11.207 | -0.833 | 63.369 | 1.00 | 58.30 | A |
| ATOM | 1616 | CE3 | TRP | A | 794 | 12.366 | 1.270 | 63.180 | 1.00 | 58.38 | A |
| ATOM | 1617 | CD1 | TRP | A | 794 | 12.204 | -1.763 | 65.124 | 1.00 | 58.40 | A |
| ATOM | 1618 | NE1 | TRP | A | 794 | 11.236 | -1.938 | 64.175 | 1.00 | 59.09 | A |
| ATOM | 1619 | CZ2 | TRP | A | 794 | 10.404 | -0.542 | 62.275 | 1.00 | 58.62 | A |
| ATOM | 1620 | CZ3 | TRP | A | 794 | 11.570 | 1.561 | 62.097 | 1.00 | 58.65 | A |

FIG. 8-8

| ATOM | 1621 | CH2 | TRP | A | 794 | 10.599 | 0.659 | 61.653 | 1.00 | 58.41 | A |
| --- | --- | --- | --- | --- | --- | --- | --- | --- | --- | --- | --- |
| ATOM | 1622 | C | TRP | A | 794 | 14.415 | -1.909 | 67.219 | 1.00 | 61.18 | A |
| ATOM | 1623 | O | TRP | A | 794 | 15.428 | -2.204 | 66.596 | 1.00 | 61.29 | A |
| ATOM | 1624 | N | PRO | A | 795 | 13.737 | -2.808 | 67.948 | 1.00 | 62.15 | A |
| ATOM | 1625 | CD | PRO | A | 795 | 12.748 | -2.448 | 68.977 | 1.00 | 62.31 | A |
| ATOM | 1626 | CA | PRO | A | 795 | 14.130 | -4.218 | 68.089 | 1.00 | 62.95 | A |
| ATOM | 1627 | CB | PRO | A | 795 | 13.339 | -4.682 | 69.315 | 1.00 | 62.69 | A |
| ATOM | 1628 | CG | PRO | A | 795 | 13.089 | -3.416 | 70.077 | 1.00 | 63.42 | A |
| ATOM | 1629 | C | PRO | A | 795 | 13.872 | -5.126 | 66.891 | 1.00 | 63.57 | A |
| ATOM | 1630 | O | PRO | A | 795 | 12.802 | -5.106 | 66.301 | 1.00 | 63.32 | A |
| ATOM | 1631 | N | ASP | A | 796 | 14.871 | -5.931 | 66.556 | 1.00 | 64.06 | A |
| ATOM | 1632 | CA | ASP | A | 796 | 14.804 | -6.888 | 65.457 | 1.00 | 64.96 | A |
| ATOM | 1633 | CB | ASP | A | 796 | 16.017 | -7.823 | 65.565 | 1.00 | 66.50 | A |
| ATOM | 1634 | CG | ASP | A | 796 | 16.136 | -8.791 | 64.408 | 1.00 | 67.68 | A |
| ATOM | 1635 | OD1 | ASP | A | 796 | 15.139 | -9.466 | 64.103 | 1.00 | 67.96 | A |
| ATOM | 1636 | OD2 | ASP | A | 796 | 17.239 | -8.889 | 63.819 | 1.00 | 68.04 | A |
| ATOM | 1637 | C | ASP | A | 796 | 13.501 | -7.678 | 65.610 | 1.00 | 65.33 | A |
| ATOM | 1638 | O | ASP | A | 796 | 13.099 | -7.988 | 66.726 | 1.00 | 66.06 | A |
| ATOM | 1639 | N | HIS | A | 797 | 12.836 | -7.998 | 64.505 | 1.00 | 65.19 | A |
| ATOM | 1640 | CA | HIS | A | 797 | 11.584 | -8.752 | 64.567 | 1.00 | 64.73 | A |
| ATOM | 1641 | CB | HIS | A | 797 | 11.813 | -10.159 | 65.130 | 1.00 | 64.81 | A |
| ATOM | 1642 | CG | HIS | A | 797 | 12.406 | -11.129 | 64.156 | 1.00 | 65.92 | A |
| ATOM | 1643 | CD2 | HIS | A | 797 | 11.851 | -12.166 | 63.486 | 1.00 | 67.43 | A |
| ATOM | 1644 | ND1 | HIS | A | 797 | 13.737 | -11.118 | 63.807 | 1.00 | 65.64 | A |
| ATOM | 1645 | CE1 | HIS | A | 797 | 13.981 | -12.107 | 62.967 | 1.00 | 67.29 | A |
| ATOM | 1646 | NE2 | HIS | A | 797 | 12.852 | -12.760 | 62.756 | 1.00 | 69.01 | A |

FIG. 8-9

| ATOM | 1647 | C | HIS A 797 | 10.506 | -8.095 | 65.423 | 1.00 | 64.75 | A |
| --- | --- | --- | --- | --- | --- | --- | --- | --- | --- |
| ATOM | 1648 | O | HIS A 797 | 9.473 | -8.701 | 65.667 | 1.00 | 63.56 | A |
| ATOM | 1649 | N | GLY A 798 | 10.734 | -6.870 | 65.884 | 1.00 | 65.06 | A |
| ATOM | 1650 | CA | GLY A 798 | 9.739 | -6.212 | 66.721 | 1.00 | 66.05 | A |
| ATOM | 1651 | C | GLY A 798 | 9.529 | -4.738 | 66.434 | 1.00 | 67.10 | A |
| ATOM | 1652 | O | GLY A 798 | 10.036 | -4.224 | 65.449 | 1.00 | 68.68 | A |
| ATOM | 1653 | N | VAL A 799 | 8.795 | -4.042 | 67.297 | 1.00 | 67.83 | A |
| ATOM | 1654 | CA | VAL A 799 | 8.524 | -2.616 | 67.077 | 1.00 | 68.01 | A |
| ATOM | 1655 | CB | VAL A 799 | 7.005 | -2.354 | 66.940 | 1.00 | 67.52 | A |
| ATOM | 1656 | CG1 | VAL A 799 | 6.426 | -3.217 | 65.840 | 1.00 | 66.85 | A |
| ATOM | 1657 | CG2 | VAL A 799 | 6.310 | -2.615 | 68.265 | 1.00 | 66.77 | A |
| ATOM | 1658 | C | VAL A 799 | 9.058 | -1.684 | 68.173 | 1.00 | 68.50 | A |
| ATOM | 1659 | O | VAL A 799 | 9.394 | -2.127 | 69.273 | 1.00 | 68.79 | A |
| ATOM | 1660 | N | PRO A 800 | 9.146 | -0.374 | 67.876 | 1.00 | 68.40 | A |
| ATOM | 1661 | CD | PRO A 800 | 9.084 | 0.222 | 66.534 | 1.00 | 66.96 | A |
| ATOM | 1662 | CA | PRO A 800 | 9.639 | 0.611 | 68.843 | 1.00 | 68.64 | A |
| ATOM | 1663 | CB | PRO A 800 | 9.795 | 1.868 | 68.002 | 1.00 | 67.44 | A |
| ATOM | 1664 | CG | PRO A 800 | 10.072 | 1.332 | 66.663 | 1.00 | 67.07 | A |
| ATOM | 1665 | C | PRO A 800 | 8.665 | 0.819 | 69.995 | 1.00 | 70.22 | A |
| ATOM | 1666 | O | PRO A 800 | 7.572 | 0.267 | 69.998 | 1.00 | 70.60 | A |
| ATOM | 1667 | N | GLU A 801 | 9.070 | 1.637 | 70.961 | 1.00 | 72.72 | A |
| ATOM | 1668 | CA | GLU A 801 | 8.259 | 1.930 | 72.146 | 1.00 | 74.14 | A |
| ATOM | 1669 | CB | GLU A 801 | 9.081 | 2.685 | 73.202 | 1.00 | 76.86 | A |
| ATOM | 1670 | CG | GLU A 801 | 10.449 | 2.100 | 73.564 | 1.00 | 79.83 | A |
| ATOM | 1671 | CD | GLU A 801 | 11.445 | 2.098 | 72.402 | 1.00 | 81.09 | A |

FIG. 8-10

| ATOM | 1672 | OE1 | GLU | A | 801 | 11.577 | 3.122 | 71.688 | 1.00 | 80.87 | A |
| ATOM | 1673 | OE2 | GLU | A | 801 | 12.110 | 1.059 | 72.217 | 1.00 | 82.07 | A |
| ATOM | 1674 | C | GLU | A | 801 | 7.038 | 2.779 | 71.825 | 1.00 | 74.12 | A |
| ATOM | 1675 | O | GLU | A | 801 | 5.973 | 2.590 | 72.410 | 1.00 | 75.37 | A |
| ATOM | 1676 | N | ASP | A | 802 | 7.196 | 3.732 | 70.916 | 1.00 | 72.61 | A |
| ATOM | 1677 | CA | ASP | A | 802 | 6.093 | 4.600 | 70.568 | 1.00 | 72.00 | A |
| ATOM | 1678 | CB | ASP | A | 802 | 6.104 | 5.839 | 71.466 | 1.00 | 73.41 | A |
| ATOM | 1679 | CG | ASP | A | 802 | 5.078 | 6.879 | 71.043 | 1.00 | 75.49 | A |
| ATOM | 1680 | OD1 | ASP | A | 802 | 3.861 | 6.599 | 71.134 | 1.00 | 75.89 | A |
| ATOM | 1681 | OD2 | ASP | A | 802 | 5.492 | 7.980 | 70.611 | 1.00 | 77.48 | A |
| ATOM | 1682 | C | ASP | A | 802 | 6.148 | 5.010 | 69.110 | 1.00 | 70.59 | A |
| ATOM | 1683 | O | ASP | A | 802 | 7.207 | 5.309 | 68.573 | 1.00 | 70.55 | A |
| ATOM | 1684 | N | PRO | A | 803 | 4.993 | 5.014 | 68.444 | 1.00 | 68.82 | A |
| ATOM | 1685 | CD | PRO | A | 803 | 3.712 | 4.440 | 68.894 | 1.00 | 68.40 | A |
| ATOM | 1686 | CA | PRO | A | 803 | 4.920 | 5.393 | 67.038 | 1.00 | 67.12 | A |
| ATOM | 1687 | CB | PRO | A | 803 | 3.422 | 5.342 | 66.764 | 1.00 | 67.38 | A |
| ATOM | 1688 | CG | PRO | A | 803 | 3.001 | 4.169 | 67.583 | 1.00 | 67.27 | A |
| ATOM | 1689 | C | PRO | A | 803 | 5.541 | 6.749 | 66.715 | 1.00 | 65.57 | A |
| ATOM | 1690 | O | PRO | A | 803 | 5.985 | 6.972 | 65.597 | 1.00 | 64.68 | A |
| ATOM | 1891 | N | SER | A | 828 | 18.653 | -2.874 | 57.425 | 1.00 | 57.33 | A |
| ATOM | 1892 | CA | SER | A | 828 | 18.613 | -3.392 | 58.771 | 1.00 | 57.64 | A |
| ATOM | 1893 | CB | SER | A | 828 | 17.168 | -3.709 | 59.194 | 1.00 | 57.54 | A |
| ATOM | 1894 | OG | SER | A | 828 | 16.516 | -4.575 | 58.286 | 1.00 | 58.16 | A |
| ATOM | 1895 | C | SER | A | 828 | 19.475 | -4.646 | 58.747 | 1.00 | 57.58 | A |
| ATOM | 1896 | O | SER | A | 828 | 20.601 | -4.618 | 58.263 | 1.00 | 56.83 | A |
| ATOM | 1897 | N | SER | A | 829 | 18.953 | -5.754 | 59.241 | 1.00 | 58.15 | A |

FIG. 8-11

| ATOM | 1898 | CA  | SER | A | 829 | 19.742 | -6.959 | 59.255 | 1.00 | 58.86 | A |
|------|------|-----|-----|---|-----|--------|--------|--------|------|-------|---|
| ATOM | 1899 | CB  | SER | A | 829 | 19.390 | -7.808 | 60.468 | 1.00 | 60.71 | A |
| ATOM | 1900 | OG  | SER | A | 829 | 20.433 | -8.718 | 60.754 | 1.00 | 61.39 | A |
| ATOM | 1901 | C   | SER | A | 829 | 19.535 | -7.746 | 57.988 | 1.00 | 59.55 | A |
| ATOM | 1902 | O   | SER | A | 829 | 20.498 | -8.059 | 57.303 | 1.00 | 60.85 | A |
| ATOM | 1903 | N   | ALA | A | 830 | 18.288 | -8.067 | 57.664 | 1.00 | 60.12 | A |
| ATOM | 1904 | CA  | ALA | A | 830 | 18.008 | -8.827 | 56.446 | 1.00 | 61.62 | A |
| ATOM | 1905 | CB  | ALA | A | 830 | 16.889 | -9.814 | 56.688 | 1.00 | 61.69 | A |
| ATOM | 1906 | C   | ALA | A | 830 | 17.643 | -7.912 | 55.286 | 1.00 | 62.46 | A |
| ATOM | 1907 | O   | ALA | A | 830 | 17.686 | -8.327 | 54.125 | 1.00 | 63.08 | A |
| ATOM | 1908 | N   | GLY | A | 831 | 17.279 | -6.672 | 55.618 | 1.00 | 62.80 | A |
| ATOM | 1909 | CA  | GLY | A | 831 | 16.902 | -5.690 | 54.621 | 1.00 | 62.02 | A |
| ATOM | 1910 | C   | GLY | A | 831 | 15.450 | -5.825 | 54.218 | 1.00 | 61.87 | A |
| ATOM | 1911 | O   | GLY | A | 831 | 15.070 | -5.459 | 53.114 | 1.00 | 62.36 | A |
| ATOM | 1912 | N   | VAL | A | 832 | 14.629 | -6.353 | 55.111 | 1.00 | 61.60 | A |
| ATOM | 1913 | CA  | VAL | A | 832 | 13.222 | -6.531 | 54.800 | 1.00 | 62.48 | A |
| ATOM | 1914 | CB  | VAL | A | 832 | 12.925 | -8.005 | 54.423 | 1.00 | 60.90 | A |
| ATOM | 1915 | CG1 | VAL | A | 832 | 13.599 | -8.350 | 53.122 | 1.00 | 57.78 | A |
| ATOM | 1916 | CG2 | VAL | A | 832 | 13.422 | -8.938 | 55.508 | 1.00 | 58.78 | A |
| ATOM | 1917 | C   | VAL | A | 832 | 12.295 | -6.096 | 55.942 | 1.00 | 64.79 | A |
| ATOM | 1918 | O   | VAL | A | 832 | 11.388 | -5.285 | 55.739 | 1.00 | 65.48 | A |
| ATOM | 1919 | N   | GLY | A | 833 | 12.540 | -6.620 | 57.143 | 1.00 | 66.52 | A |
| ATOM | 1920 | CA  | GLY | A | 833 | 11.716 | -6.310 | 58.304 | 1.00 | 65.43 | A |
| ATOM | 1921 | C   | GLY | A | 833 | 11.579 | -4.846 | 58.652 | 1.00 | 64.90 | A |
| ATOM | 1922 | O   | GLY | A | 833 | 10.802 | -4.132 | 58.034 | 1.00 | 65.69 | A |
| ATOM | 1923 | N   | ARG | A | 834 | 12.330 | -4.399 | 59.651 | 1.00 | 64.38 | A |

FIG. 8-12

| | | | | | | | | | | |
|---|---|---|---|---|---|---|---|---|---|---|
| ATOM | 1924 | CA  | ARG | A | 834 | 12.284 | -3.015 | 60.097 | 1.00 | 62.11 | A |
| ATOM | 1925 | CB  | ARG | A | 834 | 13.398 | -2.776 | 61.102 | 1.00 | 60.04 | A |
| ATOM | 1926 | CG  | ARG | A | 834 | 13.191 | -3.528 | 62.374 | 1.00 | 59.34 | A |
| ATOM | 1927 | CD  | ARG | A | 834 | 14.442 | -3.539 | 63.188 | 1.00 | 61.06 | A |
| ATOM | 1928 | NE  | ARG | A | 834 | 15.324 | -4.631 | 62.804 | 1.00 | 62.24 | A |
| ATOM | 1929 | CZ  | ARG | A | 834 | 16.559 | -4.776 | 63.262 | 1.00 | 63.06 | A |
| ATOM | 1930 | NH1 | ARG | A | 834 | 17.055 | -3.894 | 64.115 | 1.00 | 63.21 | A |
| ATOM | 1931 | NH2 | ARG | A | 834 | 17.291 | -5.803 | 62.872 | 1.00 | 63.58 | A |
| ATOM | 1932 | C   | ARG | A | 834 | 12.402 | -2.033 | 58.951 | 1.00 | 61.65 | A |
| ATOM | 1933 | O   | ARG | A | 834 | 11.691 | -1.030 | 58.902 | 1.00 | 59.66 | A |
| ATOM | 1934 | N   | THR | A | 835 | 13.306 | -2.335 | 58.027 | 1.00 | 61.78 | A |
| ATOM | 1935 | CA  | THR | A | 835 | 13.534 | -1.482 | 56.874 | 1.00 | 61.96 | A |
| ATOM | 1936 | CB  | THR | A | 835 | 14.691 | -2.010 | 56.020 | 1.00 | 61.73 | A |
| ATOM | 1937 | OG1 | THR | A | 835 | 14.517 | -1.573 | 54.671 | 1.00 | 63.32 | A |
| ATOM | 1938 | CG2 | THR | A | 835 | 14.753 | -3.509 | 56.075 | 1.00 | 62.44 | A |
| ATOM | 1939 | C   | THR | A | 835 | 12.285 | -1.313 | 56.018 | 1.00 | 62.02 | A |
| ATOM | 1940 | O   | THR | A | 835 | 11.868 | -0.192 | 55.745 | 1.00 | 62.36 | A |
| ATOM | 1941 | N   | GLY | A | 836 | 11.680 | -2.413 | 55.598 | 1.00 | 60.53 | A |
| ATOM | 1942 | CA  | GLY | A | 836 | 10.467 | -2.301 | 54.812 | 1.00 | 60.71 | A |
| ATOM | 1943 | C   | GLY | A | 836 | 9.359  | -1.602 | 55.589 | 1.00 | 59.57 | A |
| ATOM | 1944 | O   | GLY | A | 836 | 8.541  | -0.883 | 55.025 | 1.00 | 60.50 | A |
| ATOM | 1945 | N   | THR | A | 837 | 9.330  | -1.820 | 56.896 | 1.00 | 58.37 | A |
| ATOM | 1946 | CA  | THR | A | 837 | 8.334  | -1.203 | 57.750 | 1.00 | 57.43 | A |
| ATOM | 1947 | CB  | THR | A | 837 | 8.529  | -1.642 | 59.202 | 1.00 | 57.10 | A |
| ATOM | 1948 | OG1 | THR | A | 837 | 8.506  | -3.071 | 59.272 | 1.00 | 57.46 | A |

FIG. 8-13

| ATOM | 1949 | CG2 | THR | A | 837 | 7.432 | -1.089 | 60.078 | 1.00 | 55.54 | A |
|---|---|---|---|---|---|---|---|---|---|---|---|
| ATOM | 1950 | C | THR | A | 837 | 8.478 | 0.310 | 57.663 | 1.00 | 57.35 | A |
| ATOM | 1951 | O | THR | A | 837 | 7.498 | 1.028 | 57.466 | 1.00 | 57.09 | A |
| ATOM | 1952 | N | TYR | A | 838 | 9.713 | 0.783 | 57.812 | 1.00 | 57.00 | A |
| ATOM | 1953 | CA | TYR | A | 838 | 10.027 | 2.213 | 57.747 | 1.00 | 55.87 | A |
| ATOM | 1954 | CB | TYR | A | 838 | 11.545 | 2.423 | 57.757 | 1.00 | 52.22 | A |
| ATOM | 1955 | CG | TYR | A | 838 | 11.940 | 3.834 | 57.412 | 1.00 | 48.68 | A |
| ATOM | 1956 | CD1 | TYR | A | 838 | 11.803 | 4.858 | 58.330 | 1.00 | 47.77 | A |
| ATOM | 1957 | CE1 | TYR | A | 838 | 12.053 | 6.166 | 57.979 | 1.00 | 46.16 | A |
| ATOM | 1958 | CD2 | TYR | A | 838 | 12.349 | 4.158 | 56.133 | 1.00 | 48.84 | A |
| ATOM | 1959 | CE2 | TYR | A | 838 | 12.596 | 5.460 | 55.777 | 1.00 | 47.40 | A |
| ATOM | 1960 | CZ | TYR | A | 838 | 12.440 | 6.457 | 56.701 | 1.00 | 46.85 | A |
| ATOM | 1961 | OH | TYR | A | 838 | 12.623 | 7.753 | 56.322 | 1.00 | 46.33 | A |
| ATOM | 1962 | C | TYR | A | 838 | 9.461 | 2.837 | 56.480 | 1.00 | 56.33 | A |
| ATOM | 1963 | O | TYR | A | 838 | 8.717 | 3.822 | 56.519 | 1.00 | 55.54 | A |
| ATOM | 1964 | N | ILE | A | 839 | 9.859 | 2.252 | 55.355 | 1.00 | 56.22 | A |
| ATOM | 1965 | CA | ILE | A | 839 | 9.431 | 2.688 | 54.045 | 1.00 | 55.89 | A |
| ATOM | 1966 | CB | ILE | A | 839 | 9.927 | 1.704 | 52.977 | 1.00 | 55.49 | A |
| ATOM | 1967 | CG2 | ILE | A | 839 | 9.393 | 2.100 | 51.628 | 1.00 | 55.31 | A |
| ATOM | 1968 | CG1 | ILE | A | 839 | 11.461 | 1.688 | 52.970 | 1.00 | 55.77 | A |
| ATOM | 1969 | CD1 | ILE | A | 839 | 12.087 | 0.571 | 52.149 | 1.00 | 56.57 | A |
| ATOM | 1970 | C | ILE | A | 839 | 7.915 | 2.769 | 54.045 | 1.00 | 56.14 | A |
| ATOM | 1971 | O | ILE | A | 839 | 7.338 | 3.698 | 53.497 | 1.00 | 56.13 | A |
| ATOM | 1972 | N | GLY | A | 840 | 7.270 | 1.799 | 54.683 | 1.00 | 56.80 | A |
| ATOM | 1973 | CA | GLY | A | 840 | 5.824 | 1.811 | 54.754 | 1.00 | 56.89 | A |
| ATOM | 1974 | C | GLY | A | 840 | 5.357 | 3.156 | 55.258 | 1.00 | 57.39 | A |

FIG. 8-14

| ATOM | 1975 | O   | GLY | A | 840 | 4.652  | 3.885  | 54.574 | 1.00 | 56.61 | A |
|------|------|-----|-----|---|-----|--------|--------|--------|------|-------|---|
| ATOM | 1976 | N   | ILE | A | 841 | 5.774  | 3.502  | 56.464 | 1.00 | 58.58 | A |
| ATOM | 1977 | CA  | ILE | A | 841 | 5.385  | 4.773  | 57.040 | 1.00 | 60.03 | A |
| ATOM | 1978 | CB  | ILE | A | 841 | 6.105  | 5.040  | 58.370 | 1.00 | 60.25 | A |
| ATOM | 1979 | CG2 | ILE | A | 841 | 5.401  | 6.153  | 59.134 | 1.00 | 59.37 | A |
| ATOM | 1980 | CG1 | ILE | A | 841 | 6.104  | 3.773  | 59.220 | 1.00 | 61.42 | A |
| ATOM | 1981 | CD1 | ILE | A | 841 | 6.731  | 3.961  | 60.575 | 1.00 | 60.63 | A |
| ATOM | 1982 | C   | ILE | A | 841 | 5.716  | 5.901  | 56.085 | 1.00 | 60.98 | A |
| ATOM | 1983 | O   | ILE | A | 841 | 4.827  | 6.616  | 55.646 | 1.00 | 61.92 | A |
| ATOM | 1984 | N   | ASP | A | 842 | 6.992  | 6.054  | 55.749 | 1.00 | 62.10 | A |
| ATOM | 1985 | CA  | ASP | A | 842 | 7.400  | 7.133  | 54.852 | 1.00 | 64.06 | A |
| ATOM | 1986 | CB  | ASP | A | 842 | 8.839  | 6.936  | 54.379 | 1.00 | 63.91 | A |
| ATOM | 1987 | CG  | ASP | A | 842 | 9.385  | 8.154  | 53.648 | 1.00 | 64.93 | A |
| ATOM | 1988 | OD1 | ASP | A | 842 | 10.468 | 8.041  | 53.048 | 1.00 | 66.63 | A |
| ATOM | 1989 | OD2 | ASP | A | 842 | 8.744  | 9.226  | 53.679 | 1.00 | 64.36 | A |
| ATOM | 1990 | C   | ASP | A | 842 | 6.500  | 7.279  | 53.628 | 1.00 | 65.31 | A |
| ATOM | 1991 | O   | ASP | A | 842 | 5.898  | 8.336  | 53.424 | 1.00 | 64.94 | A |
| ATOM | 2211 | N   | MSE | A | 870 | 8.808  | -8.260 | 52.919 | 1.00 | 63.45 | A |
| ATOM | 2212 | CA  | MSE | A | 870 | 9.153  | -6.946 | 53.462 | 1.00 | 64.87 | A |
| ATOM | 2213 | CB  | MSE | A | 870 | 8.676  | -5.784 | 52.571 | 1.00 | 63.46 | A |
| ATOM | 2214 | CG  | MSE | A | 870 | 9.640  | -5.387 | 51.402 | 1.00 | 62.43 | A |
| ATOM | 2215 | SE  | MSE | A | 870 | 11.310 | -4.368 | 51.703 | 1.00 | 62.31 | A |
| ATOM | 2216 | CE  | MSE | A | 870 | 10.668 | -2.591 | 51.474 | 1.00 | 57.10 | A |
| ATOM | 2217 | C   | MSE | A | 870 | 8.527  | -6.862 | 54.850 | 1.00 | 66.47 | A |
| ATOM | 2218 | O   | MSE | A | 870 | 8.885  | -7.663 | 55.713 | 1.00 | 68.67 | A |
| ATOM | 2219 | N   | VAL | A | 871 | 7.605  | -5.929 | 55.087 | 1.00 | 65.94 | A |

FIG. 8-15

| ATOM | 2220 | CA | VAL A 871 | 6.988 | -5.815 | 56.417 | 1.00 | 64.60 | A |
|---|---|---|---|---|---|---|---|---|---|
| ATOM | 2221 | CB | VAL A 871 | 5.628 | -5.117 | 56.322 | 1.00 | 62.92 | A |
| ATOM | 2222 | CG1 | VAL A 871 | 5.107 | -4.824 | 57.704 | 1.00 | 62.22 | A |
| ATOM | 2223 | CG2 | VAL A 871 | 5.753 | -3.848 | 55.505 | 1.00 | 60.65 | A |
| ATOM | 2224 | C | VAL A 871 | 6.777 | -7.217 | 57.000 | 1.00 | 65.03 | A |
| ATOM | 2225 | O | VAL A 871 | 5.729 | -7.805 | 56.776 | 1.00 | 66.32 | A |
| ATOM | 2226 | N | GLN A 872 | 7.743 | -7.735 | 57.763 | 1.00 | 64.38 | A |
| ATOM | 2227 | CA | GLN A 872 | 7.667 | -9.107 | 58.285 | 1.00 | 64.88 | A |
| ATOM | 2228 | CB | GLN A 872 | 9.075 | -9.695 | 58.382 | 1.00 | 63.33 | A |
| ATOM | 2229 | CG | GLN A 872 | 9.845 | -9.248 | 59.594 | 1.00 | 62.70 | A |
| ATOM | 2230 | CD | GLN A 872 | 10.674 | -10.358 | 60.193 | 1.00 | 62.86 | A |
| ATOM | 2231 | OE1 | GLN A 872 | 11.324 | -10.170 | 61.211 | 1.00 | 64.65 | A |
| ATOM | 2232 | NE2 | GLN A 872 | 10.654 | -11.522 | 59.566 | 1.00 | 62.67 | A |
| ATOM | 2233 | C | GLN A 872 | 6.932 | -9.444 | 59.589 | 1.00 | 66.23 | A |
| ATOM | 2234 | O | GLN A 872 | 7.039 | -10.565 | 60.091 | 1.00 | 66.29 | A |
| ATOM | 2235 | N | VAL A 873 | 6.175 | -8.510 | 60.141 | 1.00 | 67.91 | A |
| ATOM | 2236 | CA | VAL A 873 | 5.480 | -8.809 | 61.382 | 1.00 | 68.58 | A |
| ATOM | 2237 | CB | VAL A 873 | 6.400 | -8.536 | 62.594 | 1.00 | 69.52 | A |
| ATOM | 2238 | CG1 | VAL A 873 | 5.570 | -8.447 | 63.871 | 1.00 | 71.66 | A |
| ATOM | 2239 | CG2 | VAL A 873 | 7.443 | -9.647 | 62.715 | 1.00 | 67.95 | A |
| ATOM | 2240 | C | VAL A 873 | 4.165 | -8.080 | 61.582 | 1.00 | 68.35 | A |
| ATOM | 2241 | O | VAL A 873 | 4.070 | -6.869 | 61.423 | 1.00 | 68.05 | A |
| ATOM | 2242 | N | GLU A 874 | 3.158 | -8.857 | 61.952 | 1.00 | 69.33 | A |
| ATOM | 2243 | CA | GLU A 874 | 1.806 | -8.387 | 62.218 | 1.00 | 71.81 | A |
| ATOM | 2244 | CB | GLU A 874 | 1.030 | -9.445 | 62.998 | 1.00 | 73.48 | A |
| ATOM | 2245 | CG | GLU A 874 | 1.472 | -10.869 | 62.668 | 1.00 | 79.16 | A |

FIG. 8-16

| | | | | | | | | | |
|---|---|---|---|---|---|---|---|---|---|
| ATOM | 2246 | CD | GLU | A | 874 | 2.995 | -11.067 | 62.780 | 1.00 82.35 | A |
| ATOM | 2247 | OE1 | GLU | A | 874 | 3.543 | -10.913 | 63.901 | 1.00 85.03 | A |
| ATOM | 2248 | OE2 | GLU | A | 874 | 3.646 | -11.360 | 61.743 | 1.00 83.51 | A |
| ATOM | 2249 | C | GLU | A | 874 | 1.874 | -7.134 | 63.052 | 1.00 71.71 | A |
| ATOM | 2250 | O | GLU | A | 874 | 1.026 | -6.259 | 62.933 | 1.00 72.75 | A |
| ATOM | 2251 | N | ALA | A | 875 | 2.884 | -7.061 | 63.910 | 1.00 70.57 | A |
| ATOM | 2252 | CA | ALA | A | 875 | 3.062 | -5.911 | 64.770 | 1.00 70.00 | A |
| ATOM | 2253 | CB | ALA | A | 875 | 4.016 | -6.254 | 65.874 | 1.00 70.67 | A |
| ATOM | 2254 | C | ALA | A | 875 | 3.587 | -4.744 | 63.952 | 1.00 70.42 | A |
| ATOM | 2255 | O | ALA | A | 875 | 3.119 | -3.617 | 64.092 | 1.00 70.73 | A |
| ATOM | 2256 | N | GLN | A | 876 | 4.562 | -5.019 | 63.092 | 1.00 70.61 | A |
| ATOM | 2257 | CA | GLN | A | 876 | 5.144 | -3.988 | 62.232 | 1.00 70.44 | A |
| ATOM | 2258 | CB | GLN | A | 876 | 6.374 | -4.548 | 61.502 | 1.00 71.47 | A |
| ATOM | 2259 | CG | GLN | A | 876 | 7.636 | -4.611 | 62.365 | 1.00 72.27 | A |
| ATOM | 2260 | CD | GLN | A | 876 | 8.529 | -5.765 | 61.994 | 1.00 72.00 | A |
| ATOM | 2261 | OE1 | GLN | A | 876 | 8.709 | -6.066 | 60.823 | 1.00 72.03 | A |
| ATOM | 2262 | NE2 | GLN | A | 876 | 9.099 | -6.417 | 62.993 | 1.00 72.43 | A |
| ATOM | 2263 | C | GLN | A | 876 | 4.084 | -3.538 | 61.237 | 1.00 68.80 | A |
| ATOM | 2264 | O | GLN | A | 876 | 4.080 | -2.400 | 60.774 | 1.00 67.61 | A |
| ATOM | 2265 | N | TYR | A | 877 | 3.185 | -4.461 | 60.920 | 1.00 68.32 | A |
| ATOM | 2266 | CA | TYR | A | 877 | 2.079 | -4.194 | 60.009 | 1.00 67.69 | A |
| ATOM | 2267 | CB | TYR | A | 877 | 1.301 | -5.487 | 59.726 | 1.00 68.75 | A |
| ATOM | 2268 | CG | TYR | A | 877 | 0.274 | -5.359 | 58.622 | 1.00 71.21 | A |
| ATOM | 2269 | CD1 | TYR | A | 877 | 0.651 | -4.980 | 57.329 | 1.00 72.02 | A |
| ATOM | 2270 | CE1 | TYR | A | 877 | -0.301 | -4.825 | 56.303 | 1.00 73.19 | A |
| ATOM | 2271 | CD2 | TYR | A | 877 | -1.086 | -5.589 | 58.873 | 1.00 72.72 | A |

FIG. 8-17

| ATOM | 2272 | CE2 | TYR | A | 877 | -2.050 | -5.440 | 57.861 | 1.00 | 73.45 | A |
| --- | --- | --- | --- | --- | --- | --- | --- | --- | --- | --- | --- |
| ATOM | 2273 | CZ | TYR | A | 877 | -1.649 | -5.055 | 56.574 | 1.00 | 74.18 | A |
| ATOM | 2274 | OH | TYR | A | 877 | -2.583 | -4.888 | 55.564 | 1.00 | 73.96 | A |
| ATOM | 2275 | C | TYR | A | 877 | 1.169 | -3.179 | 60.687 | 1.00 | 66.19 | A |
| ATOM | 2276 | O | TYR | A | 877 | 0.838 | -2.138 | 60.129 | 1.00 | 66.54 | A |
| ATOM | 2277 | N | ILE | A | 878 | 0.782 | -3.490 | 61.912 | 1.00 | 63.34 | A |
| ATOM | 2278 | CA | ILE | A | 878 | -0.082 | -2.620 | 62.668 | 1.00 | 60.77 | A |
| ATOM | 2279 | CB | ILE | A | 878 | -0.518 | -3.307 | 63.974 | 1.00 | 59.77 | A |
| ATOM | 2280 | CG2 | ILE | A | 878 | -1.477 | -2.407 | 64.738 | 1.00 | 58.85 | A |
| ATOM | 2281 | CG1 | ILE | A | 878 | -1.179 | -4.652 | 63.648 | 1.00 | 57.99 | A |
| ATOM | 2282 | CD1 | ILE | A | 878 | -1.442 | -5.545 | 64.839 | 1.00 | 57.24 | A |
| ATOM | 2283 | C | ILE | A | 878 | 0.647 | -1.324 | 62.975 | 1.00 | 60.06 | A |
| ATOM | 2284 | O | ILE | A | 878 | 0.027 | -0.278 | 63.123 | 1.00 | 59.66 | A |
| ATOM | 2285 | N | LEU | A | 879 | 1.971 | -1.389 | 63.041 | 1.00 | 59.55 | A |
| ATOM | 2286 | CA | LEU | A | 879 | 2.771 | -0.208 | 63.357 | 1.00 | 58.93 | A |
| ATOM | 2287 | CB | LEU | A | 879 | 4.259 | -0.566 | 63.466 | 1.00 | 59.61 | A |
| ATOM | 2288 | CG | LEU | A | 879 | 5.157 | 0.235 | 64.430 | 1.00 | 60.69 | A |
| ATOM | 2289 | CD1 | LEU | A | 879 | 6.619 | 0.092 | 64.008 | 1.00 | 60.78 | A |
| ATOM | 2290 | CD2 | LEU | A | 879 | 4.769 | 1.700 | 64.439 | 1.00 | 60.63 | A |
| ATOM | 2291 | C | LEU | A | 879 | 2.607 | 0.883 | 62.316 | 1.00 | 57.73 | A |
| ATOM | 2292 | O | LEU | A | 879 | 2.491 | 2.058 | 62.655 | 1.00 | 57.43 | A |
| ATOM | 2293 | N | ILE | A | 880 | 2.609 | 0.492 | 61.047 | 1.00 | 56.59 | A |
| ATOM | 2294 | CA | ILE | A | 880 | 2.474 | 1.444 | 59.957 | 1.00 | 55.67 | A |
| ATOM | 2295 | CB | ILE | A | 880 | 2.510 | 0.727 | 58.622 | 1.00 | 53.99 | A |
| ATOM | 2296 | CG2 | ILE | A | 880 | 2.576 | 1.717 | 57.513 | 1.00 | 52.97 | A |

FIG. 8-18

| ATOM | 2297 | CG1 | ILE | A | 880 | 3.743 | -0.166 | 58.558 | 1.00 | 53.59 | A |
| --- | --- | --- | --- | --- | --- | --- | --- | --- | --- | --- | --- |
| ATOM | 2298 | CD1 | ILE | A | 880 | 3.841 | -0.985 | 57.309 | 1.00 | 52.20 | A |
| ATOM | 2299 | C | ILE | A | 880 | 1.170 | 2.208 | 60.094 | 1.00 | 56.29 | A |
| ATOM | 2300 | O | ILE | A | 880 | 1.124 | 3.417 | 59.883 | 1.00 | 55.07 | A |
| ATOM | 2301 | N | HIS | A | 881 | 0.116 | 1.490 | 60.476 | 1.00 | 57.39 | A |
| ATOM | 2302 | CA | HIS | A | 881 | -1.217 | 2.071 | 60.668 | 1.00 | 58.37 | A |
| ATOM | 2303 | CB | HIS | A | 881 | -2.243 | 0.966 | 60.946 | 1.00 | 59.27 | A |
| ATOM | 2304 | CG | HIS | A | 881 | -2.387 | -0.022 | 59.826 | 1.00 | 62.16 | A |
| ATOM | 2305 | CD2 | HIS | A | 881 | -1.882 | -1.269 | 59.666 | 1.00 | 63.33 | A |
| ATOM | 2306 | ND1 | HIS | A | 881 | -3.090 | 0.255 | 58.674 | 1.00 | 62.26 | A |
| ATOM | 2307 | CE1 | HIS | A | 881 | -3.010 | -0.777 | 57.853 | 1.00 | 63.14 | A |
| ATOM | 2308 | NE2 | HIS | A | 881 | -2.282 | -1.715 | 58.430 | 1.00 | 63.26 | A |
| ATOM | 2309 | C | HIS | A | 881 | -1.241 | 3.081 | 61.808 | 1.00 | 58.39 | A |
| ATOM | 2310 | O | HIS | A | 881 | -1.695 | 4.203 | 61.625 | 1.00 | 56.91 | A |
| ATOM | 2311 | N | GLN | A | 882 | -0.752 | 2.676 | 62.983 | 1.00 | 59.51 | A |
| ATOM | 2312 | CA | GLN | A | 882 | -0.715 | 3.555 | 64.155 | 1.00 | 59.58 | A |
| ATOM | 2313 | CB | GLN | A | 882 | -0.059 | 2.847 | 65.345 | 1.00 | 59.87 | A |
| ATOM | 2314 | CG | GLN | A | 882 | -0.442 | 1.381 | 65.489 | 1.00 | 62.48 | A |
| ATOM | 2315 | CD | GLN | A | 882 | 0.266 | 0.676 | 66.644 | 1.00 | 63.57 | A |
| ATOM | 2316 | OE1 | GLN | A | 882 | 1.433 | 0.934 | 66.920 | 1.00 | 64.79 | A |
| ATOM | 2317 | NE2 | GLN | A | 882 | -0.437 | -0.234 | 67.305 | 1.00 | 62.36 | A |
| ATOM | 2318 | C | GLN | A | 882 | 0.094 | 4.784 | 63.785 | 1.00 | 59.47 | A |
| ATOM | 2319 | O | GLN | A | 882 | -0.219 | 5.900 | 64.199 | 1.00 | 58.19 | A |
| ATOM | 2320 | N | ALA | A | 883 | 1.141 | 4.555 | 62.998 | 1.00 | 60.94 | A |
| ATOM | 2321 | CA | ALA | A | 883 | 2.022 | 5.618 | 62.523 | 1.00 | 62.60 | A |
| ATOM | 2322 | CB | ALA | A | 883 | 3.039 | 5.054 | 61.544 | 1.00 | 60.53 | A |

FIG. 8-19

| ATOM | 2323 | C | ALA A 883 | 1.155 | 6.643 | 61.822 | 1.00 | 63.72 | A |
| --- | --- | --- | --- | --- | --- | --- | --- | --- | --- |
| ATOM | 2324 | O | ALA A 883 | 1.211 | 7.844 | 62.112 | 1.00 | 63.92 | A |

(8b) Active site D2 domain molecule A

| ATOM | 2840 | N | SER A 945 | -5.664 | 5.616 | 102.321 | 1.00 | 83.07 | A |
| --- | --- | --- | --- | --- | --- | --- | --- | --- | --- |
| ATOM | 2841 | CA | SER A 945 | -5.265 | 6.556 | 103.373 | 1.00 | 81.30 | A |
| ATOM | 2842 | CB | SER A 945 | -5.541 | 5.937 | 104.759 | 1.00 | 80.36 | A |
| ATOM | 2843 | OG | SER A 945 | -4.784 | 4.751 | 104.994 | 1.00 | 77.13 | A |
| ATOM | 2844 | C | SER A 945 | -3.776 | 6.899 | 103.239 | 1.00 | 81.13 | A |
| ATOM | 2845 | O | SER A 945 | -3.114 | 7.306 | 104.205 | 1.00 | 82.35 | A |
| ATOM | 2846 | N | LYS A 946 | -3.249 | 6.721 | 102.036 | 1.00 | 78.92 | A |
| ATOM | 2847 | CA | LYS A 946 | -1.858 | 7.017 | 101.783 | 1.00 | 76.60 | A |
| ATOM | 2848 | CB | LYS A 946 | -1.089 | 5.730 | 101.520 | 1.00 | 75.64 | A |
| ATOM | 2849 | CG | LYS A 946 | -1.081 | 4.730 | 102.661 | 1.00 | 74.20 | A |
| ATOM | 2850 | CD | LYS A 946 | -0.320 | 3.503 | 102.193 | 1.00 | 75.39 | A |
| ATOM | 2851 | CE | LYS A 946 | -0.179 | 2.418 | 103.242 | 1.00 | 74.90 | A |
| ATOM | 2852 | NZ | LYS A 946 | 0.648 | 1.271 | 102.703 | 1.00 | 74.14 | A |
| ATOM | 2853 | C | LYS A 946 | -1.779 | 7.928 | 100.567 | 1.00 | 76.26 | A |
| ATOM | 2854 | O | LYS A 946 | -0.697 | 8.161 | 100.020 | 1.00 | 77.46 | A |
| ATOM | 2855 | N | ASN A 947 | -2.930 | 8.448 | 100.150 | 1.00 | 73.98 | A |
| ATOM | 2856 | CA | ASN A 947 | -2.984 | 9.325 | 98.992 | 1.00 | 72.38 | A |
| ATOM | 2857 | CB | ASN A 947 | -3.936 | 8.736 | 97.943 | 1.00 | 71.17 | A |
| ATOM | 2858 | CG | ASN A 947 | -3.472 | 7.384 | 97.422 | 1.00 | 69.70 | A |
| ATOM | 2859 | OD1 | ASN A 947 | -4.155 | 6.735 | 96.634 | 1.00 | 69.84 | A |
| ATOM | 2860 | ND2 | ASN A 947 | -2.305 | 6.960 | 97.857 | 1.00 | 69.44 | A |

FIG. 8-20

| ATOM | 2861 | C | ASN A 947 | -3.420 | 10.735 | 99.376 | 1.00 | 72.36 | A |
| ATOM | 2862 | O | ASN A 947 | -4.569 | 10.970 | 99.722 | 1.00 | 71.57 | A |
| ATOM | 2863 | N | ARG A 948 | -2.486 | 11.673 | 99.324 | 1.00 | 73.57 | A |
| ATOM | 2864 | CA | ARG A 948 | -2.779 | 13.071 | 99.643 | 1.00 | 74.92 | A |
| ATOM | 2865 | CB | ARG A 948 | -1.573 | 13.959 | 99.282 | 1.00 | 76.47 | A |
| ATOM | 2866 | CG | ARG A 948 | -1.851 | 15.454 | 99.214 | 1.00 | 77.63 | A |
| ATOM | 2867 | CD | ARG A 948 | -1.905 | 16.089 | 100.574 | 1.00 | 78.75 | A |
| ATOM | 2868 | NE | ARG A 948 | -0.609 | 16.045 | 101.235 | 1.00 | 81.36 | A |
| ATOM | 2869 | CZ | ARG A 948 | -0.334 | 16.687 | 102.368 | 1.00 | 83.53 | A |
| ATOM | 2870 | NH1 | ARG A 948 | -1.273 | 17.424 | 102.959 | 1.00 | 83.39 | A |
| ATOM | 2871 | NH2 | ARG A 948 | 0.879 | 16.594 | 102.909 | 1.00 | 85.13 | A |
| ATOM | 2872 | C | ARG A 948 | -3.991 | 13.500 | 98.835 | 1.00 | 74.78 | A |
| ATOM | 2873 | O | ARG A 948 | -4.869 | 14.203 | 99.331 | 1.00 | 73.57 | A |
| ATOM | 2874 | N | ASN A 949 | -4.014 | 13.073 | 97.575 | 1.00 | 75.66 | A |
| ATOM | 2875 | CA | ASN A 949 | -5.111 | 13.387 | 96.670 | 1.00 | 76.58 | A |
| ATOM | 2876 | CB | ASN A 949 | -4.647 | 14.352 | 95.593 | 1.00 | 76.04 | A |
| ATOM | 2877 | CG | ASN A 949 | -5.788 | 14.849 | 94.749 | 1.00 | 75.87 | A |
| ATOM | 2878 | OD1 | ASN A 949 | -5.629 | 15.764 | 93.944 | 1.00 | 76.69 | A |
| ATOM | 2879 | ND2 | ASN A 949 | -6.954 | 14.247 | 94.926 | 1.00 | 74.57 | A |
| ATOM | 2880 | C | ASN A 949 | -5.726 | 12.133 | 96.023 | 1.00 | 77.55 | A |
| ATOM | 2881 | O | ASN A 949 | -5.111 | 11.443 | 95.197 | 1.00 | 77.49 | A |
| ATOM | 2882 | N | SER A 950 | -6.968 | 11.876 | 96.419 | 1.00 | 77.94 | A |
| ATOM | 2883 | CA | SER A 950 | -7.769 | 10.742 | 95.993 | 1.00 | 77.82 | A |
| ATOM | 2884 | CB | SER A 950 | -9.221 | 11.012 | 96.363 | 1.00 | 76.78 | A |

FIG. 8-21

| | | | | | | | | | | |
|---|---|---|---|---|---|---|---|---|---|---|
| ATOM | 2885 | OG  | SER | A | 950 | -10.069 | 10.073 | 95.746 | 1.00 | 79.07 | A |
| ATOM | 2886 | C   | SER | A | 950 | -7.693  | 10.339 | 94.530 | 1.00 | 78.14 | A |
| ATOM | 2887 | O   | SER | A | 950 | -7.278  | 9.222  | 94.205 | 1.00 | 77.66 | A |
| ATOM | 2888 | N   | ASN | A | 951 | -8.121  | 11.240 | 93.653 | 1.00 | 79.24 | A |
| ATOM | 2889 | CA  | ASN | A | 951 | -8.122  | 10.955 | 92.224 | 1.00 | 80.19 | A |
| ATOM | 2890 | CB  | ASN | A | 951 | -9.298  | 11.668 | 91.530 | 1.00 | 81.63 | A |
| ATOM | 2891 | CG  | ASN | A | 951 | -9.226  | 13.174 | 91.650 | 1.00 | 83.98 | A |
| ATOM | 2892 | OD1 | ASN | A | 951 | -10.111 | 13.884 | 91.164 | 1.00 | 84.48 | A |
| ATOM | 2893 | ND2 | ASN | A | 951 | -8.170  | 13.674 | 92.295 | 1.00 | 84.96 | A |
| ATOM | 2894 | C   | ASN | A | 951 | -6.793  | 11.271 | 91.519 | 1.00 | 78.93 | A |
| ATOM | 2895 | O   | ASN | A | 951 | -6.772  | 11.640 | 90.332 | 1.00 | 77.86 | A |
| ATOM | 2896 | N   | VAL | A | 952 | -5.695  | 11.124 | 92.267 | 1.00 | 77.24 | A |
| ATOM | 2897 | CA  | VAL | A | 952 | -4.345  | 11.315 | 91.732 | 1.00 | 76.25 | A |
| ATOM | 2898 | CB  | VAL | A | 952 | -3.696  | 12.634 | 92.196 | 1.00 | 76.75 | A |
| ATOM | 2899 | CG1 | VAL | A | 952 | -2.310  | 12.780 | 91.562 | 1.00 | 76.09 | A |
| ATOM | 2900 | CG2 | VAL | A | 952 | -4.573  | 13.814 | 91.788 | 1.00 | 76.10 | A |
| ATOM | 2901 | C   | VAL | A | 952 | -3.506  | 10.145 | 92.220 | 1.00 | 78.10 | A |
| ATOM | 2902 | O   | VAL | A | 952 | -2.572  | 10.305 | 93.000 | 1.00 | 74.08 | A |
| ATOM | 2903 | N   | ILE | A | 953 | -3.870  | 8.960  | 91.748 | 1.00 | 74.18 | A |
| ATOM | 2904 | CA  | ILE | A | 953 | -3.204  | 7.731  | 92.119 | 1.00 | 72.43 | A |
| ATOM | 2905 | CB  | ILE | A | 953 | -4.236  | 6.666  | 92.500 | 1.00 | 70.66 | A |
| ATOM | 2906 | CG2 | ILE | A | 953 | -3.545  | 5.327  | 92.754 | 1.00 | 70.26 | A |
| ATOM | 2907 | CG1 | ILE | A | 953 | -5.031  | 7.164  | 93.709 | 1.00 | 68.82 | A |
| ATOM | 2908 | CD1 | ILE | A | 953 | -6.093  | 6.227  | 94.195 | 1.00 | 70.20 | A |
| ATOM | 2909 | C   | ILE | A | 953 | -2.366  | 7.221  | 90.973 | 1.00 | 72.06 | A |
| ATOM | 2910 | O   | ILE | A | 953 | -2.828  | 7.161  | 89.841 | 1.00 | 68.89 | A |

FIG. 8-22

| ATOM | 2911 | N   | PRO A 954  | -1.118 | 6.838  | 91.252  | 1.00 | 68.55 | A |
|------|------|-----|------------|--------|--------|---------|------|-------|---|
| ATOM | 2912 | CD  | PRO A 954  | -0.449 | 6.716  | 92.556  | 1.00 | 68.53 | A |
| ATOM | 2913 | CA  | PRO A 954  | -0.263 | 6.334  | 90.179  | 1.00 | 69.75 | A |
| ATOM | 2914 | CB  | PRO A 954  | 1.051  | 6.040  | 90.901  | 1.00 | 68.96 | A |
| ATOM | 2915 | CG  | PRO A 954  | 0.606  | 5.689  | 92.273  | 1.00 | 68.29 | A |
| ATOM | 2916 | C   | PRO A 954  | -0.861 | 5.104  | 89.485  | 1.00 | 70.18 | A |
| ATOM | 2917 | O   | PRO A 954  | -1.596 | 4.312  | 90.096  | 1.00 | 70.66 | A |
| ATOM | 3388 | N   | THR A1037  | 6.609  | 22.978 | 96.709  | 1.00 | 67.38 | A |
| ATOM | 3389 | CA  | THR A1037  | 5.594  | 23.566 | 97.568  | 1.00 | 69.73 | A |
| ATOM | 3390 | CB  | THR A1037  | 4.520  | 22.523 | 97.930  | 1.00 | 69.03 | A |
| ATOM | 3391 | OG1 | THR A1037  | 5.129  | 21.420 | 98.618  | 1.00 | 68.49 | A |
| ATOM | 3392 | CG2 | THR A1037  | 3.843  | 22.012 | 96.676  | 1.00 | 68.88 | A |
| ATOM | 3393 | C   | THR A1037  | 6.171  | 24.139 | 98.867  | 1.00 | 71.78 | A |
| ATOM | 3394 | O   | THR A1037  | 7.391  | 24.118 | 99.098  | 1.00 | 71.96 | A |
| ATOM | 3395 | N   | GLU A1038  | 5.280  | 24.678 | 99.696  | 1.00 | 73.55 | A |
| ATOM | 3396 | CA  | GLU A1038  | 5.661  | 25.227 | 100.987 | 1.00 | 75.60 | A |
| ATOM | 3397 | CB  | GLU A1038  | 4.845  | 26.485 | 101.294 | 1.00 | 76.31 | A |
| ATOM | 3398 | CG  | GLU A1038  | 5.598  | 27.575 | 102.085 | 1.00 | 76.22 | A |
| ATOM | 3399 | CD  | GLU A1038  | 6.771  | 28.177 | 101.314 | 1.00 | 76.12 | A |
| ATOM | 3400 | OE1 | GLU A1038  | 6.628  | 28.448 | 100.101 | 1.00 | 76.20 | A |
| ATOM | 3401 | OE2 | GLU A1038  | 7.837  | 28.391 | 101.926 | 1.00 | 75.50 | A |
| ATOM | 3402 | C   | GLU A1038  | 5.279  | 24.096 | 101.927 | 1.00 | 76.52 | A |
| ATOM | 3403 | O   | GLU A1038  | 4.863  | 23.040 | 101.465 | 1.00 | 77.09 | A |
| ATOM | 3404 | N   | LEU A1039  | 5.424  | 24.279 | 103.231 | 1.00 | 78.06 | A |
| ATOM | 3405 | CA  | LEU A1039  | 5.049  | 23.198 | 104.125 | 1.00 | 79.87 | A |
| ATOM | 3406 | CB  | LEU A1039  | 5.830  | 23.285 | 105.429 | 1.00 | 79.33 | A |

FIG. 8-23

| ATOM | 3407 | CG  | LEU | A1039 | 7.214  | 22.649 | 105.306 | 1.00 | 78.29 | A |
|------|------|-----|-----|-------|--------|--------|---------|------|-------|---|
| ATOM | 3408 | CD1 | LEU | A1039 | 8.005  | 22.838 | 106.588 | 1.00 | 77.57 | A |
| ATOM | 3409 | CD2 | LEU | A1039 | 7.047  | 21.181 | 104.997 | 1.00 | 78.05 | A |
| ATOM | 3410 | C   | LEU | A1039 | 3.547  | 23.226 | 104.375 | 1.00 | 81.97 | A |
| ATOM | 3411 | O   | LEU | A1039 | 2.938  | 22.195 | 104.694 | 1.00 | 82.60 | A |
| ATOM | 3412 | N   | LYS | A1040 | 2.960  | 24.412 | 104.222 | 1.00 | 82.98 | A |
| ATOM | 3413 | CA  | LYS | A1040 | 1.522  | 24.604 | 104.375 | 1.00 | 84.51 | A |
| ATOM | 3414 | CB  | LYS | A1040 | 1.034  | 24.236 | 105.792 | 1.00 | 85.01 | A |
| ATOM | 3415 | CG  | LYS | A1040 | 1.914  | 24.663 | 106.956 | 1.00 | 86.41 | A |
| ATOM | 3416 | CD  | LYS | A1040 | 1.145  | 24.624 | 108.296 | 1.00 | 87.96 | A |
| ATOM | 3417 | CE  | LYS | A1040 | 0.458  | 23.275 | 108.571 | 1.00 | 89.79 | A |
| ATOM | 3418 | NZ  | LYS | A1040 | 1.383  | 22.143 | 108.890 | 1.00 | 89.27 | A |
| ATOM | 3419 | C   | LYS | A1040 | 1.058  | 26.011 | 104.018 | 1.00 | 85.48 | A |
| ATOM | 3420 | O   | LYS | A1040 | 1.861  | 26.921 | 103.802 | 1.00 | 84.64 | A |
| ATOM | 3421 | N   | HIS | A1041 | -0.260 | 26.160 | 103.934 | 1.00 | 87.59 | A |
| ATOM | 3422 | CA  | HIS | A1041 | -0.919 | 27.423 | 103.600 | 1.00 | 89.00 | A |
| ATOM | 3423 | CB  | HIS | A1041 | -2.018 | 27.169 | 102.561 | 1.00 | 89.58 | A |
| ATOM | 3424 | CG  | HIS | A1041 | -2.145 | 28.238 | 101.520 | 1.00 | 90.98 | A |
| ATOM | 3425 | CD2 | HIS | A1041 | -2.121 | 28.167 | 100.165 | 1.00 | 91.66 | A |
| ATOM | 3426 | ND1 | HIS | A1041 | -2.363 | 29.563 | 101.831 | 1.00 | 91.86 | A |
| ATOM | 3427 | CE1 | HIS | A1041 | -2.470 | 30.262 | 100.711 | 1.00 | 92.27 | A |
| ATOM | 3428 | NE2 | HIS | A1041 | -2.328 | 29.439 | 99.686  | 1.00 | 91.45 | A |
| ATOM | 3429 | C   | HIS | A1041 | -1.556 | 27.871 | 104.906 | 1.00 | 89.62 | A |
| ATOM | 3430 | O   | HIS | A1041 | -2.704 | 27.543 | 105.180 | 1.00 | 89.08 | A |
| ATOM | 3431 | N   | GLY | A1042 | -0.801 | 28.596 | 105.723 | 1.00 | 91.39 | A |

FIG. 8-24

| | | | | | | | | |
|---|---|---|---|---|---|---|---|---|
| ATOM | 3432 | CA | GLY | A1042 | -1.329 | 29.052 | 106.997 | 1.00 | 93.17 | A |
| ATOM | 3433 | C | GLY | A1042 | -1.758 | 27.886 | 107.870 | 1.00 | 94.83 | A |
| ATOM | 3434 | O | GLY | A1042 | -0.996 | 27.431 | 108.735 | 1.00 | 95.96 | A |
| ATOM | 3435 | N | ASP | A1043 | -2.977 | 27.393 | 107.644 | 1.00 | 95.15 | A |
| ATOM | 3436 | CA | ASP | A1043 | -3.527 | 26.263 | 108.415 | 1.00 | 94.97 | A |
| ATOM | 3437 | CB | ASP | A1043 | -5.046 | 26.424 | 108.616 | 1.00 | 95.08 | A |
| ATOM | 3438 | CG | ASP | A1043 | -5.441 | 27.820 | 109.074 | 1.00 | 95.38 | A |
| ATOM | 3439 | OD1 | ASP | A1043 | -5.202 | 28.786 | 108.311 | 1.00 | 95.25 | A |
| ATOM | 3440 | OD2 | ASP | A1043 | -5.995 | 27.946 | 110.193 | 1.00 | 94.65 | A |
| ATOM | 3441 | C | ASP | A1043 | -3.294 | 24.948 | 107.672 | 1.00 | 94.15 | A |
| ATOM | 3442 | O | ASP | A1043 | -2.605 | 24.033 | 108.154 | 1.00 | 93.40 | A |
| ATOM | 3443 | N | GLN | A1044 | -3.907 | 24.884 | 106.492 | 1.00 | 93.34 | A |
| ATOM | 3444 | CA | GLN | A1044 | -3.848 | 23.730 | 105.608 | 1.00 | 92.30 | A |
| ATOM | 3445 | CB | GLN | A1044 | -4.721 | 23.997 | 104.348 | 1.00 | 93.25 | A |
| ATOM | 3446 | CG | GLN | A1044 | -4.618 | 25.409 | 103.688 | 1.00 | 94.59 | A |
| ATOM | 3447 | CD | GLN | A1044 | -5.406 | 26.539 | 104.418 | 1.00 | 95.31 | A |
| ATOM | 3448 | OE1 | GLN | A1044 | -5.475 | 27.687 | 103.933 | 1.00 | 94.17 | A |
| ATOM | 3449 | NE2 | GLN | A1044 | -5.993 | 26.214 | 105.574 | 1.00 | 95.14 | A |
| ATOM | 3450 | C | GLN | A1044 | -2.418 | 23.305 | 105.219 | 1.00 | 90.18 | A |
| ATOM | 3451 | O | GLN | A1044 | -1.675 | 24.071 | 104.590 | 1.00 | 88.69 | A |
| ATOM | 3452 | N | GLU | A1045 | -2.043 | 22.083 | 105.616 | 1.00 | 87.91 | A |
| ATOM | 3453 | CA | GLU | A1045 | -0.724 | 21.553 | 105.303 | 1.00 | 86.07 | A |
| ATOM | 3454 | CB | GLU | A1045 | -0.327 | 20.419 | 106.272 | 1.00 | 85.95 | A |
| ATOM | 3455 | CG | GLU | A1045 | -0.957 | 19.037 | 106.012 | 1.00 | 87.50 | A |
| ATOM | 3456 | CD | GLU | A1045 | -0.107 | 17.861 | 106.548 | 1.00 | 88.03 | A |
| ATOM | 3457 | OE1 | GLU | A1045 | 0.247 | 17.857 | 107.750 | 1.00 | 88.06 | A |

FIG. 8-25

| | | | | | | | | |
|---|---|---|---|---|---|---|---|---|
| ATOM | 3458 | OE2 | GLU | A1045 | 0.203 | 16.934 | 105.763 | 1.00 88.44 | A |
| ATOM | 3459 | C | GLU | A1045 | -0.701 | 21.061 | 103.854 | 1.00 84.70 | A |
| ATOM | 3460 | O | GLU | A1045 | -1.523 | 20.233 | 103.449 | 1.00 84.31 | A |
| ATOM | 3461 | N | ILE | A1046 | 0.241 | 21.596 | 103.077 | 1.00 82.95 | A |
| ATOM | 3462 | CA | ILE | A1046 | 0.400 | 21.249 | 101.668 | 1.00 80.59 | A |
| ATOM | 3463 | CB | ILE | A1046 | 0.921 | 22.465 | 100.871 | 1.00 81.03 | A |
| ATOM | 3464 | CG2 | ILE | A1046 | 0.974 | 22.140 | 99.395 | 1.00 80.03 | A |
| ATOM | 3465 | CG1 | ILE | A1046 | -0.001 | 23.668 | 101.104 | 1.00 81.28 | A |
| ATOM | 3466 | CD1 | ILE | A1046 | 0.441 | 24.940 | 100.407 | 1.00 81.69 | A |
| ATOM | 3467 | C | ILE | A1046 | 1.379 | 20.089 | 101.544 | 1.00 78.86 | A |
| ATOM | 3468 | O | ILE | A1046 | 1.493 | 19.451 | 100.500 | 1.00 79.04 | A |
| ATOM | 3469 | N | CYS | A1047 | 2.083 | 19.816 | 102.629 | 1.00 77.11 | A |
| ATOM | 3470 | CA | CYS | A1047 | 3.037 | 18.725 | 102.659 | 1.00 76.67 | A |
| ATOM | 3471 | CB | CYS | A1047 | 4.317 | 19.116 | 101.918 | 1.00 75.79 | A |
| ATOM | 3472 | SG | CYS | A1047 | 5.544 | 17.796 | 101.739 | 1.00 73.80 | A |
| ATOM | 3473 | C | CYS | A1047 | 3.336 | 18.508 | 104.122 | 1.00 77.24 | A |
| ATOM | 3474 | O | CYS | A1047 | 3.036 | 19.377 | 104.940 | 1.00 77.40 | A |
| ATOM | 3903 | N | THR | A1098 | 10.250 | 27.990 | 96.461 | 1.00 72.39 | A |
| ATOM | 3904 | CA | THR | A1098 | 9.141 | 28.607 | 97.174 | 1.00 74.64 | A |
| ATOM | 3905 | CB | THR | A1098 | 9.689 | 29.640 | 98.150 | 1.00 74.75 | A |
| ATOM | 3906 | OG1 | THR | A1098 | 10.728 | 29.031 | 98.938 | 1.00 73.66 | A |
| ATOM | 3907 | CG2 | THR | A1098 | 8.567 | 30.173 | 99.046 | 1.00 74.93 | A |
| ATOM | 3908 | C | THR | A1098 | 8.152 | 29.263 | 96.199 | 1.00 76.46 | A |
| ATOM | 3909 | O | THR | A1098 | 6.978 | 28.877 | 96.137 | 1.00 76.49 | A |
| ATOM | 3910 | N | ASN | A1099 | 8.661 | 30.246 | 95.450 | 1.00 78.15 | A |
| ATOM | 3911 | CA | ASN | A1099 | 7.943 | 31.020 | 94.420 | 1.00 79.38 | A |
| ATOM | 3912 | CB | ASN | A1099 | 8.957 | 31.710 | 93.495 | 1.00 80.77 | A |

FIG. 8-26

| ATOM | 3913 | CG | ASN | A1099 | 9.218 | 33.140 | 93.867 | 1.00 | 81.87 | A |
|---|---|---|---|---|---|---|---|---|---|---|
| ATOM | 3914 | OD1 | ASN | A1099 | 8.326 | 33.985 | 93.794 | 1.00 | 82.73 | A |
| ATOM | 3915 | ND2 | ASN | A1099 | 10.453 | 33.428 | 94.261 | 1.00 | 82.28 | A |
| ATOM | 3916 | C | ASN | A1099 | 7.004 | 30.237 | 93.508 | 1.00 | 79.48 | A |
| ATOM | 3917 | O | ASN | A1099 | 7.109 | 30.362 | 92.293 | 1.00 | 79.25 | A |
| ATOM | 3918 | N | TRP | A1100 | 6.091 | 29.447 | 94.047 | 1.00 | 80.96 | A |
| ATOM | 3919 | CA | TRP | A1100 | 5.206 | 28.699 | 93.162 | 1.00 | 82.80 | A |
| ATOM | 3920 | CB | TRP | A1100 | 6.001 | 27.617 | 92.427 | 1.00 | 82.12 | A |
| ATOM | 3921 | CG | TRP | A1100 | 5.333 | 27.111 | 91.193 | 1.00 | 80.86 | A |
| ATOM | 3922 | CD2 | TRP | A1100 | 5.796 | 26.061 | 90.347 | 1.00 | 80.36 | A |
| ATOM | 3923 | CE2 | TRP | A1100 | 4.865 | 25.930 | 89.296 | 1.00 | 80.34 | A |
| ATOM | 3924 | CE3 | TRP | A1100 | 6.914 | 25.216 | 90.374 | 1.00 | 79.44 | A |
| ATOM | 3925 | CD1 | TRP | A1100 | 4.172 | 27.566 | 90.638 | 1.00 | 81.50 | A |
| ATOM | 3926 | NE1 | TRP | A1100 | 3.882 | 26.862 | 89.497 | 1.00 | 80.70 | A |
| ATOM | 3927 | CZ2 | TRP | A1100 | 5.016 | 24.988 | 88.279 | 1.00 | 80.22 | A |
| ATOM | 3928 | CZ3 | TRP | A1100 | 7.065 | 24.281 | 89.366 | 1.00 | 78.59 | A |
| ATOM | 3929 | CH2 | TRP | A1100 | 6.120 | 24.173 | 88.332 | 1.00 | 79.93 | A |
| ATOM | 3930 | C | TRP | A1100 | 3.995 | 28.072 | 93.844 | 1.00 | 84.27 | A |
| ATOM | 3931 | O | TRP | A1100 | 4.023 | 26.909 | 94.276 | 1.00 | 83.62 | A |
| ATOM | 3932 | N | SER | A1101 | 2.927 | 28.864 | 93.911 | 1.00 | 85.89 | A |
| ATOM | 3933 | CA | SER | A1101 | 1.660 | 28.463 | 94.520 | 1.00 | 87.61 | A |
| ATOM | 3934 | CB | SER | A1101 | 0.859 | 29.719 | 94.899 | 1.00 | 87.50 | A |
| ATOM | 3935 | OG | SER | A1101 | 1.657 | 30.669 | 95.587 | 1.00 | 88.33 | A |
| ATOM | 3936 | C | SER | A1101 | 0.844 | 27.623 | 93.526 | 1.00 | 88.58 | A |

FIG. 8-27

| | | | | | | | | | |
|---|---|---|---|---|---|---|---|---|---|
| ATOM | 3937 | O | SER | A1101 | 0.874 | 27.877 | 92.313 | 1.00 | 90.01 | A |
| ATOM | 3938 | N | VAL | A1102 | 0.105 | 26.634 | 94.023 | 1.00 | 89.13 | A |
| ATOM | 3939 | CA | VAL | A1102 | -0.708 | 25.807 | 93.130 | 1.00 | 89.47 | A |
| ATOM | 3940 | CB | VAL | A1102 | -1.320 | 24.569 | 93.865 | 1.00 | 90.59 | A |
| ATOM | 3941 | CG1 | VAL | A1102 | -0.262 | 23.915 | 94.780 | 1.00 | 91.37 | A |
| ATOM | 3942 | CG2 | VAL | A1102 | -2.554 | 24.978 | 94.657 | 1.00 | 90.44 | A |
| ATOM | 3943 | C | VAL | A1102 | -1.838 | 26.650 | 92.536 | 1.00 | 88.83 | A |
| ATOM | 3944 | O | VAL | A1102 | -2.759 | 26.117 | 91.924 | 1.00 | 88.45 | A |
| ATOM | 3945 | N | GLU | A1103 | -1.762 | 27.966 | 92.746 | 1.00 | 89.13 | A |
| ATOM | 3946 | CA | GLU | A1103 | -2.738 | 28.914 | 92.209 | 1.00 | 89.30 | A |
| ATOM | 3947 | CB | GLU | A1103 | -3.075 | 30.024 | 93.218 | 1.00 | 90.73 | A |
| ATOM | 3948 | CG | GLU | A1103 | -3.763 | 29.581 | 94.517 | 1.00 | 92.40 | A |
| ATOM | 3949 | CD | GLU | A1103 | -2.773 | 29.257 | 95.636 | 1.00 | 93.41 | A |
| ATOM | 3950 | OE1 | GLU | A1103 | -1.819 | 30.047 | 95.831 | 1.00 | 94.49 | A |
| ATOM | 3951 | OE2 | GLU | A1103 | -2.954 | 28.226 | 96.328 | 1.00 | 94.21 | A |
| ATOM | 3952 | C | GLU | A1103 | -2.112 | 29.555 | 90.973 | 1.00 | 88.54 | A |
| ATOM | 3953 | O | GLU | A1103 | -2.511 | 29.269 | 89.845 | 1.00 | 89.47 | A |
| ATOM | 3954 | N | GLN | A1104 | -1.130 | 30.425 | 91.189 | 1.00 | 87.61 | A |
| ATOM | 3955 | CA | GLN | A1104 | -0.448 | 31.086 | 90.082 | 1.00 | 87.16 | A |
| ATOM | 3956 | CB | GLN | A1104 | 0.291 | 32.344 | 90.588 | 1.00 | 86.80 | A |
| ATOM | 3957 | CG | GLN | A1104 | 0.984 | 32.226 | 91.979 | 1.00 | 87.07 | A |
| ATOM | 3958 | CD | GLN | A1104 | 2.422 | 31.634 | 91.951 | 1.00 | 86.89 | A |
| ATOM | 3959 | OE1 | GLN | A1104 | 2.618 | 30.425 | 91.801 | 1.00 | 85.42 | A |
| ATOM | 3960 | NE2 | GLN | A1104 | 3.422 | 32.503 | 92.100 | 1.00 | 86.09 | A |
| ATOM | 3961 | C | GLN | A1104 | 0.531 | 30.110 | 89.418 | 1.00 | 86.77 | A |
| ATOM | 3962 | O | GLN | A1104 | 0.468 | 28.893 | 89.641 | 1.00 | 85.76 | A |

FIG. 8-28

| ATOM | 3963 | N   | LEU | A1105 | 1.405  | 30.646 | 88.571 | 1.00 | 86.34 | A |
|------|------|-----|-----|-------|--------|--------|--------|------|-------|---|
| ATOM | 3964 | CA  | LEU | A1105 | 2.434  | 29.846 | 87.905 | 1.00 | 85.63 | A |
| ATOM | 3965 | CB  | LEU | A1105 | 2.267  | 29.880 | 86.369 | 1.00 | 85.19 | A |
| ATOM | 3966 | CG  | LEU | A1105 | 1.448  | 28.755 | 85.714 | 1.00 | 84.49 | A |
| ATOM | 3967 | CD1 | LEU | A1105 | 1.422  | 28.935 | 84.214 | 1.00 | 82.58 | A |
| ATOM | 3968 | CD2 | LEU | A1105 | 2.058  | 27.402 | 86.063 | 1.00 | 84.32 | A |
| ATOM | 3969 | C   | LEU | A1105 | 3.763  | 30.478 | 88.310 | 1.00 | 85.24 | A |
| ATOM | 3970 | O   | LEU | A1105 | 3.779  | 31.550 | 88.913 | 1.00 | 85.38 | A |
| ATOM | 3971 | N   | PRO | A1106 | 4.890  | 29.824 | 88.007 | 1.00 | 85.62 | A |
| ATOM | 3972 | CD  | PRO | A1106 | 5.102  | 28.627 | 87.179 | 1.00 | 85.86 | A |
| ATOM | 3973 | CA  | PRO | A1106 | 6.168  | 30.424 | 88.388 | 1.00 | 85.56 | A |
| ATOM | 3974 | CB  | PRO | A1106 | 7.159  | 29.717 | 87.475 | 1.00 | 85.79 | A |
| ATOM | 3975 | CG  | PRO | A1106 | 6.578  | 28.350 | 87.396 | 1.00 | 86.06 | A |
| ATOM | 3976 | C   | PRO | A1106 | 6.151  | 31.941 | 88.175 | 1.00 | 86.15 | A |
| ATOM | 3977 | O   | PRO | A1106 | 6.099  | 32.431 | 87.041 | 1.00 | 84.91 | A |
| ATOM | 3978 | N   | ALA | A1107 | 6.172  | 32.666 | 89.291 | 1.00 | 87.00 | A |
| ATOM | 3979 | CA  | ALA | A1107 | 6.153  | 34.122 | 89.294 | 1.00 | 87.15 | A |
| ATOM | 3980 | CB  | ALA | A1107 | 6.205  | 34.624 | 90.725 | 1.00 | 87.54 | A |
| ATOM | 3981 | C   | ALA | A1107 | 7.308  | 34.716 | 88.485 | 1.00 | 87.70 | A |
| ATOM | 3982 | O   | ALA | A1107 | 7.085  | 35.549 | 87.600 | 1.00 | 87.92 | A |
| ATOM | 3983 | N   | GLU | A1108 | 8.534  | 34.287 | 88.792 | 1.00 | 87.91 | A |
| ATOM | 3984 | CA  | GLU | A1108 | 9.736  | 34.765 | 88.097 | 1.00 | 88.27 | A |
| ATOM | 3985 | CB  | GLU | A1108 | 10.704 | 35.380 | 89.113 | 1.00 | 89.50 | A |
| ATOM | 3986 | CG  | GLU | A1108 | 10.022 | 36.018 | 90.337 | 1.00 | 90.96 | A |
| ATOM | 3987 | CD  | GLU | A1108 | 9.268  | 37.312 | 90.011 | 1.00 | 92.23 | A |
| ATOM | 3988 | OE1 | GLU | A1108 | 8.598  | 37.855 | 90.930 | 1.00 | 92.30 | A |

FIG. 8-29

| ATOM | 3989 | OE2 | GLU | A1108 | 9.349  | 37.787 | 88.846 | 1.00 | 92.05 | A |
| ATOM | 3990 | C   | GLU | A1108 | 10.400 | 33.566 | 87.391 | 1.00 | 87.64 | A |
| ATOM | 3991 | O   | GLU | A1108 | 11.438 | 33.057 | 87.830 | 1.00 | 87.74 | A |
| ATOM | 3992 | N   | PRO | A1109 | 9.798  | 33.100 | 86.284 | 1.00 | 86.77 | A |
| ATOM | 3993 | CD  | PRO | A1109 | 8.635  | 33.730 | 85.635 | 1.00 | 87.20 | A |
| ATOM | 3994 | CA  | PRO | A1109 | 10.270 | 31.967 | 85.482 | 1.00 | 86.31 | A |
| ATOM | 3995 | CB  | PRO | A1109 | 9.538  | 32.162 | 84.164 | 1.00 | 85.99 | A |
| ATOM | 3996 | CG  | PRO | A1109 | 8.225  | 32.676 | 84.632 | 1.00 | 86.73 | A |
| ATOM | 3997 | C   | PRO | A1109 | 11.776 | 31.834 | 85.296 | 1.00 | 85.19 | A |
| ATOM | 3998 | O   | PRO | A1109 | 12.342 | 30.795 | 85.618 | 1.00 | 85.30 | A |
| ATOM | 4176 | N   | ILE | A1142 | 10.906 | 14.466 | 92.231 | 1.00 | 52.37 | A |
| ATOM | 4177 | CA  | ILE | A1142 | 10.220 | 15.756 | 92.296 | 1.00 | 52.79 | A |
| ATOM | 4178 | CB  | ILE | A1142 | 10.038 | 16.324 | 90.901 | 1.00 | 52.45 | A |
| ATOM | 4179 | CG2 | ILE | A1142 | 9.396  | 17.694 | 90.974 | 1.00 | 51.28 | A |
| ATOM | 4180 | CG1 | ILE | A1142 | 11.393 | 16.365 | 90.203 | 1.00 | 51.84 | A |
| ATOM | 4181 | CD1 | ILE | A1142 | 11.302 | 16.627 | 88.747 | 1.00 | 51.64 | A |
| ATOM | 4182 | C   | ILE | A1142 | 8.850  | 15.618 | 92.933 | 1.00 | 53.52 | A |
| ATOM | 4183 | O   | ILE | A1142 | 8.098  | 14.730 | 92.587 | 1.00 | 53.99 | A |
| ATOM | 4184 | N   | HIS | A1143 | 8.508  | 16.495 | 93.862 | 1.00 | 55.49 | A |
| ATOM | 4185 | CA  | HIS | A1143 | 7.206  | 16.380 | 94.490 | 1.00 | 57.92 | A |
| ATOM | 4186 | CB  | HIS | A1143 | 7.301  | 15.518 | 95.755 | 1.00 | 58.73 | A |
| ATOM | 4187 | CG  | HIS | A1143 | 7.919  | 16.212 | 96.933 | 1.00 | 60.96 | A |
| ATOM | 4188 | CD2 | HIS | A1143 | 9.073  | 15.975 | 97.602 | 1.00 | 61.44 | A |
| ATOM | 4189 | ND1 | HIS | A1143 | 7.322  | 17.279 | 97.572 | 1.00 | 61.70 | A |
| ATOM | 4190 | CE1 | HIS | A1143 | 8.080  | 17.669 | 98.581 | 1.00 | 61.07 | A |

FIG. 8-30

| ATOM | 4191 | NE2 | HIS | A1143 | 9.149 | 16.895 | 98.621 | 1.00 | 61.20 | A |
|---|---|---|---|---|---|---|---|---|---|---|
| ATOM | 4192 | C | HIS | A1143 | 6.496 | 17.682 | 94.824 | 1.00 | 59.43 | A |
| ATOM | 4193 | O | HIS | A1143 | 7.090 | 18.757 | 94.865 | 1.00 | 59.78 | A |
| ATOM | 4194 | N | CYS | A1144 | 5.195 | 17.551 | 95.043 | 1.00 | 60.93 | A |
| ATOM | 4195 | CA | CYS | A1144 | 4.313 | 18.647 | 95.411 | 1.00 | 61.51 | A |
| ATOM | 4196 | CB | CYS | A1144 | 3.990 | 19.530 | 94.208 | 1.00 | 62.18 | A |
| ATOM | 4197 | SG | CYS | A1144 | 3.220 | 18.701 | 92.808 | 1.00 | 64.40 | A |
| ATOM | 4198 | C | CYS | A1144 | 3.070 | 17.952 | 95.918 | 1.00 | 60.98 | A |
| ATOM | 4199 | O | CYS | A1144 | 3.003 | 16.730 | 95.896 | 1.00 | 60.83 | A |
| ATOM | 4200 | N | ARG | A1145 | 2.096 | 18.713 | 96.381 | 1.00 | 61.04 | A |
| ATOM | 4201 | CA | ARG | A1145 | 0.885 | 18.120 | 96.911 | 1.00 | 63.07 | A |
| ATOM | 4202 | CB | ARG | A1145 | -0.303 | 18.995 | 96.603 | 1.00 | 66.07 | A |
| ATOM | 4203 | CG | ARG | A1145 | -0.211 | 20.384 | 97.136 | 1.00 | 72.73 | A |
| ATOM | 4204 | CD | ARG | A1145 | -1.523 | 21.093 | 96.844 | 1.00 | 78.48 | A |
| ATOM | 4205 | NE | ARG | A1145 | -1.649 | 22.386 | 97.507 | 1.00 | 81.72 | A |
| ATOM | 4206 | CZ | ARG | A1145 | -2.775 | 23.095 | 97.526 | 1.00 | 83.75 | A |
| ATOM | 4207 | NH1 | ARG | A1145 | -3.871 | 22.630 | 96.920 | 1.00 | 82.47 | A |
| ATOM | 4208 | NH2 | ARG | A1145 | -2.803 | 24.273 | 98.147 | 1.00 | 85.48 | A |
| ATOM | 4209 | C | ARG | A1145 | 0.589 | 16.732 | 96.376 | 1.00 | 62.90 | A |
| ATOM | 4210 | O | ARG | A1145 | 0.726 | 15.740 | 97.092 | 1.00 | 63.67 | A |
| ATOM | 4211 | N | ASP | A1146 | 0.180 | 16.678 | 95.109 | 1.00 | 61.25 | A |
| ATOM | 4212 | CA | ASP | A1146 | -0.181 | 15.431 | 94.442 | 1.00 | 59.27 | A |
| ATOM | 4213 | CB | ASP | A1146 | -1.487 | 15.603 | 93.672 | 1.00 | 58.57 | A |
| ATOM | 4214 | CG | ASP | A1146 | -1.410 | 16.690 | 92.634 | 1.00 | 58.87 | A |
| ATOM | 4215 | OD1 | ASP | A1146 | -0.352 | 16.823 | 91.993 | 1.00 | 57.69 | A |
| ATOM | 4216 | OD2 | ASP | A1146 | -2.413 | 17.406 | 92.445 | 1.00 | 61.26 | A |

FIG. 8-31

| ATOM | 4217 | C | ASP | A1146 | 0.874 | 14.888 | 93.498 | 1.00 | 59.37 | A |
| --- | --- | --- | --- | --- | --- | --- | --- | --- | --- | --- |
| ATOM | 4218 | O | ASP | A1146 | 0.742 | 13.777 | 92.993 | 1.00 | 59.61 | A |
| ATOM | 4219 | N | GLY | A1147 | 1.915 | 15.669 | 93.248 | 1.00 | 59.71 | A |
| ATOM | 4220 | CA | GLY | A1147 | 2.974 | 15.214 | 92.369 | 1.00 | 59.25 | A |
| ATOM | 4221 | C | GLY | A1147 | 2.602 | 15.154 | 90.903 | 1.00 | 59.73 | A |
| ATOM | 4222 | O | GLY | A1147 | 3.099 | 14.308 | 90.159 | 1.00 | 59.63 | A |
| ATOM | 4223 | N | SER | A1148 | 1.716 | 16.051 | 90.493 | 1.00 | 59.54 | A |
| ATOM | 4224 | CA | SER | A1148 | 1.279 | 16.142 | 89.109 | 1.00 | 60.37 | A |
| ATOM | 4225 | CB | SER | A1148 | 0.003 | 15.315 | 88.877 | 1.00 | 63.01 | A |
| ATOM | 4226 | OG | SER | A1148 | 0.247 | 13.913 | 88.864 | 1.00 | 62.60 | A |
| ATOM | 4227 | C | SER | A1148 | 1.009 | 17.610 | 88.825 | 1.00 | 59.87 | A |
| ATOM | 4228 | O | SER | A1148 | 1.392 | 18.128 | 87.783 | 1.00 | 58.71 | A |
| ATOM | 4229 | N | GLN | A1149 | 0.358 | 18.270 | 89.781 | 1.00 | 60.81 | A |
| ATOM | 4230 | CA | GLN | A1149 | 0.002 | 19.691 | 89.705 | 1.00 | 61.65 | A |
| ATOM | 4231 | CB | GLN | A1149 | -0.362 | 20.197 | 91.103 | 1.00 | 63.45 | A |
| ATOM | 4232 | CG | GLN | A1149 | -0.838 | 21.638 | 91.145 | 1.00 | 66.59 | A |
| ATOM | 4233 | CD | GLN | A1149 | -2.316 | 21.775 | 90.854 | 1.00 | 67.94 | A |
| ATOM | 4234 | OE1 | GLN | A1149 | -2.815 | 21.277 | 89.846 | 1.00 | 68.36 | A |
| ATOM | 4235 | NE2 | GLN | A1149 | -3.028 | 22.459 | 91.744 | 1.00 | 69.19 | A |
| ATOM | 4236 | C | GLN | A1149 | 1.117 | 20.571 | 89.125 | 1.00 | 61.03 | A |
| ATOM | 4237 | O | GLN | A1149 | 1.000 | 21.095 | 88.014 | 1.00 | 60.69 | A |
| ATOM | 4238 | N | GLN | A1150 | 2.188 | 20.746 | 89.894 | 1.00 | 59.49 | A |
| ATOM | 4239 | CA | GLN | A1150 | 3.317 | 21.543 | 89.448 | 1.00 | 58.15 | A |
| ATOM | 4240 | CB | GLN | A1150 | 3.815 | 22.437 | 90.584 | 1.00 | 59.99 | A |
| ATOM | 4241 | CG | GLN | A1150 | 3.001 | 22.326 | 91.851 | 1.00 | 63.00 | A |
| ATOM | 4242 | CD | GLN | A1150 | 3.182 | 23.514 | 92.775 | 1.00 | 66.11 | A |
| ATOM | 4243 | OE1 | GLN | A1150 | 2.693 | 23.506 | 93.912 | 1.00 | 67.58 | A |

FIG. 8-32

| ATOM | 4244 | NE2 | GLN | A1150 | 3.876 | 24.549 | 92.292 | 1.00 | 66.99 | A |
|------|------|-----|-----|-------|-------|--------|--------|------|-------|---|
| ATOM | 4245 | C | GLN | A1150 | 4.430 | 20.626 | 88.964 | 1.00 | 56.59 | A |
| ATOM | 4246 | O | GLN | A1150 | 5.154 | 20.965 | 88.040 | 1.00 | 55.12 | A |
| ATOM | 4247 | N | THR | A1151 | 4.548 | 19.458 | 89.589 | 1.00 | 56.31 | A |
| ATOM | 4248 | CA | THR | A1151 | 5.553 | 18.462 | 89.226 | 1.00 | 56.77 | A |
| ATOM | 4249 | CB | THR | A1151 | 5.341 | 17.153 | 89.998 | 1.00 | 57.01 | A |
| ATOM | 4250 | OG1 | THR | A1151 | 5.481 | 17.414 | 91.395 | 1.00 | 58.07 | A |
| ATOM | 4251 | CG2 | THR | A1151 | 6.344 | 16.084 | 89.568 | 1.00 | 55.19 | A |
| ATOM | 4252 | C | THR | A1151 | 5.501 | 18.145 | 87.743 | 1.00 | 57.10 | A |
| ATOM | 4253 | O | THR | A1151 | 6.506 | 17.778 | 87.145 | 1.00 | 57.63 | A |
| ATOM | 4254 | N | GLY | A1152 | 4.323 | 18.272 | 87.152 | 1.00 | 57.38 | A |
| ATOM | 4255 | CA | GLY | A1152 | 4.197 | 18.007 | 85.735 | 1.00 | 57.64 | A |
| ATOM | 4256 | C | GLY | A1152 | 4.961 | 19.048 | 84.944 | 1.00 | 58.32 | A |
| ATOM | 4257 | O | GLY | A1152 | 5.781 | 18.707 | 84.095 | 1.00 | 57.17 | A |
| ATOM | 4258 | N | ILE | A1153 | 4.705 | 20.322 | 85.241 | 1.00 | 58.81 | A |
| ATOM | 4259 | CA | ILE | A1153 | 5.359 | 21.425 | 84.545 | 1.00 | 58.53 | A |
| ATOM | 4260 | CB | ILE | A1153 | 4.948 | 22.805 | 85.096 | 1.00 | 59.42 | A |
| ATOM | 4261 | CG2 | ILE | A1153 | 5.459 | 23.896 | 84.177 | 1.00 | 58.66 | A |
| ATOM | 4262 | CG1 | ILE | A1153 | 3.432 | 22.920 | 85.181 | 1.00 | 61.16 | A |
| ATOM | 4263 | CD1 | ILE | A1153 | 2.751 | 22.708 | 83.875 | 1.00 | 61.88 | A |
| ATOM | 4264 | C | ILE | A1153 | 6.852 | 21.324 | 84.687 | 1.00 | 57.68 | A |
| ATOM | 4265 | O | ILE | A1153 | 7.586 | 21.741 | 83.800 | 1.00 | 57.58 | A |
| ATOM | 4266 | N | PHE | A1154 | 7.303 | 20.774 | 85.808 | 1.00 | 57.07 | A |
| ATOM | 4267 | CA | PHE | A1154 | 8.733 | 20.641 | 86.056 | 1.00 | 57.28 | A |

FIG. 8-33

| ATOM | 4268 | CB  | PHE | A1154 | 9.003  | 20.306 | 87.531 | 1.00 | 56.91 | A |
| ---- | ---- | --- | --- | ----- | ------ | ------ | ------ | ---- | ----- | - |
| ATOM | 4269 | CG  | PHE | A1154 | 10.367 | 20.737 | 88.015 | 1.00 | 57.19 | A |
| ATOM | 4270 | CD1 | PHE | A1154 | 10.643 | 22.076 | 88.256 | 1.00 | 57.01 | A |
| ATOM | 4271 | CD2 | PHE | A1154 | 11.382 | 19.807 | 88.207 | 1.00 | 57.12 | A |
| ATOM | 4272 | CE1 | PHE | A1154 | 11.901 | 22.476 | 88.676 | 1.00 | 56.78 | A |
| ATOM | 4273 | CE2 | PHE | A1154 | 12.644 | 20.201 | 88.625 | 1.00 | 56.34 | A |
| ATOM | 4274 | CZ  | PHE | A1154 | 12.900 | 21.537 | 88.859 | 1.00 | 57.38 | A |
| ATOM | 4275 | C   | PHE | A1154 | 9.323  | 19.556 | 85.164 | 1.00 | 56.78 | A |
| ATOM | 4276 | O   | PHE | A1154 | 10.210 | 19.810 | 84.352 | 1.00 | 55.43 | A |
| ATOM | 4277 | N   | CYS | A1155 | 8.818  | 18.343 | 85.309 | 1.00 | 55.88 | A |
| ATOM | 4278 | CA  | CYS | A1155 | 9.323  | 17.248 | 84.517 | 1.00 | 54.85 | A |
| ATOM | 4279 | CB  | CYS | A1155 | 8.465  | 16.020 | 84.739 | 1.00 | 55.30 | A |
| ATOM | 4280 | SG  | CYS | A1155 | 8.498  | 15.455 | 86.439 | 1.00 | 57.12 | A |
| ATOM | 4281 | C   | CYS | A1155 | 9.323  | 17.624 | 83.063 | 1.00 | 54.63 | A |
| ATOM | 4282 | O   | CYS | A1155 | 10.281 | 17.361 | 82.349 | 1.00 | 53.91 | A |
| ATOM | 4283 | N   | ALA | A1156 | 8.241  | 18.255 | 82.629 | 1.00 | 55.74 | A |
| ATOM | 4284 | CA  | ALA | A1156 | 8.103  | 18.676 | 81.238 | 1.00 | 56.83 | A |
| ATOM | 4285 | CB  | ALA | A1156 | 6.774  | 19.384 | 81.034 | 1.00 | 58.53 | A |
| ATOM | 4286 | C   | ALA | A1156 | 9.239  | 19.588 | 80.818 | 1.00 | 56.42 | A |
| ATOM | 4287 | O   | ALA | A1156 | 9.760  | 19.459 | 79.718 | 1.00 | 54.90 | A |
| ATOM | 4288 | N   | LEU | A1157 | 9.614  | 20.510 | 81.702 | 1.00 | 54.98 | A |
| ATOM | 4289 | CA  | LEU | A1157 | 10.685 | 21.447 | 81.417 | 1.00 | 54.10 | A |
| ATOM | 4290 | CB  | LEU | A1157 | 10.729 | 22.549 | 82.465 | 1.00 | 52.43 | A |
| ATOM | 4291 | CG  | LEU | A1157 | 9.841  | 23.763 | 82.226 | 1.00 | 51.61 | A |
| ATOM | 4292 | CD1 | LEU | A1157 | 10.140 | 24.817 | 83.251 | 1.00 | 51.87 | A |
| ATOM | 4293 | CD2 | LEU | A1157 | 10.109 | 24.321 | 80.862 | 1.00 | 49.72 | A |

FIG. 8-34

| ATOM | 4294 | C | LEU | A1157 | 12.038 | 20.782 | 81.339 | 1.00 | 55.22 | A |
|---|---|---|---|---|---|---|---|---|---|---|
| ATOM | 4295 | O | LEU | A1157 | 12.850 | 21.140 | 80.493 | 1.00 | 55.04 | A |
| ATOM | 4296 | N | LEU | A1158 | 12.285 | 19.819 | 82.227 | 1.00 | 57.32 | A |
| ATOM | 4297 | CA | LEU | A1158 | 13.563 | 19.106 | 82.253 | 1.00 | 57.84 | A |
| ATOM | 4298 | CB | LEU | A1158 | 13.597 | 18.065 | 83.355 | 1.00 | 58.10 | A |
| ATOM | 4299 | CG | LEU | A1158 | 13.671 | 18.531 | 84.797 | 1.00 | 59.37 | A |
| ATOM | 4300 | CD1 | LEU | A1158 | 13.747 | 17.310 | 85.674 | 1.00 | 60.33 | A |
| ATOM | 4301 | CD2 | LEU | A1158 | 14.873 | 19.412 | 85.008 | 1.00 | 58.63 | A |
| ATOM | 4302 | C | LEU | A1158 | 13.781 | 18.398 | 80.950 | 1.00 | 59.05 | A |
| ATOM | 4303 | O | LEU | A1158 | 14.869 | 18.437 | 80.389 | 1.00 | 59.70 | A |
| ATOM | 4516 | N | MSE | A1186 | -0.489 | 15.773 | 85.244 | 1.00 | 66.11 | A |
| ATOM | 4517 | CA | MSE | A1186 | 0.439 | 16.663 | 84.525 | 1.00 | 65.56 | A |
| ATOM | 4518 | CB | MSE | A1186 | 1.466 | 15.860 | 83.716 | 1.00 | 66.51 | A |
| ATOM | 4519 | CG | MSE | A1186 | 1.703 | 14.405 | 84.153 | 1.00 | 67.59 | A |
| ATOM | 4520 | SE | MSE | A1186 | 2.920 | 14.048 | 85.604 | 1.00 | 68.87 | A |
| ATOM | 4521 | CE | MSE | A1186 | 4.495 | 13.524 | 84.673 | 1.00 | 66.21 | A |
| ATOM | 4522 | C | MSE | A1186 | -0.272 | 17.647 | 83.590 | 1.00 | 64.89 | A |
| ATOM | 4523 | O | MSE | A1186 | -1.376 | 17.389 | 83.137 | 1.00 | 63.97 | A |
| ATOM | 4524 | N | VAL | A1187 | 0.381 | 18.768 | 83.302 | 1.00 | 64.84 | A |
| ATOM | 4525 | CA | VAL | A1187 | -0.183 | 19.824 | 82.458 | 1.00 | 64.71 | A |
| ATOM | 4526 | CB | VAL | A1187 | 0.635 | 20.019 | 81.167 | 1.00 | 65.06 | A |
| ATOM | 4527 | CG1 | VAL | A1187 | 0.211 | 21.307 | 80.477 | 1.00 | 65.30 | A |
| ATOM | 4528 | CG2 | VAL | A1187 | 2.118 | 20.043 | 81.484 | 1.00 | 64.12 | A |
| ATOM | 4529 | C | VAL | A1187 | -1.633 | 19.551 | 82.085 | 1.00 | 64.85 | A |
| ATOM | 4530 | O | VAL | A1187 | -1.930 | 18.966 | 81.043 | 1.00 | 64.81 | A |
| ATOM | 4531 | N | SER | A1188 | -2.542 | 19.973 | 82.950 | 1.00 | 64.46 | A |

FIG. 8-35

| | | | | | | | | | |
|---|---|---|---|---|---|---|---|---|---|
| ATOM | 4532 | CA | SER | A1188 | -3.953 | 19.742 | 82.708 | 1.00 | 64.57 | A |
| ATOM | 4533 | CB | SER | A1188 | -4.599 | 19.171 | 83.971 | 1.00 | 64.90 | A |
| ATOM | 4534 | OG | SER | A1188 | -4.016 | 19.742 | 85.128 | 1.00 | 67.12 | A |
| ATOM | 4535 | C | SER | A1188 | -4.694 | 20.984 | 82.237 | 1.00 | 64.51 | A |
| ATOM | 4536 | O | SER | A1188 | -5.847 | 20.902 | 81.813 | 1.00 | 64.13 | A |
| ATOM | 4537 | N | THR | A1189 | -4.024 | 22.130 | 82.285 | 1.00 | 65.18 | A |
| ATOM | 4538 | CA | THR | A1189 | -4.636 | 23.381 | 81.854 | 1.00 | 65.50 | A |
| ATOM | 4539 | CB | THR | A1189 | -4.822 | 24.339 | 83.033 | 1.00 | 64.81 | A |
| ATOM | 4540 | OG1 | THR | A1189 | -3.542 | 24.700 | 83.563 | 1.00 | 63.12 | A |
| ATOM | 4541 | CG2 | THR | A1189 | -5.670 | 23.683 | 84.115 | 1.00 | 65.50 | A |
| ATOM | 4542 | C | THR | A1189 | -3.805 | 24.085 | 80.792 | 1.00 | 66.54 | A |
| ATOM | 4543 | O | THR | A1189 | -2.581 | 24.013 | 80.801 | 1.00 | 65.71 | A |
| ATOM | 4544 | N | PHE | A1190 | -4.485 | 24.767 | 79.877 | 1.00 | 68.09 | A |
| ATOM | 4545 | CA | PHE | A1190 | -3.814 | 25.494 | 78.808 | 1.00 | 68.98 | A |
| ATOM | 4546 | CB | PHE | A1190 | -4.833 | 26.240 | 77.953 | 1.00 | 68.28 | A |
| ATOM | 4547 | CG | PHE | A1190 | -4.222 | 27.128 | 76.842 | 1.00 | 68.75 | A |
| ATOM | 4548 | CD1 | PHE | A1190 | -3.888 | 28.341 | 77.019 | 1.00 | 69.98 | A |
| ATOM | 4549 | CD2 | PHE | A1190 | -3.960 | 26.417 | 75.617 | 1.00 | 70.69 | A |
| ATOM | 4550 | CE1 | PHE | A1190 | -3.298 | 29.065 | 75.992 | 1.00 | 71.82 | A |
| ATOM | 4551 | CE2 | PHE | A1190 | -3.369 | 27.128 | 74.580 | 1.00 | 72.50 | A |
| ATOM | 4552 | CZ | PHE | A1190 | -3.037 | 28.456 | 74.767 | 1.00 | 72.35 | A |
| ATOM | 4553 | C | PHE | A1190 | -2.806 | 26.475 | 79.375 | 1.00 | 69.85 | A |
| ATOM | 4554 | O | PHE | A1190 | -1.786 | 26.764 | 78.743 | 1.00 | 70.24 | A |
| ATOM | 4555 | N | GLU | A1191 | -3.102 | 26.983 | 80.570 | 1.00 | 70.24 | A |
| ATOM | 4556 | CA | GLU | A1191 | -2.225 | 27.930 | 81.255 | 1.00 | 70.09 | A |

FIG. 8-36

| ATOM | 4557 | CB | GLU | A1191 | -2.739 | 28.226 | 82.668 | 1.00 | 71.87 | A |
|------|------|------|-----|-------|--------|--------|--------|------|-------|---|
| ATOM | 4558 | CG | GLU | A1191 | -4.052 | 28.975 | 82.700 | 1.00 | 74.67 | A |
| ATOM | 4559 | CD | GLU | A1191 | -5.196 | 28.171 | 82.109 | 1.00 | 76.53 | A |
| ATOM | 4560 | OE1 | GLU | A1191 | -5.608 | 27.161 | 82.726 | 1.00 | 78.04 | A |
| ATOM | 4561 | OE2 | GLU | A1191 | -5.681 | 28.550 | 81.021 | 1.00 | 76.96 | A |
| ATOM | 4562 | C | GLU | A1191 | -0.853 | 27.305 | 81.346 | 1.00 | 68.56 | A |
| ATOM | 4563 | O | GLU | A1191 | 0.138 | 27.892 | 80.920 | 1.00 | 67.37 | A |
| ATOM | 4564 | N | GLN | A1192 | -0.823 | 26.102 | 81.907 | 1.00 | 67.46 | A |
| ATOM | 4565 | CA | GLN | A1192 | 0.405 | 25.350 | 82.063 | 1.00 | 66.79 | A |
| ATOM | 4566 | CB | GLN | A1192 | 0.132 | 24.070 | 82.853 | 1.00 | 67.83 | A |
| ATOM | 4567 | CG | GLN | A1192 | -0.435 | 24.292 | 84.250 | 1.00 | 70.21 | A |
| ATOM | 4568 | CD | GLN | A1192 | -0.239 | 23.081 | 85.168 | 1.00 | 72.07 | A |
| ATOM | 4569 | OE1 | GLN | A1192 | -0.612 | 21.954 | 84.830 | 1.00 | 73.81 | A |
| ATOM | 4570 | NE2 | GLN | A1192 | 0.346 | 23.318 | 86.339 | 1.00 | 72.43 | A |
| ATOM | 4571 | C | GLN | A1192 | 0.991 | 25.008 | 80.693 | 1.00 | 65.80 | A |
| ATOM | 4572 | O | GLN | A1192 | 2.179 | 25.222 | 80.447 | 1.00 | 64.53 | A |
| ATOM | 4573 | N | TYR | A1193 | 0.157 | 24.478 | 79.802 | 1.00 | 64.96 | A |
| ATOM | 4574 | CA | TYR | A1193 | 0.620 | 24.125 | 78.474 | 1.00 | 64.99 | A |
| ATOM | 4575 | CB | TYR | A1193 | -0.541 | 23.764 | 77.565 | 1.00 | 63.97 | A |
| ATOM | 4576 | CG | TYR | A1193 | -0.119 | 22.988 | 76.338 | 1.00 | 64.00 | A |
| ATOM | 4577 | CD1 | TYR | A1193 | 0.218 | 21.637 | 76.423 | 1.00 | 63.64 | A |
| ATOM | 4578 | CE1 | TYR | A1193 | 0.605 | 20.915 | 75.287 | 1.00 | 63.32 | A |
| ATOM | 4579 | CD2 | TYR | A1193 | -0.053 | 23.606 | 75.085 | 1.00 | 63.58 | A |
| ATOM | 4580 | CE2 | TYR | A1193 | 0.336 | 22.890 | 73.939 | 1.00 | 63.56 | A |
| ATOM | 4581 | CZ | TYR | A1193 | 0.658 | 21.543 | 74.050 | 1.00 | 63.33 | A |
| ATOM | 4582 | OH | TYR | A1193 | 0.997 | 20.814 | 72.933 | 1.00 | 61.38 | A |

FIG. 8-37

| ATOM | 4583 | C | TYR | A1193 | 1.332 | 25.315 | 77.896 | 1.00 | 66.16 | A |
|------|------|------|-----|-------|--------|--------|--------|------|-------|---|
| ATOM | 4584 | O | TYR | A1193 | 2.538 | 25.283 | 77.682 | 1.00 | 66.38 | A |
| ATOM | 4585 | N | GLN | A1194 | 0.576 | 26.375 | 77.655 | 1.00 | 67.44 | A |
| ATOM | 4586 | CA | GLN | A1194 | 1.135 | 27.594 | 77.094 | 1.00 | 68.50 | A |
| ATOM | 4587 | CB | GLN | A1194 | 0.087 | 28.694 | 77.070 | 1.00 | 70.89 | A |
| ATOM | 4588 | CG | GLN | A1194 | 0.661 | 30.074 | 76.830 | 1.00 | 72.77 | A |
| ATOM | 4589 | CD | GLN | A1194 | -0.415 | 31.121 | 76.709 | 1.00 | 74.33 | A |
| ATOM | 4590 | OE1 | GLN | A1194 | -0.926 | 31.394 | 75.613 | 1.00 | 73.83 | A |
| ATOM | 4591 | NE2 | GLN | A1194 | -0.787 | 31.707 | 77.844 | 1.00 | 74.79 | A |
| ATOM | 4592 | C | GLN | A1194 | 2.342 | 28.090 | 77.861 | 1.00 | 67.88 | A |
| ATOM | 4593 | O | GLN | A1194 | 3.152 | 28.841 | 77.335 | 1.00 | 67.95 | A |
| ATOM | 4594 | N | PHE | A1195 | 2.461 | 27.681 | 79.111 | 1.00 | 67.67 | A |
| ATOM | 4595 | CA | PHE | A1195 | 3.587 | 28.115 | 79.913 | 1.00 | 68.54 | A |
| ATOM | 4596 | CB | PHE | A1195 | 3.321 | 27.820 | 81.386 | 1.00 | 69.76 | A |
| ATOM | 4597 | CG | PHE | A1195 | 4.470 | 28.148 | 82.288 | 1.00 | 70.75 | A |
| ATOM | 4598 | CD1 | PHE | A1195 | 5.034 | 29.412 | 82.286 | 1.00 | 71.88 | A |
| ATOM | 4599 | CD2 | PHE | A1195 | 4.983 | 27.193 | 83.152 | 1.00 | 71.64 | A |
| ATOM | 4600 | CE1 | PHE | A1195 | 6.095 | 29.718 | 83.137 | 1.00 | 71.89 | A |
| ATOM | 4601 | CE2 | PHE | A1195 | 6.042 | 27.494 | 84.003 | 1.00 | 71.84 | A |
| ATOM | 4602 | CZ | PHE | A1195 | 6.597 | 28.758 | 83.994 | 1.00 | 71.16 | A |
| ATOM | 4603 | C | PHE | A1195 | 4.872 | 27.430 | 79.454 | 1.00 | 68.27 | A |
| ATOM | 4604 | O | PHE | A1195 | 5.939 | 28.041 | 79.466 | 1.00 | 67.94 | A |
| ATOM | 4605 | N | LEU | A1196 | 4.770 | 26.169 | 79.044 | 1.00 | 66.74 | A |
| ATOM | 4606 | CA | LEU | A1196 | 5.936 | 25.433 | 78.578 | 1.00 | 64.61 | A |
| ATOM | 4607 | CB | LEU | A1196 | 5.539 | 24.028 | 78.131 | 1.00 | 65.43 | A |
| ATOM | 4608 | CG | LEU | A1196 | 4.966 | 23.114 | 79.217 | 1.00 | 66.36 | A |
| ATOM | 4609 | CD1 | LEU | A1196 | 4.532 | 21.794 | 78.618 | 1.00 | 66.48 | A |

FIG. 8-38

| ATOM | 4610 | CD2 | LEU | A1196 | 6.000 | 22.883 | 80.290 | 1.00 | 66.57 | A |
|---|---|---|---|---|---|---|---|---|---|---|
| ATOM | 4611 | C | LEU | A1196 | 6.541 | 26.184 | 77.413 | 1.00 | 63.69 | A |
| ATOM | 4612 | O | LEU | A1196 | 7.752 | 26.351 | 77.328 | 1.00 | 63.43 | A |
| ATOM | 4613 | N | TYR | A1197 | 5.678 | 26.641 | 76.515 | 1.00 | 63.87 | A |
| ATOM | 4614 | CA | TYR | A1197 | 6.099 | 27.387 | 75.333 | 1.00 | 64.22 | A |
| ATOM | 4615 | CB | TYR | A1197 | 4.878 | 27.699 | 74.446 | 1.00 | 62.77 | A |
| ATOM | 4616 | CG | TYR | A1197 | 4.545 | 26.626 | 73.430 | 1.00 | 60.97 | A |
| ATOM | 4617 | CD1 | TYR | A1197 | 5.242 | 26.535 | 72.232 | 1.00 | 60.91 | A |
| ATOM | 4618 | CE1 | TYR | A1197 | 4.967 | 25.531 | 71.316 | 1.00 | 60.88 | A |
| ATOM | 4619 | CD2 | TYR | A1197 | 3.556 | 25.682 | 73.686 | 1.00 | 60.78 | A |
| ATOM | 4620 | CE2 | TYR | A1197 | 3.272 | 24.675 | 72.778 | 1.00 | 60.71 | A |
| ATOM | 4621 | CZ | TYR | A1197 | 3.982 | 24.605 | 71.596 | 1.00 | 61.61 | A |
| ATOM | 4622 | OH | TYR | A1197 | 3.719 | 23.601 | 70.694 | 1.00 | 62.86 | A |
| ATOM | 4623 | C | TYR | A1197 | 6.791 | 28.683 | 75.767 | 1.00 | 65.24 | A |
| ATOM | 4624 | O | TYR | A1197 | 7.912 | 28.977 | 75.355 | 1.00 | 65.32 | A |
| ATOM | 4625 | N | ASP | A1198 | 6.117 | 29.448 | 76.613 | 1.00 | 65.58 | A |
| ATOM | 4626 | CA | ASP | A1198 | 6.650 | 30.705 | 77.108 | 1.00 | 66.77 | A |
| ATOM | 4627 | CB | ASP | A1198 | 5.757 | 31.237 | 78.226 | 1.00 | 69.85 | A |
| ATOM | 4628 | CG | ASP | A1198 | 4.364 | 31.593 | 77.737 | 1.00 | 72.19 | A |
| ATOM | 4629 | OD1 | ASP | A1198 | 3.464 | 31.796 | 78.590 | 1.00 | 72.52 | A |
| ATOM | 4630 | OD2 | ASP | A1198 | 4.179 | 31.674 | 76.499 | 1.00 | 71.89 | A |
| ATOM | 4631 | C | ASP | A1198 | 8.083 | 30.599 | 77.610 | 1.00 | 65.84 | A |
| ATOM | 4632 | O | ASP | A1198 | 8.958 | 31.277 | 77.084 | 1.00 | 65.81 | A |
| ATOM | 4633 | N | VAL | A1199 | 8.320 | 29.758 | 78.622 | 1.00 | 65.18 | A |

FIG. 8-39

| | | | | | | | | | |
|---|---|---|---|---|---|---|---|---|---|
| ATOM | 4634 | CA | VAL | A1199 | 9.666 | 29.597 | 79.192 | 1.00 | 64.20 | A |
| ATOM | 4635 | CB | VAL | A1199 | 9.689 | 28.725 | 80.493 | 1.00 | 63.24 | A |
| ATOM | 4636 | CG1 | VAL | A1199 | 8.964 | 29.408 | 81.619 | 1.00 | 62.63 | A |
| ATOM | 4637 | CG2 | VAL | A1199 | 9.065 | 27.401 | 80.230 | 1.00 | 65.92 | A |
| ATOM | 4638 | C | VAL | A1199 | 10.667 | 28.995 | 78.212 | 1.00 | 63.64 | A |
| ATOM | 4639 | O | VAL | A1199 | 11.806 | 29.456 | 78.131 | 1.00 | 63.57 | A |

(8c) Peptide within active site D1 domain molecule A

| | | | | | | | | | | |
|---|---|---|---|---|---|---|---|---|---|---|
| ATOM | 9458 | CB | PRO | X2002 | 22.254 | -17.372 | 59.019 | 1.00 | 78.62 | X |
| ATOM | 9459 | CG | PRO | X2002 | 23.661 | -17.389 | 58.330 | 1.00 | 79.01 | X |
| ATOM | 9460 | C | PRO | X2002 | 20.220 | -18.493 | 58.101 | 1.00 | 77.85 | X |
| ATOM | 9461 | O | PRO | X2002 | 19.911 | -18.699 | 56.934 | 1.00 | 79.40 | X |
| ATOM | 9462 | N | PRO | X2002 | 22.414 | -19.086 | 57.318 | 1.00 | 78.79 | X |
| ATOM | 9463 | CD | PRO | X2002 | 23.413 | -18.058 | 56.972 | 1.00 | 78.56 | X |
| ATOM | 9464 | CA | PRO | X2002 | 21.659 | -18.680 | 58.534 | 1.00 | 77.94 | X |
| ATOM | 9465 | N | THR | X2003 | 19.336 | -18.096 | 59.007 | 1.00 | 77.45 | X |
| ATOM | 9466 | CA | THR | X2003 | 17.934 | -17.928 | 58.622 | 1.00 | 77.48 | X |
| ATOM | 9467 | CB | THR | X2003 | 17.155 | -19.228 | 58.857 | 1.00 | 76.48 | X |
| ATOM | 9468 | OG1 | THR | X2003 | 17.103 | -19.957 | 57.629 | 1.00 | 76.69 | X |
| ATOM | 9469 | CG2 | THR | X2003 | 15.727 | -18.946 | 59.363 | 1.00 | 75.13 | X |
| ATOM | 9470 | C | THR | X2003 | 17.167 | -16.802 | 59.294 | 1.00 | 78.10 | X |
| ATOM | 9471 | O | THR | X2003 | 17.109 | -16.737 | 60.519 | 1.00 | 78.61 | X |
| ATOM | 9472 | N | PTY | X2004 | 16.548 | -15.931 | 58.505 | 1.00 | 77.44 | X |
| ATOM | 9473 | CA | PTY | X2004 | 15.788 | -14.852 | 59.110 | 1.00 | 77.43 | X |

FIG. 8-40

| | | | | | | | | | |
|---|---|---|---|---|---|---|---|---|---|
| ATOM | 9474 | CB | PTY X2004 | 16.546 | -13.532 | 59.228 | 1.00 | 75.45 | X |
| ATOM | 9475 | CG | PTY X2004 | 15.806 | -12.218 | 59.323 | 1.00 | 73.10 | X |
| ATOM | 9476 | CD1 | PTY X2004 | 16.305 | -11.282 | 60.227 | 1.00 | 73.17 | X |
| ATOM | 9477 | CE1 | PTY X2004 | 15.729 | -10.023 | 60.402 | 1.00 | 72.62 | X |
| ATOM | 9478 | CD2 | PTY X2004 | 14.659 | -11.896 | 58.533 | 1.00 | 71.69 | X |
| ATOM | 9479 | CE2 | PTY X2004 | 14.065 | -10.611 | 58.707 | 1.00 | 70.73 | X |
| ATOM | 9480 | CZ | PTY X2004 | 14.600 | -9.689 | 59.631 | 1.00 | 70.97 | X |
| ATOM | 9481 | OH | PTY X2004 | 14.246 | -8.327 | 60.043 | 1.00 | 69.88 | X |
| ATOM | 9482 | OR1 | PTY X2004 | 16.465 | -7.057 | 60.109 | 1.00 | 69.02 | X |
| ATOM | 9483 | OR2 | PTY X2004 | 14.330 | -5.866 | 60.306 | 1.00 | 69.51 | X |
| ATOM | 9484 | OR3 | PTY X2004 | 15.168 | -6.825 | 58.207 | 1.00 | 67.89 | X |
| ATOM | 9485 | PR | PTY X2004 | 15.066 | -6.959 | 59.640 | 1.00 | 70.23 | X |
| ATOM | 9486 | C | PTY X2004 | 14.388 | -15.062 | 59.694 | 1.00 | 78.92 | X |
| ATOM | 9487 | O | PTY X2004 | 13.955 | -14.405 | 60.642 | 1.00 | 77.85 | X |
| ATOM | 9488 | N | SER X2005 | 13.723 | -16.050 | 59.092 | 1.00 | 81.96 | X |
| ATOM | 9489 | CA | SER X2005 | 12.375 | -16.528 | 59.421 | 1.00 | 84.34 | X |
| ATOM | 9490 | CB | SER X2005 | 12.234 | -16.671 | 60.943 | 1.00 | 85.23 | X |
| ATOM | 9491 | OG | SER X2005 | 12.948 | -17.820 | 61.395 | 1.00 | 86.77 | X |
| ATOM | 9492 | C | SER X2005 | 11.169 | -15.770 | 58.845 | 1.00 | 84.82 | X |
| ATOM | 9493 | O | SER X2005 | 11.290 | -14.555 | 58.550 | 1.00 | 85.38 | X |
| ATOM | 9494 | OXT | SER X2005 | 10.101 | -16.420 | 58.701 | 1.00 | 85.28 | X |

(8d)   Active site D1 domain molecule B

| | | | | | | | | | |
|---|---|---|---|---|---|---|---|---|---|
| ATOM | 5137 | N | ASN B 654 | -30.913 | 51.140 | 130.739 | 1.00 | 76.14 | B |
| ATOM | 5138 | CA | ASN B 654 | -31.124 | 50.532 | 132.042 | 1.00 | 73.29 | B |

FIG. 8-41

| | | | | | | | | | |
|---|---|---|---|---|---|---|---|---|---|
| ATOM | 5139 | CB | ASN B 654 | -32.566 | 50.678 | 132.485 | 1.00 | 73.17 | B |
| ATOM | 5140 | CG | ASN B 654 | -32.847 | 52.024 | 133.051 | 1.00 | 73.24 | B |
| ATOM | 5141 | OD1 | ASN B 654 | -32.669 | 53.035 | 132.379 | 1.00 | 72.56 | B |
| ATOM | 5142 | ND2 | ASN B 654 | -33.280 | 52.059 | 134.305 | 1.00 | 73.81 | B |
| ATOM | 5143 | C | ASN B 654 | -30.794 | 49.059 | 131.969 | 1.00 | 71.70 | B |
| ATOM | 5144 | O | ASN B 654 | -30.774 | 48.377 | 132.989 | 1.00 | 71.02 | B |
| ATOM | 5145 | N | LYS B 655 | -30.538 | 48.578 | 130.755 | 1.00 | 70.65 | B |
| ATOM | 5146 | CA | LYS B 655 | -30.226 | 47.171 | 130.513 | 1.00 | 69.85 | B |
| ATOM | 5147 | CB | LYS B 655 | -30.737 | 46.770 | 129.134 | 1.00 | 69.37 | B |
| ATOM | 5148 | CG | LYS B 655 | -32.159 | 47.190 | 128.896 | 1.00 | 69.84 | B |
| ATOM | 5149 | CD | LYS B 655 | -32.632 | 46.777 | 127.529 | 1.00 | 71.51 | B |
| ATOM | 5150 | CE | LYS B 655 | -34.085 | 47.153 | 127.333 | 1.00 | 73.27 | B |
| ATOM | 5151 | NZ | LYS B 655 | -34.610 | 46.624 | 126.058 | 1.00 | 74.77 | B |
| ATOM | 5152 | C | LYS B 655 | -28.732 | 46.858 | 130.627 | 1.00 | 69.62 | B |
| ATOM | 5153 | O | LYS B 655 | -28.313 | 45.699 | 130.525 | 1.00 | 69.26 | B |
| ATOM | 5154 | N | ASN B 656 | -27.931 | 47.895 | 130.828 | 1.00 | 69.09 | B |
| ATOM | 5155 | CA | ASN B 656 | -26.503 | 47.716 | 130.983 | 1.00 | 69.22 | B |
| ATOM | 5156 | CB | ASN B 656 | -25.761 | 48.794 | 130.219 | 1.00 | 70.12 | B |
| ATOM | 5157 | CG | ASN B 656 | -25.949 | 48.671 | 128.742 | 1.00 | 70.44 | B |
| ATOM | 5158 | OD1 | ASN B 656 | -25.726 | 47.609 | 128.173 | 1.00 | 71.24 | B |
| ATOM | 5159 | ND2 | ASN B 656 | -26.360 | 49.753 | 128.103 | 1.00 | 70.40 | B |
| ATOM | 5160 | C | ASN B 656 | -26.168 | 47.810 | 132.460 | 1.00 | 69.59 | B |
| ATOM | 5161 | O | ASN B 656 | -26.906 | 48.416 | 133.233 | 1.00 | 69.84 | B |
| ATOM | 5162 | N | ARG B 657 | -25.060 | 47.201 | 132.860 | 1.00 | 69.73 | B |

FIG. 8-42

| | | | | | | | | | |
|---|---|---|---|---|---|---|---|---|---|
| ATOM | 5163 | CA | ARG | B | 657 | -24.645 | 47.239 | 134.261 | 1.00 | 70.11 | B |
| ATOM | 5164 | CB | ARG | B | 657 | -24.032 | 45.893 | 134.656 | 1.00 | 68.95 | B |
| ATOM | 5165 | CG | ARG | B | 657 | -24.507 | 45.359 | 135.976 | 1.00 | 68.89 | B |
| ATOM | 5166 | CD | ARG | B | 657 | -23.732 | 44.124 | 136.362 | 1.00 | 69.24 | B |
| ATOM | 5167 | NE | ARG | B | 657 | -24.213 | 43.553 | 137.616 | 1.00 | 69.90 | B |
| ATOM | 5168 | CZ | ARG | B | 657 | -25.424 | 43.027 | 137.772 | 1.00 | 70.48 | B |
| ATOM | 5169 | NH1 | ARG | B | 657 | -26.268 | 43.005 | 136.749 | 1.00 | 71.68 | B |
| ATOM | 5170 | NH2 | ARG | B | 657 | -25.795 | 42.515 | 138.938 | 1.00 | 69.10 | B |
| ATOM | 5171 | C | ARG | B | 657 | -23.623 | 48.372 | 134.446 | 1.00 | 71.09 | B |
| ATOM | 5172 | O | ARG | B | 657 | -23.604 | 49.048 | 135.483 | 1.00 | 70.65 | B |
| ATOM | 5173 | N | TYR | B | 658 | -22.793 | 48.568 | 133.416 | 1.00 | 70.76 | B |
| ATOM | 5174 | CA | TYR | B | 658 | -21.757 | 49.592 | 133.381 | 1.00 | 70.01 | B |
| ATOM | 5175 | CB | TYR | B | 658 | -20.391 | 48.963 | 133.575 | 1.00 | 69.38 | B |
| ATOM | 5176 | CG | TYR | B | 658 | -20.348 | 47.928 | 134.669 | 1.00 | 68.94 | B |
| ATOM | 5177 | CD1 | TYR | B | 658 | -20.413 | 48.298 | 136.016 | 1.00 | 68.64 | B |
| ATOM | 5178 | CE1 | TYR | B | 658 | -20.390 | 47.343 | 137.018 | 1.00 | 67.76 | B |
| ATOM | 5179 | CD2 | TYR | B | 658 | -20.257 | 46.576 | 134.361 | 1.00 | 66.82 | B |
| ATOM | 5180 | CE2 | TYR | B | 658 | -20.233 | 45.617 | 135.358 | 1.00 | 66.56 | B |
| ATOM | 5181 | CZ | TYR | B | 658 | -20.301 | 46.004 | 136.682 | 1.00 | 67.32 | B |
| ATOM | 5182 | OH | TYR | B | 658 | -20.291 | 45.045 | 137.664 | 1.00 | 66.98 | B |
| ATOM | 5183 | C | TYR | B | 658 | -21.809 | 50.144 | 131.986 | 1.00 | 70.93 | B |
| ATOM | 5184 | O | TYR | B | 658 | -21.937 | 49.374 | 131.050 | 1.00 | 71.35 | B |
| ATOM | 5185 | N | VAL | B | 659 | -21.707 | 51.460 | 131.836 | 1.00 | 73.08 | B |
| ATOM | 5186 | CA | VAL | B | 659 | -21.731 | 52.077 | 130.500 | 1.00 | 74.45 | B |
| ATOM | 5187 | CB | VAL | B | 659 | -22.147 | 53.579 | 130.559 | 1.00 | 75.35 | B |
| ATOM | 5188 | CG1 | VAL | B | 659 | -21.066 | 54.394 | 131.270 | 1.00 | 75.18 | B |

FIG. 8-43

| ATOM | 5189 | CG2 | VAL | B | 659 | -22.399 | 54.113 | 129.142 | 1.00 | 76.81 | B |
| --- | --- | --- | --- | --- | --- | --- | --- | --- | --- | --- | --- |
| ATOM | 5190 | C | VAL | B | 659 | -20.330 | 51.971 | 129.898 | 1.00 | 74.41 | B |
| ATOM | 5191 | O | VAL | B | 659 | -20.092 | 52.312 | 128.743 | 1.00 | 72.63 | B |
| ATOM | 5192 | N | ASP | B | 660 | -19.411 | 51.489 | 130.717 | 1.00 | 74.66 | B |
| ATOM | 5193 | CA | ASP | B | 660 | -18.035 | 51.309 | 130.322 | 1.00 | 74.73 | B |
| ATOM | 5194 | CB | ASP | B | 660 | -17.218 | 50.954 | 131.568 | 1.00 | 78.77 | B |
| ATOM | 5195 | CG | ASP | B | 660 | -15.729 | 51.175 | 131.379 | 1.00 | 82.65 | B |
| ATOM | 5196 | OD1 | ASP | B | 660 | -15.340 | 52.342 | 131.107 | 1.00 | 85.77 | B |
| ATOM | 5197 | OD2 | ASP | B | 660 | -14.953 | 50.190 | 131.505 | 1.00 | 84.14 | B |
| ATOM | 5198 | C | ASP | B | 660 | -17.958 | 50.179 | 129.287 | 1.00 | 73.66 | B |
| ATOM | 5199 | O | ASP | B | 660 | -17.152 | 50.229 | 128.358 | 1.00 | 73.43 | B |
| ATOM | 5200 | N | ILE | B | 661 | -18.817 | 49.169 | 129.456 | 1.00 | 72.74 | B |
| ATOM | 5201 | CA | ILE | B | 661 | -18.865 | 47.993 | 128.576 | 1.00 | 71.08 | B |
| ATOM | 5202 | CB | ILE | B | 661 | -18.702 | 46.659 | 129.398 | 1.00 | 71.43 | B |
| ATOM | 5203 | CG2 | ILE | B | 661 | -18.682 | 45.469 | 128.469 | 1.00 | 70.90 | B |
| ATOM | 5204 | CG1 | ILE | B | 661 | -17.389 | 46.657 | 130.191 | 1.00 | 72.25 | B |
| ATOM | 5205 | CD1 | ILE | B | 661 | -17.377 | 47.575 | 131.398 | 1.00 | 72.51 | B |
| ATOM | 5206 | C | ILE | B | 661 | -20.165 | 47.904 | 127.765 | 1.00 | 69.61 | B |
| ATOM | 5207 | O | ILE | B | 661 | -21.249 | 47.728 | 128.314 | 1.00 | 68.35 | B |
| ATOM | 5208 | N | LEU | B | 662 | -20.043 | 48.025 | 126.452 | 1.00 | 68.50 | B |
| ATOM | 5209 | CA | LEU | B | 662 | -21.198 | 47.944 | 125.571 | 1.00 | 68.44 | B |
| ATOM | 5210 | CB | LEU | B | 662 | -21.564 | 49.330 | 125.067 | 1.00 | 68.77 | B |
| ATOM | 5211 | CG | LEU | B | 662 | -21.866 | 50.362 | 126.150 | 1.00 | 69.54 | B |
| ATOM | 5212 | CD1 | LEU | B | 662 | -22.210 | 51.668 | 125.474 | 1.00 | 69.47 | B |
| ATOM | 5213 | CD2 | LEU | B | 662 | -23.013 | 49.902 | 127.035 | 1.00 | 69.29 | B |
| ATOM | 5214 | C | LEU | B | 662 | -20.905 | 47.012 | 124.389 | 1.00 | 69.14 | B |

FIG. 8-44

| ATOM | 5215 | O | LEU B 662 | -19.845 | 47.083 | 123.764 | 1.00 | 69.62 | B |
|------|------|---|-----------|---------|--------|---------|------|-------|---|
| ATOM | 5216 | N | PRO B 663 | -21.859 | 46.139 | 124.047 | 1.00 | 69.75 | B |
| ATOM | 5217 | CD | PRO B 663 | -23.248 | 46.055 | 124.532 | 1.00 | 69.79 | B |
| ATOM | 5218 | CA | PRO B 663 | -21.644 | 45.209 | 122.941 | 1.00 | 70.14 | B |
| ATOM | 5219 | CB | PRO B 663 | -22.820 | 44.256 | 123.087 | 1.00 | 69.80 | B |
| ATOM | 5220 | CG | PRO B 663 | -23.913 | 45.189 | 123.491 | 1.00 | 69.66 | B |
| ATOM | 5221 | C | PRO B 663 | -21.581 | 45.850 | 121.559 | 1.00 | 70.39 | B |
| ATOM | 5222 | O | PRO B 663 | -22.395 | 46.721 | 121.239 | 1.00 | 70.07 | B |
| ATOM | 5741 | N | THR B 727 | -18.244 | 34.146 | 138.650 | 1.00 | 65.20 | B |
| ATOM | 5742 | CA | THR B 727 | -18.354 | 35.305 | 139.528 | 1.00 | 67.01 | B |
| ATOM | 5743 | CB | THR B 727 | -18.916 | 36.530 | 138.798 | 1.00 | 66.55 | B |
| ATOM | 5744 | OG1 | THR B 727 | -18.714 | 37.700 | 139.602 | 1.00 | 65.87 | B |
| ATOM | 5745 | CG2 | THR B 727 | -20.406 | 36.361 | 138.566 | 1.00 | 66.51 | B |
| ATOM | 5746 | C | THR B 727 | -19.298 | 35.005 | 140.683 | 1.00 | 68.88 | B |
| ATOM | 5747 | O | THR B 727 | -19.853 | 33.911 | 140.792 | 1.00 | 70.15 | B |
| ATOM | 5748 | N | ARG B 728 | -19.466 | 35.984 | 141.555 | 1.00 | 69.49 | B |
| ATOM | 5749 | CA | ARG B 728 | -20.367 | 35.829 | 142.667 | 1.00 | 69.59 | B |
| ATOM | 5750 | CB | ARG B 728 | -19.618 | 35.907 | 143.991 | 1.00 | 69.51 | B |
| ATOM | 5751 | CG | ARG B 728 | -18.701 | 34.729 | 144.230 | 1.00 | 70.31 | B |
| ATOM | 5752 | CD | ARG B 728 | -18.313 | 34.634 | 145.696 | 1.00 | 73.39 | B |
| ATOM | 5753 | NE | ARG B 728 | -17.373 | 33.541 | 145.963 | 1.00 | 75.72 | B |
| ATOM | 5754 | CZ | ARG B 728 | -16.957 | 33.178 | 147.179 | 1.00 | 77.27 | B |
| ATOM | 5755 | NH1 | ARG B 728 | -17.396 | 33.816 | 148.264 | 1.00 | 77.04 | B |
| ATOM | 5756 | NH2 | ARG B 728 | -16.091 | 32.177 | 147.314 | 1.00 | 76.33 | B |
| ATOM | 5757 | C | ARG B 728 | -21.326 | 36.980 | 142.515 | 1.00 | 70.09 | B |

FIG. 8-45

| ATOM | 5758 | O | ARG B 728 | -20.981 | 38.005 | 141.928 | 1.00 | 69.58 | B |
|------|------|------|-----------|---------|--------|---------|------|-------|---|
| ATOM | 5759 | N | CYS B 729 | -22.534 | 36.800 | 143.031 | 1.00 | 71.12 | B |
| ATOM | 5760 | CA | CYS B 729 | -23.572 | 37.823 | 142.945 | 1.00 | 71.94 | B |
| ATOM | 5761 | CB | CYS B 729 | -24.900 | 37.195 | 143.356 | 1.00 | 71.08 | B |
| ATOM | 5762 | SG | CYS B 729 | -25.233 | 35.674 | 142.430 | 1.00 | 66.52 | B |
| ATOM | 5763 | C | CYS B 729 | -23.271 | 39.087 | 143.769 | 1.00 | 73.31 | B |
| ATOM | 5764 | O | CYS B 729 | -23.679 | 40.200 | 143.410 | 1.00 | 71.60 | B |
| ATOM | 5765 | N | GLU B 730 | -22.546 | 38.901 | 144.869 | 1.00 | 75.67 | B |
| ATOM | 5766 | CA | GLU B 730 | -22.157 | 39.996 | 145.743 | 1.00 | 77.79 | B |
| ATOM | 5767 | CB | GLU B 730 | -22.838 | 39.856 | 147.103 | 1.00 | 78.97 | B |
| ATOM | 5768 | CG | GLU B 730 | -24.358 | 39.885 | 147.000 | 1.00 | 81.17 | B |
| ATOM | 5769 | CD | GLU B 730 | -24.889 | 41.191 | 146.403 | 1.00 | 82.32 | B |
| ATOM | 5770 | OE1 | GLU B 730 | -26.072 | 41.229 | 145.988 | 1.00 | 82.56 | B |
| ATOM | 5771 | OE2 | GLU B 730 | -24.125 | 42.182 | 146.359 | 1.00 | 82.51 | B |
| ATOM | 5772 | C | GLU B 730 | -20.651 | 39.986 | 145.905 | 1.00 | 78.63 | B |
| ATOM | 5773 | O | GLU B 730 | -20.044 | 38.929 | 146.076 | 1.00 | 78.86 | B |
| ATOM | 5774 | N | GLU B 731 | -20.058 | 41.173 | 145.829 | 1.00 | 80.41 | B |
| ATOM | 5775 | CA | GLU B 731 | -18.615 | 41.349 | 145.961 | 1.00 | 82.72 | B |
| ATOM | 5776 | CB | GLU B 731 | -17.934 | 41.245 | 144.601 | 1.00 | 83.39 | B |
| ATOM | 5777 | CG | GLU B 731 | -17.798 | 39.831 | 144.087 | 1.00 | 84.83 | B |
| ATOM | 5778 | CD | GLU B 731 | -17.087 | 39.773 | 142.754 | 1.00 | 85.62 | B |
| ATOM | 5779 | OE1 | GLU B 731 | -16.693 | 38.657 | 142.336 | 1.00 | 85.38 | B |
| ATOM | 5780 | OE2 | GLU B 731 | -16.931 | 40.850 | 142.129 | 1.00 | 86.48 | B |
| ATOM | 5781 | C | GLU B 731 | -18.312 | 42.708 | 146.549 | 1.00 | 84.11 | B |
| ATOM | 5782 | O | GLU B 731 | -18.511 | 43.734 | 145.891 | 1.00 | 84.52 | B |
| ATOM | 5783 | N | GLY B 732 | -17.820 | 42.722 | 147.782 | 1.00 | 85.16 | B |

FIG. 8-46

| ATOM | 5784 | CA  | GLY | B | 732 | -17.515 | 43.993 | 148.413 | 1.00 | 86.65 | B |
|------|------|-----|-----|---|-----|---------|--------|---------|------|-------|---|
| ATOM | 5785 | C   | GLY | B | 732 | -18.789 | 44.750 | 148.764 | 1.00 | 87.44 | B |
| ATOM | 5786 | O   | GLY | B | 732 | -18.840 | 45.988 | 148.688 | 1.00 | 87.34 | B |
| ATOM | 5787 | N   | ASN | B | 733 | -19.825 | 44.001 | 149.141 | 1.00 | 87.33 | B |
| ATOM | 5788 | CA  | ASN | B | 733 | -21.098 | 44.601 | 149.508 | 1.00 | 87.46 | B |
| ATOM | 5789 | CB  | ASN | B | 733 | -20.907 | 45.486 | 150.738 | 1.00 | 88.84 | B |
| ATOM | 5790 | CG  | ASN | B | 733 | -20.235 | 44.736 | 151.887 | 1.00 | 89.37 | B |
| ATOM | 5791 | OD1 | ASN | B | 733 | -20.680 | 43.650 | 152.273 | 1.00 | 90.73 | B |
| ATOM | 5792 | ND2 | ASN | B | 733 | -19.160 | 45.306 | 152.433 | 1.00 | 89.50 | B |
| ATOM | 5793 | C   | ASN | B | 733 | -21.631 | 45.394 | 148.324 | 1.00 | 87.12 | B |
| ATOM | 5794 | O   | ASN | B | 733 | -22.485 | 46.270 | 148.461 | 1.00 | 87.18 | B |
| ATOM | 5795 | N   | ARG | B | 734 | -21.086 | 45.069 | 147.158 | 1.00 | 86.72 | B |
| ATOM | 5796 | CA  | ARG | B | 734 | -21.478 | 45.659 | 145.886 | 1.00 | 85.97 | B |
| ATOM | 5797 | CB  | ARG | B | 734 | -20.257 | 46.203 | 145.134 | 1.00 | 86.93 | B |
| ATOM | 5798 | CG  | ARG | B | 734 | -19.869 | 47.635 | 145.481 | 1.00 | 89.76 | B |
| ATOM | 5799 | CD  | ARG | B | 734 | -20.550 | 48.706 | 144.590 | 1.00 | 92.00 | B |
| ATOM | 5800 | NE  | ARG | B | 734 | -21.972 | 48.930 | 144.880 | 1.00 | 94.53 | B |
| ATOM | 5801 | CZ  | ARG | B | 734 | -22.983 | 48.194 | 144.405 | 1.00 | 95.34 | B |
| ATOM | 5802 | NH1 | ARG | B | 734 | -22.742 | 47.162 | 143.598 | 1.00 | 96.04 | B |
| ATOM | 5803 | NH2 | ARG | B | 734 | -24.242 | 48.496 | 144.729 | 1.00 | 94.39 | B |
| ATOM | 5804 | C   | ARG | B | 734 | -22.083 | 44.496 | 145.102 | 1.00 | 84.63 | B |
| ATOM | 5805 | O   | ARG | B | 734 | -21.573 | 43.372 | 145.156 | 1.00 | 83.91 | B |
| ATOM | 5806 | N   | ASN | B | 735 | -23.173 | 44.753 | 144.388 | 1.00 | 83.18 | B |
| ATOM | 5807 | CA  | ASN | B | 735 | -23.820 | 43.706 | 143.608 | 1.00 | 80.94 | B |
| ATOM | 5808 | CB  | ASN | B | 735 | -25.300 | 44.028 | 143.418 | 1.00 | 81.48 | B |
| ATOM | 5809 | CG  | ASN | B | 735 | -26.067 | 42.871 | 142.831 | 1.00 | 82.39 | B |

FIG. 8-47

| | | | | | | | | | |
|---|---|---|---|---|---|---|---|---|---|
| ATOM | 5810 | OD1 | ASN | B | 735 | -25.757 | 42.397 | 141.742 | 1.00 | 83.09 | B |
| ATOM | 5811 | ND2 | ASN | B | 735 | -27.079 | 42.404 | 143.553 | 1.00 | 83.49 | B |
| ATOM | 5812 | C | ASN | B | 735 | -23.141 | 43.572 | 142.255 | 1.00 | 78.91 | B |
| ATOM | 5813 | O | ASN | B | 735 | -22.926 | 44.558 | 141.549 | 1.00 | 78.53 | B |
| ATOM | 5814 | N | LYS | B | 736 | -22.793 | 42.348 | 141.895 | 1.00 | 77.22 | B |
| ATOM | 5815 | CA | LYS | B | 736 | -22.139 | 42.139 | 140.620 | 1.00 | 76.08 | B |
| ATOM | 5816 | CB | LYS | B | 736 | -20.769 | 41.469 | 140.829 | 1.00 | 76.65 | B |
| ATOM | 5817 | CG | LYS | B | 736 | -19.739 | 42.361 | 141.569 | 1.00 | 76.66 | B |
| ATOM | 5818 | CD | LYS | B | 736 | -19.674 | 43.749 | 140.942 | 1.00 | 76.68 | B |
| ATOM | 5819 | CE | LYS | B | 736 | -18.868 | 44.732 | 141.762 | 1.00 | 76.92 | B |
| ATOM | 5820 | NZ | LYS | B | 736 | -19.188 | 46.128 | 141.325 | 1.00 | 76.00 | B |
| ATOM | 5821 | C | LYS | B | 736 | -23.002 | 41.342 | 139.644 | 1.00 | 74.72 | B |
| ATOM | 5822 | O | LYS | B | 736 | -22.813 | 41.433 | 138.436 | 1.00 | 75.08 | B |
| ATOM | 5823 | N | CYS | B | 737 | -23.961 | 40.585 | 140.165 | 1.00 | 72.06 | B |
| ATOM | 5824 | CA | CYS | B | 737 | -24.839 | 39.802 | 139.318 | 1.00 | 69.95 | B |
| ATOM | 5825 | CB | CYS | B | 737 | -24.113 | 38.564 | 138.825 | 1.00 | 70.17 | B |
| ATOM | 5826 | SG | CYS | B | 737 | -25.129 | 37.496 | 137.803 | 1.00 | 72.95 | B |
| ATOM | 5827 | C | CYS | B | 737 | -26.092 | 39.386 | 140.062 | 1.00 | 69.24 | B |
| ATOM | 5828 | O | CYS | B | 737 | -26.006 | 38.859 | 141.161 | 1.00 | 69.12 | B |
| ATOM | 6273 | N | THR | B | 792 | -16.435 | 30.123 | 142.172 | 1.00 | 69.61 | B |
| ATOM | 6274 | CA | THR | B | 792 | -16.358 | 31.109 | 143.252 | 1.00 | 69.66 | B |
| ATOM | 6275 | CB | THR | B | 792 | -17.191 | 30.642 | 144.431 | 1.00 | 70.04 | B |
| ATOM | 6276 | OG1 | THR | B | 792 | -17.256 | 29.210 | 144.405 | 1.00 | 69.74 | B |
| ATOM | 6277 | CG2 | THR | B | 792 | -18.595 | 31.235 | 144.363 | 1.00 | 70.25 | B |
| ATOM | 6278 | C | THR | B | 792 | -14.989 | 31.477 | 143.783 | 1.00 | 69.67 | B |

FIG. 8-48

| | | | | | | | | |
|---|---|---|---|---|---|---|---|---|
| ATOM | 6279 | O   | THR | B | 792 | -14.876 | 32.292 | 144.688 | 1.00 | 68.73 | B |
| ATOM | 6280 | N   | SER | B | 793 | -13.952 | 30.880 | 143.224 | 1.00 | 69.94 | B |
| ATOM | 6281 | CA  | SER | B | 793 | -12.609 | 31.168 | 143.669 | 1.00 | 70.05 | B |
| ATOM | 6282 | CB  | SER | B | 793 | -11.819 | 29.869 | 143.778 | 1.00 | 70.31 | B |
| ATOM | 6283 | OG  | SER | B | 793 | -12.507 | 28.930 | 144.583 | 1.00 | 70.22 | B |
| ATOM | 6284 | C   | SER | B | 793 | -11.940 | 32.104 | 142.685 | 1.00 | 70.57 | B |
| ATOM | 6285 | O   | SER | B | 793 | -10.737 | 32.044 | 142.479 | 1.00 | 71.40 | B |
| ATOM | 6286 | N   | TRP | B | 794 | -12.728 | 32.979 | 142.076 | 1.00 | 71.19 | B |
| ATOM | 6287 | CA  | TRP | B | 794 | -12.197 | 33.922 | 141.103 | 1.00 | 71.45 | B |
| ATOM | 6288 | CB  | TRP | B | 794 | -12.667 | 33.535 | 139.718 | 1.00 | 71.37 | B |
| ATOM | 6289 | CG  | TRP | B | 794 | -11.886 | 34.156 | 138.639 | 1.00 | 72.09 | B |
| ATOM | 6290 | CD2 | TRP | B | 794 | -11.689 | 33.629 | 137.326 | 1.00 | 72.50 | B |
| ATOM | 6291 | CE2 | TRP | B | 794 | -10.913 | 34.565 | 136.613 | 1.00 | 73.10 | B |
| ATOM | 6292 | CE3 | TRP | B | 794 | -12.092 | 32.452 | 136.682 | 1.00 | 71.76 | B |
| ATOM | 6293 | CD1 | TRP | B | 794 | -11.244 | 35.355 | 138.675 | 1.00 | 72.14 | B |
| ATOM | 6294 | NE1 | TRP | B | 794 | -10.655 | 35.612 | 137.457 | 1.00 | 73.27 | B |
| ATOM | 6295 | CZ2 | TRP | B | 794 | -10.531 | 34.360 | 135.290 | 1.00 | 72.92 | B |
| ATOM | 6296 | CZ3 | TRP | B | 794 | -11.714 | 32.249 | 135.372 | 1.00 | 71.18 | B |
| ATOM | 6297 | CH2 | TRP | B | 794 | -10.941 | 33.197 | 134.689 | 1.00 | 71.95 | B |
| ATOM | 6298 | C   | TRP | B | 794 | -12.669 | 35.338 | 141.416 | 1.00 | 71.72 | B |
| ATOM | 6299 | O   | TRP | B | 794 | -13.821 | 35.684 | 141.176 | 1.00 | 72.40 | B |
| ATOM | 6300 | N   | PRO | B | 795 | -11.778 | 36.171 | 141.964 | 1.00 | 71.54 | B |
| ATOM | 6301 | CD  | PRO | B | 795 | -10.537 | 35.715 | 142.608 | 1.00 | 71.76 | B |
| ATOM | 6302 | CA  | PRO | B | 795 | -12.067 | 37.561 | 142.331 | 1.00 | 71.16 | B |
| ATOM | 6303 | CB  | PRO | B | 795 | -10.915 | 37.912 | 143.269 | 1.00 | 71.95 | B |
| ATOM | 6304 | CG  | PRO | B | 795 | -10.499 | 36.572 | 143.830 | 1.00 | 71.81 | B |

FIG. 8-49

| | | | | | | | | | |
|---|---|---|---|---|---|---|---|---|---|
| ATOM | 6305 | C | PRO | B | 795 | -12.170 | 38.550 | 141.177 | 1.00 | 70.59 | B |
| ATOM | 6306 | O | PRO | B | 795 | -11.343 | 38.553 | 140.273 | 1.00 | 70.32 | B |
| ATOM | 6307 | N | ASP | B | 796 | -13.188 | 39.399 | 141.246 | 1.00 | 70.59 | B |
| ATOM | 6308 | CA | ASP | B | 796 | -13.456 | 40.432 | 140.251 | 1.00 | 71.30 | B |
| ATOM | 6309 | CB | ASP | B | 796 | -14.544 | 41.353 | 140.803 | 1.00 | 73.32 | B |
| ATOM | 6310 | CG | ASP | B | 796 | -15.008 | 42.412 | 139.810 | 1.00 | 75.46 | B |
| ATOM | 6311 | OD1 | ASP | B | 796 | -14.156 | 43.151 | 139.277 | 1.00 | 77.24 | B |
| ATOM | 6312 | OD2 | ASP | B | 796 | -16.236 | 42.521 | 139.584 | 1.00 | 75.34 | B |
| ATOM | 6313 | C | ASP | B | 796 | -12.171 | 41.213 | 140.002 | 1.00 | 71.42 | B |
| ATOM | 6314 | O | ASP | B | 796 | -11.436 | 41.470 | 140.932 | 1.00 | 71.17 | B |
| ATOM | 6315 | N | HIS | B | 797 | -11.897 | 41.586 | 138.754 | 1.00 | 72.37 | B |
| ATOM | 6316 | CA | HIS | B | 797 | -10.683 | 42.336 | 138.414 | 1.00 | 73.20 | B |
| ATOM | 6317 | CB | HIS | B | 797 | -10.672 | 43.712 | 139.102 | 1.00 | 74.64 | B |
| ATOM | 6318 | CG | HIS | B | 797 | -11.533 | 44.747 | 138.438 | 1.00 | 78.22 | B |
| ATOM | 6319 | CD2 | HIS | B | 797 | -11.208 | 45.819 | 137.673 | 1.00 | 79.60 | B |
| ATOM | 6320 | ND1 | HIS | B | 797 | -12.908 | 44.765 | 138.554 | 1.00 | 78.95 | B |
| ATOM | 6321 | CE1 | HIS | B | 797 | -13.392 | 45.802 | 137.893 | 1.00 | 79.56 | B |
| ATOM | 6322 | NE2 | HIS | B | 797 | -12.382 | 46.458 | 137.348 | 1.00 | 80.28 | B |
| ATOM | 6323 | C | HIS | B | 797 | -9.387 | 41.612 | 138.784 | 1.00 | 72.85 | B |
| ATOM | 6324 | O | HIS | B | 797 | -8.310 | 42.171 | 138.633 | 1.00 | 72.55 | B |
| ATOM | 6325 | N | GLY | B | 798 | -9.479 | 40.376 | 139.261 | 1.00 | 72.58 | B |
| ATOM | 6326 | CA | GLY | B | 798 | -8.272 | 39.670 | 139.659 | 1.00 | 73.22 | B |
| ATOM | 6327 | C | GLY | B | 798 | -8.218 | 38.240 | 139.186 | 1.00 | 73.80 | B |
| ATOM | 6328 | O | GLY | B | 798 | -9.037 | 37.856 | 138.364 | 1.00 | 75.77 | B |
| ATOM | 6329 | N | VAL | B | 799 | -7.277 | 37.451 | 139.704 | 1.00 | 73.53 | B |
| ATOM | 6330 | CA | VAL | B | 799 | -7.123 | 36.054 | 139.285 | 1.00 | 73.27 | B |

FIG. 8-50

| ATOM | 6331 | CB  | VAL | B | 799 | -5.728 | 35.814 | 138.667 | 1.00 | 73.12 | B |
| ---- | ---- | --- | --- | - | --- | ------ | ------ | ------- | ---- | ----- | - |
| ATOM | 6332 | CG1 | VAL | B | 799 | -5.479 | 36.812 | 137.565 | 1.00 | 73.25 | B |
| ATOM | 6333 | CG2 | VAL | B | 799 | -4.650 | 35.923 | 139.730 | 1.00 | 71.14 | B |
| ATOM | 6334 | C   | VAL | B | 799 | -7.288 | 35.060 | 140.422 | 1.00 | 73.25 | B |
| ATOM | 6335 | O   | VAL | B | 799 | -7.256 | 35.444 | 141.580 | 1.00 | 74.26 | B |
| ATOM | 6336 | N   | PRO | B | 800 | -7.476 | 33.766 | 140.103 | 1.00 | 73.13 | B |
| ATOM | 6337 | CD  | PRO | B | 800 | -7.927 | 33.261 | 138.799 | 1.00 | 71.96 | B |
| ATOM | 6338 | CA  | PRO | B | 800 | -7.635 | 32.724 | 141.127 | 1.00 | 73.62 | B |
| ATOM | 6339 | CB  | PRO | B | 800 | -8.127 | 31.520 | 140.326 | 1.00 | 71.73 | B |
| ATOM | 6340 | CG  | PRO | B | 800 | -8.845 | 32.144 | 139.211 | 1.00 | 71.51 | B |
| ATOM | 6341 | C   | PRO | B | 800 | -6.327 | 32.419 | 141.885 | 1.00 | 75.03 | B |
| ATOM | 6342 | O   | PRO | B | 800 | -5.269 | 32.987 | 141.590 | 1.00 | 74.20 | B |
| ATOM | 6343 | N   | GLU | B | 801 | -6.419 | 31.511 | 142.855 | 1.00 | 76.48 | B |
| ATOM | 6344 | CA  | GLU | B | 801 | -5.282 | 31.114 | 143.683 | 1.00 | 77.43 | B |
| ATOM | 6345 | CB  | GLU | B | 801 | -5.738 | 30.213 | 144.841 | 1.00 | 78.78 | B |
| ATOM | 6346 | CG  | GLU | B | 801 | -6.861 | 30.759 | 145.723 | 1.00 | 80.70 | B |
| ATOM | 6347 | CD  | GLU | B | 801 | -8.179 | 30.932 | 144.986 | 1.00 | 80.45 | B |
| ATOM | 6348 | OE1 | GLU | B | 801 | -8.536 | 30.040 | 144.190 | 1.00 | 79.41 | B |
| ATOM | 6349 | OE2 | GLU | B | 801 | -8.860 | 31.956 | 145.218 | 1.00 | 79.73 | B |
| ATOM | 6350 | C   | GLU | B | 801 | -4.246 | 30.341 | 142.892 | 1.00 | 76.81 | B |
| ATOM | 6351 | O   | GLU | B | 801 | -3.046 | 30.583 | 143.013 | 1.00 | 77.02 | B |
| ATOM | 6352 | N   | ASP | B | 802 | -4.722 | 29.397 | 142.091 | 1.00 | 75.56 | B |
| ATOM | 6353 | CA  | ASP | B | 802 | -3.836 | 28.554 | 141.316 | 1.00 | 74.38 | B |
| ATOM | 6354 | CB  | ASP | B | 802 | -3.606 | 27.256 | 142.088 | 1.00 | 73.64 | B |
| ATOM | 6355 | CG  | ASP | B | 802 | -2.790 | 26.259 | 141.317 | 1.00 | 74.68 | B |

FIG. 8-51

| ATOM | 6356 | OD1 | ASP | B | 802 | -1.585 | 26.502 | 141.086 | 1.00 | 76.80 | B |
|------|------|-----|-----|---|-----|--------|--------|---------|------|-------|---|
| ATOM | 6357 | OD2 | ASP | B | 802 | -3.360 | 25.224 | 140.935 | 1.00 | 75.20 | B |
| ATOM | 6358 | C | ASP | B | 802 | -4.361 | 28.252 | 139.914 | 1.00 | 74.11 | B |
| ATOM | 6359 | O | ASP | B | 802 | -5.546 | 27.994 | 139.727 | 1.00 | 73.74 | B |
| ATOM | 6360 | N | PRO | B | 803 | -3.473 | 28.296 | 138.904 | 1.00 | 73.03 | B |
| ATOM | 6361 | CD | PRO | B | 803 | -2.092 | 28.818 | 138.952 | 1.00 | 72.60 | B |
| ATOM | 6362 | CA | PRO | B | 803 | -3.858 | 28.022 | 137.521 | 1.00 | 72.05 | B |
| ATOM | 6363 | CB | PRO | B | 803 | -2.525 | 28.100 | 136.785 | 1.00 | 71.93 | B |
| ATOM | 6364 | CG | PRO | B | 803 | -1.826 | 29.191 | 137.508 | 1.00 | 72.00 | B |
| ATOM | 6365 | C | PRO | B | 803 | -4.563 | 26.687 | 137.306 | 1.00 | 70.82 | B |
| ATOM | 6366 | O | PRO | B | 803 | -5.238 | 26.509 | 136.308 | 1.00 | 70.20 | B |
| ATOM | 6567 | N | SER | B | 828 | -19.865 | 37.007 | 133.697 | 1.00 | 62.05 | B |
| ATOM | 6568 | CA | SER | B | 828 | -19.360 | 37.413 | 134.985 | 1.00 | 63.58 | B |
| ATOM | 6569 | CB | SER | B | 828 | -17.866 | 37.707 | 134.895 | 1.00 | 65.17 | B |
| ATOM | 6570 | OG | SER | B | 828 | -17.592 | 38.657 | 133.886 | 1.00 | 68.65 | B |
| ATOM | 6571 | C | SER | B | 828 | -20.151 | 38.659 | 135.357 | 1.00 | 63.66 | B |
| ATOM | 6572 | O | SER | B | 828 | -21.379 | 38.633 | 135.332 | 1.00 | 63.51 | B |
| ATOM | 6573 | N | SER | B | 829 | -19.471 | 39.751 | 135.684 | 1.00 | 64.15 | B |
| ATOM | 6574 | CA | SER | B | 829 | -20.190 | 40.959 | 136.051 | 1.00 | 64.53 | B |
| ATOM | 6575 | CB | SER | B | 829 | -19.480 | 41.697 | 137.181 | 1.00 | 63.43 | B |
| ATOM | 6576 | OG | SER | B | 829 | -20.356 | 42.634 | 137.776 | 1.00 | 59.72 | B |
| ATOM | 6577 | C | SER | B | 829 | -20.385 | 41.897 | 134.868 | 1.00 | 65.92 | B |
| ATOM | 6578 | O | SER | B | 829 | -21.480 | 42.411 | 134.670 | 1.00 | 66.15 | B |
| ATOM | 6579 | N | ALA | B | 830 | -19.337 | 42.127 | 134.083 | 1.00 | 66.49 | B |
| ATOM | 6580 | CA | ALA | B | 830 | -19.455 | 43.011 | 132.925 | 1.00 | 66.89 | B |
| ATOM | 6581 | CB | ALA | B | 830 | -18.301 | 43.975 | 132.873 | 1.00 | 69.20 | B |

FIG. 8-52

| | | | | | | | | | | |
|---|---|---|---|---|---|---|---|---|---|---|
| ATOM | 6582 | C | ALA | B | 830 | -19.484 | 42.195 | 131.657 | 1.00 | 67.07 | B |
| ATOM | 6583 | O | ALA | B | 830 | -19.846 | 42.692 | 130.597 | 1.00 | 67.35 | B |
| ATOM | 6584 | N | GLY | B | 831 | -19.083 | 40.938 | 131.779 | 1.00 | 67.43 | B |
| ATOM | 6585 | CA | GLY | B | 831 | -19.078 | 40.046 | 130.641 | 1.00 | 67.72 | B |
| ATOM | 6586 | C | GLY | B | 831 | -17.844 | 40.216 | 129.798 | 1.00 | 67.95 | B |
| ATOM | 6587 | O | GLY | B | 831 | -17.860 | 39.938 | 128.611 | 1.00 | 68.97 | B |
| ATOM | 6588 | N | VAL | B | 832 | -16.761 | 40.670 | 130.407 | 1.00 | 68.57 | B |
| ATOM | 6589 | CA | VAL | B | 832 | -15.529 | 40.872 | 129.662 | 1.00 | 68.38 | B |
| ATOM | 6590 | CB | VAL | B | 832 | -15.318 | 42.384 | 129.327 | 1.00 | 66.71 | B |
| ATOM | 6591 | CG1 | VAL | B | 832 | -16.352 | 42.843 | 128.341 | 1.00 | 66.19 | B |
| ATOM | 6592 | CG2 | VAL | B | 832 | -15.426 | 43.224 | 130.572 | 1.00 | 65.14 | B |
| ATOM | 6593 | C | VAL | B | 832 | -14.311 | 40.340 | 130.416 | 1.00 | 69.46 | B |
| ATOM | 6594 | O | VAL | B | 832 | -13.546 | 39.529 | 129.884 | 1.00 | 69.18 | B |
| ATOM | 6595 | N | GLY | B | 833 | -14.155 | 40.792 | 131.658 | 1.00 | 69.60 | B |
| ATOM | 6596 | CA | GLY | B | 833 | -13.030 | 40.393 | 132.480 | 1.00 | 69.24 | B |
| ATOM | 6597 | C | GLY | B | 833 | -12.818 | 38.903 | 132.607 | 1.00 | 69.54 | B |
| ATOM | 6598 | O | GLY | B | 833 | -12.400 | 38.243 | 131.668 | 1.00 | 69.94 | B |
| ATOM | 6599 | N | ARG | B | 834 | -13.102 | 38.371 | 133.784 | 1.00 | 69.61 | B |
| ATOM | 6600 | CA | ARG | B | 834 | -12.915 | 36.956 | 134.052 | 1.00 | 69.24 | B |
| ATOM | 6601 | CB | ARG | B | 834 | -13.593 | 36.600 | 135.367 | 1.00 | 69.38 | B |
| ATOM | 6602 | CG | ARG | B | 834 | -13.027 | 37.311 | 136.564 | 1.00 | 69.18 | B |
| ATOM | 6603 | CD | ARG | B | 834 | -13.987 | 37.212 | 137.723 | 1.00 | 68.70 | B |
| ATOM | 6604 | NE | ARG | B | 834 | -14.882 | 38.359 | 137.775 | 1.00 | 69.69 | B |
| ATOM | 6605 | CZ | ARG | B | 834 | -15.900 | 38.465 | 138.620 | 1.00 | 70.33 | B |
| ATOM | 6606 | NH1 | ARG | B | 834 | -16.152 | 37.485 | 139.470 | 1.00 | 70.33 | B |
| ATOM | 6607 | NH2 | ARG | B | 834 | -16.644 | 39.559 | 138.640 | 1.00 | 70.60 | B |

FIG. 8-53

| | | | | | | | | | | |
|---|---|---|---|---|---|---|---|---|---|---|
| ATOM | 6608 | C | ARG | B | 834 | -13.453 | 36.068 | 132.944 | 1.00 | 69.58 | B |
| ATOM | 6609 | O | ARG | B | 834 | -12.842 | 35.062 | 132.586 | 1.00 | 69.42 | B |
| ATOM | 6610 | N | THR | B | 835 | -14.605 | 36.444 | 132.401 | 1.00 | 70.04 | B |
| ATOM | 6611 | CA | THR | B | 835 | -15.238 | 35.666 | 131.341 | 1.00 | 69.03 | B |
| ATOM | 6612 | CB | THR | B | 835 | -16.629 | 36.280 | 130.972 | 1.00 | 67.94 | B |
| ATOM | 6613 | OG1 | THR | B | 835 | -16.985 | 35.915 | 129.637 | 1.00 | 67.47 | B |
| ATOM | 6614 | CG2 | THR | B | 835 | -16.610 | 37.786 | 131.106 | 1.00 | 66.94 | B |
| ATOM | 6615 | C | THR | B | 835 | -14.339 | 35.518 | 130.103 | 1.00 | 68.97 | B |
| ATOM | 6616 | O | THR | B | 835 | -14.046 | 34.399 | 129.674 | 1.00 | 67.81 | B |
| ATOM | 6617 | N | GLY | B | 836 | -13.888 | 36.639 | 129.548 | 1.00 | 68.72 | B |
| ATOM | 6618 | CA | GLY | B | 836 | -13.022 | 36.587 | 128.383 | 1.00 | 68.94 | B |
| ATOM | 6619 | C | GLY | B | 836 | -11.712 | 35.882 | 128.696 | 1.00 | 69.23 | B |
| ATOM | 6620 | O | GLY | B | 836 | -11.075 | 35.286 | 127.833 | 1.00 | 69.35 | B |
| ATOM | 6621 | N | THR | B | 837 | -11.302 | 35.959 | 129.951 | 1.00 | 68.91 | B |
| ATOM | 6622 | CA | THR | B | 837 | -10.081 | 35.319 | 130.384 | 1.00 | 68.08 | B |
| ATOM | 6623 | CB | THR | B | 837 | -9.791 | 35.664 | 131.852 | 1.00 | 68.12 | B |
| ATOM | 6624 | OG1 | THR | B | 837 | -9.701 | 37.087 | 131.997 | 1.00 | 67.92 | B |
| ATOM | 6625 | CG2 | THR | B | 837 | -8.489 | 35.026 | 132.304 | 1.00 | 68.78 | B |
| ATOM | 6626 | C | THR | B | 837 | -10.293 | 33.824 | 130.251 | 1.00 | 68.06 | B |
| ATOM | 6627 | O | THR | B | 837 | -9.468 | 33.112 | 129.678 | 1.00 | 67.61 | B |
| ATOM | 6628 | N | TYR | B | 838 | -11.420 | 33.363 | 130.784 | 1.00 | 68.71 | B |
| ATOM | 6629 | CA | TYR | B | 838 | -11.767 | 31.951 | 130.754 | 1.00 | 69.24 | B |
| ATOM | 6630 | CB | TYR | B | 838 | -13.182 | 31.725 | 131.286 | 1.00 | 67.74 | B |
| ATOM | 6631 | CG | TYR | B | 838 | -13.686 | 30.329 | 130.993 | 1.00 | 67.17 | B |
| ATOM | 6632 | CD1 | TYR | B | 838 | -13.254 | 29.231 | 131.729 | 1.00 | 65.62 | B |

FIG. 8-54

| | | | | | | | | | |
|---|---|---|---|---|---|---|---|---|---|
| ATOM | 6633 | CE1 | TYR | B | 838 | -13.649 | 27.938 | 131.390 | 1.00 66.04 | B |
| ATOM | 6634 | CD2 | TYR | B | 838 | -14.531 | 30.099 | 129.914 | 1.00 67.66 | B |
| ATOM | 6635 | CE2 | TYR | B | 838 | -14.927 | 28.817 | 129.566 | 1.00 67.65 | B |
| ATOM | 6636 | CZ | TYR | B | 838 | -14.484 | 27.741 | 130.300 | 1.00 67.38 | B |
| ATOM | 6637 | OH | TYR | B | 838 | -14.866 | 26.480 | 129.903 | 1.00 67.68 | B |
| ATOM | 6638 | C | TYR | B | 838 | -11.688 | 31.431 | 129.341 | 1.00 69.97 | B |
| ATOM | 6639 | O | TYR | B | 838 | -11.020 | 30.430 | 129.071 | 1.00 70.54 | B |
| ATOM | 6640 | N | ILE | B | 839 | -12.398 | 32.116 | 128.450 | 1.00 70.26 | B |
| ATOM | 6641 | CA | ILE | B | 839 | -12.438 | 31.758 | 127.037 | 1.00 71.34 | B |
| ATOM | 6642 | CB | ILE | B | 839 | -13.265 | 32.799 | 126.237 | 1.00 71.33 | B |
| ATOM | 6643 | CG2 | ILE | B | 839 | -13.232 | 32.463 | 124.755 | 1.00 71.18 | B |
| ATOM | 6644 | CG1 | ILE | B | 839 | -14.708 | 32.836 | 126.768 | 1.00 70.47 | B |
| ATOM | 6645 | CD1 | ILE | B | 839 | -15.524 | 34.009 | 126.273 | 1.00 68.69 | B |
| ATOM | 6646 | C | ILE | B | 839 | -11.008 | 31.677 | 126.492 | 1.00 72.15 | B |
| ATOM | 6647 | O | ILE | B | 839 | -10.675 | 30.774 | 125.721 | 1.00 72.55 | B |
| ATOM | 6648 | N | GLY | B | 840 | -10.162 | 32.615 | 126.906 | 1.00 72.24 | B |
| ATOM | 6649 | CA | GLY | B | 840 | -8.786 | 32.587 | 126.463 | 1.00 71.49 | B |
| ATOM | 6650 | C | GLY | B | 840 | -8.235 | 31.199 | 126.704 | 1.00 71.64 | B |
| ATOM | 6651 | O | GLY | B | 840 | -7.875 | 30.502 | 125.763 | 1.00 71.78 | B |
| ATOM | 6652 | N | ILE | B | 841 | -8.191 | 30.782 | 127.963 | 1.00 71.66 | B |
| ATOM | 6653 | CA | ILE | B | 841 | -7.676 | 29.463 | 128.289 | 1.00 72.22 | B |
| ATOM | 6654 | CB | ILE | B | 841 | -7.917 | 29.107 | 129.764 | 1.00 72.63 | B |
| ATOM | 6655 | CG2 | ILE | B | 841 | -7.011 | 27.950 | 130.171 | 1.00 71.40 | B |
| ATOM | 6656 | CG1 | ILE | B | 841 | -7.627 | 30.321 | 130.646 | 1.00 73.08 | B |
| ATOM | 6657 | CD1 | ILE | B | 841 | -7.756 | 30.041 | 132.132 | 1.00 74.09 | B |
| ATOM | 6658 | C | ILE | B | 841 | -8.333 | 28.395 | 127.423 | 1.00 72.56 | B |

FIG. 8-55

| | | | | | | | | | |
|---|---|---|---|---|---|---|---|---|---|
| ATOM | 6659 | O   | ILE | B | 841 | -7.662  | 27.738 | 126.635 | 1.00 | 72.93 | B |
| ATOM | 6660 | N   | ASP | B | 842 | -9.646  | 28.231 | 127.559 | 1.00 | 72.85 | B |
| ATOM | 6661 | CA  | ASP | B | 842 | -10.367 | 27.216 | 126.793 | 1.00 | 73.84 | B |
| ATOM | 6662 | CB  | ASP | B | 842 | -11.884 | 27.452 | 126.881 | 1.00 | 76.03 | B |
| ATOM | 6663 | CG  | ASP | B | 842 | -12.711 | 26.293 | 126.275 | 1.00 | 77.39 | B |
| ATOM | 6664 | OD1 | ASP | B | 842 | -13.958 | 26.415 | 126.213 | 1.00 | 76.78 | B |
| ATOM | 6665 | OD2 | ASP | B | 842 | -12.120 | 25.263 | 125.870 | 1.00 | 77.59 | B |
| ATOM | 6666 | C   | ASP | B | 842 | -9.946  | 27.172 | 125.328 | 1.00 | 73.52 | B |
| ATOM | 6667 | O   | ASP | B | 842 | -9.507  | 26.145 | 124.833 | 1.00 | 73.14 | B |
| ATOM | 6887 | N   | MSE | B | 870 | -11.906 | 42.728 | 126.476 | 1.00 | 72.95 | B |
| ATOM | 6888 | CA  | MSE | B | 870 | -12.118 | 41.380 | 126.982 | 1.00 | 75.11 | B |
| ATOM | 6889 | CB  | MSE | B | 870 | -11.995 | 40.324 | 125.873 | 1.00 | 74.68 | B |
| ATOM | 6890 | CG  | MSE | B | 870 | -13.331 | 40.033 | 125.103 | 1.00 | 73.08 | B |
| ATOM | 6891 | SE  | MSE | B | 870 | -14.794 | 39.071 | 126.044 | 1.00 | 71.72 | B |
| ATOM | 6892 | CE  | MSE | B | 870 | -14.386 | 37.252 | 125.485 | 1.00 | 67.73 | B |
| ATOM | 6893 | C   | MSE | B | 870 | -11.101 | 41.168 | 128.100 | 1.00 | 76.54 | B |
| ATOM | 6894 | O   | MSE | B | 870 | -11.170 | 41.873 | 129.097 | 1.00 | 78.15 | B |
| ATOM | 6895 | N   | VAL | B | 871 | -10.168 | 40.230 | 127.976 | 1.00 | 77.93 | B |
| ATOM | 6896 | CA  | VAL | B | 871 | -9.178  | 40.029 | 129.051 | 1.00 | 79.54 | B |
| ATOM | 6897 | CB  | VAL | B | 871 | -7.935  | 39.284 | 128.517 | 1.00 | 79.88 | B |
| ATOM | 6898 | CG1 | VAL | B | 871 | -7.069  | 38.848 | 129.668 | 1.00 | 79.90 | B |
| ATOM | 6899 | CG2 | VAL | B | 871 | -8.353  | 38.090 | 127.680 | 1.00 | 79.47 | B |
| ATOM | 6900 | C   | VAL | B | 871 | -8.739  | 41.419 | 129.572 | 1.00 | 80.20 | B |
| ATOM | 6901 | O   | VAL | B | 871 | -7.861  | 42.052 | 128.978 | 1.00 | 81.38 | B |
| ATOM | 6902 | N   | GLN | B | 872 | -9.334  | 41.886 | 130.677 | 1.00 | 79.96 | B |
| ATOM | 6903 | CA  | GLN | B | 872 | -9.047  | 43.232 | 131.222 | 1.00 | 79.56 | B |
| ATOM | 6904 | CB  | GLN | B | 872 | -10.320 | 43.829 | 131.841 | 1.00 | 77.79 | B |

FIG. 8-56

| ATOM | 6905 | CG | GLN | B | 872 | -10.676 | 43.278 | 133.217 | 1.00 | 75.69 | B |
|---|---|---|---|---|---|---|---|---|---|---|---|
| ATOM | 6906 | CD | GLN | B | 872 | -11.251 | 44.340 | 134.138 | 1.00 | 74.96 | B |
| ATOM | 6907 | OE1 | GLN | B | 872 | -11.573 | 44.068 | 135.292 | 1.00 | 75.40 | B |
| ATOM | 6908 | NE2 | GLN | B | 872 | -11.379 | 45.556 | 133.632 | 1.00 | 73.78 | B |
| ATOM | 6909 | C | GLN | B | 872 | -7.906 | 43.443 | 132.234 | 1.00 | 80.01 | B |
| ATOM | 6910 | O | GLN | B | 872 | -7.781 | 44.532 | 132.807 | 1.00 | 79.97 | B |
| ATOM | 6911 | N | VAL | B | 873 | -7.079 | 42.428 | 132.468 | 1.00 | 80.38 | B |
| ATOM | 6912 | CA | VAL | B | 873 | -5.993 | 42.581 | 133.425 | 1.00 | 79.94 | B |
| ATOM | 6913 | CB | VAL | B | 873 | -6.461 | 42.209 | 134.840 | 1.00 | 78.70 | B |
| ATOM | 6914 | CG1 | VAL | B | 873 | -5.269 | 41.979 | 135.742 | 1.00 | 79.50 | B |
| ATOM | 6915 | CG2 | VAL | B | 873 | -7.314 | 43.342 | 135.397 | 1.00 | 77.84 | B |
| ATOM | 6916 | C | VAL | B | 873 | -4.707 | 41.830 | 133.090 | 1.00 | 79.76 | B |
| ATOM | 6917 | O | VAL | B | 873 | -4.709 | 40.636 | 132.800 | 1.00 | 78.93 | B |
| ATOM | 6918 | N | GLU | B | 874 | -3.615 | 42.587 | 133.129 | 1.00 | 80.34 | B |
| ATOM | 6919 | CA | GLU | B | 874 | -2.268 | 42.123 | 132.857 | 1.00 | 81.25 | B |
| ATOM | 6920 | CB | GLU | B | 874 | -1.262 | 43.139 | 133.395 | 1.00 | 83.48 | B |
| ATOM | 6921 | CG | GLU | B | 874 | -1.754 | 44.601 | 133.353 | 1.00 | 87.42 | B |
| ATOM | 6922 | CD | GLU | B | 874 | -3.122 | 44.827 | 134.054 | 1.00 | 89.25 | B |
| ATOM | 6923 | OE1 | GLU | B | 874 | -3.262 | 44.523 | 135.270 | 1.00 | 89.62 | B |
| ATOM | 6924 | OE2 | GLU | B | 874 | -4.061 | 45.313 | 133.375 | 1.00 | 90.53 | B |
| ATOM | 6925 | C | GLU | B | 874 | -2.072 | 40.808 | 133.565 | 1.00 | 80.68 | B |
| ATOM | 6926 | O | GLU | B | 874 | -1.356 | 39.945 | 133.071 | 1.00 | 80.43 | B |
| ATOM | 6927 | N | ALA | B | 875 | -2.712 | 40.675 | 134.729 | 1.00 | 80.69 | B |
| ATOM | 6928 | CA | ALA | B | 875 | -2.639 | 39.458 | 135.547 | 1.00 | 81.33 | B |

FIG. 8-57

| ATOM | 6929 | CB  | ALA | B | 875 | -3.166 | 39.735 | 136.944 | 1.00 | 80.98 | B |
| ATOM | 6930 | C   | ALA | B | 875 | -3.456 | 38.342 | 134.897 | 1.00 | 81.91 | B |
| ATOM | 6931 | O   | ALA | B | 875 | -3.026 | 37.179 | 134.827 | 1.00 | 81.39 | B |
| ATOM | 6932 | N   | GLN | B | 876 | -4.650 | 38.704 | 134.434 | 1.00 | 82.41 | B |
| ATOM | 6933 | CA  | GLN | B | 876 | -5.521 | 37.756 | 133.761 | 1.00 | 82.28 | B |
| ATOM | 6934 | CB  | GLN | B | 876 | -6.892 | 38.393 | 133.535 | 1.00 | 82.20 | B |
| ATOM | 6935 | CG  | GLN | B | 876 | -7.790 | 38.375 | 134.772 | 1.00 | 82.13 | B |
| ATOM | 6936 | CD  | GLN | B | 876 | -8.724 | 39.574 | 134.840 | 1.00 | 82.29 | B |
| ATOM | 6937 | OE1 | GLN | B | 876 | -9.259 | 40.012 | 133.823 | 1.00 | 82.39 | B |
| ATOM | 6938 | NE2 | GLN | B | 876 | -8.932 | 40.101 | 136.043 | 1.00 | 82.72 | B |
| ATOM | 6939 | C   | GLN | B | 876 | -4.838 | 37.411 | 132.439 | 1.00 | 82.11 | B |
| ATOM | 6940 | O   | GLN | B | 876 | -4.959 | 36.291 | 131.932 | 1.00 | 82.33 | B |
| ATOM | 6941 | N   | TYR | B | 877 | -4.106 | 38.384 | 131.897 | 1.00 | 81.76 | B |
| ATOM | 6942 | CA  | TYR | B | 877 | -3.365 | 38.192 | 130.659 | 1.00 | 81.65 | B |
| ATOM | 6943 | CB  | TYR | B | 877 | -2.683 | 39.505 | 130.233 | 1.00 | 82.52 | B |
| ATOM | 6944 | CG  | TYR | B | 877 | -2.082 | 39.445 | 128.833 | 1.00 | 85.16 | B |
| ATOM | 6945 | CD1 | TYR | B | 877 | -2.874 | 39.173 | 127.709 | 1.00 | 85.39 | B |
| ATOM | 6946 | CE1 | TYR | B | 877 | -2.304 | 39.047 | 126.430 | 1.00 | 85.81 | B |
| ATOM | 6947 | CD2 | TYR | B | 877 | -0.707 | 39.599 | 128.638 | 1.00 | 86.34 | B |
| ATOM | 6948 | CE2 | TYR | B | 877 | -0.131 | 39.478 | 127.362 | 1.00 | 86.77 | B |
| ATOM | 6949 | CZ  | TYR | B | 877 | -0.931 | 39.200 | 126.269 | 1.00 | 86.15 | B |
| ATOM | 6950 | OH  | TYR | B | 877 | -0.341 | 39.076 | 125.032 | 1.00 | 85.41 | B |
| ATOM | 6951 | C   | TYR | B | 877 | -2.318 | 37.103 | 130.891 | 1.00 | 80.57 | B |
| ATOM | 6952 | O   | TYR | B | 877 | -2.257 | 36.093 | 130.170 | 1.00 | 79.80 | B |
| ATOM | 6953 | N   | ILE | B | 878 | -1.509 | 37.321 | 131.922 | 1.00 | 79.68 | B |
| ATOM | 6954 | CA  | ILE | B | 878 | -0.455 | 36.395 | 132.294 | 1.00 | 79.54 | B |

FIG. 8-58

| ATOM | 6955 | CB | ILE | B | 878 | 0.394 | 36.987 | 133.439 | 1.00 | 78.29 | B |
|---|---|---|---|---|---|---|---|---|---|---|---|
| ATOM | 6956 | CG2 | ILE | B | 878 | 1.542 | 36.055 | 133.776 | 1.00 | 78.93 | B |
| ATOM | 6957 | CG1 | ILE | B | 878 | 0.944 | 38.352 | 133.009 | 1.00 | 78.22 | B |
| ATOM | 6958 | CD1 | ILE | B | 878 | 1.705 | 39.109 | 134.074 | 1.00 | 77.99 | B |
| ATOM | 6959 | C | ILE | B | 878 | -1.063 | 35.065 | 132.726 | 1.00 | 79.69 | B |
| ATOM | 6960 | O | ILE | B | 878 | -0.459 | 34.002 | 132.514 | 1.00 | 79.34 | B |
| ATOM | 6961 | N | LEU | B | 879 | -2.267 | 35.129 | 133.306 | 1.00 | 79.80 | B |
| ATOM | 6962 | CA | LEU | B | 879 | -2.973 | 33.937 | 133.785 | 1.00 | 79.45 | B |
| ATOM | 6963 | CB | LEU | B | 879 | -4.327 | 34.323 | 134.397 | 1.00 | 78.76 | B |
| ATOM | 6964 | CG | LEU | B | 879 | -4.880 | 33.428 | 135.529 | 1.00 | 80.12 | B |
| ATOM | 6965 | CD1 | LEU | B | 879 | -6.392 | 33.629 | 135.640 | 1.00 | 79.78 | B |
| ATOM | 6966 | CD2 | LEU | B | 879 | -4.576 | 31.944 | 135.274 | 1.00 | 80.22 | B |
| ATOM | 6967 | C | LEU | B | 879 | -3.193 | 32.918 | 132.660 | 1.00 | 79.08 | B |
| ATOM | 6968 | O | LEU | B | 879 | -2.995 | 31.710 | 132.843 | 1.00 | 77.91 | B |
| ATOM | 6969 | N | ILE | B | 880 | -3.603 | 33.417 | 131.499 | 1.00 | 79.40 | B |
| ATOM | 6970 | CA | ILE | B | 880 | -3.852 | 32.562 | 130.348 | 1.00 | 79.79 | B |
| ATOM | 6971 | CB | ILE | B | 880 | -4.280 | 33.406 | 129.121 | 1.00 | 79.63 | B |
| ATOM | 6972 | CG2 | ILE | B | 880 | -4.715 | 32.486 | 127.970 | 1.00 | 78.56 | B |
| ATOM | 6973 | CG1 | ILE | B | 880 | -5.429 | 34.338 | 129.526 | 1.00 | 79.69 | B |
| ATOM | 6974 | CD1 | ILE | B | 880 | -5.913 | 35.244 | 128.429 | 1.00 | 79.01 | B |
| ATOM | 6975 | C | ILE | B | 880 | -2.583 | 31.786 | 130.020 | 1.00 | 79.73 | B |
| ATOM | 6976 | O | ILE | B | 880 | -2.613 | 30.571 | 129.771 | 1.00 | 79.39 | B |
| ATOM | 6977 | N | HIS | B | 881 | -1.463 | 32.496 | 130.044 | 1.00 | 78.83 | B |
| ATOM | 6978 | CA | HIS | B | 881 | -0.178 | 31.890 | 129.744 | 1.00 | 78.19 | B |
| ATOM | 6979 | CB | HIS | B | 881 | 0.892 | 32.979 | 129.722 | 1.00 | 78.60 | B |
| ATOM | 6980 | CG | HIS | B | 881 | 0.660 | 34.035 | 128.684 | 1.00 | 79.79 | B |
| ATOM | 6981 | CD2 | HIS | B | 881 | 0.161 | 35.293 | 128.785 | 1.00 | 80.37 | B |

FIG. 8-59

| ATOM | 6982 | ND1 | HIS B 881 | 0.969 | 33.855 | 127.353 | 1.00 | 79.08 | B |
| --- | --- | --- | --- | --- | --- | --- | --- | --- | --- |
| ATOM | 6983 | CE1 | HIS B 881 | 0.678 | 34.957 | 126.680 | 1.00 | 79.48 | B |
| ATOM | 6984 | NE2 | HIS B 881 | 0.186 | 35.845 | 127.525 | 1.00 | 79.95 | B |
| ATOM | 6985 | C | HIS B 881 | 0.205 | 30.778 | 130.733 | 1.00 | 77.78 | B |
| ATOM | 6986 | O | HIS B 881 | 0.569 | 29.673 | 130.320 | 1.00 | 76.26 | B |
| ATOM | 6987 | N | GLN B 882 | 0.116 | 31.072 | 132.031 | 1.00 | 77.33 | B |
| ATOM | 6988 | CA | GLN B 882 | 0.470 | 30.098 | 133.064 | 1.00 | 77.22 | B |
| ATOM | 6989 | CB | GLN B 882 | 0.283 | 30.699 | 134.456 | 1.00 | 77.61 | B |
| ATOM | 6990 | CG | GLN B 882 | 0.683 | 32.154 | 134.562 | 1.00 | 78.83 | B |
| ATOM | 6991 | CD | GLN B 882 | 0.461 | 32.719 | 135.954 | 1.00 | 79.14 | B |
| ATOM | 6992 | OE1 | GLN B 882 | -0.509 | 32.371 | 136.633 | 1.00 | 78.54 | B |
| ATOM | 6993 | NE2 | GLN B 882 | 1.351 | 33.609 | 136.379 | 1.00 | 79.74 | B |
| ATOM | 6994 | C | GLN B 882 | -0.420 | 28.879 | 132.927 | 1.00 | 77.18 | B |
| ATOM | 6995 | O | GLN B 882 | -0.003 | 27.736 | 133.164 | 1.00 | 75.52 | B |
| ATOM | 6996 | N | ALA B 883 | -1.664 | 29.151 | 132.547 | 1.00 | 78.00 | B |
| ATOM | 6997 | CA | ALA B 883 | -2.667 | 28.115 | 132.349 | 1.00 | 77.65 | B |
| ATOM | 6998 | CB | ALA B 883 | -3.963 | 28.740 | 131.852 | 1.00 | 77.53 | B |
| ATOM | 6999 | C | ALA B 883 | -2.114 | 27.168 | 131.308 | 1.00 | 77.72 | B |
| ATOM | 7000 | O | ALA B 883 | -2.085 | 25.946 | 131.504 | 1.00 | 75.95 | B |

(8e) Active site D2 domain molecule B

| ATOM | 7516 | N | SER B 945 | 17.155 | 29.752 | 166.719 | 1.00 | 92.96 | B |
| --- | --- | --- | --- | --- | --- | --- | --- | --- | --- |

FIG. 8-60

| ATOM | 7517 | CA | SER | B | 945 | 17.157 | 28.845 | 167.877 | 1.00 | 93.21 | B |
|---|---|---|---|---|---|---|---|---|---|---|---|
| ATOM | 7518 | CB | SER | B | 945 | 17.799 | 29.533 | 169.092 | 1.00 | 93.32 | B |
| ATOM | 7519 | OG | SER | B | 945 | 17.041 | 30.660 | 169.517 | 1.00 | 93.39 | B |
| ATOM | 7520 | C | SER | B | 945 | 15.738 | 28.409 | 168.244 | 1.00 | 93.24 | B |
| ATOM | 7521 | O | SER | B | 945 | 15.475 | 27.980 | 169.381 | 1.00 | 93.40 | B |
| ATOM | 7522 | N | LYS | B | 946 | 14.834 | 28.531 | 167.271 | 1.00 | 92.71 | B |
| ATOM | 7523 | CA | LYS | B | 946 | 13.438 | 28.157 | 167.448 | 1.00 | 92.24 | B |
| ATOM | 7524 | CB | LYS | B | 946 | 12.562 | 29.402 | 167.367 | 1.00 | 92.24 | B |
| ATOM | 7525 | CG | LYS | B | 946 | 12.831 | 30.441 | 168.438 | 1.00 | 92.26 | B |
| ATOM | 7526 | CD | LYS | B | 946 | 11.895 | 31.611 | 168.205 | 1.00 | 93.68 | B |
| ATOM | 7527 | CE | LYS | B | 946 | 12.070 | 32.714 | 169.218 | 1.00 | 93.90 | B |
| ATOM | 7528 | NZ | LYS | B | 946 | 11.097 | 33.808 | 168.942 | 1.00 | 95.02 | B |
| ATOM | 7529 | C | LYS | B | 946 | 13.019 | 27.147 | 166.370 | 1.00 | 91.75 | B |
| ATOM | 7530 | O | LYS | B | 946 | 11.842 | 26.808 | 166.218 | 1.00 | 91.93 | B |
| ATOM | 7531 | N | ASN | B | 947 | 13.996 | 26.655 | 165.630 | 1.00 | 91.15 | B |
| ATOM | 7532 | CA | ASN | B | 947 | 13.711 | 25.710 | 164.577 | 1.00 | 91.18 | B |
| ATOM | 7533 | CB | ASN | B | 947 | 14.203 | 26.273 | 163.232 | 1.00 | 93.02 | B |
| ATOM | 7534 | CG | ASN | B | 947 | 13.521 | 27.606 | 162.863 | 1.00 | 93.58 | B |
| ATOM | 7535 | OD1 | ASN | B | 947 | 13.853 | 28.244 | 161.855 | 1.00 | 93.44 | B |
| ATOM | 7536 | ND2 | ASN | B | 947 | 12.565 | 28.024 | 163.689 | 1.00 | 93.25 | B |
| ATOM | 7537 | C | ASN | B | 947 | 14.342 | 24.361 | 164.848 | 1.00 | 90.64 | B |
| ATOM | 7538 | O | ASN | B | 947 | 15.557 | 24.207 | 164.755 | 1.00 | 90.16 | B |
| ATOM | 7539 | N | ARG | B | 948 | 13.504 | 23.390 | 165.204 | 1.00 | 91.11 | B |
| ATOM | 7540 | CA | ARG | B | 948 | 13.956 | 22.019 | 165.454 | 1.00 | 91.75 | B |
| ATOM | 7541 | CB | ARG | B | 948 | 12.754 | 21.070 | 165.549 | 1.00 | 91.58 | B |
| ATOM | 7542 | CG | ARG | B | 948 | 13.100 | 19.599 | 165.409 | 1.00 | 92.17 | B |
| ATOM | 7543 | CD | ARG | B | 948 | 13.601 | 19.012 | 166.702 | 1.00 | 94.19 | B |

FIG. 8-61

| | | | | | | | | | |
|---|---|---|---|---|---|---|---|---|---|
| ATOM | 7544 | NE | ARG | B | 948 | 12.562 | 19.045 | 167.735 | 1.00 | 96.16 | B |
| ATOM | 7545 | CZ | ARG | B | 948 | 12.626 | 18.390 | 168.899 | 1.00 | 96.88 | B |
| ATOM | 7546 | NH1 | ARG | B | 948 | 13.690 | 17.638 | 169.182 | 1.00 | 96.71 | B |
| ATOM | 7547 | NH2 | ARG | B | 948 | 11.629 | 18.489 | 169.784 | 1.00 | 95.97 | B |
| ATOM | 7548 | C | ARG | B | 948 | 14.854 | 21.586 | 164.288 | 1.00 | 91.94 | B |
| ATOM | 7549 | O | ARG | B | 948 | 15.884 | 20.938 | 164.495 | 1.00 | 91.74 | B |
| ATOM | 7550 | N | ASN | B | 949 | 14.451 | 21.949 | 163.069 | 1.00 | 91.88 | B |
| ATOM | 7551 | CA | ASN | B | 949 | 15.213 | 21.620 | 161.875 | 1.00 | 91.73 | B |
| ATOM | 7552 | CB | ASN | B | 949 | 14.463 | 20.604 | 161.025 | 1.00 | 91.10 | B |
| ATOM | 7553 | CG | ASN | B | 949 | 15.284 | 20.108 | 159.858 | 1.00 | 90.83 | B |
| ATOM | 7554 | OD1 | ASN | B | 949 | 14.892 | 19.163 | 159.166 | 1.00 | 91.00 | B |
| ATOM | 7555 | ND2 | ASN | B | 949 | 16.432 | 20.745 | 159.625 | 1.00 | 89.92 | B |
| ATOM | 7556 | C | ASN | B | 949 | 15.503 | 22.882 | 161.064 | 1.00 | 92.62 | B |
| ATOM | 7557 | O | ASN | B | 949 | 14.591 | 23.584 | 160.599 | 1.00 | 92.58 | B |
| ATOM | 7558 | N | SER | B | 950 | 16.803 | 23.136 | 160.906 | 1.00 | 93.84 | B |
| ATOM | 7559 | CA | SER | B | 950 | 17.364 | 24.297 | 160.208 | 1.00 | 94.08 | B |
| ATOM | 7560 | CB | SER | B | 950 | 18.880 | 24.148 | 160.120 | 1.00 | 93.10 | B |
| ATOM | 7561 | OG | SER | B | 950 | 19.419 | 25.131 | 159.258 | 1.00 | 93.58 | B |
| ATOM | 7562 | C | SER | B | 950 | 16.834 | 24.634 | 158.818 | 1.00 | 94.54 | B |
| ATOM | 7563 | O | SER | B | 950 | 16.334 | 25.743 | 158.585 | 1.00 | 94.84 | B |
| ATOM | 7564 | N | ASN | B | 951 | 16.966 | 23.696 | 157.887 | 1.00 | 94.26 | B |
| ATOM | 7565 | CA | ASN | B | 951 | 16.504 | 23.935 | 156.522 | 1.00 | 93.90 | B |
| ATOM | 7566 | CB | ASN | B | 951 | 17.406 | 23.189 | 155.533 | 1.00 | 95.22 | B |
| ATOM | 7567 | CG | ASN | B | 951 | 17.427 | 21.682 | 155.776 | 1.00 | 96.68 | B |
| ATOM | 7568 | OD1 | ASN | B | 951 | 18.157 | 20.945 | 155.099 | 1.00 | 97.50 | B |
| ATOM | 7569 | ND2 | ASN | B | 951 | 16.622 | 21.216 | 156.739 | 1.00 | 96.43 | B |

FIG. 8-62

| ATOM | 7570 | C | ASN | B | 951 | 15.030 | 23.563 | 156.296 | 1.00 | 93.16 | B |
|---|---|---|---|---|---|---|---|---|---|---|---|
| ATOM | 7571 | O | ASN | B | 951 | 14.639 | 23.141 | 155.199 | 1.00 | 92.69 | B |
| ATOM | 7572 | N | VAL | B | 952 | 14.228 | 23.712 | 157.352 | 1.00 | 91.76 | B |
| ATOM | 7573 | CA | VAL | B | 952 | 12.792 | 23.445 | 157.303 | 1.00 | 89.18 | B |
| ATOM | 7574 | CB | VAL | B | 952 | 12.413 | 22.120 | 157.993 | 1.00 | 88.58 | B |
| ATOM | 7575 | CG1 | VAL | B | 952 | 10.912 | 21.890 | 157.876 | 1.00 | 88.22 | B |
| ATOM | 7576 | CG2 | VAL | B | 952 | 13.176 | 20.971 | 157.352 | 1.00 | 87.65 | B |
| ATOM | 7577 | C | VAL | B | 952 | 12.122 | 24.613 | 158.009 | 1.00 | 88.33 | B |
| ATOM | 7578 | O | VAL | B | 952 | 11.535 | 24.483 | 159.085 | 1.00 | 87.39 | B |
| ATOM | 7579 | N | ILE | B | 953 | 12.250 | 25.770 | 157.380 | 1.00 | 88.00 | B |
| ATOM | 7580 | CA | ILE | B | 953 | 11.678 | 26.993 | 157.898 | 1.00 | 88.31 | B |
| ATOM | 7581 | CB | ILE | B | 953 | 12.713 | 28.118 | 157.862 | 1.00 | 88.44 | B |
| ATOM | 7582 | CG2 | ILE | B | 953 | 12.070 | 29.449 | 158.265 | 1.00 | 87.57 | B |
| ATOM | 7583 | CG1 | ILE | B | 953 | 13.881 | 27.734 | 158.765 | 1.00 | 89.63 | B |
| ATOM | 7584 | CD1 | ILE | B | 953 | 14.944 | 28.796 | 158.874 | 1.00 | 91.39 | B |
| ATOM | 7585 | C | ILE | B | 953 | 10.472 | 27.400 | 157.069 | 1.00 | 88.30 | B |
| ATOM | 7586 | O | ILE | B | 953 | 10.525 | 27.393 | 155.836 | 1.00 | 88.09 | B |
| ATOM | 7587 | N | PRO | B | 954 | 9.361 | 27.759 | 157.735 | 1.00 | 87.99 | B |
| ATOM | 7588 | CD | PRO | B | 954 | 9.164 | 27.978 | 159.183 | 1.00 | 87.71 | B |
| ATOM | 7589 | CA | PRO | B | 954 | 8.179 | 28.160 | 156.966 | 1.00 | 87.82 | B |
| ATOM | 7590 | CB | PRO | B | 954 | 7.138 | 28.439 | 158.052 | 1.00 | 87.80 | B |
| ATOM | 7591 | CG | PRO | B | 954 | 7.995 | 28.938 | 159.214 | 1.00 | 87.79 | B |
| ATOM | 7592 | C | PRO | B | 954 | 8.485 | 29.395 | 156.101 | 1.00 | 87.75 | B |
| ATOM | 7593 | O | PRO | B | 954 | 9.295 | 30.255 | 156.468 | 1.00 | 87.60 | B |

FIG. 8-63

| | | | | | | | | |
|---|---|---|---|---|---|---|---|---|
| ATOM | 8083 | N   | THR | B1037 | 4.559  | 11.676 | 165.992 | 1.00 | 83.21 | B |
| ATOM | 8084 | CA  | THR | B1037 | 5.821  | 11.171 | 166.531 | 1.00 | 84.49 | B |
| ATOM | 8085 | CB  | THR | B1037 | 6.928  | 12.272 | 166.502 | 1.00 | 83.09 | B |
| ATOM | 8086 | OG1 | THR | B1037 | 6.570  | 13.357 | 167.379 | 1.00 | 81.10 | B |
| ATOM | 8087 | CG2 | THR | B1037 | 7.115  | 12.801 | 165.074 | 1.00 | 83.41 | B |
| ATOM | 8088 | C   | THR | B1037 | 5.699  | 10.666 | 167.970 | 1.00 | 86.04 | B |
| ATOM | 8089 | O   | THR | B1037 | 4.628  | 10.738 | 168.594 | 1.00 | 85.84 | B |
| ATOM | 8090 | N   | GLU | B1038 | 6.811  | 10.133 | 168.472 | 1.00 | 87.84 | B |
| ATOM | 8091 | CA  | GLU | B1038 | 6.908  | 9.649  | 169.844 | 1.00 | 88.96 | B |
| ATOM | 8092 | CB  | GLU | B1038 | 7.860  | 8.460  | 169.917 | 1.00 | 88.68 | B |
| ATOM | 8093 | CG  | GLU | B1038 | 7.454  | 7.382  | 170.919 | 1.00 | 90.19 | B |
| ATOM | 8094 | CD  | GLU | B1038 | 6.134  | 6.675  | 170.556 | 1.00 | 91.11 | B |
| ATOM | 8095 | OE1 | GLU | B1038 | 5.912  | 6.383  | 169.352 | 1.00 | 92.76 | B |
| ATOM | 8096 | OE2 | GLU | B1038 | 5.324  | 6.393  | 171.478 | 1.00 | 90.75 | B |
| ATOM | 8097 | C   | GLU | B1038 | 7.518  | 10.857 | 170.554 | 1.00 | 89.87 | B |
| ATOM | 8098 | O   | GLU | B1038 | 7.692  | 11.912 | 169.929 | 1.00 | 91.26 | B |
| ATOM | 8099 | N   | LEU | B1039 | 7.843  | 10.745 | 171.837 | 1.00 | 90.88 | B |
| ATOM | 8100 | CA  | LEU | B1039 | 8.435  | 11.899 | 172.522 | 1.00 | 91.75 | B |
| ATOM | 8101 | CB  | LEU | B1039 | 8.126  | 11.846 | 174.016 | 1.00 | 90.74 | B |
| ATOM | 8102 | CG  | LEU | B1039 | 6.728  | 12.394 | 174.310 | 1.00 | 90.01 | B |
| ATOM | 8103 | CD1 | LEU | B1039 | 6.376  | 12.174 | 175.762 | 1.00 | 89.59 | B |
| ATOM | 8104 | CD2 | LEU | B1039 | 6.686  | 13.876 | 173.953 | 1.00 | 88.61 | B |
| ATOM | 8105 | C   | LEU | B1039 | 9.936  | 11.968 | 172.262 | 1.00 | 92.48 | B |
| ATOM | 8106 | O   | LEU | B1039 | 10.539 | 13.052 | 172.262 | 1.00 | 91.02 | B |
| ATOM | 8107 | N   | LYS | B1040 | 10.518 | 10.794 | 172.031 | 1.00 | 94.01 | B |
| ATOM | 8108 | CA  | LYS | B1040 | 11.928 | 10.660 | 171.700 | 1.00 | 96.23 | B |

FIG. 8-64

| ATOM | 8109 | CB | LYS | B1040 | 12.824 | 11.135 | 172.847 | 1.00 | 96.14 | B |
| --- | --- | --- | --- | --- | --- | --- | --- | --- | --- | --- |
| ATOM | 8110 | CG | LYS | B1040 | 12.442 | 10.663 | 174.227 | 1.00 | 96.33 | B |
| ATOM | 8111 | CD | LYS | B1040 | 13.637 | 10.813 | 175.187 | 1.00 | 96.49 | B |
| ATOM | 8112 | CE | LYS | B1040 | 14.263 | 12.218 | 175.163 | 1.00 | 95.67 | B |
| ATOM | 8113 | NZ | LYS | B1040 | 13.427 | 13.266 | 175.825 | 1.00 | 95.26 | B |
| ATOM | 8114 | C | LYS | B1040 | 12.311 | 9.236 | 171.298 | 1.00 | 97.89 | B |
| ATOM | 8115 | O | LYS | B1040 | 11.526 | 8.288 | 171.470 | 1.00 | 98.35 | B |
| ATOM | 8116 | N | HIS | B1041 | 13.517 | 9.113 | 170.738 | 1.00 | 99.43 | B |
| ATOM | 8117 | CA | HIS | B1041 | 14.081 | 7.838 | 170.279 | 1.00 | 99.96 | B |
| ATOM | 8118 | CB | HIS | B1041 | 14.760 | 8.044 | 168.920 | 1.00 | 99.95 | B |
| ATOM | 8119 | CG | HIS | B1041 | 14.560 | 6.924 | 167.940 | 1.00 | 99.96 | B |
| ATOM | 8120 | CD2 | HIS | B1041 | 14.087 | 6.931 | 166.667 | 1.00 | 99.97 | B |
| ATOM | 8121 | ND1 | HIS | B1041 | 14.952 | 5.626 | 168.197 | 1.00 | 99.96 | B |
| ATOM | 8122 | CE1 | HIS | B1041 | 14.731 | 4.886 | 167.122 | 1.00 | 99.95 | B |
| ATOM | 8123 | NE2 | HIS | B1041 | 14.208 | 5.653 | 166.180 | 1.00 | 99.99 | B |
| ATOM | 8124 | C | HIS | B1041 | 15.132 | 7.493 | 171.333 | 1.00 | 99.94 | B |
| ATOM | 8125 | O | HIS | B1041 | 16.291 | 7.915 | 171.220 | 1.00 | 99.91 | B |
| ATOM | 8126 | N | GLY | B1042 | 14.712 | 6.749 | 172.360 | 1.00 | 99.96 | B |
| ATOM | 8127 | CA | GLY | B1042 | 15.614 | 6.383 | 173.436 | 1.00 | 99.95 | B |
| ATOM | 8128 | C | GLY | B1042 | 16.223 | 7.634 | 174.063 | 1.00 | 99.95 | B |
| ATOM | 8129 | O | GLY | B1042 | 15.706 | 8.154 | 175.070 | 1.00 | 99.97 | B |
| ATOM | 8130 | N | ASP | B1043 | 17.317 | 8.118 | 173.456 | 1.00 | 99.96 | B |
| ATOM | 8131 | CA | ASP | B1043 | 18.042 | 9.312 | 173.921 | 1.00 | 99.98 | B |
| ATOM | 8132 | CB | ASP | B1043 | 19.541 | 9.220 | 173.573 | 1.00 | 99.95 | B |
| ATOM | 8133 | CG | ASP | B1043 | 20.159 | 7.885 | 173.951 | 1.00 | 99.95 | B |
| ATOM | 8134 | OD1 | ASP | B1043 | 19.761 | 6.858 | 173.349 | 1.00 | 99.96 | B |

FIG. 8-65

| ATOM | 8135 | OD2 | ASP | B1043 | 21.043 | 7.871 | 174.846 | 1.00 | 99.96 | B |
| ATOM | 8136 | C | ASP | B1043 | 17.495 | 10.554 | 173.233 | 1.00 | 99.67 | B |
| ATOM | 8137 | O | ASP | B1043 | 16.871 | 11.422 | 173.860 | 1.00 | 99.95 | B |
| ATOM | 8138 | N | GLN | B1044 | 17.759 | 10.611 | 171.930 | 1.00 | 99.55 | B |
| ATOM | 8139 | CA | GLN | B1044 | 17.359 | 11.721 | 171.080 | 1.00 | 98.88 | B |
| ATOM | 8140 | CB | GLN | B1044 | 17.793 | 11.446 | 169.624 | 1.00 | 99.11 | B |
| ATOM | 8141 | CG | GLN | B1044 | 17.535 | 10.011 | 169.106 | 1.00 | 99.43 | B |
| ATOM | 8142 | CD | GLN | B1044 | 18.546 | 8.958 | 169.608 | 1.00 | 99.21 | B |
| ATOM | 8143 | OE1 | GLN | B1044 | 18.502 | 7.794 | 169.184 | 1.00 | 98.13 | B |
| ATOM | 8144 | NE2 | GLN | B1044 | 19.453 | 9.365 | 170.506 | 1.00 | 98.76 | B |
| ATOM | 8145 | C | GLN | B1044 | 15.869 | 12.058 | 171.143 | 1.00 | 98.05 | B |
| ATOM | 8146 | O | GLN | B1044 | 15.023 | 11.222 | 170.807 | 1.00 | 97.02 | B |
| ATOM | 8147 | N | GLU | B1045 | 15.569 | 13.287 | 171.586 | 1.00 | 97.42 | B |
| ATOM | 8148 | CA | GLU | B1045 | 14.194 | 13.774 | 171.688 | 1.00 | 97.26 | B |
| ATOM | 8149 | CB | GLU | B1045 | 14.068 | 14.955 | 172.677 | 1.00 | 97.77 | B |
| ATOM | 8150 | CG | GLU | B1045 | 14.503 | 16.346 | 172.161 | 1.00 | 99.36 | B |
| ATOM | 8151 | CD | GLU | B1045 | 13.819 | 17.522 | 172.922 | 1.00 | 99.95 | B |
| ATOM | 8152 | OE1 | GLU | B1045 | 13.892 | 17.576 | 174.175 | 1.00 | 99.94 | B |
| ATOM | 8153 | OE2 | GLU | B1045 | 13.205 | 18.407 | 172.268 | 1.00 | 99.94 | B |
| ATOM | 8154 | C | GLU | B1045 | 13.686 | 14.195 | 170.310 | 1.00 | 96.56 | B |
| ATOM | 8155 | O | GLU | B1045 | 14.277 | 15.049 | 169.633 | 1.00 | 95.93 | B |
| ATOM | 8156 | N | ILE | B1046 | 12.589 | 13.566 | 169.903 | 1.00 | 95.78 | B |
| ATOM | 8157 | CA | ILE | B1046 | 11.968 | 13.834 | 168.615 | 1.00 | 95.11 | B |
| ATOM | 8158 | CB | ILE | B1046 | 11.251 | 12.560 | 168.111 | 1.00 | 94.79 | B |
| ATOM | 8159 | CG2 | ILE | B1046 | 10.685 | 12.781 | 166.722 | 1.00 | 95.96 | B |

FIG. 8-66

| | | | | | | | | |
|---|---|---|---|---|---|---|---|---|
| ATOM | 8160 | CG1 | ILE | B1046 | 12.244 | 11.400 | 168.082 | 1.00 | 94.74 | B |
| ATOM | 8161 | CD1 | ILE | B1046 | 11.663 | 10.105 | 167.557 | 1.00 | 95.42 | B |
| ATOM | 8162 | C | ILE | B1046 | 10.967 | 14.992 | 168.776 | 1.00 | 94.74 | B |
| ATOM | 8163 | O | ILE | B1046 | 10.534 | 15.640 | 167.803 | 1.00 | 94.63 | B |
| ATOM | 8164 | N | CYS | B1047 | 10.619 | 15.253 | 170.030 | 1.00 | 93.58 | B |
| ATOM | 8165 | CA | CYS | B1047 | 9.685 | 16.313 | 170.353 | 1.00 | 91.74 | B |
| ATOM | 8166 | CB | CYS | B1047 | 8.241 | 15.866 | 170.032 | 1.00 | 91.82 | B |
| ATOM | 8167 | SG | CYS | B1047 | 6.952 | 17.161 | 170.198 | 1.00 | 90.61 | B |
| ATOM | 8168 | C | CYS | B1047 | 9.843 | 16.569 | 171.846 | 1.00 | 90.21 | B |
| ATOM | 8169 | O | CYS | B1047 | 10.404 | 15.735 | 172.573 | 1.00 | 89.22 | B |
| ATOM | 8598 | N | THR | B1098 | 1.349 | 6.557 | 167.096 | 1.00 | 81.28 | B |
| ATOM | 8599 | CA | THR | B1098 | 2.652 | 6.010 | 167.442 | 1.00 | 83.22 | B |
| ATOM | 8600 | CB | THR | B1098 | 2.501 | 5.022 | 168.592 | 1.00 | 83.90 | B |
| ATOM | 8601 | OG1 | THR | B1098 | 1.783 | 5.659 | 169.666 | 1.00 | 84.27 | B |
| ATOM | 8602 | CG2 | THR | B1098 | 3.873 | 4.537 | 169.058 | 1.00 | 83.80 | B |
| ATOM | 8603 | C | THR | B1098 | 3.272 | 5.304 | 166.237 | 1.00 | 83.96 | B |
| ATOM | 8604 | O | THR | B1098 | 4.360 | 5.670 | 165.785 | 1.00 | 83.90 | B |
| ATOM | 8605 | N | ASN | B1099 | 2.554 | 4.302 | 165.732 | 1.00 | 84.65 | B |
| ATOM | 8606 | CA | ASN | B1099 | 2.947 | 3.501 | 164.573 | 1.00 | 86.07 | B |
| ATOM | 8607 | CB | ASN | B1099 | 1.736 | 2.710 | 164.068 | 1.00 | 87.91 | B |
| ATOM | 8608 | CG | ASN | B1099 | 1.706 | 1.288 | 164.569 | 1.00 | 89.11 | B |
| ATOM | 8609 | OD1 | ASN | B1099 | 2.558 | 0.469 | 164.197 | 1.00 | 89.95 | B |
| ATOM | 8610 | ND2 | ASN | B1099 | 0.714 | 0.974 | 165.413 | 1.00 | 89.37 | B |
| ATOM | 8611 | C | ASN | B1099 | 3.516 | 4.259 | 163.372 | 1.00 | 86.09 | B |
| ATOM | 8612 | O | ASN | B1099 | 3.053 | 4.048 | 162.250 | 1.00 | 86.26 | B |
| ATOM | 8613 | N | TRP | B1100 | 4.510 | 5.114 | 163.561 | 1.00 | 86.52 | B |

FIG. 8-67

| ATOM | 8614 | CA  | TRP | B1100 | 5.030  | 5.819  | 162.402 | 1.00 | 87.77 | B |
|------|------|-----|-----|-------|--------|--------|---------|------|-------|---|
| ATOM | 8615 | CB  | TRP | B1100 | 3.984  | 6.810  | 161.903 | 1.00 | 88.12 | B |
| ATOM | 8616 | CG  | TRP | B1100 | 4.216  | 7.275  | 160.504 | 1.00 | 88.87 | B |
| ATOM | 8617 | CD2 | TRP | B1100 | 3.457  | 8.262  | 159.804 | 1.00 | 89.10 | B |
| ATOM | 8618 | CE2 | TRP | B1100 | 4.042  | 8.414  | 158.524 | 1.00 | 89.79 | B |
| ATOM | 8619 | CE3 | TRP | B1100 | 2.339  | 9.038  | 160.133 | 1.00 | 88.62 | B |
| ATOM | 8620 | CD1 | TRP | B1100 | 5.207  | 6.868  | 159.642 | 1.00 | 89.45 | B |
| ATOM | 8621 | NE1 | TRP | B1100 | 5.108  | 7.552  | 158.449 | 1.00 | 90.06 | B |
| ATOM | 8622 | CZ2 | TRP | B1100 | 3.542  | 9.314  | 157.576 | 1.00 | 89.79 | B |
| ATOM | 8623 | CZ3 | TRP | B1100 | 1.845  | 9.930  | 159.193 | 1.00 | 88.56 | B |
| ATOM | 8624 | CH2 | TRP | B1100 | 2.447  | 10.061 | 157.930 | 1.00 | 89.10 | B |
| ATOM | 8625 | C   | TRP | B1100 | 6.362  | 6.523  | 162.609 | 1.00 | 88.85 | B |
| ATOM | 8626 | O   | TRP | B1100 | 6.424  | 7.715  | 162.952 | 1.00 | 88.43 | B |
| ATOM | 8627 | N   | SER | B1101 | 7.424  | 5.759  | 162.368 | 1.00 | 89.99 | B |
| ATOM | 8628 | CA  | SER | B1101 | 8.802  | 6.223  | 162.499 | 1.00 | 91.30 | B |
| ATOM | 8629 | CB  | SER | B1101 | 9.740  | 5.014  | 162.667 | 1.00 | 92.49 | B |
| ATOM | 8630 | OG  | SER | B1101 | 9.331  | 4.177  | 163.744 | 1.00 | 94.02 | B |
| ATOM | 8631 | C   | SER | B1101 | 9.223  | 7.019  | 161.262 | 1.00 | 91.35 | B |
| ATOM | 8632 | O   | SER | B1101 | 8.849  | 6.673  | 160.136 | 1.00 | 90.44 | B |
| ATOM | 8633 | N   | VAL | B1102 | 10.004 | 8.079  | 161.469 | 1.00 | 91.64 | B |
| ATOM | 8634 | CA  | VAL | B1102 | 10.476 | 8.885  | 160.343 | 1.00 | 92.48 | B |
| ATOM | 8635 | CB  | VAL | B1102 | 11.217 | 10.177 | 160.822 | 1.00 | 92.65 | B |
| ATOM | 8636 | CG1 | VAL | B1102 | 10.456 | 10.824 | 161.993 | 1.00 | 93.03 | B |
| ATOM | 8637 | CG2 | VAL | B1102 | 12.657 | 9.847  | 161.208 | 1.00 | 92.81 | B |
| ATOM | 8638 | C   | VAL | B1102 | 11.427 | 8.047  | 159.458 | 1.00 | 92.84 | B |
| ATOM | 8639 | O   | VAL | B1102 | 12.133 | 8.585  | 158.603 | 1.00 | 92.33 | B |
| ATOM | 8640 | N   | GLU | B1103 | 11.446 | 6.732  | 159.687 | 1.00 | 93.46 | B |

FIG. 8-68

| | | | | | | | | | |
|---|---|---|---|---|---|---|---|---|---|
| ATOM | 8641 | CA | GLU | B1103 | 12.276 | 5.802 | 158.913 | 1.00 | 93.70 | B |
| ATOM | 8642 | CB | GLU | B1103 | 12.951 | 4.768 | 159.817 | 1.00 | 94.18 | B |
| ATOM | 8643 | CG | GLU | B1103 | 13.971 | 5.314 | 160.817 | 1.00 | 95.89 | B |
| ATOM | 8644 | CD | GLU | B1103 | 13.386 | 5.580 | 162.218 | 1.00 | 96.47 | B |
| ATOM | 8645 | OE1 | GLU | B1103 | 12.557 | 4.762 | 162.705 | 1.00 | 96.05 | B |
| ATOM | 8646 | OE2 | GLU | B1103 | 13.780 | 6.601 | 162.838 | 1.00 | 97.45 | B |
| ATOM | 8647 | C | GLU | B1103 | 11.354 | 5.067 | 157.944 | 1.00 | 94.23 | B |
| ATOM | 8648 | O | GLU | B1103 | 11.415 | 5.263 | 156.724 | 1.00 | 93.59 | B |
| ATOM | 8649 | N | GLN | B1104 | 10.499 | 4.212 | 158.501 | 1.00 | 94.75 | B |
| ATOM | 8650 | CA | GLN | B1104 | 9.539 | 3.466 | 157.696 | 1.00 | 95.22 | B |
| ATOM | 8651 | CB | GLN | B1104 | 9.064 | 2.225 | 158.473 | 1.00 | 95.40 | B |
| ATOM | 8652 | CG | GLN | B1104 | 8.835 | 2.427 | 160.002 | 1.00 | 96.74 | B |
| ATOM | 8653 | CD | GLN | B1104 | 7.418 | 2.920 | 160.381 | 1.00 | 97.28 | B |
| ATOM | 8654 | OE1 | GLN | B1104 | 7.118 | 4.124 | 160.317 | 1.00 | 97.26 | B |
| ATOM | 8655 | NE2 | GLN | B1104 | 6.545 | 1.980 | 160.776 | 1.00 | 96.99 | B |
| ATOM | 8656 | C | GLN | B1104 | 8.335 | 4.364 | 157.333 | 1.00 | 95.76 | B |
| ATOM | 8657 | O | GLN | B1104 | 8.387 | 5.612 | 157.469 | 1.00 | 95.82 | B |
| ATOM | 8658 | N | LEU | B1105 | 7.268 | 3.730 | 156.840 | 1.00 | 94.97 | B |
| ATOM | 8659 | CA | LEU | B1105 | 6.030 | 4.443 | 156.513 | 1.00 | 93.89 | B |
| ATOM | 8660 | CB | LEU | B1105 | 5.702 | 4.361 | 155.023 | 1.00 | 92.67 | B |
| ATOM | 8661 | CG | LEU | B1105 | 6.238 | 5.519 | 154.178 | 1.00 | 91.66 | B |
| ATOM | 8662 | CD1 | LEU | B1105 | 5.782 | 5.322 | 152.749 | 1.00 | 90.88 | B |
| ATOM | 8663 | CD2 | LEU | B1105 | 5.739 | 6.856 | 154.722 | 1.00 | 91.05 | B |
| ATOM | 8664 | C | LEU | B1105 | 4.928 | 3.790 | 157.332 | 1.00 | 93.68 | B |

FIG. 8-69

| ATOM | 8665 | O | LEU B1105 | 5.140 | 2.719 | 157.910 | 1.00 | 93.77 | B |
| --- | --- | --- | --- | --- | --- | --- | --- | --- | --- |
| ATOM | 8666 | N | PRO B1106 | 3.740 | 4.418 | 157.399 | 1.00 | 93.94 | B |
| ATOM | 8667 | CD | PRO B1106 | 3.222 | 5.571 | 156.639 | 1.00 | 93.87 | B |
| ATOM | 8668 | CA | PRO B1106 | 2.675 | 3.804 | 158.192 | 1.00 | 94.00 | B |
| ATOM | 8669 | CB | PRO B1106 | 1.414 | 4.442 | 157.614 | 1.00 | 94.37 | B |
| ATOM | 8670 | CG | PRO B1106 | 1.886 | 5.839 | 157.325 | 1.00 | 94.15 | B |
| ATOM | 8671 | C | PRO B1106 | 2.702 | 2.287 | 158.078 | 1.00 | 94.22 | B |
| ATOM | 8672 | O | PRO B1106 | 2.441 | 1.720 | 157.006 | 1.00 | 93.78 | B |
| ATOM | 8673 | N | ALA B1107 | 3.057 | 1.652 | 159.195 | 1.00 | 94.94 | B |
| ATOM | 8674 | CA | ALA B1107 | 3.160 | 0.197 | 159.289 | 1.00 | 96.29 | B |
| ATOM | 8675 | CB | ALA B1107 | 3.557 | -0.192 | 160.703 | 1.00 | 96.27 | B |
| ATOM | 8676 | C | ALA B1107 | 1.857 | -0.506 | 158.900 | 1.00 | 97.18 | B |
| ATOM | 8677 | O | ALA B1107 | 1.847 | -1.412 | 158.040 | 1.00 | 96.94 | B |
| ATOM | 8678 | N | GLU B1108 | 0.769 | -0.082 | 159.549 | 1.00 | 97.75 | B |
| ATOM | 8679 | CA | GLU B1108 | -0.578 | -0.623 | 159.311 | 1.00 | 97.27 | B |
| ATOM | 8680 | CB | GLU B1108 | -1.158 | -1.198 | 160.620 | 1.00 | 98.32 | B |
| ATOM | 8681 | CG | GLU B1108 | -0.112 | -1.788 | 161.582 | 1.00 | 99.68 | B |
| ATOM | 8682 | CD | GLU B1108 | 0.599 | -3.027 | 161.025 | 1.00 | 99.95 | B |
| ATOM | 8683 | OE1 | GLU B1108 | 1.557 | -3.504 | 161.691 | 1.00 | 99.95 | B |
| ATOM | 8684 | OE2 | GLU B1108 | 0.202 | -3.524 | 159.935 | 1.00 | 99.92 | B |
| ATOM | 8685 | C | GLU B1108 | -1.458 | 0.542 | 158.816 | 1.00 | 96.09 | B |
| ATOM | 8686 | O | GLU B1108 | -2.271 | 1.099 | 159.578 | 1.00 | 96.67 | B |
| ATOM | 8687 | N | PRO B1109 | -1.296 | 0.931 | 157.534 | 1.00 | 94.20 | B |
| ATOM | 8688 | CD | PRO B1109 | -0.356 | 0.323 | 156.573 | 1.00 | 93.30 | B |
| ATOM | 8689 | CA | PRO B1109 | -2.042 | 2.025 | 156.897 | 1.00 | 92.35 | B |
| ATOM | 8690 | CB | PRO B1109 | -1.734 | 1.817 | 155.420 | 1.00 | 92.15 | B |

FIG. 8-70

| | | | | | | | | |
|---|---|---|---|---|---|---|---|---|
| ATOM | 8691 | CG | PRO | B1109 | -0.304 | 1.369 | 155.477 | 1.00 92.75 B |
| ATOM | 8692 | C | PRO | B1109 | -3.546 | 2.094 | 157.189 | 1.00 90.86 B |
| ATOM | 8693 | O | PRO | B1109 | -4.048 | 3.114 | 157.669 | 1.00 89.19 B |
| ATOM | 8948 | N | ILE | B1142 | -1.358 | 19.771 | 162.869 | 1.00 72.76 B |
| ATOM | 8949 | CA | ILE | B1142 | -0.623 | 18.516 | 162.747 | 1.00 73.51 B |
| ATOM | 8950 | CB | ILE | B1142 | -0.873 | 17.886 | 161.370 | 1.00 73.02 B |
| ATOM | 8951 | CG2 | ILE | B1142 | -0.199 | 16.545 | 161.274 | 1.00 72.31 B |
| ATOM | 8952 | CG1 | ILE | B1142 | -2.368 | 17.759 | 161.130 | 1.00 72.42 B |
| ATOM | 8953 | CD1 | ILE | B1142 | -2.699 | 17.452 | 159.716 | 1.00 72.36 B |
| ATOM | 8954 | C | ILE | B1142 | -0.872 | 18.759 | 162.883 | 1.00 74.86 B |
| ATOM | 8955 | O | ILE | B1142 | 1.415 | 19.681 | 162.275 | 1.00 74.27 B |
| ATOM | 8956 | N | HIS | B1143 | 1.546 | 17.928 | 163.668 | 1.00 77.03 B |
| ATOM | 8957 | CA | HIS | B1143 | 2.982 | 18.111 | 163.832 | 1.00 78.80 B |
| ATOM | 8958 | CB | HIS | B1143 | 3.277 | 19.047 | 165.028 | 1.00 79.79 B |
| ATOM | 8959 | CG | HIS | B1143 | 3.106 | 18.402 | 166.375 | 1.00 81.82 B |
| ATOM | 8960 | CD2 | HIS | B1143 | 2.221 | 18.643 | 167.375 | 1.00 82.43 B |
| ATOM | 8961 | ND1 | HIS | B1143 | 3.903 | 17.363 | 166.813 | 1.00 82.44 B |
| ATOM | 8962 | CE1 | HIS | B1143 | 3.514 | 16.992 | 168.022 | 1.00 82.28 B |
| ATOM | 8963 | NE2 | HIS | B1143 | 2.496 | 17.752 | 168.386 | 1.00 82.19 B |
| ATOM | 8964 | C | HIS | B1143 | 3.816 | 16.838 | 163.967 | 1.00 79.28 B |
| ATOM | 8965 | O | HIS | B1143 | 3.319 | 15.727 | 164.234 | 1.00 77.86 B |
| ATOM | 8966 | N | CYS | B1144 | 5.106 | 17.041 | 163.751 | 1.00 80.42 B |
| ATOM | 8967 | CA | CYS | B1144 | 6.105 | 16.000 | 163.866 | 1.00 81.96 B |
| ATOM | 8968 | CB | CYS | B1144 | 6.086 | 15.060 | 162.648 | 1.00 82.04 B |
| ATOM | 8969 | SG | CYS | B1144 | 6.457 | 15.840 | 161.064 | 1.00 82.13 B |
| ATOM | 8970 | C | CYS | B1144 | 7.393 | 16.790 | 163.927 | 1.00 81.98 B |

FIG. 8-71

| ATOM | 8971 | O   | CYS B1144 | 7.364  | 18.021 | 163.857 | 1.00 | 81.45 | B |
| ---- | ---- | --- | --------- | ------ | ------ | ------- | ---- | ----- | - |
| ATOM | 8972 | N   | ARG B1145 | 8.507  | 16.087 | 164.073 | 1.00 | 82.60 | B |
| ATOM | 8973 | CA  | ARG B1145 | 9.812  | 16.717 | 164.142 | 1.00 | 83.21 | B |
| ATOM | 8974 | CB  | ARG B1145 | 10.841 | 15.834 | 163.455 | 1.00 | 85.51 | B |
| ATOM | 8975 | CG  | ARG B1145 | 10.961 | 14.446 | 164.021 | 1.00 | 89.67 | B |
| ATOM | 8976 | CD  | ARG B1145 | 12.144 | 13.742 | 163.361 | 1.00 | 94.81 | B |
| ATOM | 8977 | NE  | ARG B1145 | 12.559 | 12.500 | 164.028 | 1.00 | 98.48 | B |
| ATOM | 8978 | CZ  | ARG B1145 | 13.695 | 11.849 | 163.753 | 1.00 | 99.96 | B |
| ATOM | 8979 | NH1 | ARG B1145 | 14.530 | 12.324 | 162.820 | 1.00 | 99.96 | B |
| ATOM | 8980 | NH2 | ARG B1145 | 14.007 | 10.730 | 164.416 | 1.00 | 99.97 | B |
| ATOM | 8981 | C   | ARG B1145 | 9.842  | 18.088 | 163.481 | 1.00 | 82.40 | B |
| ATOM | 8982 | O   | ARG B1145 | 9.846  | 19.118 | 164.155 | 1.00 | 81.72 | B |
| ATOM | 8983 | N   | ASP B1146 | 9.858  | 18.081 | 162.152 | 1.00 | 81.99 | B |
| ATOM | 8984 | CA  | ASP B1146 | 9.919  | 19.308 | 161.371 | 1.00 | 81.94 | B |
| ATOM | 8985 | CB  | ASP B1146 | 10.918 | 19.143 | 160.224 | 1.00 | 81.67 | B |
| ATOM | 8986 | CG  | ASP B1146 | 10.581 | 17.972 | 159.328 | 1.00 | 81.81 | B |
| ATOM | 8987 | OD1 | ASP B1146 | 9.379  | 17.758 | 159.087 | 1.00 | 82.64 | B |
| ATOM | 8988 | OD2 | ASP B1146 | 11.505 | 17.272 | 158.856 | 1.00 | 81.73 | B |
| ATOM | 8989 | C   | ASP B1146 | 8.575  | 19.758 | 160.798 | 1.00 | 82.44 | B |
| ATOM | 8990 | O   | ASP B1146 | 8.481  | 20.839 | 160.197 | 1.00 | 82.27 | B |
| ATOM | 8991 | N   | GLY B1147 | 7.542  | 18.935 | 160.975 | 1.00 | 82.46 | B |
| ATOM | 8992 | CA  | GLY B1147 | 6.225  | 19.284 | 160.464 | 1.00 | 81.64 | B |
| ATOM | 8993 | C   | GLY B1147 | 6.136  | 19.294 | 158.945 | 1.00 | 81.03 | B |
| ATOM | 8994 | O   | GLY B1147 | 5.400  | 20.090 | 158.365 | 1.00 | 81.48 | B |
| ATOM | 8995 | N   | SER B1148 | 6.897  | 18.410 | 158.304 | 1.00 | 79.77 | B |

FIG. 8-72

| ATOM | 8996 | CA | SER | B1148 | 6.916 | 18.272 | 156.849 | 1.00 | 78.07 | B |
|---|---|---|---|---|---|---|---|---|---|---|
| ATOM | 8997 | CB | SER | B1148 | 8.058 | 19.096 | 156.242 | 1.00 | 77.00 | B |
| ATOM | 8998 | OG | SER | B1148 | 7.774 | 20.479 | 156.277 | 1.00 | 76.21 | B |
| ATOM | 8999 | C | SER | B1148 | 7.126 | 16.796 | 156.528 | 1.00 | 77.65 | B |
| ATOM | 9000 | O | SER | B1148 | 6.462 | 16.221 | 155.665 | 1.00 | 76.99 | B |
| ATOM | 9001 | N | GLN | B1149 | 8.067 | 16.204 | 157.253 | 1.00 | 78.25 | B |
| ATOM | 9002 | CA | GLN | B1149 | 8.442 | 14.804 | 157.125 | 1.00 | 79.22 | B |
| ATOM | 9003 | CB | GLN | B1149 | 9.246 | 14.383 | 158.365 | 1.00 | 82.00 | B |
| ATOM | 9004 | CG | GLN | B1149 | 9.797 | 12.956 | 158.320 | 1.00 | 84.35 | B |
| ATOM | 9005 | CD | GLN | B1149 | 11.095 | 12.845 | 157.535 | 1.00 | 85.53 | B |
| ATOM | 9006 | OE1 | GLN | B1149 | 11.181 | 13.258 | 156.368 | 1.00 | 85.59 | B |
| ATOM | 9007 | NE2 | GLN | B1149 | 12.116 | 12.281 | 158.176 | 1.00 | 85.51 | B |
| ATOM | 9008 | C | GLN | B1149 | 7.231 | 13.891 | 156.964 | 1.00 | 78.48 | B |
| ATOM | 9009 | O | GLN | B1149 | 6.984 | 13.368 | 155.878 | 1.00 | 77.95 | B |
| ATOM | 9010 | N | GLN | B1150 | 6.490 | 13.689 | 158.056 | 1.00 | 78.73 | B |
| ATOM | 9011 | CA | GLN | B1150 | 5.298 | 12.837 | 158.041 | 1.00 | 78.81 | B |
| ATOM | 9012 | CB | GLN | B1150 | 5.245 | 11.954 | 159.295 | 1.00 | 78.53 | B |
| ATOM | 9013 | CG | GLN | B1150 | 6.370 | 12.198 | 160.286 | 1.00 | 80.98 | B |
| ATOM | 9014 | CD | GLN | B1150 | 6.555 | 11.045 | 161.280 | 1.00 | 83.04 | B |
| ATOM | 9015 | OE1 | GLN | B1150 | 7.395 | 11.117 | 162.193 | 1.00 | 83.40 | B |
| ATOM | 9016 | NE2 | GLN | B1150 | 5.779 | 9.973 | 161.102 | 1.00 | 82.69 | B |
| ATOM | 9017 | C | GLN | B1150 | 4.033 | 13.690 | 157.937 | 1.00 | 78.20 | B |
| ATOM | 9018 | O | GLN | B1150 | 3.027 | 13.259 | 157.366 | 1.00 | 77.56 | B |
| ATOM | 9019 | N | THR | B1151 | 4.102 | 14.905 | 158.479 | 1.00 | 76.89 | B |
| ATOM | 9020 | CA | THR | B1151 | 2.992 | 15.850 | 158.431 | 1.00 | 76.02 | B |

FIG. 8-73

| | | | | | | | | | |
|---|---|---|---|---|---|---|---|---|---|
| ATOM | 9021 | CB | THR | B1151 | 3.404 | 17.196 | 159.044 | 1.00 | 75.72 | B |
| ATOM | 9022 | OG1 | THR | B1151 | 3.781 | 16.996 | 160.409 | 1.00 | 76.47 | B |
| ATOM | 9023 | CG2 | THR | B1151 | 2.259 | 18.193 | 158.981 | 1.00 | 76.23 | B |
| ATOM | 9024 | C | THR | B1151 | 2.545 | 16.078 | 156.982 | 1.00 | 75.50 | B |
| ATOM | 9025 | O | THR | B1151 | 1.374 | 16.327 | 156.718 | 1.00 | 75.83 | B |
| ATOM | 9026 | N | GLY | B1152 | 3.484 | 16.005 | 156.046 | 1.00 | 75.31 | B |
| ATOM | 9027 | CA | GLY | B1152 | 3.139 | 16.179 | 154.652 | 1.00 | 74.31 | B |
| ATOM | 9028 | C | GLY | B1152 | 2.225 | 15.051 | 154.201 | 1.00 | 74.28 | B |
| ATOM | 9029 | O | GLY | B1152 | 1.161 | 15.303 | 153.641 | 1.00 | 74.83 | B |
| ATOM | 9030 | N | ILE | B1153 | 2.630 | 13.807 | 154.444 | 1.00 | 73.23 | B |
| ATOM | 9031 | CA | ILE | B1153 | 1.829 | 12.651 | 154.049 | 1.00 | 73.13 | B |
| ATOM | 9032 | CB | ILE | B1153 | 2.490 | 11.321 | 154.474 | 1.00 | 73.70 | B |
| ATOM | 9033 | CG2 | ILE | B1153 | 1.736 | 10.129 | 153.863 | 1.00 | 72.54 | B |
| ATOM | 9034 | CG1 | ILE | B1153 | 3.951 | 11.314 | 154.035 | 1.00 | 73.47 | B |
| ATOM | 9035 | CD1 | ILE | B1153 | 4.131 | 11.592 | 152.578 | 1.00 | 72.97 | B |
| ATOM | 9036 | C | ILE | B1153 | 0.446 | 12.691 | 154.674 | 1.00 | 72.94 | B |
| ATOM | 9037 | O | ILE | B1153 | -0.517 | 12.187 | 154.097 | 1.00 | 72.63 | B |
| ATOM | 9038 | N | PHE | B1154 | 0.354 | 13.282 | 155.859 | 1.00 | 72.33 | B |
| ATOM | 9039 | CA | PHE | B1154 | -0.919 | 13.373 | 156.554 | 1.00 | 71.67 | B |
| ATOM | 9040 | CB | PHE | B1154 | -0.721 | 13.780 | 158.009 | 1.00 | 70.15 | B |
| ATOM | 9041 | CG | PHE | B1154 | -1.831 | 13.339 | 158.903 | 1.00 | 68.50 | B |
| ATOM | 9042 | CD1 | PHE | B1154 | -1.922 | 12.017 | 159.311 | 1.00 | 68.83 | B |
| ATOM | 9043 | CD2 | PHE | B1154 | -2.802 | 14.233 | 159.318 | 1.00 | 67.54 | B |
| ATOM | 9044 | CE1 | PHE | B1154 | -2.964 | 11.594 | 160.119 | 1.00 | 68.83 | B |
| ATOM | 9045 | CE2 | PHE | B1154 | -3.849 | 13.821 | 160.125 | 1.00 | 66.70 | B |
| ATOM | 9046 | CZ | PHE | B1154 | -3.930 | 12.501 | 160.527 | 1.00 | 68.10 | B |

FIG. 8-74

| | | | | | | | | |
|---|---|---|---|---|---|---|---|---|
| ATOM | 9047 | C | PHE B1154 | -1.821 | 14.385 | 155.875 | 1.00 | 72.35 | B |
| ATOM | 9048 | O | PHE B1154 | -2.924 | 14.049 | 155.460 | 1.00 | 73.44 | B |
| ATOM | 9049 | N | CYS B1155 | -1.354 | 15.625 | 155.767 | 1.00 | 72.62 | B |
| ATOM | 9050 | CA | CYS B1155 | -2.129 | 16.679 | 155.115 | 1.00 | 72.98 | B |
| ATOM | 9051 | CB | CYS B1155 | -1.285 | 17.948 | 154.963 | 1.00 | 73.58 | B |
| ATOM | 9052 | SG | CYS B1155 | -0.730 | 18.695 | 156.498 | 1.00 | 74.98 | B |
| ATOM | 9053 | C | CYS B1155 | -2.593 | 16.219 | 153.731 | 1.00 | 72.60 | B |
| ATOM | 9054 | O | CYS B1155 | -3.762 | 16.381 | 153.366 | 1.00 | 72.13 | B |
| ATOM | 9055 | N | ALA B1156 | -1.664 | 15.650 | 152.967 | 1.00 | 72.00 | B |
| ATOM | 9056 | CA | ALA B1156 | -1.962 | 15.157 | 151.630 | 1.00 | 71.84 | B |
| ATOM | 9057 | CB | ALA B1156 | -0.726 | 14.492 | 151.027 | 1.00 | 71.93 | B |
| ATOM | 9058 | C | ALA B1156 | -3.137 | 14.176 | 151.656 | 1.00 | 71.91 | B |
| ATOM | 9059 | O | ALA B1156 | -4.013 | 14.251 | 150.802 | 1.00 | 72.84 | B |
| ATOM | 9060 | N | LEU B1157 | -3.158 | 13.264 | 152.627 | 1.00 | 70.33 | B |
| ATOM | 9061 | CA | LEU B1157 | -4.240 | 12.294 | 152.744 | 1.00 | 68.53 | B |
| ATOM | 9062 | CB | LEU B1157 | -3.894 | 11.239 | 153.787 | 1.00 | 68.58 | B |
| ATOM | 9063 | CG | LEU B1157 | -3.073 | 10.040 | 153.335 | 1.00 | 68.24 | B |
| ATOM | 9064 | CD1 | LEU B1157 | -3.045 | 9.013 | 154.459 | 1.00 | 68.13 | B |
| ATOM | 9065 | CD2 | LEU B1157 | -3.697 | 9.436 | 152.100 | 1.00 | 67.57 | B |
| ATOM | 9066 | C | LEU B1157 | -5.580 | 12.929 | 153.110 | 1.00 | 67.86 | B |
| ATOM | 9067 | O | LEU B1157 | -6.620 | 12.526 | 152.601 | 1.00 | 67.21 | B |
| ATOM | 9068 | N | LEU B1158 | -5.557 | 13.907 | 154.009 | 1.00 | 67.19 | B |
| ATOM | 9069 | CA | LEU B1158 | -6.782 | 14.578 | 154.413 | 1.00 | 66.55 | B |
| ATOM | 9070 | CB | LEU B1158 | -6.509 | 15.708 | 155.399 | 1.00 | 63.90 | B |
| ATOM | 9071 | CG | LEU B1158 | -6.105 | 15.335 | 156.814 | 1.00 | 62.55 | B |
| ATOM | 9072 | CD1 | LEU B1158 | -6.005 | 16.608 | 157.618 | 1.00 | 61.87 | B |

FIG. 8-75

| ATOM | 9073 | CD2 | LEU | B1158 | -7.110 | 14.386 | 157.428 | 1.00 | 60.36 | B |
|---|---|---|---|---|---|---|---|---|---|---|
| ATOM | 9074 | C | LEU | B1158 | -7.422 | 15.168 | 153.187 | 1.00 | 67.35 | B |
| ATOM | 9075 | O | LEU | B1158 | -8.618 | 14.989 | 152.963 | 1.00 | 68.89 | B |
| ATOM | 9288 | N | MSE | B1186 | 7.900 | 18.942 | 152.664 | 1.00 | 80.61 | B |
| ATOM | 9289 | CA | MSE | B1186 | 6.808 | 17.987 | 152.467 | 1.00 | 82.71 | B |
| ATOM | 9290 | CB | MSE | B1186 | 5.707 | 18.675 | 151.672 | 1.00 | 83.95 | B |
| ATOM | 9291 | CG | MSE | B1186 | 5.304 | 20.012 | 152.263 | 1.00 | 85.35 | B |
| ATOM | 9292 | SE | MSE | B1186 | 4.337 | 19.748 | 153.890 | 1.00 | 87.12 | B |
| ATOM | 9293 | CE | MSE | B1186 | 2.926 | 21.069 | 153.689 | 1.00 | 86.49 | B |
| ATOM | 9294 | C | MSE | B1186 | 7.235 | 16.691 | 151.754 | 1.00 | 83.19 | B |
| ATOM | 9295 | O | MSE | B1186 | 8.429 | 16.358 | 151.708 | 1.00 | 83.90 | B |
| ATOM | 9296 | N | VAL | B1187 | 6.264 | 15.953 | 151.216 | 1.00 | 82.37 | B |
| ATOM | 9297 | CA | VAL | B1187 | 6.587 | 14.731 | 150.494 | 1.00 | 80.98 | B |
| ATOM | 9298 | CB | VAL | B1187 | 5.477 | 14.333 | 149.535 | 1.00 | 80.83 | B |
| ATOM | 9299 | CG1 | VAL | B1187 | 5.809 | 12.995 | 148.903 | 1.00 | 81.49 | B |
| ATOM | 9300 | CG2 | VAL | B1187 | 4.159 | 14.289 | 150.257 | 1.00 | 80.23 | B |
| ATOM | 9301 | C | VAL | B1187 | 7.799 | 15.093 | 149.658 | 1.00 | 80.60 | B |
| ATOM | 9302 | O | VAL | B1187 | 7.841 | 16.172 | 149.065 | 1.00 | 80.36 | B |
| ATOM | 9303 | N | SER | B1188 | 8.791 | 14.219 | 149.619 | 1.00 | 79.89 | B |
| ATOM | 9304 | CA | SER | B1188 | 9.984 | 14.528 | 148.847 | 1.00 | 79.89 | B |
| ATOM | 9305 | CB | SER | B1188 | 10.991 | 15.309 | 149.706 | 1.00 | 79.64 | B |
| ATOM | 9306 | OG | SER | B1188 | 10.500 | 16.599 | 150.034 | 1.00 | 77.36 | B |
| ATOM | 9307 | C | SER | B1188 | 10.618 | 13.265 | 148.309 | 1.00 | 80.22 | B |
| ATOM | 9308 | O | SER | B1188 | 11.571 | 13.304 | 147.532 | 1.00 | 79.32 | B |
| ATOM | 9309 | N | THR | B1189 | 10.083 | 12.133 | 148.729 | 1.00 | 81.20 | B |
| ATOM | 9310 | CA | THR | B1189 | 10.602 | 10.867 | 148.247 | 1.00 | 82.63 | B |

FIG. 8-76

| ATOM | 9311 | CB | THR B1189 | 11.173 | 10.018 | 149.380 | 1.00 | 83.72 | B |
|---|---|---|---|---|---|---|---|---|---|
| ATOM | 9312 | OG1 | THR B1189 | 10.133 | 9.722 | 150.326 | 1.00 | 84.82 | B |
| ATOM | 9313 | CG2 | THR B1189 | 12.324 | 10.749 | 150.058 | 1.00 | 84.11 | B |
| ATOM | 9314 | C | THR B1189 | 9.491 | 10.082 | 147.574 | 1.00 | 82.85 | B |
| ATOM | 9315 | O | THR B1189 | 8.345 | 10.081 | 148.025 | 1.00 | 83.53 | B |
| ATOM | 9316 | N | PHE B1190 | 9.840 | 9.408 | 146.492 | 1.00 | 83.37 | B |
| ATOM | 9317 | CA | PHE B1190 | 8.870 | 8.628 | 145.760 | 1.00 | 84.36 | B |
| ATOM | 9318 | CB | PHE B1190 | 9.556 | 7.902 | 144.617 | 1.00 | 84.91 | B |
| ATOM | 9319 | CG | PHE B1190 | 8.633 | 7.035 | 143.834 | 1.00 | 87.12 | B |
| ATOM | 9320 | CD1 | PHE B1190 | 8.418 | 5.705 | 144.202 | 1.00 | 87.50 | B |
| ATOM | 9321 | CD2 | PHE B1190 | 7.936 | 7.555 | 142.749 | 1.00 | 87.86 | B |
| ATOM | 9322 | CE1 | PHE B1190 | 7.521 | 4.906 | 143.498 | 1.00 | 87.89 | B |
| ATOM | 9323 | CE2 | PHE B1190 | 7.033 | 6.765 | 142.035 | 1.00 | 88.61 | B |
| ATOM | 9324 | CZ | PHE B1190 | 6.826 | 5.435 | 142.411 | 1.00 | 88.71 | B |
| ATOM | 9325 | C | PHE B1190 | 8.153 | 7.625 | 146.657 | 1.00 | 84.88 | B |
| ATOM | 9326 | O | PHE B1190 | 7.014 | 7.223 | 146.372 | 1.00 | 84.37 | B |
| ATOM | 9327 | N | GLU B1191 | 8.823 | 7.219 | 147.734 | 1.00 | 85.30 | B |
| ATOM | 9328 | CA | GLU B1191 | 8.246 | 6.266 | 148.681 | 1.00 | 86.39 | B |
| ATOM | 9329 | CB | GLU B1191 | 9.180 | 6.044 | 149.876 | 1.00 | 87.71 | B |
| ATOM | 9330 | CG | GLU B1191 | 10.498 | 5.364 | 149.524 | 1.00 | 90.19 | B |
| ATOM | 9331 | CD | GLU B1191 | 11.390 | 6.198 | 148.592 | 1.00 | 91.23 | B |
| ATOM | 9332 | OE1 | GLU B1191 | 11.905 | 7.247 | 149.034 | 1.00 | 91.83 | B |
| ATOM | 9333 | OE2 | GLU B1191 | 11.577 | 5.804 | 147.418 | 1.00 | 92.25 | B |
| ATOM | 9334 | C | GLU B1191 | 6.935 | 6.845 | 149.177 | 1.00 | 86.59 | B |
| ATOM | 9335 | O | GLU B1191 | 5.875 | 6.199 | 149.085 | 1.00 | 86.67 | B |
| ATOM | 9336 | N | GLN B1192 | 7.026 | 8.072 | 149.694 | 1.00 | 86.02 | B |

FIG. 8-77

| ATOM | 9337 | CA | GLN | B1192 | 5.874 | 8.799 | 150.218 | 1.00 | 84.97 | B |
| --- | --- | --- | --- | --- | --- | --- | --- | --- | --- | --- |
| ATOM | 9338 | CB | GLN | B1192 | 6.330 | 10.127 | 150.815 | 1.00 | 85.61 | B |
| ATOM | 9339 | CG | GLN | B1192 | 7.343 | 9.995 | 151.932 | 1.00 | 87.40 | B |
| ATOM | 9340 | CD | GLN | B1192 | 7.410 | 11.245 | 152.797 | 1.00 | 88.82 | B |
| ATOM | 9341 | OE1 | GLN | B1192 | 7.551 | 12.367 | 152.282 | 1.00 | 89.64 | B |
| ATOM | 9342 | NE2 | GLN | B1192 | 7.308 | 11.061 | 154.121 | 1.00 | 89.16 | B |
| ATOM | 9343 | C | GLN | B1192 | 4.849 | 9.054 | 149.115 | 1.00 | 83.63 | B |
| ATOM | 9344 | O | GLN | B1192 | 3.653 | 8.810 | 149.299 | 1.00 | 82.61 | B |
| ATOM | 9345 | N | TYR | B1193 | 5.328 | 9.559 | 147.978 | 1.00 | 82.47 | B |
| ATOM | 9346 | CA | TYR | B1193 | 4.461 | 9.818 | 146.843 | 1.00 | 81.79 | B |
| ATOM | 9347 | CB | TYR | B1193 | 5.278 | 10.195 | 145.606 | 1.00 | 79.94 | B |
| ATOM | 9348 | CG | TYR | B1193 | 4.457 | 10.899 | 144.541 | 1.00 | 79.63 | B |
| ATOM | 9349 | CD1 | TYR | B1193 | 4.086 | 12.237 | 144.687 | 1.00 | 79.27 | B |
| ATOM | 9350 | CE1 | TYR | B1193 | 3.305 | 12.883 | 143.715 | 1.00 | 79.45 | B |
| ATOM | 9351 | CD2 | TYR | B1193 | 4.028 | 10.216 | 143.394 | 1.00 | 79.10 | B |
| ATOM | 9352 | CE2 | TYR | B1193 | 3.245 | 10.853 | 142.413 | 1.00 | 78.65 | B |
| ATOM | 9353 | CZ | TYR | B1193 | 2.890 | 12.188 | 142.579 | 1.00 | 79.30 | B |
| ATOM | 9354 | OH | TYR | B1193 | 2.145 | 12.839 | 141.613 | 1.00 | 77.62 | B |
| ATOM | 9355 | C | TYR | B1193 | 3.662 | 8.552 | 146.543 | 1.00 | 82.03 | B |
| ATOM | 9356 | O | TYR | B1193 | 2.436 | 8.514 | 146.712 | 1.00 | 82.29 | B |
| ATOM | 9357 | N | GLN | B1194 | 4.361 | 7.515 | 146.097 | 1.00 | 82.16 | B |
| ATOM | 9358 | CA | GLN | B1194 | 3.707 | 6.255 | 145.784 | 1.00 | 83.20 | B |
| ATOM | 9359 | CB | GLN | B1194 | 4.750 | 5.201 | 145.435 | 1.00 | 83.17 | B |
| ATOM | 9360 | CG | GLN | B1194 | 4.206 | 3.793 | 145.519 | 1.00 | 83.33 | B |
| ATOM | 9361 | CD | GLN | B1194 | 5.204 | 2.771 | 145.059 | 1.00 | 83.81 | B |

FIG. 8-78

| ATOM | 9362 | OE1 | GLN | B1194 | 5.313 | 2.486 | 143.863 | 1.00 | 84.39 | B |
|------|------|-----|-----|-------|-------|-------|---------|------|-------|---|
| ATOM | 9363 | NE2 | GLN | B1194 | 5.956 | 2.218 | 146.000 | 1.00 | 84.22 | B |
| ATOM | 9364 | C | GLN | B1194 | 2.820 | 5.742 | 146.928 | 1.00 | 83.35 | B |
| ATOM | 9365 | O | GLN | B1194 | 1.899 | 4.951 | 146.711 | 1.00 | 82.72 | B |
| ATOM | 9366 | N | PHE | B1195 | 3.105 | 6.190 | 148.145 | 1.00 | 83.75 | B |
| ATOM | 9367 | CA | PHE | B1195 | 2.326 | 5.777 | 149.305 | 1.00 | 83.93 | B |
| ATOM | 9368 | CB | PHE | B1195 | 3.060 | 6.178 | 150.583 | 1.00 | 85.59 | B |
| ATOM | 9369 | CG | PHE | B1195 | 2.306 | 5.864 | 151.833 | 1.00 | 86.98 | B |
| ATOM | 9370 | CD1 | PHE | B1195 | 1.881 | 4.570 | 152.090 | 1.00 | 87.75 | B |
| ATOM | 9371 | CD2 | PHE | B1195 | 2.024 | 6.864 | 152.758 | 1.00 | 87.80 | B |
| ATOM | 9372 | CE1 | PHE | B1195 | 1.181 | 4.270 | 153.255 | 1.00 | 88.38 | B |
| ATOM | 9373 | CE2 | PHE | B1195 | 1.326 | 6.575 | 153.927 | 1.00 | 88.45 | B |
| ATOM | 9374 | CZ | PHE | B1195 | 0.902 | 5.271 | 154.175 | 1.00 | 88.43 | B |
| ATOM | 9375 | C | PHE | B1195 | 0.918 | 6.391 | 149.283 | 1.00 | 83.19 | B |
| ATOM | 9376 | O | PHE | B1195 | -0.047 | 5.758 | 149.730 | 1.00 | 82.50 | B |
| ATOM | 9377 | N | LEU | B1196 | 0.814 | 7.621 | 148.767 | 1.00 | 82.40 | B |
| ATOM | 9378 | CA | LEU | B1196 | -0.467 | 8.328 | 148.658 | 1.00 | 80.51 | B |
| ATOM | 9379 | CB | LEU | B1196 | -0.268 | 9.720 | 148.065 | 1.00 | 79.73 | B |
| ATOM | 9380 | CG | LEU | B1196 | 0.560 | 10.685 | 148.909 | 1.00 | 79.98 | B |
| ATOM | 9381 | CD1 | LEU | B1196 | 0.747 | 11.966 | 148.141 | 1.00 | 80.50 | B |
| ATOM | 9382 | CD2 | LEU | B1196 | -0.131 | 10.956 | 150.237 | 1.00 | 79.97 | B |
| ATOM | 9383 | C | LEU | B1196 | -1.380 | 7.530 | 147.750 | 1.00 | 79.62 | B |
| ATOM | 9384 | O | LEU | B1196 | -2.567 | 7.366 | 148.030 | 1.00 | 79.82 | B |
| ATOM | 9385 | N | TYR | B1197 | -0.811 | 7.033 | 146.657 | 1.00 | 78.05 | B |
| ATOM | 9386 | CA | TYR | B1197 | -1.554 | 6.221 | 145.705 | 1.00 | 77.08 | B |
| ATOM | 9387 | CB | TYR | B1197 | -0.650 | 5.870 | 144.526 | 1.00 | 76.59 | B |

FIG. 8-79

| ATOM | 9388 | CG | TYR | B1197 | -0.701 | 6.888 | 143.415 | 1.00 | 76.44 | B |
| --- | --- | --- | --- | --- | --- | --- | --- | --- | --- | --- |
| ATOM | 9389 | CD1 | TYR | B1197 | -1.732 | 6.876 | 142.476 | 1.00 | 76.22 | B |
| ATOM | 9390 | CE1 | TYR | B1197 | -1.805 | 7.837 | 141.474 | 1.00 | 76.34 | B |
| ATOM | 9391 | CD2 | TYR | B1197 | 0.257 | 7.890 | 143.322 | 1.00 | 76.49 | B |
| ATOM | 9392 | CE2 | TYR | B1197 | 0.194 | 8.862 | 142.320 | 1.00 | 76.63 | B |
| ATOM | 9393 | CZ | TYR | B1197 | -0.837 | 8.830 | 141.399 | 1.00 | 76.25 | B |
| ATOM | 9394 | OH | TYR | B1197 | -0.889 | 9.779 | 140.401 | 1.00 | 75.36 | B |
| ATOM | 9395 | C | TYR | B1197 | -2.044 | 4.944 | 146.384 | 1.00 | 77.02 | B |
| ATOM | 9396 | O | TYR | B1197 | -3.238 | 4.626 | 146.365 | 1.00 | 76.11 | B |
| ATOM | 9397 | N | ASP | B1198 | -1.100 | 4.229 | 146.992 | 1.00 | 77.71 | B |
| ATOM | 9398 | CA | ASP | B1198 | -1.369 | 2.979 | 147.695 | 1.00 | 78.52 | B |
| ATOM | 9399 | CB | ASP | B1198 | -0.139 | 2.546 | 148.498 | 1.00 | 79.84 | B |
| ATOM | 9400 | CG | ASP | B1198 | 1.046 | 2.199 | 147.615 | 1.00 | 80.95 | B |
| ATOM | 9401 | OD1 | ASP | B1198 | 2.159 | 2.036 | 148.162 | 1.00 | 81.67 | B |
| ATOM | 9402 | OD2 | ASP | B1198 | 0.865 | 2.086 | 146.383 | 1.00 | 80.74 | B |
| ATOM | 9403 | C | ASP | B1198 | -2.561 | 3.070 | 148.636 | 1.00 | 78.37 | B |
| ATOM | 9404 | O | ASP | B1198 | -3.542 | 2.343 | 148.445 | 1.00 | 78.86 | B |
| ATOM | 9405 | N | VAL | B1199 | -2.471 | 3.944 | 149.648 | 1.00 | 77.54 | B |
| ATOM | 9406 | CA | VAL | B1199 | -3.556 | 4.111 | 150.625 | 1.00 | 76.89 | B |
| ATOM | 9407 | CB | VAL | B1199 | -3.185 | 5.087 | 151.788 | 1.00 | 76.65 | B |
| ATOM | 9408 | CG1 | VAL | B1199 | -2.108 | 4.490 | 152.663 | 1.00 | 75.68 | B |
| ATOM | 9409 | CG2 | VAL | B1199 | -2.725 | 6.406 | 151.236 | 1.00 | 76.55 | B |
| ATOM | 9410 | C | VAL | B1199 | -4.856 | 4.597 | 149.996 | 1.00 | 76.25 | B |
| ATOM | 9411 | O | VAL | B1199 | -5.922 | 4.055 | 150.294 | 1.00 | 76.14 | B |

FIG. 8-80

(8f) Peptide within active site D1 domain molecule B

| | | | | | | | | | |
|---|---|---|---|---|---|---|---|---|---|
| ATOM | 9495 | CB | PRO | Y2002 | -21.678 | 51.418 | 137.840 | 1.00 | 81.76 | Y |
| ATOM | 9496 | CG | PRO | Y2002 | -23.149 | 51.580 | 138.086 | 1.00 | 82.24 | Y |
| ATOM | 9497 | C | PRO | Y2002 | -20.316 | 52.628 | 136.171 | 1.00 | 82.64 | Y |
| ATOM | 9498 | O | PRO | Y2002 | -20.624 | 52.893 | 135.007 | 1.00 | 82.93 | Y |
| ATOM | 9499 | N | PRO | Y2002 | -22.532 | 53.399 | 136.720 | 1.00 | 82.05 | Y |
| ATOM | 9500 | CD | PRO | Y2002 | -23.665 | 52.486 | 136.929 | 1.00 | 82.64 | Y |
| ATOM | 9501 | CA | PRO | Y2002 | -21.312 | 52.788 | 137.286 | 1.00 | 82.41 | Y |
| ATOM | 9502 | N | THR | Y2003 | -19.122 | 52.183 | 136.535 | 1.00 | 82.30 | Y |
| ATOM | 9503 | CA | THR | Y2003 | -18.061 | 51.979 | 135.566 | 1.00 | 81.61 | Y |
| ATOM | 9504 | CB | THR | Y2003 | -17.111 | 53.206 | 135.487 | 1.00 | 81.51 | Y |
| ATOM | 9505 | OG1 | THR | Y2003 | -17.741 | 54.249 | 134.730 | 1.00 | 82.48 | Y |
| ATOM | 9506 | CG2 | THR | Y2003 | -15.775 | 52.826 | 134.826 | 1.00 | 80.87 | Y |
| ATOM | 9507 | C | THR | Y2003 | -17.221 | 50.750 | 135.856 | 1.00 | 80.89 | Y |
| ATOM | 9508 | O | THR | Y2003 | -16.824 | 50.479 | 136.999 | 1.00 | 81.37 | Y |
| ATOM | 9509 | N | PTY | Y2004 | -16.975 | 49.987 | 134.807 | 1.00 | 79.51 | Y |
| ATOM | 9510 | CA | PTY | Y2004 | -16.138 | 48.835 | 134.959 | 1.00 | 78.46 | Y |
| ATOM | 9511 | CB | PTY | Y2004 | -16.820 | 47.523 | 135.375 | 1.00 | 76.21 | Y |
| ATOM | 9512 | CG | PTY | Y2004 | -16.185 | 46.178 | 135.070 | 1.00 | 73.13 | Y |
| ATOM | 9513 | CD1 | PTY | Y2004 | -16.431 | 45.156 | 135.985 | 1.00 | 73.00 | Y |
| ATOM | 9514 | CE1 | PTY | Y2004 | -15.921 | 43.871 | 135.842 | 1.00 | 72.68 | Y |
| ATOM | 9515 | CD2 | PTY | Y2004 | -15.376 | 45.916 | 133.917 | 1.00 | 71.98 | Y |
| ATOM | 9516 | CE2 | PTY | Y2004 | -14.848 | 44.605 | 133.761 | 1.00 | 71.74 | Y |
| ATOM | 9517 | CZ | PTY | Y2004 | -15.123 | 43.599 | 134.719 | 1.00 | 72.22 | Y |
| ATOM | 9518 | OH | PTY | Y2004 | -14.781 | 42.188 | 134.931 | 1.00 | 73.90 | Y |

FIG. 8-81

| ATOM | 9519 | OR1 | PTY | Y2004 | -16.699 | 40.842 | 135.943 | 1.00 | 72.30 | Y |
| ATOM | 9520 | OR2 | PTY | Y2004 | -14.603 | 39.722 | 135.259 | 1.00 | 72.65 | Y |
| ATOM | 9521 | OR3 | PTY | Y2004 | -16.158 | 40.718 | 133.599 | 1.00 | 74.43 | Y |
| ATOM | 9522 | PR | PTY | Y2004 | -15.613 | 40.765 | 134.936 | 1.00 | 74.26 | Y |
| ATOM | 9523 | C | PTY | Y2004 | -14.660 | 49.018 | 134.742 | 1.00 | 79.21 | Y |
| ATOM | 9524 | O | PTY | Y2004 | -13.812 | 48.306 | 135.285 | 1.00 | 79.01 | Y |
| ATOM | 9525 | N | SER | Y2005 | -14.423 | 50.090 | 133.977 | 1.00 | 80.04 | Y |
| ATOM | 9526 | CA | SER | Y2005 | -13.137 | 50.598 | 133.509 | 1.00 | 81.28 | Y |
| ATOM | 9527 | CB | SER | Y2005 | -12.541 | 51.627 | 134.510 | 1.00 | 81.62 | Y |
| ATOM | 9528 | OG | SER | Y2005 | -12.264 | 51.109 | 135.806 | 1.00 | 81.25 | Y |
| ATOM | 9529 | C | SER | Y2005 | -12.104 | 49.540 | 133.102 | 1.00 | 82.26 | Y |
| ATOM | 9530 | O | SER | Y2005 | -11.863 | 48.564 | 133.863 | 1.00 | 82.18 | Y |
| ATOM | 9531 | OXT | SER | Y2005 | -11.548 | 49.709 | 131.986 | 1.00 | 83.91 | Y |
| ATOM | 9532 | OH2 | TIP | W2501 | 3.206 | -12.377 | 55.589 | 1.00 | 36.05 | W |
| END | | | | | | | | | | |

FIG. 8-82

RECEPTOR LINKED PROTEIN TYROSINE PHOSPHATASES

The present application claims the benefit of U.S. provisional application No. 60/362,594 filed Mar. 8, 2002, and which is incorporated herein by reference in its entirety.

BACKGROUND OF THE INVENTION

1. Field of the Invention

The present invention provides crystal structures of cellular molecules that play important roles in immunity, phosphorylation events, and disease initiation mechanisms. The isolated crystals and methods for crystallization thereof, are also important in identifying small molecule interactions with cellular molecules for new drug discovery.

2. Background

Protein tyrosine phosphorylation is an important molecular switching mechanism that regulates a variety of cellular functions including cell proliferation, differentiation, and activation. Tyrosine phosphorylation is not only an essential part of the signal transduction mediated by various growth factor receptors, but it is also involved in intracellular signal transduction and nuclear cell cycle regulation. Disturbances of these processes are known to be causes of cancer. For example, overexpression and/or hyper-activation of many protein tyrosine kinases are oncogenic. Thus, knowledge about the regulation of protein tyrosine phosphorylation provides valuable information about the control of basic cellular processes and is essential to understanding the generation of cancer. In this regard, the ultimate goal of many converging lines of research is the eventual development of rational therapeutic agents.

Protein tyrosine phosphorylation is a reversible process that involves both protein tyrosine kinases (PTKs) and protein tyrosine phosphatases (PTPases). Protein phosphorylation is now well recognized as an important mechanism utilized by cells to transduce signals during different stages of cellular function (Fischer et al, *Science* 253:401–6 (1991); Flint et al., *The EMBO J.* 12:1937–46 (1993)). There are at least two major classes of phosphatases: (1) those that dephosphorylate proteins (or peptides) that contain a phosphate group(s) on a serine or threonine moiety (termed Ser/Thr phosphatases) and (2) those that remove a phosphate group(s) from the amino acid tyrosine (termed protein tyrosine phosphatases or PTPases). The PTPases can be further subdivided into two groups: a) intracellular or non-transmembrane PTPases and b) receptor-type or transmembrane PTPases.

Most known intracellular type PTPases contain a single conserved catalytic phosphatase domain consisting of 220–240 amino acid residues. The regions outside the PTPase domains are believed to play important roles in localizing the intracellular PTPases subcellularly (Mauro, L. J. and Dixon, J. E. *TIBS* 19: 151–155 (1994)). The first intracellular PTPase to be purified and characterized was PTP1B which was isolated from human placenta (Tonks et al., *J. Biol. Chem.* 263: 6722–6730 (1988)). Other examples of intracellular PTPases include (1) T-cell PTPase (Cool et al. *Proc. Natl. Acad. Sci.* USA 86: 5257–5261 (1989)), (2) rat brain PTPase (Guan et al., *Proc. Natl. Acad. Sci.* USA 87:1501–1502 (1990)), (3) neuronal phosphatase STEP (Lombroso et al., *Proc. Natl. Acad. Sci.* USA 88: 7242–7246 (1991)), (4) ezrin-domain containing PTPases: PTPMEG1 (Guet al., *Proc. Natl. Acad. Sci.* USA 88: 5867–57871 (1991)), PTPH1 (Yang and Tonks, *Proc. Natl. Acad. Sci.* USA 88: 5949–5953 (1991)), PTPD1 and PTPD2 (M. Oller et al., *Proc. Natl. Acad. Sci.* USA 91: 7477–7481 (1994)), FAP-1/BAS (Sato et al., *Science* 268: 411–415 (1995); Banville et al., *J. Biol. Chem.* 269: 22320–22327 (1994); Maekawa et al., *FEBS Letters* 337: 200–206 (1994)), and SH2 domain containing PTPases: PTP1C/SH-PTP1/SHP-1 (Plutzky et al., *Proc. Natl. Acad. Sci.* USA 89: 1123–1127 (1992); Shen et al., *Nature* Lond. 352: 736–739 (1991)) and PTP1D/Syp/SH-PTP2/SHP-2 (Vogel et al., *Science* 259: 1611–1614 (1993); Feng et al., *Science* 259: 1607–1611 (1993); Bastein et al., *Biochem. Biophys. Res. Comm.* 196: 124–133 (1993)).

Receptor-type PTPases (RPTPases) consist of a) a putative ligand-binding extracellular domain, b) a transmembrane segment, and c) an intracellular catalytic region. The structures and sizes of the putative ligand-binding extracellular domains of receptor-type PTPases are quite divergent. In contrast, the intracellular catalytic regions of receptor-type PTPases are very homologous to each other and to the intracellular PTPases. Most receptor-type PTPases have two tandemly duplicated catalytic PTPase domains.

The first receptor-type PTPases to be identified were (1) CD45 also known as Leukocyte Common Antigen (LCA) ((Ralph, S. J., *EMBO J.* 6: 1251–1257 (1987)) and (2) Leukocyte common Antigen Related (LAR)(Streuli et al., *J. Exp. Med.* 168: 1523–1530 (1988)) that were recognized to belong to this class of enzymes based on homology to PTP1B (Charbonneau et al., *Proc. Natl. Acad. Sci.* USA 86: 5252–5256 (1989)). CD45 is a member of a family of high molecular weight glycoproteins, is one of the most abundant leukocyte cell surface glycoproteins, and appears to be exclusively expressed upon cells of the hematopoietic system (Trowbridge and Thomas, *Ann. Rev. Immunol.* 12: 85–116 (1994)).

The identification of CD45 and LAR as members of the PTPase family was quickly followed by identification and cloning of several different members of the receptor-type PTPase group. Thus, 5 different PTPases, (3) PTPα, (4) PTPβ, (5) PTPδ, (6) PTPε, and (7) PTPζ, were identified in one early study (Krueger et al., *EMBO J.* 9: 3241–3252 (1990)). Other examples of receptor-type PTPases include (8) PTPγ (Barnea et al., *Mol. Cell. Biol.* 13: 1497–1506 (1995)) which, like PTPζ (Krueger and Saito, *Proc. Natl. Acad. Sci.* USA 89: 7417–7421 (1992)) contains a carbonic anhydrase-like domain in the extracellular region, (9) PTPμ (Gebbink et al., *FEBS Letters* 290: 123–130 (1991)), (10) PTPκ (Jiang et al., *Mol. Cell. Biol.* 13: 2942–2951 (1993)). Based on structural differences the receptor-type PTPases may be classified into subtypes (Fischer et al., *Science* 253: 401–406 (1991)): (I) CD45; (II) LAR, PTPδ, (11) PTPσ; (III) PTPβ, (12) SAP-1 (Matozaki et al., *J. Biol. Chem.* 269: 2075–2081 (1994)), (13) PTP-U2/GLEPP1 (Seimiya et al., *Oncogene* 10: 1731–1738 (1995); Thomas et al., *J. Biol. Chem.* 269: 19953–19962 (1994)), and (14) DEP-1; (IV) PTPα, PTPε. All receptor-type PTPases except Type IV contain two PTPase domains. Novel PTPases are continuously identified, and it is anticipated that more than 500 different species will be found in the human genome, i.e. close to the predicted size of the protein tyrosine kinase superfamily (Hanks and Hunter, *FASEB J.* 9: 576–596 (1995)).

Considerable information regarding the interactions of specific PTKases in various cellular pathways has led to a general understanding of their roles and the regulation of such. However, much less is known about the specific functions or the control of PTPases in these pathways.

There is thus a need to determine the structural basis of the function of significant representatives of protein tyrosine phosphatases such as the human leukocyte PTPases, LAR and CD45 (CD45).

SUMMARY OF THE INVENTION

The present invention provides for methods in determining the three-dimensional structure of certain receptor protein tyrosine phosphatases (RPTPases) for the understanding of the mechanism and regulation of human receptor protein tyrosine phosphatases RPTPases, such as for example CD45, LAR.

In particular, provided is the structure solution of the two domain Leukocyte common Antigen Related D1/D2 protein (LAR). This represents the first structural determination of both individual PTPase domains tandemly arranged within the same protein molecule.

Methods of the invention include obtaining a series of three dimensional structure determinations using x-ray crystallography. Knowledge about the regulation of protein tyrosine phosphorylation provides valuable information about the control of basic cellular processes and is essential to understanding the mechanisms of a wide range of diseases such as the generation of cancer as well as diseases resulting from the improper control of the body's defensive and autoimmune responses.

In one preferred aspect, the amino terminal segment of LAR protein is extended to include additional residues expected to complete the initial alpha helix. These residues are identified in other PTPase structures as possible sites for stabilizing the terminal segment of the protein as well as for directing protein-protein interactions. Therefore, determining the amino terminal segment for LAR is important in understanding the mechanisms of diseases in which PTPases play a role. Preferably, the protein is crystallized to provide the structure of this slightly longer variant.

In another preferred aspect, methods of the invention provide for the co-crystallization of both of these LAR D1/D2 proteins with phosphate analogues and in the presence of potential phosphopeptide substrates. Generally these methods provide for constructing the active site mutant forms in which the critical active site cysteine residues are substituted with serine residues, in either or both domains, in order to bind but not cleave the phosphate groups during co-crystallization. Crystals achieved in this way can be screened for the presence of desired complexes and complete structure determinations carried out for any co-crystals.

In another embodiment, mutants of LAR D1/D2 are provided, to probe the details of the proposed active site and other loop regions in D2 as well as the linker segment between D1 and D2. Exact residues that are mutated are dictated by the crystal structures obtained using the above methods. It is desirable that mutants of LAR D1/D2 are co-crystallized with substrates and to determine the structures of these proteins and protein complexes.

In another embodiment, constructs of CD45 D1/D2 are generated by altering both the amino and carboxy termini as well as by removing the 16 residue insertion in D2 that is not found in the conserved D1 domains or in D2 of LAR. The protein is crystallized and complete structures of any proteins that diffract to a high resolution are obtained.

In another preferred embodiment, the crystallization and structure solution for CD45/LAR chimeric proteins that comprise about one phosphatase domain from each parent protein are provided. To verify exact positioning of the interfaces of the two proteins, reconstruction of the domain interfaces is preferred, such that the exact position of the junction between the two parent proteins corresponds to conservation of structural integrity as seen in the wild type structures.

Crystals comprising CD45 or LAR molecular structures wherein the crystals effectively diffract X-rays (i.e. the lower the angstrom number, the greater the resolution) for the determination of at least one of the structures to a resolution of about 5 Angstroms or less, more preferably a resolution of about 4 or 3 Angstroms or less, most preferred is a crystal wherein the crystal effectively diffracts X-rays for the determination of at least one of the structures to a resolution of about 2 Angstroms or less.

In preferred embodiments, the crystals comprise CD45 molecular structure or an LAR molecular structure, CD45 and LAR molecular structures, CD45/LAR chimeric structure, mutants and fragments thereof.

In one aspect the crystals comprise the entire molecule, including the N-terminal region to the PTPase domains that extend towards and into the cell membrane. This N-terminal or tail region can include about 10, 15, 20, 25 or 30 amino acids, or varying lengths of the tail region, fragments or amino acids that are juxtapositioned to the cell membrane.

In preferred embodiments, the method of making a crystal comprising CD45 or LAR molecular structures, produces a crystal which effectively diffracts X-rays for the determination of said structures to a resolution about 5 Angstroms or better, e.g. about 4, 3 or 2 Angstroms, and sufficient to determine atomic co-ordinates of said crystals.

In another preferred embodiment, a method of making crystals comprising cloning of CD45 or LAR molecules from cells producing these molecules into suitable expression vectors is provided. Suitable host cells are contacted with expression vectors wherein, the host cells express CD45 or LAR gene products. The gene products are purified the gene products are mixed with reservoir solutions. The crystals of the gene products are grown by hanging drop micro vapor diffusion; wherein, the crystals effectively diffract X-rays for the determination of said crystal structures to a resolution about 5 Angstroms or less and sufficient to determine atomic co-ordinates of said crystals. Wild-type CD45 crystals or wild type Leukocyte common Antigen Related (LAR) crystals are obtained using reservoir solutions containing Hepes, Ammonium Sulfate, DTT and PEG. Furthermore, mutant CD45 or LAR are crystallized with reservoir solutions containing Sodium Acetate, Magnesium Sulfate, DTT, glycerol and PEG. Preferably, the crystal is grown in a reservoir solution that comprises about 10% to about 20% PEG in molecular ranges of about PEG4K to about PEG20K, about 100 mM Hepes in a pH range of about pH5 to about pH9, and about 100 mM of ammonium sulfate to about 500 mM of ammonium sulfate.

Preferably, the wild type and mutant crystals effectively diffract X-rays to a resolution of at least about 5 Angstroms, more preferably diffract X-rays to a resolution of at least about 3 Angstroms most preferably diffract X-rays to a resolution of at least about 2 Angstroms.

A preferred method of producing the crystals comprises growing a crystal by vapor diffusion. Crystallization is preferably achieved in the presence of propylene ethylene glycol (PEG) and/or glycerol, preferably to generate a crystal of sufficient resolution to determine atomic co-ordinates of said crystals.

In one aspect, the reservoir solutions to generate a crystal comprises about 10% to about 20% PEG in molecular ranges of about PEG4K to about PEG20K. In another aspect, the reservoir solutions comprise about 100 mM Hepes in a pH range of about pH 5 to about pH 9. In another aspect, the reservoir solutions comprise about 100 mM of ammonium sulfate to about 500 mM of ammonium sulfate.

In preferred embodiments, the crystals comprise D1 and D2 PTPase domains, wherein the crystal effectively diffracts X-rays for the determination of the atomic coordinates to a resolution of at least about 3.0 Angstroms; and wherein said crystal has a space group of P1 with unit cell dimensions of: a=86 Å, b=60 Å, c=161 Å, $\alpha=90°$, $\beta=100°$ and $\gamma=90°$.

The crystals of the invention are preferably a CD45 crystal comprising an LAR PTPase domain or the crystal is an LAR crystal wherein the LAR crystal comprises a CD45 PTPase domain or the crystals comprise mutant LAR and CD45 proteins and LAR/CD45 chimeras, combinations and fragments thereof. The crystals can be mutated in an active site, in loop regions, in the D1 region, in the D2 region, in the D1/D2 region, in linker regions between the D1 and D2 regions, or combinations thereof.

In another aspect, a preferred crystal comprises the D1 and D2 PTPase domains, wherein the crystal effectively diffracts X-rays for the determination of the atomic coordinates to a resolution of at least about 2.0 Angstroms; and wherein said crystal has a space group of P2(1) with unit cell dimensions of: a=86.0 Å, b=59.7 Å, c=160.0 Å and $\beta=99.9°$.

In another aspect, a preferred crystal comprises the D1 and D2 PTPase domains, wherein the crystal effectively diffracts X-rays for the determination of the atomic coordinates to a resolution of at least about 2.0 Angstroms; and wherein said crystal has a space group of P2(1) with unit cell dimensions of: a=66.92 Å, b=62.73 Å, c=161.59 Å.

In other preferred embodiments, preferred crystal structures include, but not limited to, a crystal structure wherein LAR is co-crystallized with phosphate analogues in the presence of phosphopeptide substrates; a crystal structure wherein CD45 is co-crystallized with phosphate analogues in the presence of phosphopeptide substrates or analogs thereof.

Preferred phosphopeptide substrates are tyrosine kinases or components of the TCR CD3 complex, preferably the zeta chain.

Preferred mutant crystal structures, include but are not limited to mutations of amino acid residues in any loop and/or linker region; mutations of amino terminal and carboxy terminal ends; deletions in the D2 domain.

In other preferred embodiments, methods are provided for visualizing molecules that bind to any of the molecules which make up the crystals of the invention. Identified molecules are co-crystallized by the methods described herein.

A preferred method for identifying potential molecules that bind to, for example CD45, LAR and the like, is by molecular replacement techniques. Preferred co-crystallized complexes effectively diffract X-rays to a resolution of at least about 5 Angstroms, more preferably said crystals effectively diffract X-rays to a resolution of at least about 3 Angstroms, most preferably said crystals effectively diffract X-rays to a resolution of at least about 2 Angstroms.

In another preferred embodiment, molecules that bind to a CD45 and/or LAR molecule are identified. The method comprises selecting a potential compound through use of the set of atomic coordinates in FIGS. 4A through D and FIGS. 8A through F, wherein the selecting is performed in conjunction with computer modeling. The potential compound is contacted with a CD45 and/or LAR molecules or fragments thereof, and, measuring the binding affinity of, for example, the CD45 molecule or fragments thereof. The complex is co-crystallized, wherein the complex comprises, for example, CD45 molecule or fragments thereof and the potential compound. A potential compound is identified when the crystal effectively diffracts X-rays for the determination of the structures to a resolution of about 5 Angstroms or greater, sufficient to determine atomic co-ordinates of the crystals.

Preferred molecules or molecular complexes to which potential binding molecules can bind to, but are not limited to, comprise CD45, CD45/LAR chimeric protein, CD45-like polypeptides or LAR-like polypeptides, wherein said CD45 or LAR-like polypeptides belongs to the family of PTPases or homologues thereof.

Other aspects of the invention are disclosed infra.

Definitions

If appearing herein, the following terms shall have the definitions set out below.

As used herein, "active site" refers to those amino acids which bind to other molecules or ligands.

As used herein, the term "crystals effectively diffract X-rays" or "effectively diffract X-rays" refers to the measurement of X rays diffracted by the crystals such that, the lower the angstrom number, the greater the resolution.

As used herein, "tail region" or "N-terminal region" are used interchangeably and refer to the region of the molecule which extends from the looped domains to the cellular membrane spanning region. The tail or N-terminal region is the N-terminal region to the PTPase domains, or the cytoplasmic region N-terminal to the D1 PTPase domain.

As used herein, the term "gene" refers to an assembly of nucleotides that encode a polypeptide, and includes cDNA and genomic DNA nucleic acids.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., infra). The conditions of temperature and ionic strength determine the "stringency" of the hybridization. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA: RNA, DNA:RNA, DNA:DNA. For hybrids of greater than 100 nucleotides in length, equations for calculating $T_m$ have been derived (see Sambrook et al., infra, 9.50–0.51). For hybridization with shorter nucleic acids, i.e., oligonucleotides, the position of mismatches becomes more important, and the length of the oligonucleotide determines its specificity (see Sambrook et al., infra, 11.7–11.8). Preferably a minimum length for a hybridizable nucleic acid is at least about 12 nucleotides; preferably at least about 18 nucleotides; and more preferably the length is at least about 27 nucleotides; and most preferably 36 nucleotides.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences and synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

As used herein, the term "homologous" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667). Such proteins have sequence homology as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

The term "corresponding to" is used herein to refer to homologous amino acid (or nucleotide) sequences in which the relative positions of the amino acid residues (or nucleotides) is equivalent though the numbering of the amino acid residues or nucleotide bases of the sequences may not be the same.

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

The term "variant," when used in the context of a polynucleotide sequence, may encompass a polynucleotide sequence related to a wild type gene. This definition may also include, for example, "allelic", "splice," "species," "mutant" or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target genes. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant or mutant is a variation or mutation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

As used herein, the term "mRNA" means the presently known mRNA transcript(s) of a targeted gene, and any further transcripts which may be elucidated.

The term, "complementary" means that two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. Normally, the complementary sequence of the oligonucleotide has at least 80% or 90%, preferably 95%, most preferably 100%, complementarity to a defined sequence. Preferably, alleles or variants thereof can be identified. A BLAST program also can be employed to assess such sequence identity.

The term "complementary sequence" as it refers to a polynucleotide sequence, relates to the base sequence in another nucleic acid molecule by the base-pairing rules. More particularly, the term or like term refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 95% of the nucleotides of the other strand, usually at least about 98%, and more preferably from about 99% to about 100%. Complementary polynucleotide sequences can be identified by a variety of approaches including use of well-known computer algorithms and software, for example the BLAST program.

A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell. A cell is "transformed" by a nucleic acid when the nucleic acid is transduced into the cell and stably replicated. A vector includes a nucleic acid (ordinarily RNA or DNA) to be expressed by the cell. A vector optionally includes materials to aid in achieving entry of the nucleic acid into the cell, such as a viral particle, liposome, protein coating or the like. A "cell transduction vector" is a vector which encodes a nucleic acid capable of stable replication and expression in a cell once the nucleic acid is transduced into the cell.

As used herein, a "target cell" or "recipient cell" refers to an individual cell or cell which is desired to be, or has been, a recipient of exogenous nucleic acid molecules, polynucleotides and/or proteins. The term is also intended to include progeny of a single cell.

As used herein, the term "fragment or segment", as applied to a nucleic acid sequence, gene or polypeptide, will ordinarily be at least about 5 contiguous nucleic acid bases (for nucleic acid sequence or gene) or amino acids (for polypeptides), typically at least about 10 contiguous nucleic acid bases or amino acids, more typically at least about 20 contiguous nucleic acid bases or amino acids, usually at least about 30 contiguous nucleic acid bases or amino acids, preferably at least about 40 contiguous nucleic acid bases or amino acids, more preferably at least about 50 contiguous nucleic acid bases or amino acids, and even more preferably at least about 60 to 80 or more contiguous nucleic acid bases or amino acids in length. "Overlapping fragments" as used herein, refer to contiguous nucleic acid or peptide fragments which begin at the amino terminal end of a nucleic acid or protein and end at the carboxy terminal end of the nucleic acid or protein. Each nucleic acid or peptide fragment has at least about one contiguous nucleic acid or amino acid position in common with the next nucleic acid or peptide fragment, more preferably at least about three contiguous nucleic acid bases or amino acid positions in common, most preferably at least about ten contiguous nucleic acid bases amino acid positions in common.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides.

BRIEF DESCRIPTION OF THE DRAWINGS

FIGS. 4(A–D) shows the atomic coordinates corresponding to each of the active sites (a) (b) (c) and (d) from the two molecules that comprise one asymmetric unit. The bound ligands, either sulfate ion or pTyr residue, are included with their respective active sites.

FIGS. 8(A–F) shows the atomic coordinates corresponding to each of the active sites (a) (b) (c) and (d) from the two molecules that comprise one asymmetric unit as well as the phosphopeptide residues bound within each D1 site (e) and (f). These refined coordinates are from the seleno-met crystals in space group P2(1).

DETAILED DESCRIPTION OF THE INVENTION

Figure 1:
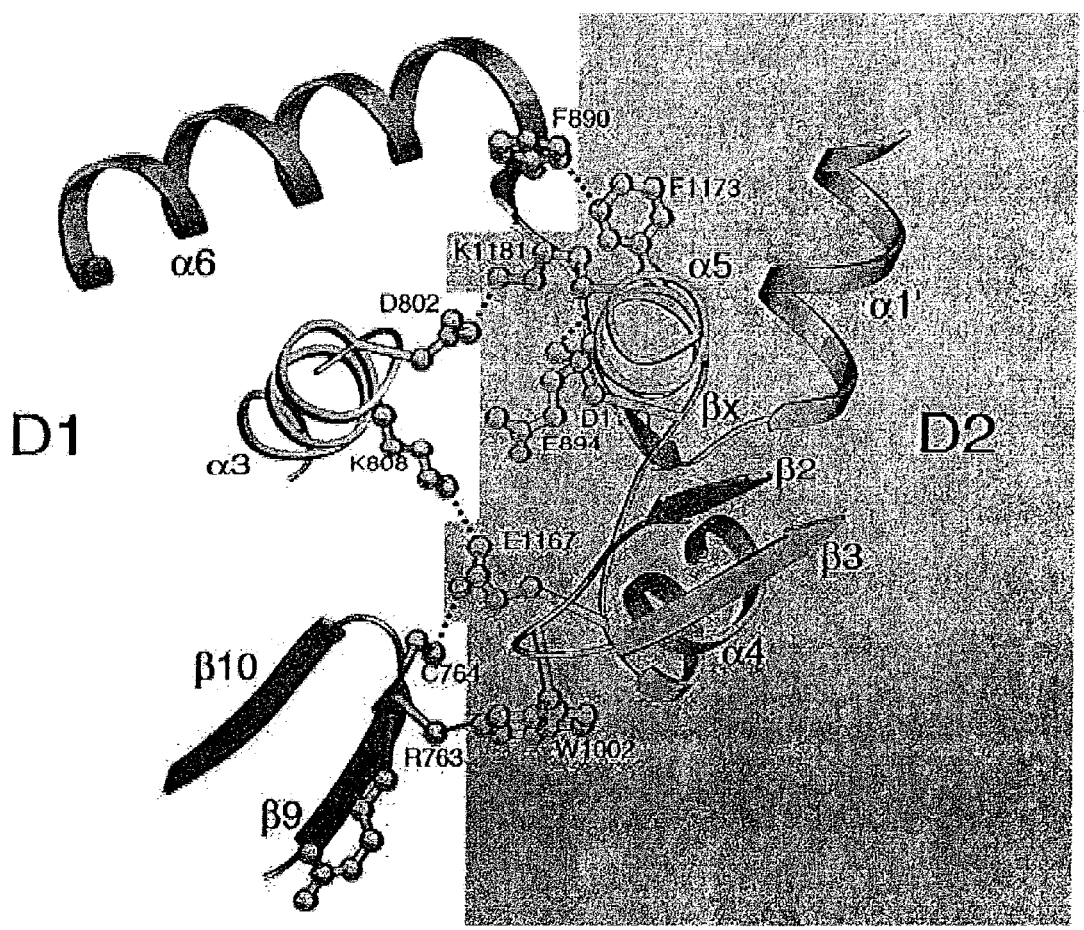
FIG. 1 is a schematic representation, depicting the interface between the D1 and D2 domains of CD45 as a ribbon diagram. Parts of D1 and D2 are shown on the left and on the right, respectively. For clarity, D2 domain is shown with a shaded background. Amino acid residues involved in hydrogen bonding between the two domains are shown. Potential hydrogen bonds (2.5 Å-3.1 Å) are drawn as dotted lines.

The present invention provides methods for determining the crystallographic structures of receptor-like protein tyrosine phosphatases. Crystallographic structures, to date, have yielded low quality crystals that are not useful in determining structure-function relationships. This is especially important in, for example, elucidating disease causing mechanisms and drug discovery.

The crystal structures presented herein, are the first to provide clear, stable, high quality crystals, visualization of the membrane distal PTPase (D2) domain and the structures of the two consecutive PTPase domains within the same polypeptide chain. The crystal structures are of high significance in determining the mechanisms of protein tyrosine phosphorylation associated with various disease states.

In particular, the structure of the cytoplasmic portion of CD45 as determined by x-ray crystallography, is described. This provides the first direct structural information for this important RPTPase and a framework from which to analyze the array of previous cellular-function data. The presence of both PTPase domains within the same molecule offers new insight into the critical questions of the role of D2 and the possible intra- and inter-molecular interactions of both domains. In addition to providing the fine details regarding the catalytic centers of CD45 and LAR, the determination of the 3-D structure of an entire cytoplasmic region of the RPTP is essential to answer many questions related to the role of the D2 domain.

Protein tyrosine phosphorylation is an important molecular switching mechanism that regulates a variety of cellular functions including cell proliferation, differentiation, and activation. Tyrosine phosphorylation is not only an essential part of the signal transduction mediated by various growth factor receptors, but it is also involved in intracellular signal transduction and nuclear cell cycle regulation. Disturbances of these processes are known to be causes of disease. For example, overexpression and/or hyper-activation of many protein tyrosine kinases are oncogenic. Thus, knowledge about the regulation of protein tyrosine phosphorylation provides valuable information about the control of basic cellular processes and is essential to understanding the generation of the diseased state. In this regard, the ultimate goal of many converging lines of research is the eventual development of rational drug design. Also, particularly in the case of CD45, the direct link to control of the immune response makes auto-immune diseases a major focus for drug development based on the invention described herein.

A description of the PTPases, described below, is important to understand the urgency for the crystallization of these molecules.

The roughly 100PTPases identified to date can be broadly divided into receptor-like (RPTP) and cytosolic (non-receptor) proteins. Each member of the cytosolic PTPase subfamily contains a conserved PTPase domain of ~240 amino acids, and may also contain various accessory domains such as an SH2 domain. Members of the RPTPs are type-I integral membrane proteins composed of an extracellular receptor-like domain and a cytoplasmic region containing one or two PTPase domains connected by a single membrane-spanning segment. CD45 (also known as Leukocyte Common Antigen, CD45) and LAR (Leukocyte Common Antigen Related) molecules are the prototypic members of the RPTP family, which now includes numerous proteins such as transmembrane PTPases-α, -β, -γ, -δ, -ε, -ζ, -μ, and -κ. The extracellular regions vary in size and structure, among members of RPTPs as well as among isoforms of a given molecule.

Structural characteristics of the extracellular regions of many RPTPs suggest that they may function in ligand binding mediated by these segments. For example, the extracellular region of LAR is composed of three immunoglobulin (Ig)-like domains and eight repeats of fibronectin type III (FnIII) domains (see the schematic diagram below). Ig domains are thought to function as cell surface recognition structures and are found in several growth factor receptors such as PDGFR, FGFR, and IL-6R and in cell-adhesion molecules, including the Neural-Cell Adhesion Molecule (N-CAM). FnIII domains are approximately 90 amino acids long and contain a characteristic sequence motif identified initially in fibronectin. The combination of Ig and FnIII domains is found in a number of known cell-adhesion molecules (CAMs) and matrix-adhesion molecules (MAMs). The CAM/MAM-like extracellular region of LAR suggests that it may be an adhesion receptor.

Figure 9:
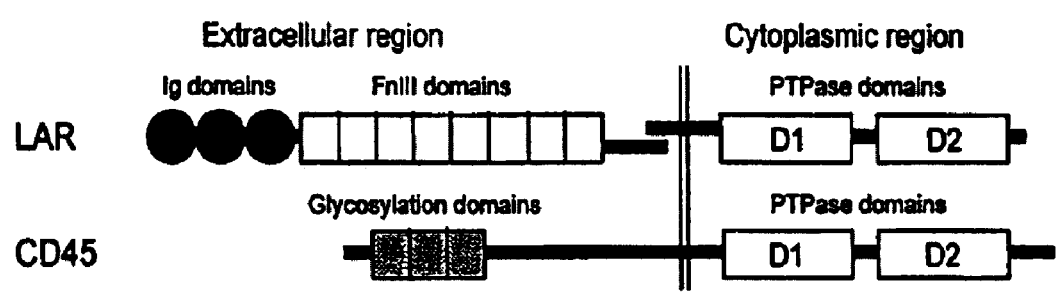
FIG. 9 shows extracellular and cytoplasmic regions of LAR and CD45.

The extracellular regions of CD45 on the other hand is composed of alternate arrangements of several exon segments that incorporate sites for glycosylation. Within this region there are also two segments of conserved cysteine repeats that are thought to function in some sort of protein recognition. See FIG. 9.

To date all previous PTPase structure determinations have shown that the overall phosphatase domain structure as well as the active site region is highly conserved. As described herein, the catalytic domain (D1) of CD45 exhibits this common three-dimensional structure. The active site itself appears to be in a "closed" conformation as defined by comparison to structures of peptide and phosphate analogues complexed with PTP1B and the *Yersinia* PTPase. The presence of a sulfate ion from the crystallization solution within the active site pocket seems to mimic the position of a substrate phosphate group and is hydrogen bonded to the serine residues within the signature sequence. In addition, the WPD loop is shifted toward the binding site and is in a position that would be comparable to that seen in an intermediate of the catalytic reaction.

The overall domain architecture of the membrane distal (D2) domain of CD45 also maintains the expected conserved PTPase fold. There has been only one other D2 domain structure published, that of the closely related RPTPase, LAR, and in this case the active site structure of D2 was nearly superimposable with that of its respective D1 domain. Only small localized changes, resulting from the substitution of two key residues, were identified as critical for blocking catalytic activity. For most RPTPases, the respective D1 and D2 domains share overall primary sequence homology of ~70%. However, in the case of CD45, there is a much greater degree of substitution at the active site region and there are potentially important deviations within the signature motif itself.

Figure 5:
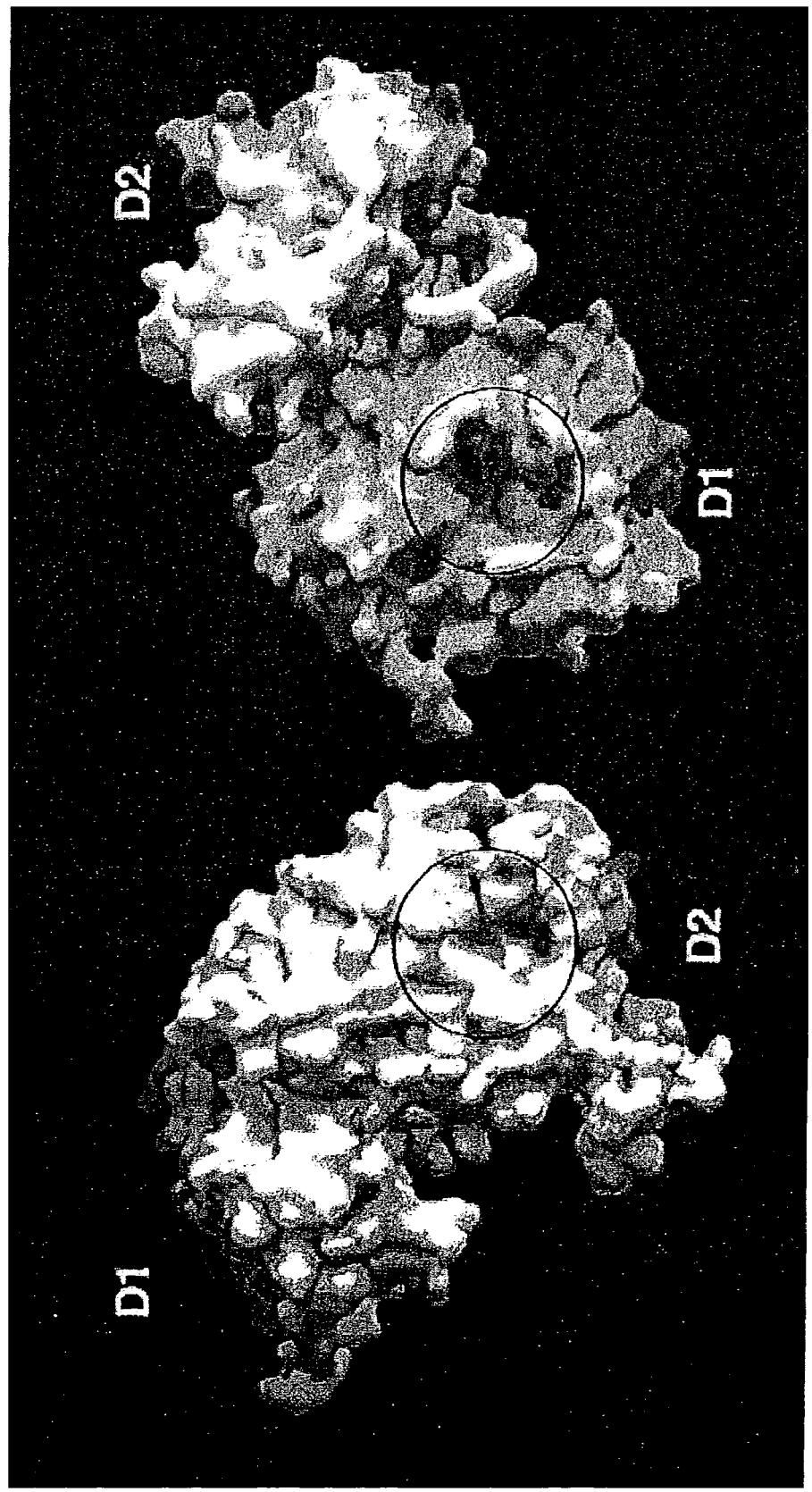
FIG. 5 is a schematic representation showing surface diagrams of the active sites of D1 and D2. The entire D1D2 molecules are shown with the D1 active site facing toward viewers on the right, and the D2 active site on the left. (Active site regions are circled.) Positive charges on the surface of the molecules are shown in gray scale; the darker shade indicates stronger positive charge.

As illustrated in FIGS. 4 and 5, there are more significant structural changes associated with these differences. A surface diagram of the D1 active site shows a positively charged pocket which can have high affinity for a phosphotyrosine moiety. On the other hand, the D2 active site C1143 is not exposed and is instead blocked from incoming substrates by the side chain of Q1149. The D2 active site is also positively charged, however this results from the presence of a unique arginine residue, R1145, as opposed to the invariant R834 in D1. The otherwise invariant Q869 is also substituted by Ser in the D2 domain of CD45. The short side chain of S1144 may not be able to contribute to the catalytic activity as in the case of the corresponding Q869. Instead, this role is served by nearby Q1149, whose position in D2 mimics that of Q869 in D1. The combined effects of these subtle changes result in a blocked binding pocket which may be able to open up to accommodate specific substrates, but in general appears to display very low affinity for phosphotyrosine containing substrates.

One other important feature that is specific for CD45 can be seen in the primary sequence comparison of these PTPase domains. There is a 19-residue insertion within the D2 domain that falls at the position corresponding to the β1–β2 loop in the LAR D2 domain. This sequence is highly acidic and by secondary structure prediction could not be characterized as any regular structure element. There have been reports that the presence of this segment affects the phosphatase activity of D1 and might be responsible for altering the binding of CD45 with respect to various other cellular components. From the present structure the spatial orientation of this acidic loop can be visualized for the first time.

In the crystallized structure, the intramolecular domain orientation seen here would not be consistent with the model of the symmetrical dimerization of CD45 that has been postulated previously. As with its close relative LAR, the presence of the D2 domain would preclude the interlocking insertion of the N-terminal "wedge" of each receptor into the active site pocket of the other molecule. Instead, the positioning of D2 against the back side of the D1 active site may account for the influence of the second domain on the activity of D1.

Another distinctive feature of the present invention is that one intermolecular contact seen in this crystal form does involve the N-terminal region of one molecule and the equivalent of the "WPD" loop in D2 of an adjacent molecule. The crystallized structure has a crystal packing interaction between Lys618 in D1, and Gln1104 from a neighboring D2 domain. In the structure, this interaction appears to be only a fortuitous packing artifact, however, it may resemble a possible D1–D2 interaction in solution. Regardless, it does not involve the same spatial relationship of the "wedge" and active site pocket, nor does it utilize the specific residues, that had been previously implicated in the proposed dimer interaction.

Finally, this structure gives one clear picture of the intramolecular domain orientations for the cytoplasmic portion of CD45. There is an extended contact surface comprising portions of the last helices of D1 and the beta sheet loops and helices of D2. This interaction is stabilized by overall surface complementarity of the two domains comprising van der Waal's and hydrogen bonding interactions. The short linker segment is involved in hydrogen bonds to both domains utilizing backbone atoms as well as side chains of conserved residues. The two individual molecules in the crystallographic asymmetric unit each adopt a slightly different orientation while maintaining the same bonding interactions. The overall shift in position of D2 for the two molecules is only 1.5 Å resulting from a 4 degree rotation about the linker segment.

The methods used for the crystallization of the LAR/CD45 are particularly important as they can be applied to other surface molecules, especially, for example classes of receptor protein tyrosine phosphatases. This is especially important as the balance of protein phosphorylation and dephosphorylation is recognized as a major key in the control of cellular processes and their response to the outer environment. Furthermore, it has become increasingly important to determine the structures of PTPases, for their role in diseases such as autoimmunity, malignancies and the like, especially since PTPases most likely are varied in class, specificity, and mechanism of regulation. The methods used herein, will be important in the understanding of the PTPases's true cellular substrate specificities or the regulation of their catalytic activity.

Leukocyte Common Antigen (LCA), or more commonly, CD45 is associated with specific disease states, determined by the phenotypic consequences of the inactivation or mutation of CD45. The pivotal role this protein plays at the interface of a lymphatic cell's response to external immune stimulation and the subsequent activation of the T Cell Receptor coupled with the crystal structure of the invention provides a major driving force for understanding the details of this critical component. The leukocyte-specific CD45 PTPase, is important for T-cell antigen receptor-mediated signaling as well as for B-lymphocyte development and the present invention is highly useful in investigating these properties. CD45 is thought to play a role in the termination of signaling by the T-cell antigen receptor (TCR) by the identification of another high affinity substrate of CD45 among tyrosine phosphorylated T-cell proteins. Furthermore, there is a need to determine the connection between CD45 and the src family kinases. CD45 is able to dephosphorylate several members of this group of proteins and shows some substrate preference for these kinases when compared with the activity of other PTPases. It is important to determine that CD45 functions directly in signal pathways by dephosphorylation and activating cytosolic PTKases.

The characteristic RPTPase domain organization poses certain very interesting structural questions that are unique to this family of proteins. Unlike the soluble PTPases, the cytoplasmic portion of these proteins comprises tandem conserved PTPase domains, with only the membrane proximal (D1) domain exhibiting any significant catalytic activity. The methods of the invention are useful in determining the role of the high degree of sequence conservation of D2. The present data show that the membrane distal (D2) domain has an additional binding domain and/or that it affects the activity or regulation of the neighboring D1 domain. It is well established in the prior art that the primary sequence proximity and the conservation of catalytic residues have made it difficult to actually define the roles of either domain independently in solution. Structural data have been used to infer a possible mechanism of regulation for the D1 domain of a related RPTPase, RPTP-α, and a series of experiments with engineered chimeric receptors has been described in an attempt to extend this possible regulatory mode to explain the cellular activity of CD45 as well.

As mentioned, the present invention describes the structure of the cytoplasmic portion of CD45 as determined by x-ray crystallography. This represents the first direct structural information for this important RPTPase and provides a framework from which to analyze the array of previous cellular function data. The presence of both PTPase domains within the same molecule is useful in defining the role of D2 and the possible intra and inter-molecular interactions of both domains.

With respect to LAR, LAR has a broad tissue distribution and is expressed as multiple isoforms that are generated by apparent tissue-specific splicing of four small exons coding for 4–16 residues within the extracellular and immediate membrane proximal segments of the full length protein. In addition, the protein is thought to be expressed on the cell surface as a complex of two non-covalently associated subunits generated by cleavage of a proprotein just ahead of the transmembrane segment. During cell growth the shedding of the extracellular portion may provide a mechanism for control of phosphatase activity, for example, the activation of insulin receptor (IR), both receptors for epidermal growth factor (EGF) and hepatocyte growth factor (HGF). Antisense-mediated suppression of LAR showed increased levels of phosphorylation of prominent immunoregulatory substrates as well as significant increases in autophosphorylation of growth factor receptors. In addition, LAR knockout mice have developmental defects in the mammary gland, and knock-out of PTPσ (which is highly related to LAR) causes neuroendocrine defects. These multiple roles of this family of proteins underscores the immediate urgency for identifying the three-dimensional structures in order to understand the mechanism involved.

In contrast to the divergent extracellular region, the cytoplasmic region and in particular the PTPase domains themselves, of RPTPs are all similar. Most of the RPTPs contain two tandem phosphatase (PTPase) domains, although a few RPTPs such as PTPβ, DEP-1, and U2 have only one PTPase domain. The PTPase domains each consist of a conserved segment of approximately 240 amino acid residues, within which is the sequence motif (I/V)HCXAGXXR(S/T)G that uniquely defines the PTPase family. For both LAR and CD45, mutational analyses suggest that the conserved Cys residue is essential for the PTPase activity.

Whereas both PTPase domains in the two-PTPase-domain RPTPs are highly homologous, catalytic activity is thought to be associated mainly with the membrane proximal phosphatase domain (D1). In the cases of CD45 and LAR, it is generally thought that the D2 domain is not active, whereas their D1 domain is thought to be highly active.

Although the D2 domains are thought not to be catalytically active for most RPTPs, the D2 sequences are very well conserved suggesting that they must have functionally important roles. For example, the D2 domains of human LAR and its *Drosophila* homologue, DLAR, are as much as 83% identical in amino acid sequences. In comparison, their catalytically active D1 domains are only 71% identical to each other. This high level of conservation of the D2 sequences seems implausible unless they have a vital function. Thus, a fundamental question concerning many RPTPs is the role of the D2 domain.

As an illustrative example of use for the present invention for determining function, and discussed in detail in the examples which follow, it is shown that purified LAR-D1 (which comprises the D1 domain) and LAR-D1D2 (which comprises both the D1 and D2 domains) proteins have identical specific activity. However, only LAR-D1D2 was sensitive to the effect of stimulators such as poly(Lys) and poly(Arg). Evidence from phosphatase activity studies based on a series of deletion mutations suggests that the inclusion of some amino terminal portion of the D2 domain might be necessary for maximal activity and can alter the ratios of affinities for different phospho-peptide or protein substrates. Thus, by virtue of obtaining the crystal structure, data regarding the membrane distal phosphatase domain (D2) indicates that D2 does have a function which may be regulatory in nature, and will aid in defining the interactions of these molecules in disease associated states.

A preferred method for the growth of high quality crystals for structure determination is to, first, express and purify sufficient quantities of CD45-D1D2 and LAR-D1D2 with a high degree of purity. Recombinant CD45-D1D2 and LAR-D1D2 proteins are preferably expressed in an *E. coli* cell line BL21(DE3) using the T7 RNA polymerase expression system. The cytoplasmic sequences of CD45 and LAR are preferably aligned and the N- and C-termini are chosen to minimize the presence of any unwanted flexible amino acid residues outside of the conserved predicted D1 and D2 domains. The plasmid of choice comprising these sequences is introduced into cells suitable for expression of the proteins. Other methods and cell lines can also be used which are well-known to one of skill in the art.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

A gene encoding a CD 45 or LAR protein, whether genomic DNA or cDNA, can be isolated from any animal source, particularly from a mammal. Methods for obtaining the CD 45 or LAR molecule are well known in the art, as described above (see, e.g., Sambrook et al., 1989, supra).

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion proteins. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed.

In still another such embodiment the heterologous nucleotide can function as a means of detecting a nucleotide sequence of the present invention. A heterologous nucleotide sequence comprises non-coding sequences including restriction sites, regulatory sites, promoters and the like.

To further determine structure/function relationships, the invention provides for mutants of LAR D1/D2 and CD45 D1/D2 in the proposed active site and other loop regions in D2 as well as the linker segment between D1 and D2.

Additionally, the CD45 or LAR protein-encoding nucleic acid sequences of choice can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, *J. Biol. Chem.* 253:6551; Zoller and Smith, 1984, *DNA* 3:479–488; Oliphant et al., 1986, *Gene* 44:177; Hutchinson et al., 1986, *Proc. Natl. Acad. Sci.* U.S.A. 83:710), etc. PCR techniques are preferred for site directed mutagenesis (see Higuchi, 1989, "Using PCR to Engineer DNA", in PCR Technology: Principles and Applications for DNA Amplification, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2µ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

The nucleotide sequence coding for a CD45 or LAR protein, or functional fragments, derivatives or analogs thereof, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding a CD45 or LAR protein of the invention or functional fragment, derivatives or analogs thereof, is operationally associated with a promoter in an expression vector of the invention. Both cDNA and genomic sequences can be cloned and expressed under control of such regulatory sequences. An expression vector also preferably includes a replication origin. The necessary transcriptional and translational signals can be provided on a recombinant expression vector.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant CD45 or LAR protein of the invention, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding CD45 or LAR protein is cultured in an appropriate cell culture medium under conditions that provide for expression of CD45 or LAR protein by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of CD45 or LAR protein may be controlled by any promoter/enhancer element known in the art, but these regulatory elements must be functional in the host selected for expression.

Expression vectors containing a nucleic acid encoding a CD45 or LAR protein of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding CD45 or LAR protein is inserted within the "selection marker" gene sequence of the vector, recombinants containing the CD45 or LAR protein insert can be identified by the absence of the CD45 or LAR protein gene function. In the fourth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, nonchromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., 1988, *Gene* 67:31–40), pMB9 and their derivatives, plasmids such as RP4; phage DNAs, e.g., the numerous derivatives of λ phage, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoRI, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAC700 (BamH1 and KpnI cloning site, in which the BamH1 recognition site begins with the initiation codon; Summers), pAC701 and pAC702 (same as pAc700, with different reading frames), pAC360 (BamH1 cloning site 36 base pairs downstream of a polyhedron initiation codon; Invitrogen (195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, Current Protocols in Molecular Biology, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindIII, SbaI, BamHI, and Hpa cloning site, TK or XPRT selection).

Yeast expression systems can also be used according to the invention to express CD45 or LAR polypeptide. For example, the non-fusion pYES2 vector (XbaI, SphI, ShoI, NotI, GstXI, EcoRI, BstXI, BamH1, SacI, KpnI, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the present invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, *J. Biol. Chem.* 267:963–967; Wu and Wu, 1988, *J. Biol. Chem.* 263:14621–14624; Hartmut et al., Canadian Patent Application No. 2,012,311, filed Mar. 15, 1990).

The following is an illustrative example for producing purified proteins of the invention, leading to the crystallization of these proteins. *E. coli* cells carrying the recombinant plasmid are cultured in a 1medium and the proteins are induced when the optical absorbance at 600 nm reaches 0.6 Å. After induction, the cells are harvested and lysed using sonication. The cellular debris is separated by low speed centrifugation and the soluble cell extract containing either LAR-D1D2 or CD45-D1D2 is retained.

Depending on the construct used for the expression, the cellular proteins are initially separated by immobilized metal ion affinity chromatography or by ion exchange chromatography. Proteins expressed with a six histidine tag at their N- or C-terminus are first run through a Ni— or Zn column, and proteins without a tag are first separated using a DEAE Sepharose Fast Flow column. Crude fractions of proteins are collected and further purified using a FPLC Mono-Q column. The proteins are next run through a gel filtration column to remove additional impurities and final pooled fractions, as run on polyacrylamide gels, are judged to be >95% pure by staining. Typical yields from a 4 L cell culture can vary anywhere from between about 3 mg to at least about 40 mg of highly pure protein depending on the different constructs. LAR-D1D2 or CD45-D1D2 purified in this manner displays phosphatase activity in a standard colorimetric assay using PNPP (p-Nitrophenyl phosphate).

The next step in this illustrative example is the crystallization step. This step can be performed using at least about 15 mg/ml protein solutions in standard vapor diffusion set-ups. Factorial screening of crystallization solutions including variations of buffers and their pH, salts, additives, and precipitants are performed to determine general growth conditions. This allows for determining exact conditions required for the different proteins to improve crystal quality. For example, in a preferred embodiment, PEG with molecular weight cut offs used in the buffers, range from about 4K to about 20K and the percentage of PEG in the buffer ranges from about 10% to about 20%. Ranges of buffer pH are from about pH 5 to about pH 9. Molar amounts of ammonium sulfate range from about 100 mM to about 500 mM.

Using this method, four different forms of wild type CD45-D1D2 crystals have been observed. For example, thin plate-like crystal clusters have been obtained from conditions with 0.1M Tris pH 8.0 and 2M ammonium sulfate, and long rod shaped crystals have been observed from a condition with 0.1M Tris pH 8.0 and 1M sodium citrate. Hexagonal crystals have been obtained from a condition with 0.1M MOPS pH 6.5, 15% PEG 8K and 0.5M ammonium sulfate.

Another form of thin plate-like crystal clusters have been obtained for wild type and mutant CD45-D1D2 proteins. These crystals typically grow from a condition with 0.1M Sodium Acetate pH 5.0, 10–14% PEG 4K and 0.1M MgSO4. The mutant CD45-D1D2 protein was also crystallized with phosphotyrosine (pTyr) in the solution. The crystallization solution contains 0.1M Sodium Acetate pH 5.0, 10–14% PEG 4K and 10 mM phosphotyrosine. Typically, the thin plate-like crystals grow to the size of about 0.2×0.1×0.0005 mm, the rod shaped ones to the size of about 0.3×0.1×0.05 mm, and the hexagonal shaped crystals grow to about 0.3×0.2×0.1 mm. Varying conditions, such as for example, including varying additives and macro and micro seeding techniques, allow for growth of larger crystals.

Two kinds of LAR-D1D2 crystals have also been obtained. Both crystal forms can appear in the same crystallization conditions, and a wide range of conditions gives rise to these crystals. The protein is crystallized as either a thin plate cluster form or a hexagonal form with typical dimensions of about 0.2×0.1×0.0005 mm and about 0.005× 0.005×0.005 mm for the plate and the hexagonal forms, respectively. The plate-like form crystals, despite their thin morphology, diffract well and as described below are suitable for structure solution. Preferred methods for crystallization are described in detail in the examples which follow.

Other methods well known to those skilled in the art can also be used. Crystals can be grown by a number of techniques including batch crystallization, vapor diffusion (either by sitting drop or hanging drop) and by microdialysis. Seeding of the crystals in some instances is required to obtain X-ray quality crystals. Standard micro and/or macro seeding of crystals may therefore be used. An initial crystal can be allowed to grow over several months, for example, at 4° C. from a hanging drop. Crystals then can be subsequently grown by macroseeding from the initial crystal.

Once a crystal of the present invention is grown, X-ray diffraction data can be collected. A MARresearch imaging plate detector for X-ray diffraction data collection can be used for example. Crystals can be characterized by using X-rays produced in a conventional source (such as a sealed tube or a rotating anode) or using a synchrotron source. Initially, diffraction patterns have been collected from rod shaped and hexagonal CD45-D1D2 crystals. Both capillary mounted and cryogenically frozen crystals diffracted weakly at our home x-ray source. Typically, diffraction patterns up to 6 Å could be obtained from a 2 hour exposure for a 1° oscillation. Diffraction data were collected from a small hexagonal crystal at the Brookhaven National Laboratory (BNL) Synchrotron facility. At this source diffraction intensities could be clearly observed up to a resolution of 4 Å. The Rsymm (the agreement between symmetry related reflections, $\Sigma hkl \Sigma i |Ii(hkl) - <Ii(hkl)>|/\Sigma hkl \Sigma i Ii(hkl)$) of the data between 50 Å and 6 Å is about 9%. However, because of the weak intensity beyond 6 Å resolution, the Rsymm was higher than 20% in the 6 Å–4 Å resolution shell. These data were processed using DENZO and it was determined that the crystal belongs to a hexagonal space group with the unit cell dimensions of a=165 Å, b=165 Å and c=144 Å. Later, diffraction patterns have been collected from thin plate-like crystals grown at pH 5.0. There crystals diffracted up to 3.5 Å at our home x-ray source and diffracted up to 3.2 Å at Advanced Photon Source (APS) Synchrotron facility. The crystals of the mutant CD45-D1D2/pTyr complex diffracted up to 3.0 Å at the Cornell High Energy Synchrotron Source (CHESS) facility. The Rsymm was approximately 10% overall. The data were processed using DENZO and it was determined that the crystals belong to a triclinic space group with the unit cell dimension of: a=86 Å, b=60 Å, c=161 Å, α=90°, β=100° and γ=90°.

An illustrative example using the methods of the invention is described and is not meant to construe or limit the invention in any way. Diffraction data sets were collected from the thin-plate like crystals and the hexagonal crystals of LAR-D1D2, both using flash frozen crystals under cryogenic conditions. The small sized hexagonal crystals diffracted only up to 7 Å at our laboratory. Well ordered diffraction intensities from the thin plate crystal, on the other hand, were observed up to the resolution of 3 Å in the laboratory. A diffraction data set was collected from a thin plate like crystal at the F1 line of Cornell High Energy Synchrotron Source (CHESS). The crystal diffracted up to a resolution of 2.0 Å. This data set is 90.7% complete and, after processing, the Rsymm of the data between 20 Å and 2.0 Å is 6.4%. The crystal belongs to space group P2(1) with the unit cell dimensions of a=66.92 Å, b=62.73 Å and c=161.59 Å.

Amino acid sequence analyses showed that the D1 and D2 domains of LAR are very close to the D1 domain of RPTPα; the sequence identities between the D1 domain of LAR and RPTPα-D1, and between LAR-D2 and RPTPα-D1 are about 49% and about 38%, respectively. Therefore initial phase information for structure solution was obtained by molecular replacement techniques. Using the LAR data collected from CHESS, a search for the molecular replacement solutions using the RPTPα D1 structure as a search model, was conducted. The program AMoRe was used for rotation and then translation searches. From the size of the unit cell, two molecules (four phosphatase domains) were expected in an asymmetric unit. The search gave unambiguous results such that each domain could be held constant and used to search for the subsequent positions. The molecular packing in the unit cell was then examined to ensure the absence of overlapping molecules or the presence of large empty spaces and by such criteria judged to be ideal and sufficient to begin model building and refinement.

After the four phosphatase domains were positioned according to the molecular replacement solutions, the amino acid residues were replaced with poly-serine and a 2Fo-Fc map was generated using this model. That model was rebuilt to reflect the actual amino acid sequence of LAR D1D2 as the model showed clear side chain densities. Based on these side chain densities each domain could be unambiguously assigned. Crystallographic refinement was performed using X-PLOR applying noncrystallographic symmetry (NCS) restraints. Calculated phases using the model were improved by several cycles of combined solvent flattening and multidomain NCS averaging using the CCP4 computer package. Interactive rounds of positional and simulated annealing refinement were applied to improve the quality of the model.

The final model has 1108 of the total 1148 residues and 472 ordered water molecules with working and free R-factors 22.2% and 27.4%, respectively.

Methods of crystal data characterization include, but are not limited to, precision photography, oscillation photography, and image plate or CCD detector data collection, as described above. Preferred methods are exemplified in the examples which follow. Alternatively, the CD45 or LAR proteins can also be synthesized with selenium-methionine (Se-Met) in place of methionine, and the Se-Met multiwavelength anomalous dispersion data [Hendrickson, *Science,* 254:51–58 (1991)] can be collected on CHESS F2, using reverse-beam geometry to record Friedel pairs at four X-ray wavelengths, corresponding to two remote points above and below the Se absorption edge, such as for example, $\lambda 1$ and $\lambda 4$ and the absorption edge inflection point $\lambda 2$ and peak $\lambda 3$. Selenium sites can be located using SHELXS-90 in Patterson search mode (G. M. Sheldrick). Experimental phases (alphaMAD) can be estimated via a multiple isomorphous replacement/anomalous scattering strategy using, for example, MLPHARE (Z. Otwinowski, Southwestern University of Texas, Dallas) with three of the wavelengths treated as derivatives and one, $\lambda 2$, treated as the parent for example.

Data processing and reduction can be carried out using programs such as for example, HKL, DENZO, and SCALEPACK [Otwinowski and Minor, *Meth. Enzymol.* 276:307–326 (1997)]. As exemplified in the examples which follow, X-PLOR applying noncrystallographic symmetry restraints is the preferred method, [Bruger, X-PLOR v.3.1 Manual, New Haven: Yale University, (1993B)] and may be utilized for bulk solvent correction and B-factor scaling. Electron density maps can be calculated using SHARP [La Fortelle, E. D. and Bricogne, G., Methods in Enzymology 276:472–494 1997)] and SOLOMON. Molecular models can be built into this map using O [Jones, T. A., et al., *ACTA Crystallogr.* A47: 110–119 (1991)]. A complete molecular model for the protein can be built on the basis of the experimental electron density map. Model building interspersed with positional and simulated annealing refinement [Bruger, 1993B, supra] or with CNS, using a maximum likelihood residual [Brunger, A. T. et al., *Acta Cryst. D* (1998)] can permit an unambiguous trace and sequence assignment of the proteins.

Once the three-dimensional structure of a crystal comprising CD45 or LAR is determined, a potential ligand (antagonist or agonist) can be examined through the use of computer modeling using a docking program such as GRAM, DOCK, or AUTODOCK [Dunbrack et al., 1997, supra]. This procedure can include computer fitting of potential ligands to the pTyr binding domain for example to ascertain how well the shape and the chemical structure of the potential ligand will complement or interfere with the CD45 or LAR ligand binding [Bugg et al., *Scientific American*, December:92–98 (1993); West et al., *TIPS,* 16:67–74 (1995)]. Computer programs can also be employed to estimate the attraction, repulsion, and steric hindrance of the ligand to the CD45 or LAR D1/D2 domain(s).

Preferably, once mutants are generated, they can be used in crystallization and structure solution experiments, as described in the examples which follow. Individual protein constructs are examined alone and in the presence of various ligands so that the effects of these substitutions on the ability to bind substrates and the associated structural changes can be seen. For previous PTPase domains similar structural comparisons have demonstrated the potential flexibility of certain segments, i.e. the WPD loop, and confirmed the participation of specific key residues in the reaction mechanism. Co-crystallization with phosphopeptide substrates offers an excellent way to assess binding capabilities of both D1 and D2 domains. If the second PTPase domain is important as a kind of silent phosphotyrosine binding site then crystallization and structure determination is a very direct way simultaneously to observe and to characterize interactions at both sites. Any interaction between the two binding sites can be described as well.

For binding studies, several different peptides based on the available biochemical data as described above, are chosen. LAR has been shown to be directly involved in the inactivation of insulin receptor and EGF receptor and therefore the pTyr sites in these proteins are excellent candidates. Similarly, the observation the CD3$\zeta$ chain is a specific ligand for CD45 suggests that it is also a good initial substrate to test. The zeta chain has three sets of pTyr residues so that a peptide centered around each of these sites can be used. Due to the observations that CD45 associates with both PTKases Lck and Fyn in vivo, decapeptides composed of sequences flanking the terminal phosphotyrosine that is defined as the negative regulatory site of each can be used.

Analyses of in vitro binding studies have also defined the relative affinities of both LAR and CD45 for a series of IR peptides with one or two pTyr residues as well as peptides from growth factor receptors. In addition, due to the very prominent role of Src itself in signaling pathways and the cellular evidence that both LAR and Src are localized within the focal adhesion areas, Src peptides can be used as possible substrates, one flanking the critical pTyr residue in the kinase domain and finally one based on the inhibitory tail peptide containing pTry527. The peptides used in these studies are obtained from commercial sources and their purity checked by HPLC analysis. Preferably, the protein constructs used for co-crystallization include the critical cys to ser mutation in one or both domains as needed to prevent substrate cleavage. Solution binding to peptides used are monitored by affinity measurements, as described below, as a means of correlating with and directing crystallization with respect to choice and molar ratio of peptide to PTPase domain.

Alternatively, for binding studies or identification of a potential ligand could be obtained by screening a random peptide library produced by recombinant bacteriophage for example, [Scott and Smith, *Science,* 249:386–390 (1990); Cwirla et al., *Proc. Natl. Acad. Sci.,* 87:6378–6382 (1990); Devlin et al., *Science,* 249:404–406 (1990)] or a chemical library. A ligand selected in this manner could then be systematically modified by computer modeling programs until one or more promising potential ligands are identified. Such analysis has been shown to be effective in the development of HIV protease inhibitors [Lam et al., *Science* 263:380–384 (1994); Wlodawer et al., *Ann. Rev. Biochem.* 62:543–585 (1993); Appelt, Perspectives in Drug Discovery and Design 1:23–48 (1993); Erickson, Perspectives in Drug Discovery and Design 1: 109–128 (1993)].

Such computer modeling allows the selection of a finite number of rational chemical modifications, as opposed to the countless number of essentially random chemical modifications that could be made, and of which any one might lead to a useful drug. Each chemical modification requires additional chemical steps, which while being reasonable for the synthesis of a finite number of compounds, quickly becomes overwhelming if all possible modifications needed to be synthesized. Thus, through the use of the three-dimensional structures disclosed herein, and computer modeling, a large number of these compounds can be rapidly screened on the computer monitor screen, and a few likely candidates can be determined without the laborious synthesis of untold numbers of compounds.

Once a potential ligand is identified it can be either selected from a library of chemicals as are commercially available from most large chemical companies including Merck, Glaxo Welcome, Bristol Meyers Squib, Monsanto/Searle, Eli Lilly, Novartis and Pharmacia UpJohn, or alternatively the potential ligand may be synthesized de novo. As mentioned above, the de novo synthesis of one or even a relatively small group of specific compounds is reasonable in the art of drug design. The ligand can be placed into any standard binding assay exemplified below to test its effect on any particular CD45 or LAR function.

Preferably the crystal effectively diffracts X-rays allowing the determination of the atomic coordinates of the protein-ligand complex to a resolution of at least about 3 Å and the three-dimensional structure of the supplemental crystal can be determined by molecular replacement analysis. As described above, molecular replacement involves using a known three-dimensional structure as a search model to determine the structure of a closely related molecule or protein-ligand complex in a new crystal form. The measured X-ray diffraction properties of the new crystal are compared with the search model structure to compute the position and orientation of the protein in the new crystal. Computer programs that can be used include: X-PLOR and AMORE [J. Navaza, Acta Crystallographics ASO, 157–163 (1994)]. Once the position and orientation are known an electron density map can be calculated using the search model to provide X-ray phases. Thereafter, the electron density is inspected for structural differences and the search model is modified to conform to the new structure. The methods for structure determination are described in the examples which follow. Other computer programs that can be used to solve the structures of such CD45 or LAR crystals include QUANTA, CHARMM; INSIGHT; SYBYL; MACROMODE; and ICM.

For the first time, the present invention also permits the use of structure-based or rational drug design techniques to design, select, and synthesize chemical entities, including inhibitory compounds that are capable of binding to CD45, LAR, CD45-chimeric protein complexes, LAR-chimeric protein complexes or any portion thereof.

One particularly useful drug design technique enabled by this invention is iterative drug design. Iterative drug design is a method for optimizing associations between a protein and a compound by determining and evaluating the three-dimensional structures of successive sets of protein/compound complexes.

Those of skill in the art will realize that association of natural ligands or substrates with the binding pockets of their corresponding receptors or enzymes is the basis of many biological mechanisms of action. The term "binding pocket", as used herein, refers to a region of a molecule or molecular complex, that, as a result of its shape, favorably associates with another chemical entity or compound. Similarly, many drugs exert their biological effects through association with the binding pockets of receptors and enzymes. Such associations may occur with all or any parts of the binding pockets. An understanding of such associations will help lead to the design of drugs having more favorable associations with their target receptor or enzyme, and thus, improved biological effects.

The term "associating with" refers to a condition of proximity between chemical entities or compounds, or portions thereof. The association may be non-covalent—wherein the juxtaposition is energetically favored by hydrogen bonding or van der Waal's or electrostatic interactions—or it may be covalent.

In iterative drug design, crystals of a series of protein/compound complexes are obtained and then the three-dimensional structure of each complex is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affect the protein/compound associations, these associations may be optimized.

In some cases, iterative drug design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex. Advantageously, the CD45, LAR, CD45-chimeric protein complexes, LAR-chimeric protein complexes or any portions thereof, of these peptide crystals, may be soaked in the presence of a compound or compounds, to provide CD45/polypeptide, LAR/polypeptide, CD45-chimeric protein complexes/polypeptide, LAR-chimeric protein compound/polypeptide crystal complexes.

As used herein, the term "soaked" refers to a process in which the crystal is transferred to a solution containing the compound of interest.

In another embodiment of this invention is provided a method for preparing the compositions of the invention comprising the steps described in the methods section and exemplified in Examples 1 to 8.

The present invention provides for structure coordinates of the crystal complexes and can also be used to aid in obtaining structural information about another crystallized molecule or molecular complex. This may be achieved by any of a number of well-known techniques, including molecular replacement.

Therefore, in another embodiment this invention provides a method of utilizing molecular replacement to obtain structural information about a crystallized molecule or molecular complex whose structure is unknown comprising the steps of:

a) generating an X-ray diffraction pattern from said crystallized molecule or molecular complex; and, b) applying at least a portion of the structure coordinates to the X-ray diffraction pattern to generate a three-dimensional electron density map of the molecule or molecular complex whose structure is unknown.

As used herein, "portion" refers to the use of the least number of structure co-ordinates to the X-ray diffraction pattern for generating a three-dimensional electron density map of the molecule or molecular complex whose structure is unknown.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of the crystal complexes of the present invention within the unit cell of the crystal of the unknown molecule or molecular complex, for example other PTPases, so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in *Meth. Enzymol.*, 115, pp. 55–77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of the crystal complex of the invention can be solved by this method.

In a preferred embodiment, the method of molecular replacement is utilized to obtain structural information about a molecule or molecular complex, wherein the complex comprises a CD45, CD45/LAR chimeric protein and the like. Preferably the CD45 or LAR-like polypeptide belongs to the family of PTPases or homologues thereof.

The structure coordinates are also particularly useful to solve the structure of crystals co-complexed with a variety of chemical entities. This approach enables the determination of the optimal sites for interaction between chemical entities, including interaction of candidate molecules that interact with the molecules derived in the present invention. For example, high resolution X-ray diffraction data collected from crystals exposed to different types of solvent allows the determination of where each type of solvent molecule resides. Small molecules that bind tightly to those sites can then be designed and synthesized and tested for their biological activity.

In another preferred embodiment, once the three-dimensional structure of a crystal comprising, for example, a CD45 complex, is determined, (e.g., see the coordinates in FIGS. 4A through 4D) a potential compound that binds to CD45, can be examined through the use of computer modeling using a docking program such as GRAM, DOCK, or AUTODOCK (Dunbrack et al., 1997), to identify potential interactions. This procedure can include computer fitting of potential compounds to, for example, CD45 complex, to ascertain how well the shape and the chemical structure of the potential molecule will bind, e.g., to act as a stabilizer. [Bugg et al., Scientific American, December:92–98 (1993); West et al., TIPS, 16:67–74 (1995)]. Computer programs can also be employed to estimate the attraction, repulsion, and steric hindrance of two binding partners. Generally the tighter the fit, the lower the steric hindrances, and the greater the attractive forces, the more potent the potential modulator since these properties are consistent with a tighter binding constant. Furthermore, the more specificity in the design of a potential drug the more likely that the drug will not interact as well with other proteins. This will minimize potential side-effects due to unwanted interactions with other proteins.

Initially CD45 or LAR mutants, for example, can be systematically modified by computer modeling programs until one or more promising mutants are identified. In addition systematic modification of selected mutants can then be systematically modified by computer modeling programs until one or more potential mutants are identified. Using the crystallization methods described infra and detailed in the examples which follow, crystals of the mutant molecules can be obtained.

Alternatively a potential binding compound can be obtained by initially screening a random peptide library produced by recombinant bacteriophage for example, [Scott and Smith, *Science*, 249:386–390 (1990); Cwirla et al., *Proc. Natl. Acad. Sci.*, 87:6378–6382 (1990); Devlin et al., *Science*, 249:404–406 (1990)]. A peptide selected in this manner would then be systematically modified by computer modeling programs as described above. Through the use of the three-dimensional structure disclosed herein and computer modeling, a large number of these compounds can be rapidly screened on the computer monitor screen, and a few likely candidates can be determined without the laborious synthesis of untold numbers of compounds.

Once a potential binding molecule is identified it can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively the potential compound may be synthesized de novo. The de novo synthesis of one or even a relatively small group of specific compounds is reasonable in the art of drug design. The potential binding molecule can be placed into a standard binding assay with CD45, LAR, mutants of CD45 or LAR, chimeric CD45/LAR molecules and/or fragments thereof which contain the binding domains of these proteins involved in their protein-protein interaction. The CD45 fragments and LAR fragments, chimeric CD45/LAR, mutants and the like can be synthesized by either standard peptide synthesis, or generated through recombinant DNA technology or classical proteolysis. Alternatively the corresponding full-length proteins may be used in these assays.

In a particular embodiment, isothermal calorimetry can be used to determine the stability of any of the complexes of the invention, for example, CD45, LAR and the like, in the absence and presence of a potential binding molecule.

In another embodiment, a Biacore machine can be used to determine the binding constant of the complexes in the presence and absence of a potential binding molecule.

When suitable potential modulators are identified, a supplemental crystal can be grown which comprises the complexes of the invention and a potential binding molecule. Preferably the crystal effectively diffracts X-rays for the determination of the atomic coordinates of the protein-ligand complex to a resolution of better than 5.0 Angstroms, more preferably better than 3.0 Angstroms, most preferably better than 2 Angstroms.

The following non-limiting examples are illustrative of the invention. All documents mentioned herein are incorporated herein by reference.

EXAMPLES

Materials and Methods

The following materials and methods were employed in the examples which follow.

CD45 Constructs

Oligonucleotides (from Sigma-Genosys) were designed to amplify by PCR the DNA sequence encoding residues 597 to 1213. The resulting product was subcloned into a modified pRSET vector (Invitrogen) to express an N-terminal 6-histidine tagged protein. To generate an inactive form of CD45, another set of oligos was designed to change Cysteine828 to Serine828 (Stratagene QuikChange Site-directed Mutagenesis kit).

Protein Expression and Purification

CD45 expression constructs were transformed into E. coli strain BL21 (DE3)/pLysS (Novagen). LB cultures were grown at 37° C. to an OD600–0.700 before being transferred to a room temperature shaker. Protein expression was induced by the addition of 0.4 mM IPTG. The cells were harvested after 18 hours, resuspended in 50 mM Tris-HCl (pH 8)/150 mM NaCl and stored at −80° C. When thawed, 1 mM PMSF and 5 mM β-ME was added to the cell suspension. Cells were lysed by sonication; unbroken cells and cell debris were removed by centrifugation. Nucleic acids were precipitated from the lysate by the addition of 0.1% PEI and another round of centrifugation. The cleared lysate was passed through a filter and allowed to mix with a slurry of Nickel-charged metal-chelating Sepharose (Amersham Pharmacia Biotech).

The beads were washed with 20 mM Tris-HCl (pH 8)/200 mM NaCl/5 mM βME (buffer A) and then with buffer A containing 40 mM Imidazole (pH 8). His6-CD45 was eluted from the beads with buffer B containing 200 mM Imidazole (pH 8). 10 mM EDTA was added to the eluate, which was then diluted four-fold by the addition of 20 mM Tris-HCl (pH 8)/5 mM DTT. The protein was loaded onto a Q-Hitrap column (APBiotech) and eluted with a salt gradient from 50 mM to 1M NaCl in a base buffer of 20 mM Tris-HCl (pH 8)/5 mM DTT. Fractions containing His6-CD45 were pooled, concentrated and passed over a PD10 desalting column (APBiotech) equilibrated with 20 mM Tris-HCl (pH 8)/200 mM NaCl/10 mM DTT. The purified protein was concentrated to 12 mg ml−1 for crystallization trials.

Crystallization

Crystals were grown at room temperature by the method of hanging drop vapor diffusion. 2 μL of protein was mixed with 2 μl of reservoir solution on a siliconized glass cover slip; the cover slip was then inverted and placed over the reservoir. CD45 crystallized over a wide pH range, with various salts, and over a range of salt, PEG4K and glycerol concentrations. Wild-type CD45 crystals were obtained with reservoir solutions containing 100 mM Hepes (pH 7)/200 mM Ammonium Sulfate/10 mM DTT and 12–18% PEG4K. Mutant CD45 was crystallized with reservoir solutions containing 100 mM Sodium Acetate (pH 5)/100 mM Magnesium Sulfate/10 mM DTT/20% glycerol and 12–18% PEG4K. Mutant CD45 and pTyr complex crystals were grown in solutions containing 100 mM Sodium Acetate (pH 5)/10 mM DTT/20% glycerol and 12–18% PEG4K/10 mM pTyr.

All crystallization trials use standard methods of micro vapor diffusion. Initial experiments with all new proteins include a series of screening trials based on commercial and in-house factorial combinations of various additives, salts, and precipitants. Since most proposed new trials are with proteins that closely resemble those for which at least some useable conditions have already been determined (mutants with single or small numbers of amino acid changes), screens clustered around these most successful conditions for either LAR or CD45, are conducted. In the case of CD45, based on the knowledge obtained during previous crystallization trials, modifications were made in the exact protein expressed, i.e. including different N- and/or C-termini leading to improvements in crystal quality. Refining conditions for these native protein constructs as well as all new variants of both proteins generated as described above will include standard changes such as, slowing the speed of crystal growth and varying additives, including phosphate analogues. For co-crystallization with phosphopeptides the ratios and concentrations of the two components are adjusted and varied in attempts to obtain the best quality crystals. As mentioned above, the crystallization of similar complexes has been achieved for other PTPases.

Generation of Mutant LAR and CD45 Proteins and LARCD45 Chimeras by Site-Directed Mutagenesis Site-directed mutants are generated by a sequential PCR-method as described previously (Maeda et al, Nature 1994). In the first step, a short (up to several hundred bp) segment of DNA centering at the nucleotide to be mutated is amplified in two separate pieces using a 5' (+) primer and a mutagenic (−) primer; and a mutagenic (+) primer and a 3' (−) primer. In the second step, the two PCR products are mixed and amplified using the 5' (+) primer and the 3' (−) primer. The PCR product from the second step is subcloned, sequenced, and used to replace the relevant segment of a PTP expression plasmid.

Phosphatase Assay

Catalytic activity vs. peptide substrates is determined for new protein constructs. Synthetic peptide substrates are labeled at their unique tyrosine residue using [γ-32P]ATP (125 Ci/mmol) and Src or Lck tyrosine kinase as described previously (Tsai, et al. JBC 1991). The phosphatase assay mixture (50 μl) contained 60 mM Tris/HCl (pH 7.2), 5 mM EDTA, 10 mM DTT, 50 mM NaCl, 50 mg/ml BSA, 50 nCi of 32P-labelled substrate, and appropriately diluted PTPase protein. After incubation at 37° C. for appropriate time, the reactions are terminated by the addition of 0.75 ml of acidic charcoal mixture (0.9 M HCl, 90 mM sodium pyrophosphate, 2 mM NaH2PO4, and 4% (v/v) Norit A). After centrifugation in a microfuge, the amount of radioactivity in 0.4 ml of supernatant will be measured.

Data Collection and Processing

With improved crystals of LAR-D1D2 and CD45-D1D2 we are able to screen crystals and collect initial data sets on our home x-ray sources. We have demonstrated the collection of complete high resolution data sets from LAR-D1D2 crystals using a synchrotron x-ray source. The same process is used with the existing CD45 crystals as described. Synchrotron radiation for all final high resolution data collection as is now common practice is used. Data is collected from flash frozen crystals and the use and variation of different cryogenic solvents for the preservation of crystal integrity is another standard means for improving diffraction quality. Data is processed with standard software packages depending on the detector and radiation source.

Strategy for Structure Determination

Due to the highly conserved nature of the structure of individual PTPase domains determined to date and the availability of our existing LAR-D1D2 structure, methods of molecular replacement to obtain initial phasing information are utilized. It is still possible that in some cases a significant deviation in domain structure might result in a failure to use these methods, in which case the standard methods of heavy atom isomorphous replacement are used as well. In this case specific modifications to the protein as well as potentially to substrates can be combined with standard crystal soaking techniques to yield the required substitutions. Patterson and difference Fourier methods are used for location of heavy atom sites.

Once initial phases are obtained model building and structure refinement is carried out. This consists of an interactive process using the positional and simulated annealing options of the program XPLOR and aided by high resolution graphical display programs, O and Main, whereby amino acid residues, either individual ones or secondary structure elements, are fitted to segments of well defined electron density, their positions refined to take into account steric and chemical constraints and new electron density calculated with this information included. Models are visually adjusted and positions refined at increasing resolution to the limit of the data. Solvent molecules are added and accuracy of the structure analyzed using standard crystallographic software.

Initially, diffraction patterns have been collected from rod shaped and hexagonal CD45-D1D2 crystals. Both capillary mounted and cryogenically frozen crystals diffracted weakly at our home X-ray source. Typically, diffraction patterns up to 6 Å could be obtained from a 2 hour exposure for a 1° oscillation. However, a complete diffraction data set was collected from a small hexagonal crystal at the Brookhaven National Laboratory (BNL) Synchrotron facility. At this source diffraction intensities could be clearly observed up to a resolution of 4 Å. This data set is over 98% complete and the Rsymm of the data between 50 Å and 6 Å is approximately 9%. However, because of the weak intensity beyond 6 Å resolution, the Rsymm was higher than 20% in the 6 Å–4 Å resolution shell. These data were processed using DENZO and it was determined that the crystal belongs to an hexagonal space group with the unit cell dimensions of a=165 Å, b=165 Å and c=144 Å. Later, diffraction patterns have been collected from thin plate-like crystals grown at pH 5.0. There crystals diffracted up to 3.5 Å at our home x-ray source and diffracted up to 3.2 Å at Advanced Photon Source (APS) Synchrotron facility. This data set and the Rsymm of the data between 50 Å and 3.2 Å is approximately 10%. These data (originally processed as monoclinic) were reprocessed using DENZO in the lower symmetry triclinic space group (P1) with unit cell dimensions of a=86.0 Å, b=59.7 Å, c=160.0 Å, $\alpha=90°$, $\beta=100°$ and $\gamma=90°$. The crystals of the mutant CD45-D1D2/pTyr complex diffracted up to 3.0 Å at the Cornell High Energy Synchrotron Source (CHESS) facility. The Rsymm was approximately 10% overall with 91% completeness. These crystals belong to a triclinic space group with the unit cell dimension of a=86 Å, b=60 Å, c=161 Å, $\alpha=90°$, $\beta=100°$ and $\gamma=90°$.

(ii) LAR-D1D2 Crystals

Diffraction data have been collected from the thin-plate like crystals and the hexagonal crystals of LAR-D1D2, both using flash frozen crystals under cryogenic conditions. The small sized hexagonal crystals diffracted only up to 7 Å at our laboratory. Well ordered diffraction intensities from the thin plate crystal, on the other hand, were observed up to the resolution of 3 Å in the laboratory. A diffraction data set has been collected from a thin plate like crystal at the F1 line of Cornell High Energy Synchrotron Source (CHESS). The crystal diffracted up to a resolution of 2.0 Å. This data set is 90.7% complete and after processing the Rsymm of the data between 20 Å and 2.0 Å is 6.4%. The crystal belongs to space group P2(1) with the unit cell dimensions of a=66.92 Å, b=62.73 Å and c=161.59 Å.

Example 1

Structure of PTPase Domains of CD45

The crystallization data obtained show that the catalytic domain (D1) of CD45 exhibits a common three-dimensional structure. The active site itself appears to be in a partially "closed" conformation as defined by comparison to structures of peptide and phosphate analogues complexed with PTP1B and the Yersinia PTPase. The presence of a sulfate ion or phosphotyrosine molecule from the crystallization solution within the active site pocket seems to mimic the position of a substrate phosphate group and is hydrogen bonded to the serine residues within the signature sequence. In addition, the WPD loop is shifted toward the binding site and is in a position that would be comparable to that seen in an intermediate of the catalytic reaction.

The overall domain architecture of the membrane distal (D2) domain of CD45 also maintains the conserved PTPase fold. There has been only one other D2 domain structure published, that of the closely related RPTPase, LAR, and in this case the active site structure of D2 was nearly superimposable with that of its respective D1 domain. Only small localized changes, resulting from the substitution of two key residues, were identified as critical for blocking catalytic activity. For most RPTPases, the respective D1 and D2 domains share overall primary sequence homology of 70%. However, in the case of CD45, there is a much greater degree of substitution at the active site region and there are potentially important deviations within the signature motif itself. The combined effects of these subtle changes results in an "open" yet blocked binding pocket which would be expected to display its own substrate specificities.

Example 2

CD45 Specific Structural Features

Figure 3:
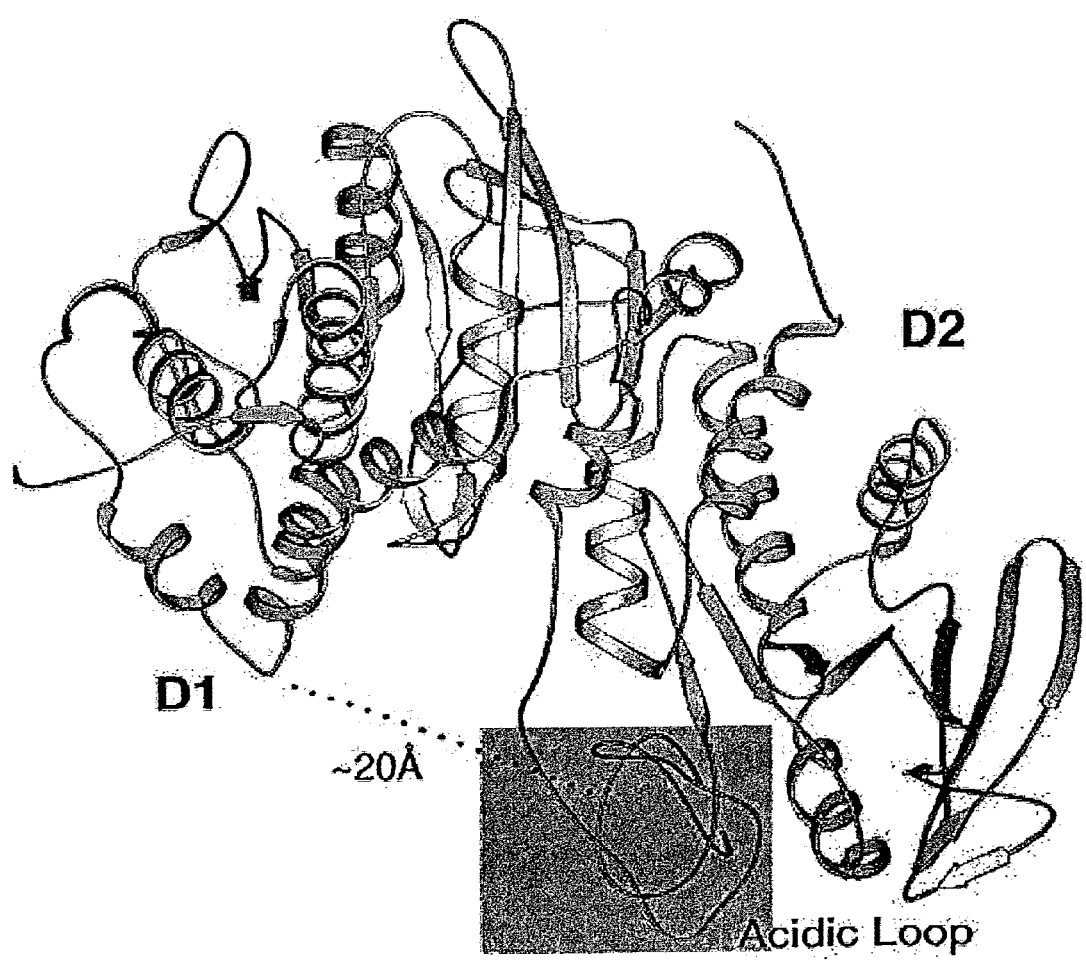
FIG. 3 is a schematic representation depicting the relative position of the acidic loop in the D2 domain crystal structure, the closest intramolecular contact is about 20 Å

One other important feature that is specific for CD45 can be seen in the sequence comparison of the PTPase domains. There is a 19-residue insertion within the D2 domain that falls at the position corresponding to the β1 to β2 loop in the LAR D2 domain. This sequence is highly acidic (FIG. 3) and by secondary structure prediction could not be characterized as any regular structure element. The relative orientation of this loop within the context of the two phosphatase domains is first seen in this structure.

Finally, this structure gives one clear picture of the intramolecular domain orientations for the cytoplasmic portion of CD45. There is an extended contact surface comprising portions of the last helices of D1 and the beta sheet loops of D2. This interaction is stabilized by overall surface complementarity of the two domains comprising van der Waal's and hydrogen bonding interactions. The short linker segment is involved in hydrogen bonds to both domains utilizing backbone atoms as well as side chains of conserved residues. The individual molecules in the crystallographic asymmetric unit each adopt a slightly different orientation while maintaining the same bonding interactions.

The results, described herein, show that the intramolecular domain orientation seen here would not be consistent with the model of the symmetrical dimerization of CD45 that has been postulated previously. As with its close relative LAR, the presence of the D2 domain would preclude the interlocking insertion of the N-terminal "wedge" of each receptor into the active site pocket of the other molecule. Instead it appears that the positioning of D2 against the back side of the D1 active site might account for the influence of the second domain on the activity of D1.

One intermolecular contact seen in our crystal form does involve the N-terminal region of one molecule and the equivalent of the "WPD" loop in D2 of an adjacent molecule. There appears to be a crystal packing interaction between Lys618 in D1 and Gln1104 from a neighboring D2 domain which may resemble a possible D1–D2 interaction. However, observation of this interaction appears to be only a fortuitous packing artifact. It does not involve the same spatial relationship of the "wedge" and active site pocket, nor does it utilize the specific residues, that had been previously implicated in the proposed dimer interaction.

Example 3

LAR-D1D2 Structure Determination

To complete the LAR-D1D2 structure determination, the amino terminus of the protein is extended to include the proline rich segment just upstream of the current start site. This segment is important for several reasons—this segment has slightly different conformations from other PTPase structures and is also involved in potentially biologically relevant protein-protein interactions. The data show that the structure of the amino terminus begins as part of an alpha helix, however the density for one molecule is disordered in this region. Extending this segment to include what can be the rest of this helical region can improve the existing structure and provide reliable information about the exact conformation of this region of the protein. The crystal structure includes the membrane proximal residues up to and including Leu1311.

Mutational studies also identified a number of temperature sensitive mutations within the amino terminal half of the first PTPase domain (clustered between residues 1329–1407). In particular a change from tyrosine to phenylalanine at position 1379 yielded a protein that demonstrated enhanced structural stability and a revertant second-site mutation, C1446-Y, was identified that suppressed several other mutants and appeared to contribute to enhanced protein folding and production. These mutations are incorporated in the extended construct.

Example 4

Catalytic Activity for the Individual PTPase Domains

Comparing the structures of the two domains can aid in the understanding of the potential function of the D2 domain. It is not known whether this domain has the structural components necessary to function as an active phosphatase itself. From the highly homologous nature of the sequences within these two regions of LAR, it is expected that the three dimensional structures are very similar and yet biochemical data have uniformly indicated that this domain does not have catalytic activity. From the present structure it appears that these two active site regions are generally well conserved structurally. Careful analysis of this structure, will allow the determination of which key positions can be changed in order to bring a currently dormant phosphatase domain to a potentially active conformation. The amino acid candidates for mutation are within the P-loop where hydrophobic residues are critical for shaping the cleft for phosphate moiety interaction and the order and orientation of charged residues is required for optimal binding to residues of peptide substrates amino terminal to the pTyr position.

The second set of mutations are in the WPD loop or the residues responsible for stabilizing its orientation with respect to the oxyanion binding pocket, as the ability of this segment to shift into hydrogen bonding distance is critical for activity. It is also possible that the existing structure will reveal other structural regions that might be responsible for repressing the activity of the wild type D2 domain and therefore the alteration of residues in any such identified regions are to be examined.

Regarding the regulation of the activity of individual domains or the total cytoplasmic region is addressed by specific targets within another area of the LAR D1D2 protein, the linker segment between the two domains. Subtle changes in sequence in this region might alter the orientation of two domains and thereby affect the active sites. This short region, essentially residues 1585 to 1590, is well ordered and seems to form a short beta strand in the current structure. In keeping with this, certain residues do appear to be in direct hydrogen bonding geometry with respect to an alpha helical structure of D2. Modifying one or more of these residues will generate the desired small local effects and this could then be directly examined with respect to other catalytically important areas of the protein. The sequence of this linker segment is well conserved between LAR and CD45 however, two somewhat complementary changes have occurred, a Lys to Asp and Ser to Arg, within the critical contact points between elements at the junction of the domains. These targets are used for CD45 mutagenesis.

Example 5

D2 "Active Site" Mutant Studies with CD45

For the D2 "active site" mutant studies with CD45 the same general scheme for designing specific targets will apply. There is less direct sequence conservation between D1 and D2 for CD45 than for LAR and therefore it is expected that these differences will manifest as more distinct differences in the structure. Structure determination of the CD45 allows for identifying certain specific residues to mutate.

An additional area that is modified to improve crystal quality and as a means to understand the functional significance of this region itself, is a single 19 residue long insertion within the D2 sequence (at residues 964–984) that is not present in either the D1 domain of CD45 or the D1 or D2 domains of most other PTPases. Interestingly, to date only D1 domains and our D1D2 domain of LAR have yielded diffraction quality crystals and since this is a region of significant difference between all these proteins it suggests that perhaps omission of the region might help to stabilize the protein for structural studies. Other sites include the carboxy terminal stretch of D2 which has been shown to inhibit the activity of D1.

Example 6

Chimeric PTPase Domains of LAR and CD45

Chimeric molecules comprising the swapped individual PTPase domains of LAR and CD45 are generated with slight adjustments in the exact break between each parent protein.

Using site directed mutations ensures optimum stability of each domain. Existing constructs are used to generate non-GST fusion proteins for co-crystallization trials.

These mutants are used for a concerted set of crystallization and structure solution experiments. Individual protein constructs are examined alone and in the presence of various ligands so that the effects of these substitutions on the ability to bind substrates and the associated structural changes can be seen. Co-crystallization with phosphopeptide substrates is an excellent way to assess binding capabilities of both D1 and D2 domains. If the second PTPase domain is important as a kind of silent phosphotyrosine binding site then crystallization and structure determination is a very direct way simultaneously to observe and to characterize interactions at both sites. Any interaction between the two binding sites can be described as well. Recently the identification of a second low affinity phospho-substrate binding site was achieved by this same strategy for another PTPase.

Example 7

Binding Studies

For binding studies several different peptides are chosen based on the available biochemical data. LAR has been shown to be directly involved in the inactivation of insulin receptor and EGF receptor and therefore the pTyr sites in these proteins are excellent candidates. Similarly, the observation that CD3ζ chain is a specific ligand for CD45 is another substrate used in the binding studies. The CD3ζ chain has three sets of pTyr residues so that a peptide centered around each of these sites can be used. Due to the observations that CD45 associates with both PTKases Lck and Fyn in vivo, decapeptides composed of sequences flanking the terminal phosphotyrosine that is defined as the negative regulatory site of each are used as well.

Due to the very prominent role of Src itself in signaling pathways and the cellular evidence that both LAR and Src are localized within the focal adhesion areas, use of two Src peptides as substrates, one flanking the critical pTyr in the kinase domain and one based on the inhibitory tail peptide containing pTry527 is desirable. The peptides used in these studies are obtained from commercial sources and their purity checked by HPLC analysis.

The protein constructs used for co-crystallization include the critical Cys to Ser mutation in one or both domains as needed to prevent substrate cleavage. Solution binding to peptides used are also monitored by affinity measurements, as described below, as a means of correlating with and directing our crystallization trials with respect to choice and molar ratio of peptide to PTPase domain.

Example 8

Determination of Phospho-Peptide Structure within Active Sites

Structure Determination

Initially, the structure of C828S mutant with sulfate ion was determined. The structure was determined by molecular replacement using an unaltered model of D2 domains of RPTP LAR as a search model with the program AMoRe. An initial search revealed four unambiguous positions of phosphatase domains. After rigid-body refinement, the identity of the PTP domains was determined based on the locations of the N- and C-termini, and amino acid sequence was changed to reflect the CD45 molecule. Several iterative cycles of refinement were performed using minimization and anisotropic temperature factor refinement options of CNS followed by manual rebuilding. Noncrystallographic symmetry restraints were used through out refinement. Composite omit map (CNS) has been used for most of refinement steps.

Refined model of C828S mutant/sulfate was used for determining other crystal structures. Sel-Met data set was collected with an intention of confirming the refined structure. Because of the anisomorphism, the Sel-Met data could not be used for phase determination. Instead, an Fo-Fc map was generated using C828S mutant model and Sel-Met data. The map showed strong (over 3.5 σ) corresponding densities at most of the Met positions validating the structure. For structure determination of Sel-Met C828S mutant/phosphopeptide complex, refined model of Sel-Met C828S mutant was used to generate a Fo-Fc map. The initial map revealed clear peptide density at each D1 active site, and four residues including phosphotyrosine could be positioned based on the density. Refinement procedures include minimization and individual temperature factor refinement. The current model includes 604 residues (601–1205) excluding the disordered acidic loop part of D2. The final refinement statistics are shown in Table 1.

For the structure determination of the hexagonal crystal, the refined model of the C828S mutant was used for molecular replacement. The CD45 D1 and D2 domains were used both together and separately for the search. In both cases, the highest solutions turned out to be the same as in monoclinic crystals. The positioned model has been further refined using rigid-body to be the exact same positions. The relative orientation of the D1 and D2 domains are the refinement of CNS. The final refinement statistics are summarized in Table 1.

TABLE 1

Crystallographic Data and Refinement Statistics

Crystallographic Data

| | |
|---|---|
| Space group | P2(1) |
| Cell parameters | a = 85Å, b = 58Å, c = 159Å, α = 90°, β = 99°, γ = 90° |
| Z | 4 |
| X-ray source | X11, BNL |
| Resolution | 30–2.9 Å |
| Observations (n) | 85,661 |
| Unique reflections (complete) | 32,064 (92.8%) |
| $R_{sym}$ | 0.079 |

Current refinement statistics

| | |
|---|---|
| Resolution | 30–2.9 Å |
| Protein atoms (n) | 9,531 |
| Water molecules | 1 |
| $R_{cryst}$ (work/free) | 0.264/0.308 |
| Rmsd bond lengths | 0.010 Å |
| Rmsd bond angles | 1.60° |

Two different crystal forms of CD45 D1D2 protein have been obtained. Monoclinic crystals have been obtained using of the substrate-trapping mutant (C828S) of CD45 D1D2 (597–1213) protein. The recombinant fragment was expressed with cleavable N-terminal 6-histidine tag using T7 expression system. First, the protein was purified using a Ni-affinity column followed by cleaving of the N-terminal 6His. The protein was further purified using anion exchange column. After desalting, the protein was concentrated to the final concentration of 10 mg/ml. The expression of Sel-Met substituted protein was performed, and the purification scheme, as described above, was followed. The C828S crystals were grown by vapor diffusion in hanging drops in 100 mM Sodium Acetate (pH 5.0), 10–13% (w/v) PEG 4000, 10 mM DTT, and 25% glycerol with various additives such as ammonium sulfate, phosphotyrosine and phosphotyrosine-containing peptides.

Hexagonal crystals have been grown using wild type CD45 D1D2 (603–1203) with non-cleavable C-terminal 6 His tag. Expression and purification methods follow those of the mutant protein except cleaving of 6His tag. The hexagonal crystals were grown by vapor diffusion in hanging drops in 100 mM MOPS/NaOH (pH 6.5), 13–15% (w/v) PEG 8000, 0.5M Ammonium sulfate, 10 mM DTT, and 15% glycerol.

Crystals were flash-frozen with the crystallization solution. Diffraction data were collected at various synchrotron sources including the F1 station of the Cornell High Energy Synchrotron Source (CHESS), the SBC-CAT of Advanced Photon Source in Argon National Laboratory, and the X11 station of Brookhaven National Laboratory. Images were processed with DENZO, and data were scaled and processed with SCALEPACK. Best quality data have been collected from monoclinic crystals of Sel-Met C828S mutant with phosphotyrosine-containing peptides. For monoclinic crystal form, two molecules were found in an asymmetric unit, and for hexagonal crystals one molecule (see Table 1).

Here we report crystal structures of the native CD45 cytoplasmic region alone as well as with a substrate bound at its active site. In these structures, CD45 exists as a monomer with both D1 and D2 "active site" regions clearly unobstructed by the relative orientation of the rest of the protein chain. The observed intramolecular domain orientation is such that the previously proposed model for dimer formation utilizing the N-terminal helix-wedge-helix segment of D1 would be impossible to accommodate because of significant steric hindrance from the D2 domain position. With this structure the relationship between D1 and D2 in CD45 can be visualized and also compare this orientation to that of the only other tandem RPTP whose structure has been determined. For the first time, questions regarding the differences in D1 and D2 activity not only within a particular molecule but also with respect to the activity of another protein with a very closely related D1 domain, but very different biological roles, can be addressed.

Overview of the Structure

A series of cytoplasmic fragments of CD45 protein have been used to optimize the domain boundaries for crystallization (Table 1). The relative orientation of the two domains is also very similar to that of LAR D1D2 protein. LAR is a RPTP present in non blood cell types, and the crystal structure of the tandem phosphatase domains has been previously reported by this group. In the current structure, the two PTP domains are connected by a four-residue linker and the inter-domain orientation is stabilized by extensive inter-domain interactions. The overall structures of CD45 and previously reported LAR cytoplasmic regions are very close reflecting the high homology of amino acid sequence.

Domain Structure of D1 and D2

Figure 6:
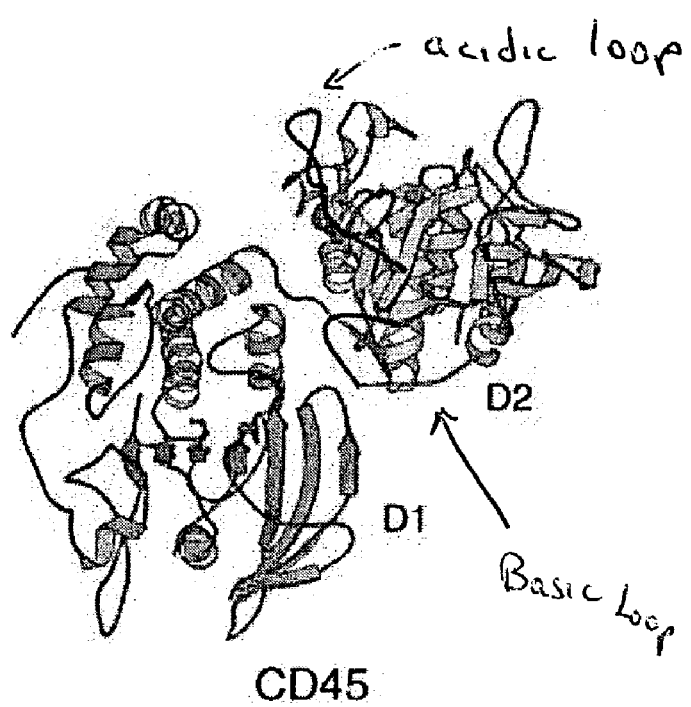
FIG. 6 is a schematic representation showing the overall two domain structure as well as the position of the acidic and the basic loops relative to the active site of D1.

Both D1 and D2 PTP domains have the same tertiary fold, which consists of a highly twisted nine-stranded mixed β-sheet flanked by four α-helices on one side and two on the other. The CD45 D2 domain has similar architectures as that of D2 domain of RPTP LAR including the protruding loop between the helices α1' and α2'. The major differences between the D2 domains of CD45 and LAR are the loops between the strands β1 and β2, and between α3 and β12. There is a 19 amino acid, mostly acidic, insertion in the loop (acidic loop) between the strands β1 and β2 and 8 amino acids insertion in the loop (basic loop) between α3 and β12. In the current structure, the acidic loop is mostly disordered, presumably forming a flexible loop. The loop between α3 and β12 could be refined in one of the two molecules in P2(1) space group, but the temperature factor is quite high (average main chain B-factor is 20 Å higher than the rest of the molecule) reflecting the flexible nature of this loop as shown in FIG. 6. FIG. 6 shows the acidic and the basic loops relative to the active site. Both loops are located at the same side with the D1 active site, and are long enough to be involved with substrate interactions. Since both loops are located at the surface of the molecule and have charged nature, they could easily serve as initial substrate recruiting motifs. Also, from sequence analyses, both loops have many potential post-translational modification motives. The crystal structure shows that they are fully accessible for such modifications. Phosphorylation of Ser residues in the acidic loop by casein kinase II was shown to be important for CD45 functions. Deletion or substitution to Ala of residues in the acidic loop cause diminished T-cell responses. It is not clear how these post-translational modifications may affect the catalytic activity of CD45. Since they are very close to the active site, once phosphorylated, these loops may serve as docking or recruiting sites for incoming substrates.

The Active Site of the D1 and Phosphopeptide Binding

When CD45 was crystallized in the presence of pTyr, there was clear well defined density corresponding to this moiety present in the D1 active site pocket. Within these same crystals, individual solvent molecules could be seen in the respective pocket of the D2 domain. However, they were not ordered in any way to suggest the presence of the phospho-substrate. The positions of the oxygen atoms of the pTyr and that of their corresponding ligands in D1 are similar to the structures of PTP1B, Yersinia PTP, and RPTP alpha. The conserved Arg and Glu residues are positioned surrounding the active site in a manner to generate the required charge distribution and pocket shape to accommodate the pTyr leaving group.

However, what is more surprising or novel is the fact that despite a significant molar excess of this potential small molecule substrate present in the crystallization mix, there is no evidence of its presence in any of the D2 domains in any of the crystal forms obtained. This is true even in the structures that were obtained of CD45 cocrystallized with sulfate or tungstate ions. In the active sites of D1, on the other hand, well-defined extra densities have been visible in all C828S mutant structures. In addition, use of a phosphopeptide in the crystallization mix, clear binding to D1 but not D2 is seen.

Figure 7:
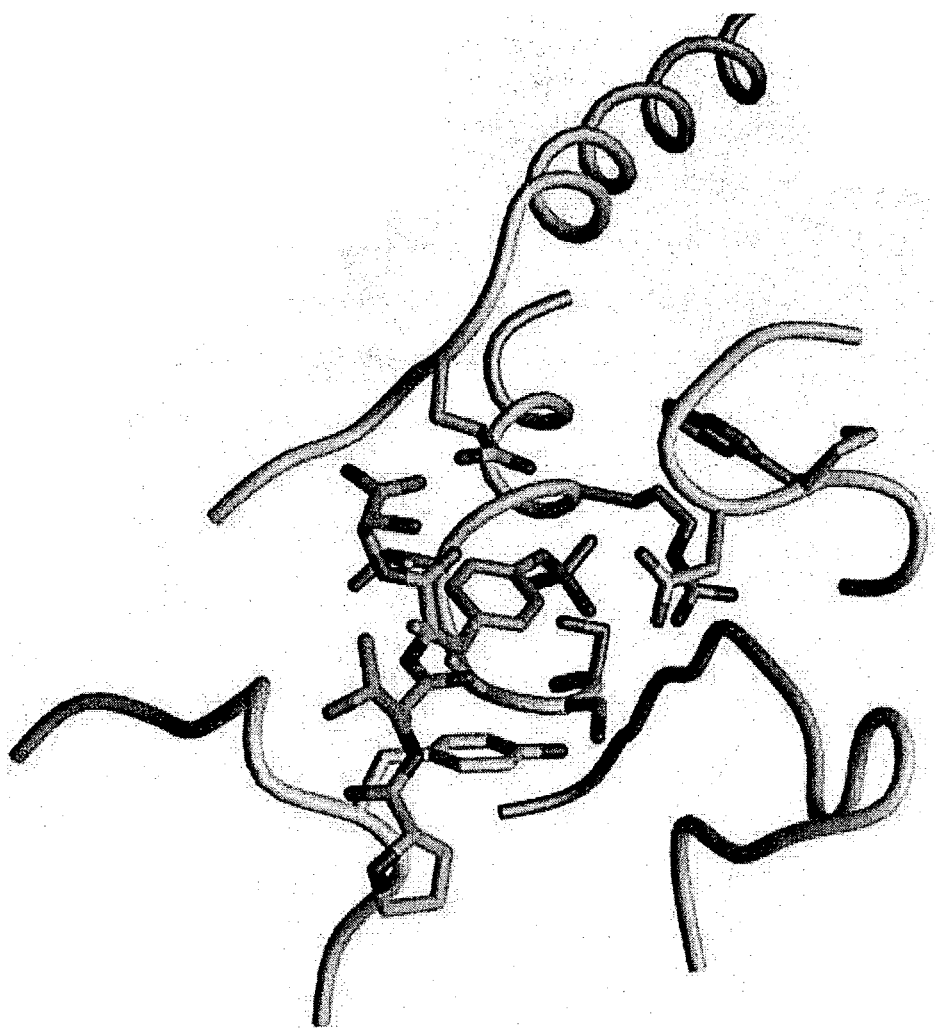
FIG. 7 is a schematic representation showing the structure of CD45 with the phosphotyrosine peptide. The key active site residues from D1 are shown as smooth ribbon diagrams (analogous to FIG. 2 above) and the peptide is shown as a stick representation. The peptide residues shown are, from top to bottom, Pro-Thr-pTyr-Ser.

In the structure of CD45 with the phosphotyrosine peptide (FIG. 7, FIG. 8a, FIG. 8c), densities for the four-peptide residues have been visible from the initial stage of refinement. The presence of the proline in the sequence aided the sequence assignment of the peptide. The position of the phosphotyrosine is the same as that of the CD45 cocrystallized with phosphotyrosine. Extensive hydrogen bonding occurs between the phosphoryl group and the backbone amide group of the active site. Additional hydrogen bonds are observed between the phosphoryl moiety and the side chain amide groups of R834. The tyrosine ring is stabilized by ring stacking effect from the Y658 of pTyr loop. The H797 of the WPD loop is also in a position to make hydrophobic contact with the tyrosine ring of the pTyr. The carbonyl group of the pTyr hydrogen bonds with the side chain of H797, and the side chain of the H797 with the side chain of D796. An additional interaction was observed with the carbonyl group of S (Y+1) and the side chain Q872 of α6. Most interactions observed between the pTyr and active site are similar to those with PTP1B and peptide complexes except the one between the carbonyl of pTyr and the side chain of H797. The H797 residue is substituted with Phenylalanine in PTP1B. Most of active PTPs have His or Phe at this position. Together with Tyr in the pTyr loop, these residues function to interact with tyrosine ring of the pTyr. Having His at this position may strengthen the binding of the pTyr through an added hydrogen bond.

The Active Site of D2

Figure 2:
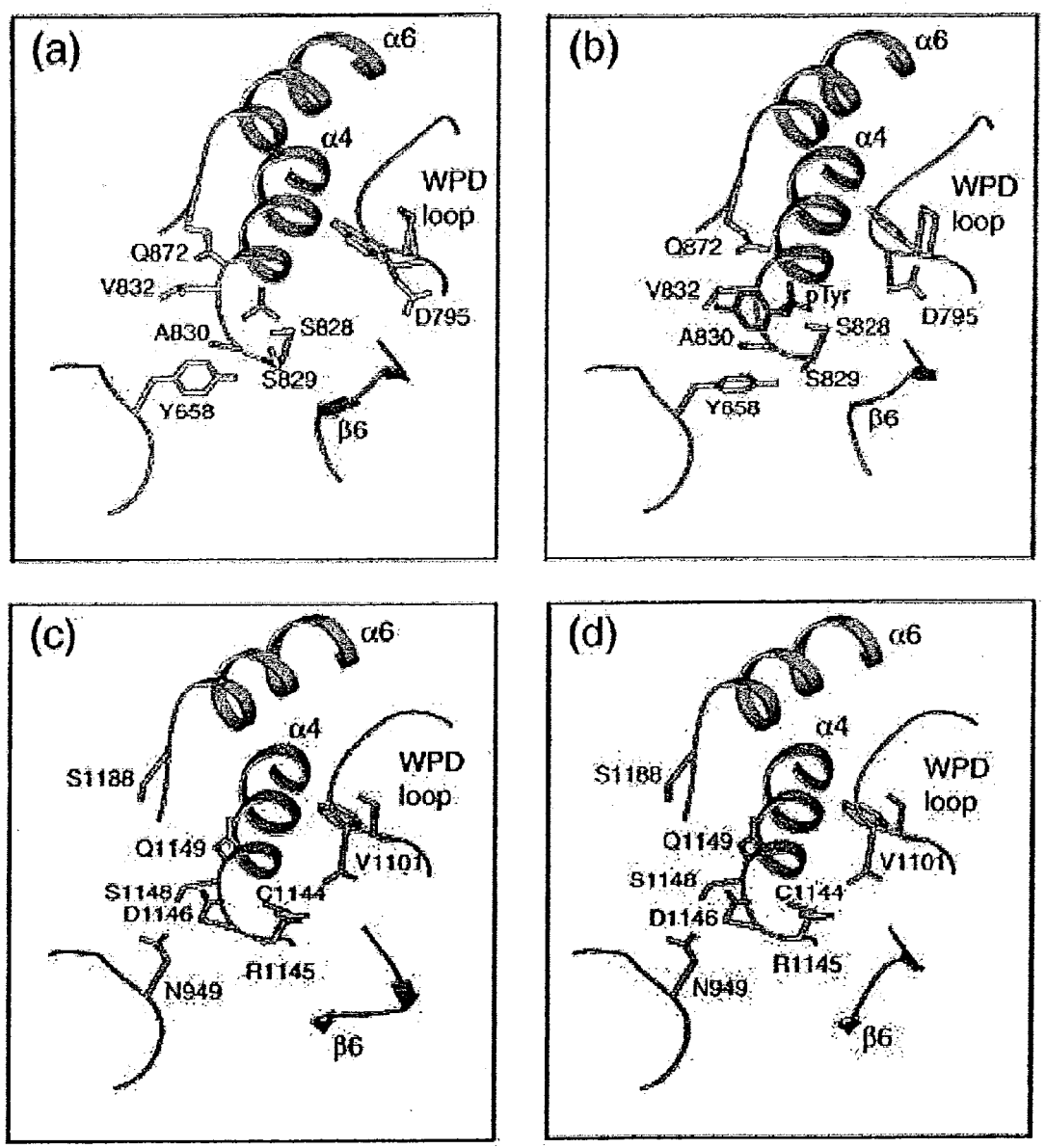
FIG. 2 is a schematic representation depicted as ribbon diagrams of the two crystallographically unique D1 domains, panels (a) and (b), and the two D2's panels (c) and (d). The active site nucleophile position in CD45 D1 is 828. The equivalent position in D2 is a cys, C1144. The two loops, as seen in all PTPases, that flank the PTPase active site, contribute to binding (Km) and activity (Kcat) with respect to phospho-substrates.

In the LAR D1D2 structure, the D2 domain maintains a similar active site topology with that of D1 with only the substitution of two key residues in the surrounding loops. In comparison, in the structure of CD45, the active site of D2 deviates from the signature PTP motif to the extent it can no longer accommodate a phosphoryl group. The substitutions of key residues in the CD45 D2 domain have reduced the number of available ligands for oxygen binding and significantly altered the shape of the "active site" pocket and resulting accessibility of the Cys nucleophile. In other PTP structures and in the CD45 D1 domain, the side chain of the highly conserved R834 makes two hydrogen bonds with the phosphoryl group, and is very important for substrate binding and transition state stabilization. The very critical substitution of this arginine to a glutamine (Q1150 is the equivalent of R834) results in the presence of a shorter side chain that is not able to interact with phosphoryl group in the same manner as R834. In addition, as shown in FIG. 2(d), the bulky side chains of D1146 and Q1149 are protruding toward what would be the phosphoryl group binding site. The Nδ1 of D1146 also hydrogen bonds with a backbone amide group, another potential binding partner of the phosphoryl group. The presence of these negative charges in the potential binding site must repel any incoming phosphoryl group.

From the structure, it is apparent that the substitution of these three residues will abolish any affinity for an incoming phosphoryl group. This can be easily visualized by the surface representation of the active sites with their respective charge distributions (see FIG. 2(c), (d), and FIG. 5). The structure of the loops surrounding the active site is also quite different from that of the D1 active site. The so-called WPD loop shows a partially open conformation, and the invariant Asp, which act as general acid/base in active PTPs is substituted with valine. This substitution will certainly impair catalytic activity. The pTyr-binding loop also shows a quite different conformation in D2. The tyrosine involved in the interactions with tyrosine ring of the pTyr is substituted with Asn. The presence of polar Asn side chain at this position will affect pTyr binding negatively. One of the two conserved Gln in the active site is also changed to Ser in the D2. In the case of yersinia PTP, the Q446 and Q450 are important for catalytic activity. Both Glns position water molecules. The substitution of Q446 to residues with smaller side chain does not have drastic effect on the catalytic activity. Thus, presence of Ser at the equivalent position may not be the main reason for the loss of catalytic activity of CD45 D2 domain.

The specific differences seen in the CD45 D2 structure suggest a distinctly different function than that of any other PTP domain whose structure has been determined to date. Although the overall PTP architecture is well conserved, however, the structural changes seen here seem to preclude both phospho-substrate binding and a catalytic mechanism based on the nucleophilic attack of the conserved Cys residue. Unlike the LAR D2 domain where the overall pocket shape and potential for a similar catalytic mechanism to that of D1 domains is still possible, the CD45 D2 structure strongly suggests that this is not the case for all D2 domains. Comparison of LAR and CD45 demonstrates very strikingly how several different and seemingly small individual sequence changes can actually lead to very dramatic differences in effect on potential function in these two respective protein molecules.

Relative Intramolecular Domain Orientation

As described in Table 1, crystals of sufficient quality for structure solution were obtained in two different space groups. In all of the crystals, the intramolecular orientation of the two domains is very similar. It is particularly noteworthy that while the crystallographic contacts in the crystals of the two different space groups are totally different, the inter-domain orientation is very similar. These results show that the intramolecular orientation reported here truly reflects preferred state of the molecule in the cell. This relative orientation of the D1 and D2 domains of CD45 is very similar to what we observe for LAR. There are significant complementary surfaces between the two domains comprising both H-bonds and van der Waals surfaces (FIG. 5). Some of the specific inter-domain contacts are conserved between CD45 and LAR while others are analogous type interactions. The four-residue linker segment is bound to both D1 and D2 domains in a similar fashion as seen with LAR and varies only slightly in its orientation between the different CD45 crystals.

The relative orientation of the two domains is of particular interest, because it is in direct disagreement with some of the models suggested for the regulation of CD45. Many experiments are performed in an attempt to explain how binding of ligands at the extacellular portion of the CD45 may affect the catalytic mechanism of its cytoplasmic part. A model has been proposed based on the crystal structure of the D1 domain of RPTPα. The D1 domain of RPTPα crystallized as a dimer, and in the crystal each active site was blocked by an N-terminal helix-turn-helix segment (wedge) of an opposing monomer, thus preventing substrate access to the active site. In this model, it was suggested that as in the case of receptor tyrosine kinases (RPTKs), ligand binding would lead to dimerization of the RPTPs, and this dimerization may cause inactivation of RPTPs. This model was also supported by in vivo and biochemical analyses of chimeric CD45/EGF receptor. More complete structure of cytoplasmic regions of another RPTP LAR (leukocyte antigen related), however, showed that the presence of the D2 domain might hinder such dimeric interactions. This led to speculations that the dimeric inactivation mechanism may only apply to some of the RPTPs including RPTP α and CD45.

The structures described herein, however, show that the cytoplasmic region of CD45 does not dimerize even when highly concentrated, and the dimeric interaction observed in the RPTPα D1 structure would be impossible. As in the case of LAR, in CD45, steric hindrance from D2 domain will prevent such dimer formation. A recent study from the same group showed that the extracellular and membrane portion is sufficient for the CD45 dimerization. In this study, CD45 with the smallest extracellular isoform dimerizes with the highest efficiency, resulting in decreased T-cell receptor signaling. Although in vivo studies showed that a mutation in the N-terminal helix-turn-helix has a significant effect on the regulation of CD45, presumably by inhibiting dimerization, the same mutation did not affect the dimerization in this study. These results and our data strongly suggest that the regulation of CD45 cannot be summarized in a simple dimeric inhibition model mediated by an N-terminal wedge.

Example 9

Characterization of the Impact of TCR-ζ ITAM Phosphorylation on its Interaction with CD45

The effect of CD45 is thought to be related to a positive regulation of the src-family kinases p56lck (lck) and p59fyn (fyn), important initiators of downstream signaling.12 Another molecule that has been shown to have a direct association with CD45 is p70zap (ZAP-70), a syk family kinase often found associated with TCR-zeta whose substrate, SLP-76, interacts with phospholipase Cγl (PLC).4,14 It is unclear whether the connection between CD45 and ZAP-70 occurs due to a dephosphorylation of zeta by CD45 which stops ZAP-70 binding or because ZAP-70 is a direct substrate.14 ZAP-70 is also noted for its ability to help double positive thymocytes develop into single positive populations, an important step in thymocyte differentiation.

With the importance of CD45 and ZAP-70, the role of the zeta protein from the TCR gains extra significance. Zeta contains three immune receptor tyrosine-based activation motifs (ITAMs), which each consist of two tyrosine phosphorylation sites and is most commonly seen in its activated phosphorylation state as either a 21 kD or 23 kD molecule.

TCR-ζ is mutated using site-directed mutagenesis to knockout the dual tyrosine residues in one of its three immune receptor tyrosine-based activation motifs (ITAMs). The zeta chains, containing only two wildtype ITAMs, are purified and interacted with mutant CD45 containing a D1 catalytic site cysteine→serine mutation. The resulting complex is run on a gel and immunoblotted to qualitatively determine the specificity of binding. Further mutation experiments are determined by the initial results seen in whole ITAM mutation. The data concerning the interaction between zeta and CD45 are used for crystallization of the complex for structure determination.

Initial constructs involve mutating each of the three ITAMs separately to examine their individual impact. Stratagene's QuikChange Site-Directed Mutagenesis kit is used to mutate the wild-type cytoplasmic domain of zeta using a primer encoding the mutation of an ITAM. A Glutathione S-Transferase (GST) tag is used to allow for purification in later steps. Results from individual ITAMs are extended to include combinations of mutant ITAMs (to establish baseline requirements for interaction) or will move to mutating individual tyrosines in an ITAM to determine the impact that each tyrosine in an ITAM has on the interaction.

Mutant constructs are transformed into Stratagene Epicurian Coli TKB 1 Competent Cells which in its genome has encoded a kinase that is used to phosphorylate zeta. Using this system and immunoblotting, a functional kinase was identified for wild-type zeta by comparing pre- and post-induction states. Protein is collected through the use of GST beads to selectively bind to the GST tag on zeta. The collected zeta is then concentrated to and tested by a Bradford assay.

Mutant CD45 comprising residues 620–1236 and an 851 Cys→Ser D1 active site mutation was constructed using a PRSET vector, Stratagene's QuikChange Site-Directed Mutagenesis, and a mutant primer from Sigma-Genosys. The mutant protein was purified through the use of a histidine tag encoded in the construct and has been shown to be catalytically inactive through a phosphatase assay. Similar to the purification of zeta alone, GST beads are used to purify the interaction between the mutant CD45 and zeta.

For immunoblotting procedures, the desired sample is run on an SDS-PAGE gel and then placed in the Trans-Blot SD Semi-Dry Electrophoretic Transfer Cell from Bio-Rad. A mouse antiphosphotyrosine antibody is used to detect phospho-zeta and an anti-mouse antibody is used as the second antibody. With zeta in excess and with a constant known concentration as well as a constant known concentration of CD45, the ratio of intensities of bands (CD45+zeta complex versus just zeta alone) give a clear indication of binding affinity. All buffers, blocking solution, color development reagents, and the protocol are provided by Bio-Rad.

The following specific references, also incorporated herein by reference, are indicated in the examples and discussion above by a superscript number.

1 Kashio, N. Matsumoto, W., Parker, S., Rothstein, D. M. (1998) The Second Domain of the CD45 Protein Tyrosine Phosphatase Is Critical for Interleukin-2 Secretion and Substrate Recruitment of TCR-ζ in Vivo. *The Journal of Biological Chemistry* 273, 33856–33863.

2 Shenoi, H., Seavitt J., Zheleznyak, A., Thomas, M. L., Brown., E. J. (1999) Regulation of Integrin-Mediated T Cell Adhesion by the Transmembrane Protein Tyrosine Phosphatase CD45. *Journal of Immunology* 162, 7120–7127.

3 Koretzky, G. A., Picus, J., Thomas, M. L., Weiss, A. (1990) Tyrosine phosphatase CD45 is essential for coupling T-cell antigen receptor to the phosphatidyl inositol pathway. *Nature* 346, 66–68.

4 Altin, J. G., Sloan, E. K. (1997) The role of CD45 and CD45-associated molecules in T cell activation. *Immunology and Cell Bio.* 75, 430–445.

5 Koretzky, G. A., Picus, J., Schultz, T. Weiss, A. (1991) Tyrosine phosphatase CD45 is required for T-cell antigen receptor and CD2-mediated activation of a protein tyrosine kinase and interleukin 2 production. *Proc. Nat. Acad. Sci. US* 88, 2037–2041.

6 Verhagen, A. M., Schraven, B., Wild, M., Wallich, R., Meuer S. C. (1996) Differential interaction of the CD2 extracellular and intracellular domains with the tyrosine phosphatase CD45 and the ζ chain of the TCR/CD3/ζ complex. *Eur. J. Immunol.* 26, 2841–2849.

7 Kung, C., Pingel, J. T., Heikinheimo, M., Klemola, T., Varkila, K., Yoo, L. I., Vuopala, K., Poyhonen, M., Uhari, M., Rogers, M, Speck, S. H., Chatila, T., Thomas, M. L (2000) Mutations in the tyrosine phosphatase CD45 gene in a child with sever combined immunodeficiency disease. *Nature Medicine* 6, 343–345.

8 Cale, C. M., Klein, N. J., Novelli, V., Veys, P., Jones, A. M., Morgan, G. (1997) Severe combined immunodeficiency with abnormalities in expression of the common leucocyte antigen, CD45. *Archives of Disease in Childhood* 76, 163–164.

9 Mahalingam, M., Pozniak, A., McManus, T. J., Senaldi, G., Vergani, D., Peakman, M. (1996) Abnormalities of CD45 Isoform Expression in HIV Infection. *Clinical Immunology and Immunopathology* 81, 210–214.

10 Guntermann, C., Amft, N., Murphy, B. J., Nye, K. E. (1998) Impaired CD45-Associated Tyrosine Phosphatase Activity during HIV-1 Infection: Implications for CD3 and CD4 Receptor Signalling. *Biochemical and Biophysical Research Communications* 252, 69–77.

11 Klaus, S. J., Sidorenko, S. P., Clark, E. A. (1996) CD45 Ligation Induces Programmed Cell Death in T and B Lymphocytes. *Journal of immunology* 156, 2743–2753.

12 Johnson, K. G., Bromley, S. K., Dustin, M. L., Thomas, M. L. (2000) A supramolecular basis for CD45 tyrosine phosphatase rgulation in sustained T cell activation. *Proc. Nat. Acad. Sci.* 97 10138–10143.

13 Stone, J. D., Conroy, L. A., Byth, K. F., Hederer, R. A., Howlett, S., Takemoto, Y., Holmes, N., Alexander, D. R. (1997) Aberrant TCR-Mediated Signaling in CD45-Null Thymocytes Involves Dysfunctional Regulation of Lck, Fyn, TCR-ζ, and ZAP-70. *The Journal of Immunology* 158, 5773–5782.

14 Mustelin, T., Williams, S., Tailor, P., Couture, C., Zenner, G., Bum, P., Ashwell, J. D., Altman, A. (1995) Regulation of the p70zap tyrosine protein kinase in T cells by the CD45 phosphotyrosine phosphatase. *Eur. J. Immunol.* 25, 942–946.

15 Negishi, I., Motoyama, N., Nakayama K., Nakayama, K., Senju, S., Hatakeyama, S., Zhang, Q., Chan, A. C., and Loh, D. Y. (1995) Essential Role for ZAP-70 in both positive and negative selection of thymocytes. *Nature* 376, 435–438.

16 Kersh, E. N., Shaw, A. S., Allen, P. M. (1998) Fidelity of T Cell Activation Through Multistep T Cell Receptor ζ Phosphorylation. *Science* 281, 572–574.

17 van Oers, N. S. C., Tohlen, B., Malissen, B., Moomaw, C. R., Afendis, S., Slaughter, C. A. (2000) The 21- and 23-kD forms of TCRζ are generated by specific ITAM phosphorylations. *Nature Immunology* 1:4, 322–328.

18 Furakawa, T., Itoh, M., Krueger, N. X., Streuli, M., Saito, H. (1994) Specific interaction of the CD45 protein tyrosine phosphatase with tyrosine-phosphorylated CD3 ζ chain. *Proc. Natl. Acad. Sci* 91, 10928–10932.

This invention has been described with reference to preferred embodiments thereof. However, it will be appreciated that those skilled in the art, upon consideration of this disclosure, may make modifications and improvements within the spirit and scope of the invention.

What is claimed is:

1. A crystal comprising CD45 molecular structures wherein the crystal effectively diffracts X-rays for the determination of at least one of the structures to a resolution of about 5 Angstroms to about 2 Angstroms.

2. A crystal of claim 1, wherein the crystal comprises CD45 and LAR molecular structures.

3. A crystal comprising D1 and D2 PTPase domains of CD45, wherein the crystal effectively diffracts X-rays for the determination of the atomic coordinates to a resolution of at least about 3.0 Angstroms; and wherein said crystal has a space group of P1 with the unit cell dimensions of a=86 Å, b=60 Å, c=161 Å, $\alpha=90°$, $\beta=100°$ and $\gamma=90°$.

4. The crystal of claim 3 wherein the crystal is CD45.

5. The crystal of claim 3, wherein the CD45 crystal comprises an LAR PTPase domain.

6. The crystal of claim 3 wherein the crystal comprises mutant LAR and CD45 proteins and LAR/CD45 chimeras, combinations and fragments thereof.

7. The crystal of claim 6 wherein the crystal is mutated in an active site.

8. The crystal of claim 6 wherein the crystal is mutated in loop regions.

9. The crystal of claim 6 wherein the crystal is mutated in the D1 region.

10. The crystal of claim 6 wherein the crystal is mutated in the D2 region.

11. The crystal of claim 6 wherein the crystal is mutated in the D1/D2 region.

12. The crystal of claim 6 wherein the crystal is mutated in linker regions between the D1 and D2 regions.

13. A crystal comprising the D1 and D2 PTPase domains of CD45, wherein the crystal effectively diffracts X-rays for the determination of the atomic coordinates to a resolution of about 5 Angstroms or greater; and wherein said crystal has a space group of P2(1) with the unit cell dimensions of a=86.0 Å, b=59.7 Å, c=160.0 Å and $\beta=89.9°$.

14. The crystal of claim 13 wherein the crystal effectively diffracts X-rays for the determination of the atomic coordinates to a resolution of about 3 Angstroms or greater.

15. The crystal of claim 13 wherein the crystal effectively diffracts X-rays for the determination of the atomic coordinates to a resolution of about 2 Angstroms or greater.

16. A crystal structure wherein CD45 is co-crystallized with phosphate analogues in the presence of phosphopeptide substrates.

17. The crystal structures of claim 16 wherein the phosphopeptide substrates are tyrosine kineses.

18. The crystal structure of claim 16 wherein the crystal comprises mutated active sites.

19. The crystal structure of claim 16 wherein the crystal is co-crystallized with phosphates substrates.

20. The crystal structure of claim 16 wherein the crystal comprises mutated amino acid residues in any loop and/or linker region.

21. A crystal structure of CD45 wherein the crystal comprises mutated amino terminal and carboxy terminal ends.

22. The crystal structure of claim 21 wherein about sixteen amino acid residues are deleted from the D2 domain.

23. The crystal structure of claim 21 or 22 wherein the crystal structure is co-crystallized with phosphate substrates.

24. A crystal comprising CD45 molecular structures wherein the crystal effectively diffracts X-rays for the determination of at least one of the structures to a resolution of about 2 Angstroms or less.

* * * * *